US011447521B2

(12) United States Patent
Mullick et al.

(10) Patent No.: US 11,447,521 B2
(45) Date of Patent: Sep. 20, 2022

(54) COMPOUNDS AND METHODS FOR MODULATING ANGIOTENSINOGEN EXPRESSION

(71) Applicant: Ionis Pharmaceuticals, Inc., Carlsbad, CA (US)

(72) Inventors: Adam Mullick, Carlsbad, CA (US); Susan M. Freier, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 17/529,897

(22) Filed: Nov. 18, 2021

(65) Prior Publication Data

US 2022/0153775 A1 May 19, 2022

Related U.S. Application Data

(60) Provisional application No. 63/232,109, filed on Aug. 11, 2021, provisional application No. 63/115,499, filed on Nov. 18, 2020.

(51) Int. Cl.
| | | |
|---|---|---|
| *C07H 21/02* | (2006.01) | |
| *A61P 9/12* | (2006.01) | |
| *C12N 15/113* | (2010.01) | |

(52) U.S. Cl.
CPC .............. *C07H 21/02* (2013.01); *A61P 9/12* (2018.01); *C12N 15/113* (2013.01); *C12N 2310/11* (2013.01); *C12N 2310/315* (2013.01); *C12N 2310/3341* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,751,219 A | 6/1988 | Kempen et al. |
| 4,845,205 A | 7/1989 | Huynh Dinh et al. |
| 4,973,679 A | 11/1990 | Caruthers et al. |
| 4,981,957 A | 1/1991 | Lableu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |

(Continued)

FOREIGN PATENT DOCUMENTS

| | | |
|---|---|---|
| WO | WO 1997/020563 | 6/1997 |
| WO | WO 1997/033623 | 9/1997 |

(Continued)

OTHER PUBLICATIONS

Acelajado et al., "Refractory Hypertension: Definition, Prevalence, and Patient Characteristics." J. Clin. Hypertens (2012) 14(1):7-12.

Albaek et al., "Analogues of a Locked Nucleic Acid with Three-Carbon 2′,4′-Linkages: Synthesis by Ring-Closing Metathesis and Influence of Nucleic Acid Duplex Stability" J. Org. Chem. (2006) 71:7731-7740.

Altmann et al., "Second Generation Antisense Oligonucleotides—Inhibition of PKC-α and c-raf Kinase Expression by Chimeric Oligonucleotides Incorporating 6″-Substituted Carbocyclic Nucleosides and 2″-O-Ethylene Glycol Substituted Ribonucleosides" Nuclewsodies Nucleotides. (1997) 16:917-926.

Altmann et al., "Second Generation of Antisense Oligonucleotides: From Nuclease Resistance to Biological Efficacy in Animals" Chimia. (1996) 50(4):168-176.

(Continued)

*Primary Examiner* — Tracy Vivlemore
(74) *Attorney, Agent, or Firm* — Sheppard, Mullin, Richter & Hampton LLP

(57) ABSTRACT

Provided are compounds, methods, and pharmaceutical compositions for reducing the amount or activity of AGT RNA in a cell or subject, and in certain instances reducing the amount of AGT in a cell or subject. Such compounds, methods, and pharmaceutical compositions are useful to ameliorate at least one symptom or hallmark of a cardiovascular disease. Such compound and pharmaceutical compositions are useful to ameliorate at least one symptom or hallmark of a RAAS pathway-related disease or disorder. Such symptoms and hallmarks include hypertension, chronic kidney disease, stroke, myocardial infarction, heart failure, valvular heart disease, aneurysms of the blood vessels, peripheral artery disease, and organ damage. Such cardiovascular diseases include hypertension, resistant hypertension, Marfan syndrome, and heart failure.

25 Claims, No Drawings

Specification includes a Sequence Listing.

(56) References Cited

U.S. PATENT DOCUMENTS

| | | | |
|---|---|---|---|
| 5,366,878 | A | 11/1994 | Pederson et al. |
| 5,367,066 | A | 11/1994 | Urdea et al. |
| 5,378,825 | A | 1/1995 | Cook et al. |
| 5,386,023 | A | 1/1995 | Sanghvi et al. |
| 5,393,878 | A | 2/1995 | Leumann |
| 5,399,676 | A | 3/1995 | Froehler |
| 5,403,711 | A | 4/1995 | Walder et al. |
| 5,405,938 | A | 4/1995 | Sumerton et al. |
| 5,405,939 | A | 4/1995 | Suhadolnik et al. |
| 5,432,272 | A | 7/1995 | Benner |
| 5,434,257 | A | 7/1995 | Matteucci |
| 5,446,137 | A | 8/1995 | Maag et al. |
| 5,453,496 | A | 9/1995 | Caruthers et al. |
| 5,455,233 | A | 10/1995 | Spielvogel et al. |
| 5,457,187 | A | 10/1995 | Gmelner et al. |
| 5,457,191 | A | 10/1995 | Cook et al. |
| 5,459,255 | A | 10/1995 | Cook et al. |
| 5,466,677 | A | 11/1995 | Baxter et al. |
| 5,466,786 | A | 11/1995 | Buhr et al. |
| 5,470,967 | A | 11/1995 | Huie et al. |
| 5,476,925 | A | 12/1995 | Letsinger et al. |
| 5,484,908 | A | 1/1996 | Froehler et al. |
| 5,489,677 | A | 2/1996 | Sanghvi et al. |
| 5,491,133 | A | 2/1996 | Walder et al. |
| 5,502,177 | A | 3/1996 | Matteucci et al. |
| 5,508,270 | A | 4/1996 | Baxter et al. |
| 5,514,785 | A | 5/1996 | Van Ness et al. |
| 5,519,126 | A | 5/1996 | Hecht |
| 5,519,134 | A | 5/1996 | Acevedo et al. |
| 5,525,711 | A | 6/1996 | Hawkins et al. |
| 5,527,899 | A | 6/1996 | Froehler |
| 5,536,821 | A | 7/1996 | Agrawal et al. |
| 5,541,306 | A | 7/1996 | Agrawal et al. |
| 5,541,307 | A | 7/1996 | Cook et al. |
| 5,550,111 | A | 8/1996 | Suhadolnik et al. |
| 5,552,540 | A | 9/1996 | Haralambidis |
| 5,561,225 | A | 10/1996 | Maddry et al. |
| 5,563,253 | A | 10/1996 | Agrawal et al. |
| 5,565,350 | A | 10/1996 | Kmiec |
| 5,565,555 | A | 10/1996 | Froehler et al. |
| 5,567,811 | A | 10/1996 | Mistura et al. |
| 5,571,799 | A | 11/1996 | Tkachuk et al. |
| 5,576,427 | A | 11/1996 | Cook et al. |
| 5,587,361 | A | 12/1996 | Cook et al. |
| 5,587,469 | A | 12/1996 | Cook et al. |
| 5,587,470 | A | 12/1996 | Cook et al. |
| 5,591,722 | A | 1/1997 | Montgomery et al. |
| 5,594,121 | A | 1/1997 | Froehler et al. |
| 5,596,086 | A | 1/1997 | Matteucci |
| 5,596,091 | A | 1/1997 | Switzer |
| 5,597,909 | A | 1/1997 | Urdea et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,610,300 | A | 3/1997 | Altmann et al. |
| 5,614,617 | A | 3/1997 | Cook et al. |
| 5,618,704 | A | 4/1997 | Sanghvi et al. |
| 5,623,065 | A | 4/1997 | Cook et al. |
| 5,623,070 | A | 4/1997 | Cook et al. |
| 5,625,050 | A | 4/1997 | Beaton et al. |
| 5,627,053 | A | 5/1997 | Usman et al. |
| 5,633,360 | A | 5/1997 | Bishofberger et al. |
| 5,639,873 | A | 6/1997 | Barascut et al. |
| 5,645,985 | A | 7/1997 | Froehler et al. |
| 5,646,265 | A | 7/1997 | McGee |
| 5,646,269 | A | 7/1997 | Matteucci |
| 5,652,355 | A | 7/1997 | Metelev et al. |
| 5,652,356 | A | 7/1997 | Agrawal |
| 5,663,312 | A | 9/1997 | Chaturvedula |
| 5,670,633 | A | 9/1997 | Cook et al. |
| 5,672,697 | A | 9/1997 | Buhr et al. |
| 5,677,437 | A | 10/1997 | Teng et al. |
| 5,677,439 | A | 10/1997 | Weis et al. |
| 5,681,941 | A | 10/1997 | Cook et al. |
| 5,698,685 | A | 12/1997 | Summerton et al. |
| 5,700,920 | A | 12/1997 | Altmann et al. |
| 5,700,922 | A | 12/1997 | Cook |
| 5,721,218 | A | 2/1998 | Froehler |
| 5,750,692 | A | 5/1998 | Cook et al. |
| 5,763,588 | A | 6/1998 | Matteucci et al. |
| 5,792,608 | A | 8/1998 | Swaminathan et al. |
| 5,792,847 | A | 8/1998 | Buhr et al. |
| 5,801,154 | A | 9/1998 | Baracchini et al. |
| 5,808,027 | A | 9/1998 | Cook et al. |
| 5,811,534 | A | 9/1998 | Cook et al. |
| 5,830,653 | A | 11/1998 | Froehler et al. |
| 5,859,221 | A | 1/1999 | Cook et al. |
| 5,948,903 | A | 9/1999 | Cook et al. |
| 5,994,517 | A | 11/1999 | Ts'O |
| 6,005,087 | A | 12/1999 | Cook et al. |
| 6,005,096 | A | 12/1999 | Matteucci et al. |
| 6,166,199 | A | 12/2000 | Cook et al. |
| 6,268,490 | B1 | 7/2001 | Imanishi et al. |
| 6,300,319 | B1 | 10/2001 | Manoharan |
| 6,383,812 | B1 | 5/2002 | Chen et al. |
| 6,426,220 | B1 | 7/2002 | Bennett et al. |
| 6,525,031 | B2 | 2/2003 | Manoharan |
| 6,525,191 | B1 | 2/2003 | Ramasamy |
| 6,531,584 | B1 | 3/2003 | Cook et al. |
| 6,582,908 | B2 | 6/2003 | Fodor et al. |
| 6,600,032 | B1 | 7/2003 | Manoharan et al. |
| 6,620,916 | B1 | 9/2003 | Takahara et al. |
| 6,660,720 | B2 | 12/2003 | Manoharan |
| 6,670,461 | B1 | 12/2003 | Wengel et al. |
| 6,770,748 | B2 | 8/2004 | Imanishi et al. |
| 6,794,499 | B2 | 9/2004 | Wengel et al. |
| 6,902,888 | B1 | 6/2005 | McGrail et al. |
| 6,906,182 | B2 | 6/2005 | Ts'o et al. |
| 6,908,903 | B1 | 6/2005 | Theodore et al. |
| 7,015,315 | B1 | 3/2006 | Cook et al. |
| 7,034,133 | B2 | 4/2006 | Wengel et al. |
| 7,053,207 | B2 | 5/2006 | Wengel |
| 7,101,993 | B1 | 9/2006 | Cook et al. |
| 7,262,177 | B2 | 8/2007 | Ts'o et al. |
| 7,374,884 | B2 | 5/2008 | McGrail et al. |
| 7,399,845 | B2 | 7/2008 | Seth et al. |
| 7,427,672 | B2 | 9/2008 | Imanishi et al. |
| 7,491,805 | B2 | 2/2009 | Vargeese et al. |
| 7,547,684 | B2 | 6/2009 | Seth et al. |
| 7,569,686 | B1 | 8/2009 | Bhat et al. |
| 7,572,582 | B2 | 8/2009 | Wengel et al. |
| 7,582,744 | B2 | 9/2009 | Manoharan et al. |
| 7,666,854 | B2 | 2/2010 | Seth et al. |
| 7,696,345 | B2 | 4/2010 | Allerson et al. |
| 7,723,509 | B2 | 5/2010 | Manoharan et al. |
| 7,741,457 | B2 | 6/2010 | Swayze et al. |
| 7,750,131 | B2 | 7/2010 | Seth et al. |
| 7,851,615 | B2 | 12/2010 | Manoharan et al. |
| 7,875,733 | B2 | 1/2011 | Bhat et al. |
| 7,939,677 | B2 | 5/2011 | Bhat et al. |
| 8,022,193 | B2 | 9/2011 | Swayze et al. |
| 8,030,467 | B2 | 10/2011 | Seth et al. |
| 8,034,909 | B2 | 10/2011 | Wengel et al. |
| 8,080,644 | B2 | 12/2011 | Wengel et al. |
| 8,088,746 | B2 | 1/2012 | Seth et al. |
| 8,088,904 | B2 | 1/2012 | Swayze et al. |
| 8,106,022 | B2 | 1/2012 | Manoharan et al. |
| 8,124,745 | B2 | 2/2012 | Allerson et al. |
| 8,137,695 | B2 | 3/2012 | Rozema et al. |
| 8,153,365 | B2 | 4/2012 | Wengel et al. |
| 8,158,601 | B2 | 4/2012 | Chen et al. |
| 8,268,980 | B2 | 9/2012 | Seth et al. |
| 8,278,283 | B2 | 10/2012 | Seth et al. |
| 8,278,425 | B2 | 10/2012 | Prakash et al. |
| 8,278,426 | B2 | 10/2012 | Seth et al. |
| 8,313,772 | B2 | 11/2012 | Rozema et al. |
| 8,344,125 | B2 | 1/2013 | Manoharan et al. |
| 8,349,308 | B2 | 1/2013 | Yurkovetskiy et al. |
| 8,404,862 | B2 | 3/2013 | Manoharan et al. |
| 8,435,491 | B2 | 5/2013 | Wang et al. |
| 8,440,803 | B2 | 5/2013 | Swayze et al. |
| 8,450,467 | B2 | 5/2013 | Manoharan et al. |
| 8,501,805 | B2 | 8/2013 | Seth et al. |
| 8,501,930 | B2 | 8/2013 | Rozema et al. |

(56) References Cited

U.S. PATENT DOCUMENTS

| | | |
|---|---|---|
| 8,530,640 B2 | 9/2013 | Seth et al. |
| 8,541,548 B2 | 9/2013 | Rozema |
| 8,546,556 B2 | 10/2013 | Seth et al. |
| 8,552,163 B2 | 10/2013 | Lee et al. |
| RE44,779 E | 2/2014 | Imanishi et al. |
| 8,796,437 B2 | 8/2014 | Swayze et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,290,760 B2 | 3/2016 | Rajeev et al. |
| 10,912,792 B2 | 2/2021 | Mullick et al. |
| 2001/0053519 A1 | 12/2001 | Fodor et al. |
| 2003/0077829 A1 | 4/2003 | MacLachlan |
| 2003/0119724 A1 | 6/2003 | Ts'o et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0077611 A1 | 4/2004 | Alexander et al. |
| 2004/0171570 A1 | 9/2004 | Allerson et al. |
| 2005/0130923 A1 | 6/2005 | Bhat et al. |
| 2005/0164235 A1 | 7/2005 | Manoharan et al. |
| 2006/0063730 A1 | 3/2006 | Monia et al. |
| 2006/0148740 A1 | 7/2006 | Platenburg |
| 2006/0183886 A1 | 8/2006 | Tso et al. |
| 2007/0031844 A1 | 2/2007 | Khvorova et al. |
| 2008/0039618 A1 | 2/2008 | Allerson et al. |
| 2008/0108801 A1 | 5/2008 | Manoharan et al. |
| 2008/0206869 A1 | 8/2008 | Smith et al. |
| 2008/0261231 A1 | 10/2008 | McGrail et al. |
| 2008/0281041 A1 | 11/2008 | Rozema et al. |
| 2008/0281044 A1 | 11/2008 | Manoharan et al. |
| 2009/0012281 A1 | 1/2009 | Swayze et al. |
| 2009/0105177 A1 | 4/2009 | Monia et al. |
| 2009/0203132 A1 | 8/2009 | Swayze et al. |
| 2009/0203135 A1 | 8/2009 | Forst et al. |
| 2009/0286973 A1 | 11/2009 | Manoharan et al. |
| 2010/0130595 A1 | 5/2010 | Dean et al. |
| 2010/0190837 A1 | 7/2010 | Migawa et al. |
| 2010/0197762 A1 | 8/2010 | Swayze et al. |
| 2010/0240730 A1 | 9/2010 | Beigelman et al. |
| 2011/0097264 A1 | 4/2011 | Wang et al. |
| 2011/0097265 A1 | 4/2011 | Wang et al. |
| 2011/0123520 A1 | 5/2011 | Manoharan et al. |
| 2011/0207799 A1 | 8/2011 | Rozema et al. |
| 2011/0269814 A1 | 11/2011 | Manoharan et al. |
| 2012/0035115 A1 | 2/2012 | Manoharan et al. |
| 2012/0095075 A1 | 4/2012 | Manoharan et al. |
| 2012/0101148 A1 | 4/2012 | Akinc et al. |
| 2012/0128760 A1 | 5/2012 | Manoharan et al. |
| 2012/0136042 A1 | 5/2012 | Manoharan et al. |
| 2012/0157509 A1 | 6/2012 | Hadwiger et al. |
| 2012/0165393 A1 | 6/2012 | Rozema et al. |
| 2012/0230938 A1 | 9/2012 | Rozema et al. |
| 2013/0004427 A1 | 1/2013 | El-Sayed et al. |
| 2013/0109817 A1 | 5/2013 | Yurkovetskiy et al. |
| 2013/0121954 A1 | 5/2013 | Wakefield et al. |
| 2013/0130378 A1 | 5/2013 | Manoharan et al. |
| 2013/0178512 A1 | 7/2013 | Manoharan et al. |
| 2013/0203836 A1 | 8/2013 | Rajeev et al. |
| 2013/0236968 A1 | 9/2013 | Manoharan et al. |
| 2014/0107330 A1 | 4/2014 | Freier et al. |
| 2015/0018540 A1 | 1/2015 | Prakash et al. |
| 2015/0031130 A1 | 1/2015 | Bhat |
| 2015/0184153 A1 | 7/2015 | Freier et al. |
| 2015/0191727 A1 | 7/2015 | Migawa et al. |
| 2015/0267195 A1 | 9/2015 | Seth et al. |
| 2015/0275212 A1 | 10/2015 | Albaek et al. |
| 2015/0297629 A1 | 10/2015 | Mullick et al. |
| 2017/0189541 A1 | 7/2017 | Foster et al. |
| 2018/0169129 A1 | 6/2018 | Hinkle et al. |
| 2019/0160090 A1 | 5/2019 | Mullick et al. |
| 2019/0233827 A1 | 8/2019 | Freier et al. |
| 2019/0338281 A1 | 11/2019 | Seth et al. |
| 2022/0000901 A1 | 1/2022 | Mullick et al. |

FOREIGN PATENT DOCUMENTS

| | | |
|---|---|---|
| WO | WO 1997/046098 | 12/1997 |
| WO | WO 1998/013381 | 4/1998 |
| WO | WO 1998/039352 | 9/1998 |
| WO | WO 1999/014226 | 3/1999 |
| WO | WO 2000/071751 | 11/2000 |
| WO | WO 2001/049687 | 7/2001 |
| WO | WO 2002/043771 | 6/2002 |
| WO | WO 2003/004602 | 1/2003 |
| WO | WO 2004/024757 | 3/2004 |
| WO | WO 2004/101619 | 11/2004 |
| WO | WO 2004/106356 | 12/2004 |
| WO | WO 2005/021570 | 3/2005 |
| WO | WO 2005/121371 | 12/2005 |
| WO | WO 2006/047842 | 5/2006 |
| WO | WO 2007/134181 | 11/2007 |
| WO | WO 2008/098788 | 8/2008 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |
| WO | WO 2009/082607 | 7/2009 |
| WO | WO 2009/100320 | 8/2009 |
| WO | WO 2009/126933 | 10/2009 |
| WO | WO 2009/134487 | 11/2009 |
| WO | WO 2010/036696 | 4/2010 |
| WO | WO 2010/036698 | 4/2010 |
| WO | WO 2010/054406 | 5/2010 |
| WO | WO 2010/088537 | 8/2010 |
| WO | WO 2010/129709 | 11/2010 |
| WO | WO 2010/144740 | 12/2010 |
| WO | WO 2010/148013 | 12/2010 |
| WO | WO 2011/017521 | 2/2011 |
| WO | WO 2011/038356 | 3/2011 |
| WO | WO 2011/041545 | 4/2011 |
| WO | WO 2011/100131 | 8/2011 |
| WO | WO 2011/120053 | 9/2011 |
| WO | WO 2011/133876 | 10/2011 |
| WO | WO 2011/163121 | 12/2011 |
| WO | WO 2012/007327 | 1/2012 |
| WO | WO 2012/037254 | 3/2012 |
| WO | WO 2012/068187 | 5/2012 |
| WO | WO 2012/083046 | 6/2012 |
| WO | WO 2012/083185 | 6/2012 |
| WO | WO 2012/089352 | 7/2012 |
| WO | WO 2012/089602 | 7/2012 |
| WO | WO 2012/177947 | 12/2012 |
| WO | WO 2013/033230 | 3/2013 |
| WO | WO 2013/075035 | 5/2013 |
| WO | WO 2013/165816 | 11/2013 |
| WO | WO 2013/166121 | 11/2013 |
| WO | WO 2014/018930 | 1/2014 |
| WO | WO 2014/179620 | 11/2014 |
| WO | WO 2015/106128 | 7/2015 |
| WO | WO 2015/179724 | 11/2015 |
| WO | WO 2017/015555 | 1/2017 |
| WO | WO 2017/062816 | 4/2017 |
| WO | WO 2019/157531 | 8/2019 |

OTHER PUBLICATIONS

Altmann et al., "Second-generation antisense oligonucleotides: structure—activity relationships and the design of improved signal-transduction inhibitors" Biochem. Soc. Trans. (1996) 24:630-637.

Altschul et al., "Basic Local Alignment Search Tool" J. Mol. Biol. (1990) 215:403-410.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.

Baker et al., "Integrated Assessment of GalNAc3-Conjugated Phosphorothioate Modified 2'-O-Methoxyethyl Chimeric Antisense Oligonucleotides in Healthy Human Volunteers" Abstract for Nature Conference: RNA at the Bench and Bedside (Oct. 8-10, 2018) La Jolla, CA.

(56) References Cited

OTHER PUBLICATIONS

Baker et al., "Integrated Assessment of GalNAc3-Conjugated Phosphorothioate Modified 2'-O-Methoxyethyl Chimeric Antisense Oligonucleotides in Healthy Human Volunteers" Poster presentation for Nature Conference: RNA at the Bench and Bedside (Oct. 8-10, 2018) La Jolla, CA.

Baker et al., "Integrated Assessment of Phase 2 Studies on GalNAC3-Conjugated 2'-O-Methoxyethyl Modified Chimeric Antisense Oligonucleotides" Abstract for RNA at the Bench and Bedside II Conference—Virtual (Nov. 11-13, 2020).

Baker et al., "Integrated Assessment of Phase 2 Studies on GalNAC3-Conjugated 2'-O-Methoxyethyl Modified Chimeric Antisense Oligonucleotides" Poster for RNA at the Bench and Bedside II Conference—Virtual (Nov. 11-13, 2020).

Balakrishnan et al., "Comparative Effects of Angiotensinogen versus Renin Inhibition on Established Atherosclerosis and Obesity in Hypercholesterolemic Mice" Abstract for Poster for Arteriosclerosis, Thrombosis, and Vascular Biology (2013) Orlando, FL.

Balakrishnan et al., "Angiotensinogen Inhibition Reduces Atherosclerosis and Body Weight Gain Induced by High-Carbohydrate Diet" Abstract for Poster for Arteriosclerosis, Thrombosis, and Vascular Biology (2014).

Balakrishnan et al., "Angiotensinogen Inhibition by Antisense Oligonucleotides Decreases Atherosclerosis and Obesity in a Dose-Dependent Manner" Abstract for Arteriosclerosis, Thrombosis, and Vascular Biology Annual Conference (2012) Chicago, IL.

Balakrishnan, et al., "Inhibition of Angiotensinogen Synthesis by Antisense Oligonucleotides Decreases Atherosclerosis and Obesity in Male LDL Receptor Deficient Mice fed a Saturated Fat-enriched Diet" Poster presented ATVB 2011 Scientific Sessions (Apr. 28-30, 2021) Chicago, IL.

Biessen et al., "Novel hepatotrophic prodrugs of the antiviral nucleoside 9-(2-phosphonylmethoxyethyl)adenine with improved pharmacokinetics and antiviral activity" FASEB J (2000) 14, 1784-1792.

Biessen et al., "Synthesis of Cluster Galactosides with High Affinity for the Hepatic Asialoglycoprotein Receptor" J Med Chem (1995) 38, 1538-1546.

Biessen et al.,"The Cholesterol Derivative of a Triantennary Galactoside with High Affinity for the Hepatic Asialoglycoprotein Receptor: a Potent Cholesterol Lowering Agent" J Med Chem (1995) 38, 1846-1852.

Braasch et al., "Locked nucleic acid (LNA): fine-tuning the recognition of DNA and RNA" Chem. Biol. (2001) 8:1-7.

Braasch et al., "Novel antisense and peptide nucleic acid strategies for controlling gene expression" Biochemistry (2002) 41(14):4503-4510.

Brambatti, M., "Antisense Oligonucleotides Targeting the Angiotensinogen: A Novel Therapeutic Approach in the Cardiovascular Space" Presentation for TIDES Europe (Nov. 15-17, 2021) Brussels, Belgium.

Branch et al., "A good antisense molecule is hard to find," TIBS (1998) 23:45-50.

Chen et al., "Inhibition of Ligand Dependent AT1a Receptor Activity Attenuates Thoracic Aortic Aneurysms in a Marfan Mouse Model" Abstract for (Virtual) Vascular Discovery: From Genes to Medicine Scientific Sessions May 5-7, 2020.

Chen et al., "Deletion of AT1a (Angiotensin II Type 1a) Receptor or Inhibition of Angiotensinogen Synthesis Attenuates Thoracic Aortopathies in Fibrillin1C1041G/+ Mice" Arteriosclerosis, Thrombosis, and Vascular Biology (2021) 41: 2538-2550.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

ClinicalTrials.gov Study Record: NCT04836182 "A Study to Assess the Safety, Tolerability and Efficacy of IONIS-AGT-LRx in Participants With Chronic Heart Failure With Reduced Ejection Fraction (ASTRAAS-HF)" (2021).

ClinicalTrials.gov Study Record: NCT03714776 "A Study to Assess the Safety, Tolerability and Efficacy of IONIS-AGT-LRx, an Antisense Inhibitor Administered Subcutaneously to Hypertensive Subjects With Controlled Blood Pressure" (2018).

ClinicalTrials.gov Study Record: NCT04714320 "A Study to Assess the Safety, Tolerability and Efficacy of IONIS-AGT-LRx in Hypertensive Participants With Uncontrolled Blood Pressure" (2021).

ClinicalTrials.gov Study Record: NCT04731623 "A Study to Assess the Safety, Tolerability, Pharmacokinetics and Pharmacodynamics of ION904" (2021).

ClinicalTrials.gov Study Record: NCT03101878 "Safety, Tolerability, Pharmacokinetics, and Pharmacodynamics of Ionis AGT-LRx in Healthy Volunteers" (2017).

ClinicalTrials.gov Study Record: NCT04083222 "A Study to Assess the Safety, Tolerability and Efficacy of IONIS-AGT-LRx" (2019).

Connolley et al., "Binding and Endocytosis of Cluster Glycosides by Rabbit Hepatocytes" J Biol Chem (1982) 257, 939-945.

Cowley et al., "Genetically defined risk of salt sensitivity in an intercross of Brown Norway and Dahl S rats" Physiol Genomics (2000) 2(3):107-115.

Crooke et al., "Basic Principles of Antisense Therapeutics" Antisense Research and Application (1998) Chapter 1:1-50.

Crooke et al., "Pharmacokinetic Properties of Several Novel Oligonucleotide Analogs in mice" J. Pharmacol. Exp. Ther. (1996) 277, 923-937.

Crooke, ST., et al., "Antisense Drug Technology" Second Edition, CRC Press (2008) Chapters 1-28.

Crooke et al., "Integrated Assessment of the Clinical Performance of GalNAc3-Conjugated 2'-O-Methoxyethyl Chimeric Antisense Oligonucleotides: I. Human Volunteer Experience" Nucl Ac Ther (2018) 1-69.

Duff et al., "Intrabody Tissue-Specific Delivery of Antisense Conjugates in Animals: Ligand-Linker-Antisense Oligomer Conjugates" Methods Enzymol (2000) 313, 297-321.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

Eide et al., "Low-renin status in therapy-resistant hypertension: a clue to efficient treatment" Journ of Hypertension (2004) 22: 2217-2226.

Elayadi et al., "Application of PNA and LNA oligomers to chemotherapy" Curr. Opinion Invens. Drugs (2001) 2:558-561.

Englisch et al., "Chemically Modified Oligonucleotides as Probes and Inhibitors" Angewandte Chemie Intl Edition (1991) 30: 613-722.

European search report for 13823783.9 dated Feb. 12, 2016.

Extended search report for 19216534.8 dated Jun. 19, 2020.

Ferrario et al., "Renin angiotensin aldosterone inhibition in the treatment of cardiovascular disease" Pharmacological Res (2017) 125: 57-71.

Fitzgibbon et al., "Attenuation of accelerated renal cystogenesis in Pkd1 mice by renin-angiotensin system blockade" Am J Physiol Renal Physiol (2018) 314: F210-F218.

Freier et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21):6365-6372.

Gautschi et al., "Activity of a novel bcl-2/bcl-xLbispecific antisense oligonucleotide against tumors of diverse histologic origins" J. Natl. Cancer Inst. (2001) 93:463-471.

Geary et al., "GalNAc Conjugated Antisense: IONIS-FXI-LRX Safety and Activity in Human Subjects" Presentation for DIA Oligonucleotide-Based Therapeutics Conference (Oct. 28-30, 2019) North Bethesda, MD.

GenBank Accession No. NC_000001.11 truncated from nucleotides 230700001 to 230718000.

GenBank Accession No. NM_000029.3.

(56) References Cited

OTHER PUBLICATIONS

Graham, M., "Pronounced Effects of Angiotensinogen Synthesis Inhibition on Atherosclerosis and Body Weight." Abstract for International Society for Applied Cardiovascular Biology (Sep. 22-25, 2010) Boston, MA.
Gu et al., "Base pairing properties of D- and L-cyclohexene nucleic acids (CeNA)" Oligonucleotides (2003) 13(6):479-489.
Gu et al., "Enzymatic resolution and base pairing properties of D- and L-cyclohexenyl nucleic acids (CeNA)" Nucleosides Nucleotides Nucleic Acids (2005) 24(5-7):993-998.
Gu et al., "Synthesis of enantiomeric-pure cyclohexenyl nucleoside building blocks for oligonucleotide synthesis" Tetrahedron (2004) 60(9):2111-2123.
Gyurko et al., "Antisense inhibition of AT1 receptor mRNA and angiotensinogen mRNA in the brain of spontaneously hypertensive rats reduces hypertension of neurogenic origin" Reg. Pep. (1993) 49:167-174.
Horvath et al., "Stereoselective synthesis of (-)-ara-cyclohexenyl-adenine" Tetrahedron Letters (2007) 48:3621-3623.
Hung "Recent Progress on Antisense Technology Research and Development" Presentation for RNAi China, Kunshan (2015).
Jayaprakash et al., "Non-Nucleoside Building Blocks for Copper-Assisted and Copper-Free Click Chemistry for the Efficieny Synthesis of RNA Conjugates" Org Lett (2010) 12, 5410-5413.
Jones et al., "RNA quantitation by fluorescence-based solution assay: RiboGreen reagent characterization" Anal. Biochem. (1998) 265(2):368-374.
Judd et al., "Apparent and true resistant hypertension: definition, prevalence and outcomes." J. Hum. Hypertens. (2014) 28(8):463-468.
Kabanov et al., "A new class of antivirals: antisense oligonucleotides combined with a hydrophobic substituent effectively inhibit influenza virus reproduction and synthesis of virus-specfic proteins in MDCK cells" FEBS Lett. (1990) 259, 327-330.
Kato et al., "N-acetylgalactosamine incorporation into a peptide containing consecutive threonine residues by UDP-N-acetyl-D-galactosaminide:polypeptide N-acetylgalactosaminyltransferases" Glycobiol (2001) 11, 821-829.
Khorev et al., "Trivalent, Gal/GalNAc-containing ligands designed for the asialoglycoprotein receptor" Bioorg Med Chem (2008) 16, 5216-5231.
Kim et al., "Oligomeric Glycopeptidomimetics Bearing the Cancer Related TN-Antigen" Tetrahedron Lett (1997) 38, 3487-3490.
Kornilova et al., "Development of a fluorescence polarization binding assay for asialoglycoprotein receptor" Analyt Biochem (2012) 425, 43-46.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kroschwitz The Concise Encyclopedia Of Polymer Science And Engineering, John Wiley & Sons (1990) 858-859.
Kukida et al., "Renal Angiotensinogen Is Predominantly Liver Derived in Nonhuman Primates" Arterioscler Thromb Vasc Biol (2021) 41: 2851-2853.
Kumar et al., "Design, synthesis, biophysical and primer extension studies of novel acyclic butyl nucleic acid (BuNA)" Org. Biomol. Chem. (2013) 11, 5853-5865.
Kumar et al., "The first analogues of LNA (locked nucleic acids): phosphorothioate-LNA and 2'-thio-LNA" Bioorg Med Chem Lett. (1998) 8:2219-2222.
Kuo et al., "Enhanced Antisense Oligonucleotide Delivery via AGTR1 Targeting" Abstract for TIDES: Oligonucleotides and Peptide Therapeutics (May 20-23, 2019) San Diego, CA.
Kuo et al., "Enhanced Antisense Oligonucleotide Delivery via AGTR1 Targeting" Poster for TIDES: Oligonucleotides and Peptide Therapeutics (May 20-23, 2019) San Diego, CA.
Kuo et al. "Enhancing Antisense Oligonucleotide Delivery Via AGTR1 Targeting" Abstract for RNA at the Bench and Bedside II Conference—Virtual (Nov. 11-13, 2020).

Lee "Synthesis of some cluster glycosides for attachment to proteins or solid matrices" Carbohydr Res (1978) 67: 509-514.
Lee et al. "New and more efficient multivalent glyco-ligands for asialoglycoprotein receptor of mammalian hepatocytes" Bioorganic & Medicinal Chemistry (2011) 19: 2494-2500.
Lee et al., "Facile Synthesis of a High-Affinity Ligand for Mammalian Hepatic Lectin Containing Three Terminal N-Acetylgalactosamine Residues" Bioconjug Chem. (1997) 8: 762-765.
Lee et al., "New Synthetic Cluster Ligands for Galactose/N-Acetylgalactosamine-Specific Lectin of Mammalian Liver" Biochem. (1984) 23: 4255-4261.
Lee et al., "Preparation of Cluster Glycosides of N-Acetylgalactosamine That Have Subnanomolar Binding Constants Towards the Mammalian Hepatic Gal/GalNAc-specific Receptor" Glycoconjugate J (1987) 4: 317-328.
Lee et al., "Protein microarrays to study carbohydrate-recognition events" Bioorg Med Chern Lett (2006) 16(19): 5132-5135.
Lee et al., "Synthesis of Multivalent Neoglyconjugates of MUC1 by the Conjugation of Carbohydrate-Centered, Triazole-Linked Glycoclusters to MUC1 Peptides Using Click Chemistry" J Org Chem (2012) 77: 7564-7571.
Lee et al., "Synthesis of Peptide-Based Trivalent Scaffold for Preparation of Cluster Glycosides" Methods Enzymol (2003) 362: 38-43.
Letsinger et al., "Cholesteryl-conjugated oligonucleotides: Synthesis, properties, and activity as inhibitors of replication of human immunodeficiency virus in cell culture" Proc. Natl. Acad. Sci. USA (1989) 86, 6553-6556.
Leumann et al., "DNA Analogues: From Supramolecular Principles to Biological Properties" Bioorganic & Medicinal Chemistry (2002) 10:841-854.
Lu et al., "Angiotensinogen Exerts Effects Independent of Angiotensin II" Arterioscler Thromb Vasc Biol (2015) 256-317.
Lu et al., "Megalin Inhibition Regulates Angiotensinogen and Angiotensin II in Mice" Abstract for AHA Annual Scientific Sessions (Nov. 12-16, 2016) New Orleans, LA.
Maher et al., "Comparative hybrid arrest by tandem antisense oligodeoxyribonucleotides or oligodeoxyribonucleoside methylpbosphonates in a cell-free system" Nucl. Acid. Res. (1988) 16(8):3341-3358.
Maier et al. "Synthesis of Antisense Oligonucleotides Conjugated to a Multivalent Carbohydrate Cluster for Cellular Targeting" Bioconjugate Chemistry (2003) 14: 18-29.
Maierhofer et al., "Probing multivalent carbohydrate-lectin interactions by an enzyme-linked lectin assay employing covalently immobilized carbohydrates" Bioorg Med Chem (2007) 15, 7661-7676.
Makino et al., "Chronic antisense therapy for angiotensinogen on cardiac hypertrophy in spontaneously hypertensive rats" Cardiovasc Res (1999) 44: 543-548.
Manoharan et al., "Chemical Modifications to Improve Uptake and Bioavailability of Antisense Oligonucleotides" Ann. N.Y. Acad. Sci. (1992) 660, 306-309.
Manoharan et al., "Cholic Acid-Oligonucleotide Conjugates for Antisense Applications" Bioorg. Med. Chem. Lett. (1994) 4, 1053-1060.
Manoharan et al., "Introduction of a Lipophilic Thioether Tether in the Minor Groove of Nucleic Acids for Antisense Applications" Bioorg. Med. Chem. Lett. (1993) 3, 2765-2770.
Manoharan et al., "Lipidic Nucleic Acids" Tetrahedron Lett. (1995) 36, 3651-3654.
Manoharan et al., "Oligonucleotide Conjugates: Alteration of the Pharmacokinetic Properties of Antisense Agents" Nucleosides & Nucleotides (1995) 14, 969-973.
Manoharan, "Oligonucleotide Conjugates as Potential Antisense Drugs with Improved Uptake, Biodistribution, Targeted Delivery, and Mechanism of Action" Antisense Nucleic Acid Drug Dev (2002) 12, 103-128.
Martin, "New acces to 2'-O-alkylated ribonucleosides and properties of 2'-O-alkylated oligoribonucleotides" Helv. Chim. Acta. (1995) 78:486-504.

(56) References Cited

OTHER PUBLICATIONS

Merwin et al., "Targeted Delivery of DNA Using YEE(GalNAcAH)3, a Synthetic Glycopeptide Ligand for the Asialoglycoprotein Receptor" *Bioconjug Chem* (1994) 5, 612-620.

Mishra et al., "Improved leishmanicidal effect of phosphorotioate antisense oligonucleotides by LDL-mediated delivery" *Biochim. Biophys. Acta* (1995) 1264, 229-237.

Morgan et al., "Antisense Inhibition of Angiotensinogen With IONIS-AGT-L Rx: Results of Phase 1 and Phase 2 Studies" JACC Basic Transl Sci (2021) 6: 485-496.

Morgan et al., "Effect of IONIS-AGT-LRX in subjects with uncontrolled hypertension on 2-3 medications: Results of a Phase 2 study" Abstract for 2021 American College of Cardiology Annual Meeting—Virtual (May 15-17, 2021).

Morgan et al., "Effect of IONIS-AGT-LRX in subjects with uncontrolled hypertension on 2-3 medications: Results of a Phase 2 study" Poster presentation, 2021 American College of Cardiology Annual Meeting, Virtual (May 15-17, 2021) Poster #17601.

Morgan et al., "Effect of IONIS-AGT-LRX, an antisense inhibitor of angiotensinogen production, in healthy volunteers and in subjects with hypertension: Results of Phase 1 and Phase 2 studies" Abstract for 2021 American College of Cardiology Annual Meeting—Virtual (May 15-17, 2021).

Morgan et al., "Effect of IONIS-AGT-Lrx, An Antisense Inhibitor of Angiotensinogen Production, in Healty Volunteers and in Subjects With Hypertension: Results of Phase 1 and Phase 2 Studies." Poster presentation, 2021 American College of Cardiology Annual Meeting, Virtual (May 15-17, 2021) Poster #17627.

Mullick et al., "Blood Pressure Lowering and Safety Improvements with Liver Angiotensinogen Inhibition in Models of Hypertension and Kidney Injury" Hypertension (2017) 566-576.

Mullick et al., "Antisense Inhibition Of Angiotensinogen Reduces BP In Normotensive Sprague-Dawley Rats And Effectively Eliminates RAS-dependent BP Control In Hypertensive Rats" Abstract for AHA High Blood Pressure Research Scientific Sessions (Sep. 19.

Mullick et al., "Antisense Inhibition Of Angiotensinogen Reduces BP In Normotensive Sprague-Dawley Rats And Effectively Eliminates RAS-dependent BP Control In Hypertensive Rats" Poster for AHA High Blood Pressure Research Scientific Sessions (Sep. 19-22, 2012).

Mullick et al., "Liver-Specific Antisense Inhibition of Angiotensinogen Reduced BP in a Hypertensive Rat Model Resistant to Standard RAS Inhibitors" Abstract for AHA—Council on Hypertension 2015 Scientific Sessions (Sep. 16-19, 2015) Washington, DC.

Mullick et al., "Liver-Specific Antisense Inhibition of Angiotensinogen Reduced BP in a Hypertensive Rat Model Resistant to Standard RAS Inhibitors" Presentation for AHA—Council on Hypertension 2015 Scientific Sessions (Sep. 16-19, 2015) Washington, DC.

Mullick et al., "LICA-Antisense Oligonucleotide Inhibition of Angiotensinogen: A New Therapeutic Approach for Treatment-Resistant Hypertension" Presentation for Gordon Research Conference (Jun. 5-10, 2016) Easton, MA.

Nanavati et al., "Interspecies Scaling of Human Clearance and Plasma Trough Exposure for Antisense Oligonucleotides: A Retrospective Analysis of Triantennary N-Acetyl Galactosamine-Conjugated and Unconjugated-Antisense Oligonucleotides" Nucl Ac Ther (2021) 1-11.

Nauwelaerts et al., "Cyclohexenyl nucleic acids: conformationally flexible oligonucleotides" Nucleic Acids Res. (2005) 33(8):2452-2463.

Nauwelaerts et al., "Structural characterization and biological evaluation of small interfering RNAs containing cyclohexenyl nucleosides" J. Am. Chem. Soc. (2007) 129(30):9340-9348.

New England Biolabs 1998/99 Catalog (cover page and pp. 121 and 284).

Nguyen et al., "The biology of the (pro)renin receptor" J. Am. Soc. Nephrol. (2010) 21(1):18-23.

Nishina et al., "Chimeric Antisense Oligonucleotide Conjugated to α-Tocopherol" *Molecular Therapy Nucleic Acids* (2015) 4, e220.

Nishina et al., "Efficient In Vivo Delivery of siRNA to the Liver by Conjugation of α-Tocopherol" *Molecular Therapy* (2008) 16, 734-740.

Nobakht et al., "Limitations of angiotensin inhibition" Nat. Rev. Nephrol. (2011) 7(6):356-359.

Oberhauser et al., "Effective incorporation of 2'-O-methyl-oligonucleotides into liposomes and enhanced cell association through modification with thiocholesterol" *Nucl. Acids Res.* (1992) 20, 533-538.

Oka et al., "An oxazaphospholidine approach for the stereocontrolled synthesis of oligonucleoside phosphorothioates" J Am Chern Soc (2003) 125: 8307-8317.

Okamoto et al., "Development of a strain of spontaneously hypertensive rats" Jpn. Circ. J. (1963) 27:282-293.

Orum et al., "Locked nucleic acids: A promising molecular family for gene-function analysis and antisense drug development" Curr. Opinion Mol. Ther. (2001) 3:239-243.

Partridge et al., "Improvements in the Tolerability Profile of 2'-O-Methoxyethyl Chimeric Antisense Oligonucleotides in Parallel with Advances in Design, Screening, and Other Methods" Nucl Ac Ther (2021) 31: 417-426.

Paulis et al., "Key advances in antihypertensive treatment" Nat. Rev. Cardiol. (2012) 9(5):276-285.

Pavia et al., "Synthetic TN glycopeptide related to human glycophorin AM" Int J Pep Protein Res (1983) 22: 539-548.

Phillips et al., "Antisense inhibition of hypertension: A new strategy for renin-angiotensin candidate genes" Kidney International (1994) 46:1554-1556.

Pilla et al., "Resistant Hypertension: An Incurable Disease or Just a Challenge For Our Medical Skill?" High Blood Press Cardiovasc Pre. (2016) 23(4);347-353.

Prakash, TP., "Multivalent N-Acetylgalactosamine Conjugates Improve Potency of Antisense Oligonucleotides" Presentation for IBC's 16th Annual TIDES (May 12-15, 2014) Providence, RI.

Pujol et al., "A Sulfur Tripod Glycoconjugate that Releases a High-Affinity Copper Chelator in Hepatocytes" *Angew Chemie Int Ed Engl* (2012) 51, 7445-7448.

Raasch et al., "Combined blockade of AT1-receptors and ACE synergistically potentiates antihypertensive effects in SHR" Journal of Hypertension (2004) 22:611-618.

Rajur et al., "Covalent Protein-Oligonucleotide Conjugates for Efficient Delivery of Antisense Molecules" Bioconjug Chem (1997) 8, 935-940.

Ravichandran et al., "Antisense-mediated angiotensinogen inhibition slows polycystic kidney disease in mice with a targeted mutation in Pkd2" Am J Physiol Renal Physiol (2015) 308: F349-F357.

Ravichandran et al., "Angiotensinogen inhibition slows polycystic kidney disease in mice with a targeted mutation in Pkd2" Abstract for American Society of Nephrology Kidney Week (Nov. 11-16, 2014) Philadelphia, PA.

Rensen et al., "Design and Synthesis of Novel N-Acetylgalactosamine-Terminated Glycolipids for Targeting of Lipoproteins to the Hepatic Asiaglycoprotein Receptor" J. Med. Chem. (2004) 47: 5798-5808.

Rensen et al., "Determination of the Upper Size Limit for Uptake and Processing of Ligands by the Asialoglycoprotein Receptor on Hepatocytes in Vitro and in Vivo" *J Biol Chem* (2001) 276, 37577-37584.

Rensen et al., "Stimulation of Liver-Directed Cholesterol Flux in Mice by Novel N-Acetylgalactosamine-Terminated Glycolipids with High Affinity for the Asialoglycoprotein Receptor" *Arterioscler Thromb Vasc Biol* (2006) 26, 169-175.

Reynolds et al., "Rational siRNA design for RNA interference" Nature Biotechnology (2004) 22(3):326-330.

Robeyns et al., "Oligonucleotides with cyclohexene-nucleoside building blocks: crystallization and preliminary X-ray studies of a left-handed sequence GTGTACAC" Acta. Crystallogr. Sect. F. Struct. Biol. Cryst. Commun. (2005) 61(Pt 6):585-586.

Robeyns et al., "Structure of the fully modified left-handed cyclohexene nucleic acid sequence GTGTACAC" J. Am. Chem. Soc. (2008) 130(6):1979-1984.

(56) References Cited

OTHER PUBLICATIONS

Rong et al., "Loss of Hepatic Angiotensinogen Attenuates Sepsis-Induced Myocardial Dysfunction" Circulation Research (2021) 129: 547-564.

Saigusa et al., "Suppressing angiotensinogen synthesis attenuates kidney cyst formation in a Pkd1 mouse model" FASEB J (2015) 1-10.

Saigusa et al., "Suppressing angiotensinogen synthesis attenuates kidney cyst formation in a Pkd1 mouse model" Abstract for American Society of Nephrology Kidney Week (Nov. 11-16, 2014) Philadelphia, PA.

Saison-Behmoaras et al., "Short modified antisense oligonucleotides directed against Ha-ras point mutation induce selective cleavage of the mRNA and inhibit T24 cells proliferation" *EMBO J.* (1991) 10, 1111-1118.

Sander et al., "Resistant hypertension: concepts and approach to management" Current Hypertension Reports (2011) 13:347-355.

Sanghvi et al., "Heterocyclic Base Modifications in Nucleic Acids and Their Applications in Antisense Oligonucleotides" Antisense Research and Applications (1993) pp. 273-288.

Sanghvi et al., Carbohydrate Modifications in Antisense Research (1994) ACS Symposium Series 580; Chapters 3 and 4, 40-65.

Sarafidis et al., "Resistant hypertension—its identification and epidemiology." Nat. Rev. Nephrol. (2013) 9(1):51-58.

Sato et al., "Glycoinsulins: Dendritic Sialyloligosaccharide-Displaying Insulins Showing a Prolonged Blood-Sugar-Lowering Activity" *J Am Chem Soc* (2004) 126, 14013-14022.

Schinke et al., "Permanent inhibition of angiotensinogen synthesis by antisense RNA expression" Hypertension (1996) 27: 508-513.

Scozzari "Oligonucleotides for Large Market Indications, what needs to happen or be considered?" Abstract for Innovations in Oligonucleotides Therapeutics Manufacturing Conference (Feb. 17, 2021).

Scozzari "Oligonucleotides for Large Market Indications, what needs to happen or be considered?" Presentation for Innovations in Oligonucleotides Therapeutics Manufacturing Conference (Feb. 17, 2021).

Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.

Shea et al., "Synthesis, hydridization properties and antiviral activity of lipid-oligodeoxynucleotide conjugates" *Nucl. Acids Res.* (1990) 18, 3777-3783.

Sigmund et al., "Report of the National Heart, Lung, and Blood Institute Working Group on Hypertension: Barriers to Translation" Hypertension (2020) 75: 902-917.

Singh et al., "LNA (locked nucleic acids): synthesis and high-affinity nucleic acid recognition" Chem. Commun. (1998) 455-456.

Singh et al., "Synthesis of 2'-amino-LNA: A novel conformationally restricted high-affinity oligonucleotide analogue with a handle" J. Org. Chem. (1998) 63: 10035-10039.

Sliedregt et al., "Design and Synthesis of Novel Amphiphilic Dendritic Galactosides for Selective Targeting of Liposomes to Hepatic Asialoglycoprotein Receptor" *J Med Chem* (1999) 42, 609-618.

Smith et al., "Comparison of biosequences" Adv. Appl. Math. (1981) 2(4):482-489.

Smith et al., "Epidemiology, Prognosis, and Treatment of Resistant Hypertension." Pharmacotherapy (2013) 33(10):1071-1086.

Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.

Svinarchuk et al., "Inhibition of HIV proliferation in MT-4 cells by antisense oligonucleotide conjugated to lipophilic groups" *Biochimie* (1993) 75, 49-54.

Tang et al., "Intravaneous angiotensingogen antisense in AAV-based vector decreases hypertension" American Jour of Physiology (1999) 277: H2392-H2399.

Tomita et al., "Effect of angiotensinogen on blood pressure regulation in normotensive rats: application of a loss of function approach" J. Hypertens. (1995) 13:1767-1774.

Tomita et al., "Transient decrease in high blood pressure by in vivo transfer of antisense oligodeoxynucleotides against rat angiotensinogen" Hypertension (1995) 26:131-136.

Tomiya et al., "Liver-targeting of primaquine-( poly-γ-glutamic acid) and its degradation in rat hepatocytes" Bioorg Med Chem (2013) 21, 5275-5281.

Toyokuni et al., "Synthetic Vaccines: I. Synthesis of Multivalent Tn Antigen Cluster-Lysyllysine Conjugates" *Tetrahedron Lett* (1990) 31, 2673-2676.

Trainor et al., "Relationship Between Circulating Levels of Angiotensinogen and Hypertension—The Multi-Ethic Study of Atherosclerosis" Presentation for AHA Scientific Sessions: Nov. 13-15, 2021.

Trainor et al., "Relationship Between Circulating Levels of Angiotensinogen and Hypertension—The Multi-Ethic Study of Atherosclerosis" Abstract for AHA Scientific Sessions: Nov. 13-15, 2021.

Tsimikas "Ongoing Clinical Trials In Cardiovascular Disease With Antisense Oligonucleotides: Targeting ApoB-100, ApoC-III, Lp(a), ANGPTL3, FXI and Angiotensinogen" Abstract for 12th Global CardioVascular Clinical Trialists Forum (CVCT): Dec. 3-5, 2015 (Washington, DC).

Tsimikas "Ongoing Clinical Trials In Cardiovascular Disease With Antisense Oligonucleotides: Targeting ApoB-100, ApoC-III, Lp(a), ANGPTL3, FXI and Angiotensinogen" Presentation for 12th Global Cardiovascular Clinical Trialists Forum (CVCT): Dec. 3-5, 2015 (Washington, DC).

Tsimikas, S., "Rna Targeted Therapeutics For Cardiovascular Disease", Abstract for RNA at the Bench and Bedside II Conference—Virtual (Nov. 11-13, 2020).

Tsimikas "Antisense inhibition of angiotensinogen to treat hypertension and heart failure" Presentation for Severance Cardio-Cerebrovascular Diseases Research Cluster International Symposium (2021).

Valentijn et al., "Solid-phase Synthesis of Lysine-Based Cluster Galactosides with High Affinity for the Asialoglycoprotein Receptor" *Tetrahedron* (1997) 53, 759-770.

Van De Wal et al., "Determinants of increased angiotensin II levels in severe chronic heart failure patients despite ACE inhibition" International Journal of Cardiology (2006) 106: 367-372.

Van Rossenberg et al., "Stable polyplexes based on arginine-containing oligopeptides for in vivo gene delivery" *Gene Ther* (2004) 11, 457-464.

Verbeure et al., "RNase H mediated cleavage of RNA by cyclohexene nucleic acid (CeNA)" Nucleic Acids Res. (2001) 29(24):4941-4947.

Viera, AJ, "Resistant Hypertension" J. Am. Board Fam. Med. (2012) 25(4):487-495.

Wahlestedt et al., "Potent and nontoxic antisense oligonucleotide containing locked nucleic acids" Proc. Natl. Acad. Sci. USA (2000) 97: 5633-5638.

Wan et al., "Synthesis, biophysical properties and biological activity of second generation antisense oligonucleotides containing chiral phosphorothioate linkages" Nucleic Acids Res (2014) 42: 13456-13468.

Wang et al., "A straightforward stereoselective synthesis of D- and L-5-hydroxy-4-hydroxymethyl-2-cyclohexenylguanine" J. Org. Chem. (2001) 66(25):8478-8482.

Wang et al., "Cyclohexene nucleic acids (CeNA) form stable duplexes with RNA and induce RNase H activity" Nucleosides Nucleotides Nucleic Acids (2001) 20(4-7):785-788.

Wang et al., "Cyclohexene Nucleic Acids (CeNA): Serum Stable Oligonucleotides that Activate RNase H and Increase Duplex Stability with Complementary RNA" J. Am. Chem. Soc. (2000) 122(36):8595-8602.

Wang et al., "Stereocontrolled synthesis of ara-type cyclohexenyl nucleosides" J. Org. Chem. (2003) 68(11):4499-4505.

Westerlind et al., "Ligands of the asialoglycoprotein receptor for targeted gene delivery, part 1: Synthesis of and binding studies with biotinylated cluster glycosides containaing N-acetylgalactosamine" *Glycoconj J* (2004) 21, 227-241.

(56) References Cited

OTHER PUBLICATIONS

Wielbo et al., "Antisense inhibition of angiotensinogen in hepatoma cell culture is enhanced by cationic liposome delivery" Biochem Biophys. Res. Commun. (1997) 232(3):794-799.

Wielbo et al., "Antisense inhibition of hypertension in the spontaneously hypertensive rat" Hypertension (1995) 25:314-319.

Wielbo et al., "Inhibition of hypertension by peripheral administration of antisense oligodeoxy nucleotides" Hypertension (1996) 28:147-151.

Woolf et al., "Specificity of antisense oligonucleotides in vivo" Proc. Natl. Acad. Sci. (1992) 89(16):7305-7309.

Wu et al., "Antisense oligonucleotides targeting angiotensinogen: insights from animal studies" Biosci Rep (2019) 39: 1-10.

Wu et al., "Effects of Renin-Angiotensin Inhibition on ACE2 and TMPRSS2 Expression: Insights into COVID-19" bioRxiv (2020) 3: Preprint.

Ye et al., "Angiotensinogen and Megalin Interactions Contribute to Atherosclerosis—Brief Report" Arterioscler Thromb Vasc Biol (2018) 150-155.

Ye et al., "Megalin Regulates Angiotensinogen and Contributes to Atherosclerosis" Abstract for Arteriosclerosis, Thrombosis and Vascular Biology | Peripheral Vascular Disease (May 4-6, 2017) Minneapolis, MN.

Ye et al., "Angiotensinogen and Megalin Interaction Contributes to Renal Angiotensin II Production and Hypercholesterolemia-induced Atherosclerosis" Poster for Arteriosclerosis, Thrombosis and Vascular Biology Annual Conference (2018) San Francisco, CA.

Ye et al., "Angiotensinogen and Megalin Interaction Contributes to Renal Angiotensin II Production and Hypercholesterolemia-induced Atherosclerosis" Abstract for Vascular Discovery: From Genes to Medicine Scientific Sessions (May 10-12, 2018) San Francisco, CA.

Ye et al., "Angiotensinogen and Megalin Interaction Contributes to Hypercholesterolemia-induced Atherosclerosis" Abstract for 12th Qianjiang International Cardiovascular Conference (Sep. 6-9, 2018) Hangzhou International Expo Center, Zhejiang Province.

Ye et al., "Antisense Oligonucleotides Targeting Hepatic Angiotensinogen Dose-Dependently Reduce Atherosclerosis and Liver Steatosis in Hypercholesterolemic Mice" Abstract for 31st European Meeting on Hypertension and Cardiovascular Protection (Jun. 17-20, 2022) Athens, Greece.

Yeh et al., "Antisense Inhibition of Angiotensinogen Reduced BP in a Hypertensive Rat Model Recalcitrant to Standard RAS Inhibitors" Abstract for 10th Annual Meeting of the Oligonucleotide Therapeutics Society (Oct. 12-15, 2014) San Diego, CA.

Yeh et al., "Antisense Inhibition of Angiotensinogen Reduced BP in a Hypertensive Rat Model Recalcitrant to Standard RAS Inhibitors" Poster for 10th Annual Meeting of the Oligonucleotide Therapeutics Society (Oct. 12-15, 2014) San Diego, CA.

Yoshitomi et al., "Effectiveness of the Direct Renin Inhibitor, Aliskiren, in Patients With Resistant Hypertension" Int Heart J. (2013) 54(2):88-92.

Zhang et al., "PowerBLAST: A New Network BLAST Application for Interactive or Automated Sequence Analysis and Annotation" Genome Res. (1997) 7:649-656.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

International Search Report for PCT/US13/52399 dated Dec. 20, 2013.

International Serch Report for PCT/US2016/056068 dated Apr. 4, 2017.

International Search Report and Written Opinion dated Mar. 29, 2022 in PCT Application No. PCT/US2021/059896.

COMPOUNDS AND METHODS FOR MODULATING ANGIOTENSINOGEN EXPRESSION

SEQUENCE LISTING

The present application is being filed along with a Sequence Listing in electronic format. The Sequence Listing is provided as a file entitled BIOL0393USSEQ_ST25.txt, created on Nov. 3, 2021, which is 32 KB in size. The information in the electronic format of the sequence listing is incorporated herein by reference in its entirety.

FIELD

Provided are compounds, methods, and pharmaceutical compositions for reducing the amount or activity of Angiotensinogen RNA in a cell or subject, and in certain instances reducing the amount of Angiotensinogen (AGT) in a cell or subject. Such compounds and pharmaceutical compositions are useful to ameliorate at least one symptom or hallmark of a RAAS pathway-related disease or disorder. Such diseases and disorders include hypertension, hypertensive emergency (i.e. malignant hypertension), resistant hypertension, kidney disease (e.g., chronic kidney disease, polycystic kidney disease), pre-eclampsia, Marfan Syndrome, stroke, cardiac disease (e.g., myocardial infarction, heart failure, congestive heart failure, valvular heart disease), aneurysms of the blood vessels, abdominal aneurysm, peripheral artery disease, organ damage, pulmonary arterial hypertension, obesity, metabolic syndrome, NASH, NAFLD and other RAAS related diseases, disorders and/or conditions or symptoms thereof.

BACKGROUND

Angiotensinogen (AGT), also known as SERPINA8 or ANHU, is a member of the serpin family and is a component of the renin-angiotensin-aldosterone system (RAAS). It is primarily produced in the liver and is released into the circulation where renin converts it into angiotensin I. Angiotensin I is subsequently converted into angiotensin II by angiotension converting enzyme (ACE). Angiotensin II is a peptide hormone which causes vasoconstriction which, in turn, can increase blood pressure. Angiotensin II also stimulates secretion of the hormone aldosterone from the adrenal cortex. Aldosterone causes the kidneys to increase reabsorption of sodium and water leading to an increase of the fluid volume in a body which, in turn, can increase blood pressure. Over stimulation or activity of the RAAS pathway can lead to high blood pressure. Chronic high blood pressure is known as hypertension. The high blood pressure in a hypertensive subject requires the heart to work harder to circulate blood through the blood vessels.

Hypertension remains a leading cause of global death and disability from cardiovascular disease and stroke. Despite extensive research and the existence of multiple effective therapeutic interventions, hypertension remains an important public health challenge in the United States (Sigmund et al., Hypertension 2020, 75: 902-917). There are limitations to the therapies currently approved for treating hypertension as a significant subset of all hypertensive patients do not achieve adequate blood pressure control. For example, drugs such as ACE inhibitors and angiotensin receptor blockers (ARBs) that target parts of the renin-angiotensin system (RAS) pathway are limited in their ability to inhibit the RAAS pathway (Nobakht et al., Nat Rev Nephrol, 2011, 7:356-359). Additionally, certain anti-hypertensive drugs such as ACE inhibitors are contra-indicated in hypertensive patients with renal disease due to their potential to compromise renal function in patients.

Accordingly, there is a need to find alternative treatments to inhibit the RAAS pathway and treat hypertension. It is therefore an object herein to provide compounds, methods, and pharmaceutical compositions for the treatment of such diseases.

SUMMARY OF THE INVENTION

Provided herein are compounds, methods and pharmaceutical compositions for reducing the amount or activity of AGT RNA and, in certain embodiments, reducing the expression of AGT protein in a cell or subject. In certain embodiments, the subject has a cardiovascular disease. In certain embodiments, the subject has hypertension. In certain embodiments, the subject has resistant hypertension. In certain embodiments, the subject has Marfan syndrome. In certain embodiments, the subject has kidney disease. In certain embodiments, compounds useful for reducing the amount or activity of AGT RNA are oligomeric compounds. In certain embodiments, compounds useful for reducing the amount or activity of AGT RNA are modified oligonucleotides. In certain embodiments, compounds useful for decreasing expression of AGT protein are oligomeric compounds. In certain embodiments, compounds useful for decreasing expression of AGT protein are modified oligonucleotides.

Also provided are methods useful for ameliorating at least one symptom or hallmark of an RAAS pathway-related disease or indication. In certain embodiments, the disease is hypertension. In certain embodiments, the disease is resistant hypertension. In certain embodiments, the disease is Marfan syndrome. In certain embodiments, the indication is heart failure. In certain embodiments, the symptom or hallmark includes hypertension, hypertensive emergency (i.e. malignant hypertension), pre-eclampsia, stroke, cardiac disease (e.g., myocardial infarction, heart failure, congestive heart failure, valvular heart disease), aneurysms of the blood vessels, abdominal aneurysm, organ damage, pulmonary arterial hypertension, obesity, and other RAAS pathway-related diseases, disorders and/or conditions or symptoms thereof.

DETAILED DESCRIPTION OF THE INVENTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, treatises, and GenBank, ENSEMBL, and NCBI reference sequence records, are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well-known and commonly used in the art. Where permitted, all patents, applications, published applications and other publications and other data referred to throughout in the disclosure are incorporated by reference herein in their entirety.

Unless otherwise indicated, the following terms have the following meanings:

Definitions

As used herein, "2'-deoxynucleoside" means a nucleoside comprising a 2'-H(H) deoxyfuranosyl sugar moiety. In certain embodiments, a 2'-deoxynucleoside is a 2'-β-D-deoxynucleoside and comprises a 2'-β-D-deoxyribosyl sugar moiety, which has the β-D configuration as found in naturally occurring deoxyribonucleic acids (DNA). In certain embodiments, a 2'-deoxynucleoside may comprise a modified nucleobase or may comprise an RNA nucleobase (uracil).

As used herein, "2'-MOE" means a 2'-OCH$_2$CH$_2$OCH$_3$ group in place of the 2'-OH group of a furanosyl sugar moiety. A "2'-MOE sugar moiety" means a sugar moiety with a 2'-OCH$_2$CH$_2$OCH$_3$ group in place of the 2'-OH group of a furanosyl sugar moiety. Unless otherwise indicated, a 2'-MOE sugar moiety is in the β-D-ribosyl configuration. "MOE" means O-methoxyethyl.

As used herein, "2'-MOE nucleoside" means a nucleoside comprising a 2'-MOE sugar moiety.

As used herein, "2'-OMe" means a 2'-OCH$_3$ group in place of the 2'-OH group of a furanosyl sugar moiety. As used herein, "2'-O-methyl sugar moiety" or "2'-OMe sugar moiety" means a sugar moiety with a 2'-OCH$_3$ group in place of the 2'-OH group of a furanosyl sugar moiety. Unless otherwise indicated, a 2'-OMe sugar moiety is in the β-D-ribosyl configuration.

As used herein, "2'-OMe nucleoside" means a nucleoside comprising a 2'-OMe sugar moiety.

As used herein, "2'-substituted nucleoside" means a nucleoside comprising a 2'-substituted sugar moiety. As used herein, "2'-substituted" in reference to a sugar moiety means a sugar moiety comprising at least one 2'-substituent group other than H or OH.

As used herein, "5-methyl cytosine" means a cytosine modified with a methyl group attached to the 5 position. A 5-methyl cytosine is a modified nucleobase.

As used herein, "About" means within ±10% of a value. For example, if it is stated, "the compounds affected about 70% inhibition of AGT", it is implied that AGT levels are inhibited within a range of 63% and 77%.

As used herein, "administering" means providing a pharmaceutical agent to a subject.

As used herein, "Angiotensinogen" and "AGT" is used interchangeably herein. Angiotensinogen is also known as SERPINA8 and ANHU.

As used herein, "Anti-hypertensive drug" refers to a drug capable of lowering blood pressure. Examples of such drugs include, but are not limited to, RAAS inhibitors, diuretics, calcium channel blockers, adrenergic receptor antagonists, adrenergic agonists and vasodilators. In one example, the anti-hypertensive drug captopril can be used in combination with the AGT compound described herein to treat an animal having or at risk of having a RAAS pathway related disease, disorder and/or condition.

As used herein, "antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound.

As used herein, "antisense compound" means an oligomeric compound or oligomeric duplex capable of achieving at least one antisense activity.

As used herein, "ameliorate" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom. The progression or severity of indicators may be determined by subjective or objective measures, which are known to those skilled in the art.

As used herein, "Blood pressure" refers to the pressure of the blood in the circulatory system against the walls of the blood vessel. The blood pressure is due mainly to the beating of the heart in an animal. During each heartbeat, the blood pressure varies between a maximum (systolic) blood pressure (SBP) and minimum (diastolic) blood pressure (DBP). The mean arterial pressure (MAP) is the average arterial pressure during a heartbeat cycle. Blood pressure can be measure by a blood pressure meter (i.e., a sphygmomanometer) Normal blood pressure at rest is less than 120 mmHg systolic and less than 80 mmHg diastolic and is commonly expressed as the systolic pressure (top reading)/diastolic pressure (bottom reading) mmHg.

As used herein, "bicyclic nucleoside" or "BNA" means a nucleoside comprising a bicyclic sugar moiety.

As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the furanosyl sugar moiety is a ribosyl moiety. In certain embodiments, the bicyclic sugar moiety does not comprise a furanosyl moiety.

As used herein, "cEt" means a 4' to 2' bridge in place of the 2'OH-group of a ribosyl sugar moiety, wherein the bridge has the formula of 4'-CH(CH$_3$)—O-2', and wherein the methyl group of the bridge is in the S configuration. A "cEt sugar moiety" is a bicyclic sugar moiety with a 4' to 2' bridge in place of the 2'OH-group of a ribosyl sugar moiety, wherein the bridge has the formula of 4'-CH(CH$_3$)—O-2', and wherein the methyl group of the bridge is in the S configuration. "cEt" means constrained ethyl.

As used herein, "cEt nucleoside" means a nucleoside comprising a cEt sugar moiety.

As used herein, "cleavable moiety" means a bond or group of atoms that is cleaved under physiological conditions, for example, inside a cell, a subject, an animal, or a human.

As used herein, "complementary" in reference to an oligonucleotide means that at least 70% of the nucleobases of the oligonucleotide or one or more portions thereof and the nucleobases of another nucleic acid or one or more portions thereof are capable of hydrogen bonding with one another when the nucleobase sequence of the oligonucleotide and the other nucleic acid are aligned in opposing directions. As used herein, "complementary nucleobases" means nucleobases that are capable of forming hydrogen bonds with one another. Complementary nucleobase pairs include adenine (A) and thymine (T), adenine (A) and uracil (U), cytosine (C) and guanine (G), and 5-methyl cytosine (mC) and guanine (G). Complementary oligonucleotides and/or target nucleic acids need not have nucleobase complementarity at each nucleoside. Rather, some mismatches are tolerated. As used herein, "fully complementary" or "100% complementary" in reference to an oligonucleotide, or a portion thereof, means that the oligonucleotide, or portion thereof, is complementary to another oligonucleotide or target nucleic acid at each nucleobase of the shorter of the two oligonucleotides, or at each nucleoside if the oligonucleotides are the same length.

As used herein, "conjugate group" means a group of atoms that is directly or indirectly attached to an oligonucleotide. Conjugate groups include a conjugate moiety and a conjugate linker that attaches the conjugate moiety to the oligonucleotide.

As used herein, "conjugate linker" means a single bond or a group of atoms comprising at least one bond that connects a conjugate moiety to an oligonucleotide.

As used herein, "conjugate moiety" means a group of atoms that is attached to an oligonucleotide via a conjugate linker.

As used herein, "contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

As used herein, "chirally enriched population" means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom. Chirally enriched populations of molecules having multiple chiral centers within each molecule may contain one or more stereorandom chiral centers. In certain embodiments, the molecules are modified oligonucleotides. In certain embodiments, the molecules are compounds comprising modified oligonucleotides.

As used herein, "chirally controlled" in reference to an internucleoside linkage means chirality at that linkage is enriched for a particular stereochemical configuration.

As used herein, "deoxy region" means a region of 5-12 contiguous nucleotides, wherein at least 70% of the nucleosides are 2'-β-D-deoxynucleosides. In certain embodiments, each nucleoside is selected from a 2'-β-D-deoxynucleoside, a bicyclic nucleoside, and a 2'-substituted nucleoside. In certain embodiments, a deoxy region supports RNase H activity. In certain embodiments, a deoxy region is the gap or internal region of a gapmer.

As used herein, "gapmer" means a modified oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings." The internal region is a deoxy region. The positions of the internal region or gap refer to the order of the nucleosides of the internal region and are counted starting from the 5'-end of the internal region. Unless otherwise indicated, "gapmer" refers to a sugar motif. In certain embodiments, each nucleoside of the gap is a 2'-β-D-deoxynucleoside. In certain embodiments, the gap comprises one 2'-substituted nucleoside at position 1, 2, 3, 4, or 5 of the gap, and the remainder of the nucleosides of the gap are 2'-β-D-deoxynucleosides. As used herein, the term "MOE gapmer" indicates a gapmer having a gap comprising 2'-β-D-deoxynucleosides and wings comprising 2'-MOE nucleosides. As used herein, the term "mixed wing gapmer" indicates a gapmer having wings comprising modified nucleosides comprising at least two different sugar modifications. Unless otherwise indicated, a gapmer may comprise one or more modified internucleoside linkages and/or modified nucleobases and such modifications do not necessarily follow the gapmer pattern of the sugar modifications.

As used herein, "hotspot region" is a range of nucleobases on a target nucleic acid that is amenable to oligomeric compound-mediated reduction of the amount or activity of the target nucleic acid.

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, "Hypertension" or "HTN" refers to a chronic medical condition where the blood pressure in an animal is elevated. The elevated blood pressure requires the heart to work harder to circulate blood through the blood vessels. High blood pressure is said to be present if it is persistently at or above 130/80 mmHg (Stage 1) or 140/90 mmHg (Stage 2). Hypertension is classified as primary (essential) or secondary. Primary hypertension has no clear cause and is thought to be linked to genetics, diet, lack of exercise and obesity. Secondary hypertension is caused by another medical condition. Hypertension is a major risk factor for shortened life expectancy, chronic kidney disease, stroke, myocardial infarction, heart failure, aneurysms of the blood vessels (e.g. aortic aneurysm), peripheral artery disease, organ damage (e.g., heart enlargement or hypertrophy) and other cardiovascular diseases, disorders and/or conditions or symptoms thereof. Anti-hypertensive drugs, diet changes and lifestyle changes may reduce hypertension and reduce the diseases, disorders and/or conditions associated with hypertension. Hypertension can be nonresistant to drug intervention (i.e., controllable by commercially available drug therapies) or resistant to drug intervention.

As used herein, "internucleoside linkage" means the covalent linkage between contiguous nucleosides in an oligonucleotide. As used herein, "modified internucleoside linkage" means any internucleoside linkage other than a phosphodiester internucleoside linkage. "Phosphorothioate internucleoside linkage" is a modified internucleoside linkage in which one of the non-bridging oxygen atoms of a phosphodiester internucleoside linkage is replaced with a sulfur atom.

As used herein, "linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, "non-bicyclic modified sugar moiety" means a modified sugar moiety that comprises a modification, such as a substituent, that does not form a bridge between two atoms of the sugar to form a second ring.

As used herein, "mismatch" or "non-complementary" means a nucleobase of a first oligonucleotide that is not complementary with the corresponding nucleobase of a second oligonucleotide or target nucleic acid when the first and second oligonucleotide are aligned.

As used herein, "motif" means the pattern of unmodified and/or modified sugar moieties, nucleobases, and/or internucleoside linkages, in an oligonucleotide.

As used herein, "nucleobase" means an unmodified nucleobase or a modified nucleobase. As used herein an "unmodified nucleobase" is adenine (A), thymine (T), cytosine (C), uracil (U), or guanine (G). As used herein, a "modified nucleobase" is a group of atoms other than unmodified A, T, C, U, or G capable of pairing with at least one unmodified nucleobase. A "5-methyl cytosine" is a modified nucleobase. A universal base is a modified nucleobase that can pair with any one of the five unmodified nucleobases. As used herein, "nucleobase sequence" means the order of contiguous nucleobases in a target nucleic acid or oligonucleotide independent of any sugar or internucleoside linkage modification.

As used herein, "nucleoside" means a compound, or a fragment of a compound, comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase. "Linked nucleosides" are nucleosides that are connected in a contiguous sequence (i.e., no additional nucleosides are presented between those that are linked).

As used herein, "oligomeric compound" means an oligonucleotide and optionally one or more additional features, such as a conjugate group or terminal group. An oligomeric compound may be paired with a second oligomeric compound that is complementary to the first oligomeric compound or may be unpaired. A "singled-stranded oligomeric compound" is an unpaired oligomeric compound. The term "oligomeric duplex" means a duplex formed by two oligomeric compounds having complementary nucleobase sequences. Each oligomeric compound of an oligomeric duplex may be referred to as a "duplexed oligomeric compound."

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "Organ damage" or "end organ damage" refers to damage occurring in major organs fed by the circulatory system such as the heart (e.g., heart muscle hypertrophy, reduced heart function and/or heart failure), kidney (e.g., albuminurea, proteinurea, reduced renal function and/or renal failure), eyes (e.g., hypertensive retinopathy), brain (e.g., stroke) and the like. The organs can be damaged by hypertension in an animal. In certain embodiments, the heart damage is fibrosis, heart cell and/or muscle hypertrophy leading to heart enlargement.

As used herein, "pharmaceutically acceptable carrier or diluent" means any substance suitable for use in administering to a subject. Certain such carriers enable pharmaceutical compositions to be formulated as, for example, tablets, pills, dragees, capsules, liquids, gels, syrups, slurries, suspension and lozenges for the oral ingestion by a subject. In certain embodiments, a pharmaceutically acceptable carrier or diluent is sterile water, sterile saline, sterile buffer solution or sterile artificial cerebrospinal fluid.

As used herein, "pharmaceutically acceptable salts" means physiologically and pharmaceutically acceptable salts of compounds. Pharmaceutically acceptable salts retain the desired biological activity of the parent compound and do not impart undesired toxicological effects thereto.

As used herein, "pharmaceutical composition" means a mixture of substances suitable for administering to a subject. For example, a pharmaceutical composition may comprise an oligomeric compound and a sterile aqueous solution. In certain embodiments, a pharmaceutical composition shows activity in free uptake assay in certain cell lines.

As used herein, "prodrug" means a therapeutic agent in a form outside the body that is converted to a different form within a subject or cells thereof. Typically, conversion of a prodrug within the subject is facilitated by the action of an enzymes (e.g., endogenous or viral enzyme) or chemicals present in cells or tissues and/or by physiologic conditions.

As used herein, "reducing the amount or activity" refers to a reduction or blockade of the transcriptional expression or activity relative to the transcriptional expression or activity in an untreated or control sample and does not necessarily indicate a total elimination of transcriptional expression or activity.

As used herein, "Renin-angiotensin-aldosterone system", "Renin-angiotensin-aldosterone system pathway", "RAAS pathway" or "RAAS" refer to a multi-component enzymatic pathway where a precursor component (angiotensinogen) is converted by various enzymes such as renin and enzyme angiotensin-converting-enzyme (ACE) into downstream components such as angiotensin I and angiotensin II. Angiotensin I stimulates secretion of the steroid aldosterone in the pathway. The RAAS pathway regulates blood pressure and fluid balance.

As used herein, "Renin-angiotensin System", or "RAS" or "RAS pathway" refer to a portion of the RAAS pathway. Various components of this pathway have been targeted by agonists or antagonists to block the production of the components. For example renin inhibitors, ACE inhibitors, angiotensin-receptor blockers (ARBs) and the like have been developed to inhibit or block the RAS pathway. However, commercially available therapies targeting various RAS pathway components have been ineffective in completely inhibiting or blocking the RAS pathway due to various mechanisms or adverse effects (Nobakht et al., Nat Rev Nephrol, 2011, 7:356-359).

As used herein, "RAAS related disease, disorder and/or condition" or "RAAS pathway related disease, disorder and/or condition" refers to any disease, disorder or condition related to RAAS in an animal. Examples of RAAS related diseases, disorders and/or conditions include shortened life expectancy, hypertension (e.g. nonresistant hypertension, resistant hypertension), kidney disease (e.g., chronic kidney disease, polycystic kidney disease), stroke, heart disease (e.g., myocardial infarction, heart failure, valvular heart disease), aneurysms of the blood vessels (e.g. aortic aneurysm), peripheral artery disease, organ damage (e.g., heart damage or hypertrophy), tissue fibrosis and other cardiovascular diseases, disorders and/or conditions or symptoms thereof. In certain embodiments, RAAS related disease, disorder and/or condition does not include hypertension.

As used herein, "Resistant hypertension" or "RHTN" is defined as either a) blood pressure above the therapeutic goal (typically ≥130/80 mmHg) despite concurrent use of 3 or more anti-hypertensive agents from different drug classes administered at maximal tolerated doses; or b) blood pressure that is controlled at or below the therapeutic goal only after administration of at least 4 anti-hypertensive agents of different classes to achieve control.

As used herein, "RNA" means an RNA transcript and includes pre-mRNA and mature mRNA unless otherwise specified.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense compounds that act through RNase H.

As used herein, "self-complementary" in reference to an oligonucleotide means an oligonucleotide that at least partially hybridizes to itself.

As used herein, "standard in vitro assay" means the assays described in Examples and reasonable variations thereof.

As used herein, "standard in vivo assay" means the assays described in Examples and reasonable variations thereof.

As used herein, "stereorandom chiral center" in the context of a population of molecules of identical molecular formula means a chiral center having a random stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the result of a synthetic method that is not designed to control the stereochemical configuration. In certain embodiments, a stereorandom chiral center is a stereorandom phosphorothioate internucleoside linkage.

As used herein, "subject" means a human or non-human animal.

As used herein, "sugar moiety" means an unmodified sugar moiety or a modified sugar moiety. As used herein, "unmodified sugar moiety" means a 2'-OH(H)β-D-ribosyl moiety, as found in RNA (an "unmodified RNA sugar moiety"), or a 2'-H(H)β-D-deoxyribosyl sugar moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" or "modified sugar" means a modified furanosyl sugar moiety or a sugar surrogate.

As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or target nucleic acids.

As used herein, "symptom" or "hallmark" means any physical feature or test result that indicates the existence or extent of a disease or disorder. In certain embodiments, a symptom is apparent to a subject or to a medical professional examining or testing the subject. In certain embodiments, a hallmark is apparent upon invasive diagnostic testing, including, but not limited to, post-mortem tests.

As used herein, "target nucleic acid" and "target RNA" mean a nucleic acid that an antisense compound is designed to affect.

As used herein, "target region" means a portion of a target nucleic acid to which an oligomeric compound is designed to hybridize.

As used herein, "terminal group" means a chemical group or group of atoms that is covalently linked to a terminus of an oligonucleotide.

As used herein, "therapeutically effective amount" means an amount of a pharmaceutical agent that provides a therapeutic benefit to a subject. For example, a therapeutically effective amount improves a symptom of a disease.

CERTAIN EMBODIMENTS

The present disclosure provides the following non-limiting numbered embodiments:

Embodiment 1: An oligomeric compound comprising a modified oligonucleotide consisting of 14 to 30 linked nucleosides and having a nucleobase sequence comprising at least 14, at least 15, or 16 contiguous nucleobases of any of the nucleobase sequences of SEQ ID NOs: 12-15, wherein the modified oligonucleotide comprises at least one modification selected from a modified sugar moiety and a modified internucleoside linkage.

Embodiment 2: An oligomeric compound comprising a modified oligonucleotide consisting of 14 to 30 linked nucleosides and having a nucleobase sequence comprising at least 14, at least 15, or at least 16 contiguous nucleobases complementary to:
  an equal length portion of nucleobases 2046-2061 of SEQ ID NO: 1;
  an equal length portion of nucleobases 2271-2286 of SEQ ID NO: 1;
  an equal length portion of nucleobases 2272-2287 of SEQ ID NO: 1;
wherein the modified oligonucleotide comprises at least one modification selected from a modified sugar moiety and a modified internucleoside linkage.

Embodiment 3: An oligomeric compound comprising a modified oligonucleotide consisting of 16 linked nucleosides and having a nucleobase sequence comprising the nucleobase sequence of SEQ ID NO: 12, wherein the modified oligonucleotide comprises at least one modification selected from a modified sugar moiety and a modified internucleoside linkage.

Embodiment 4: An oligomeric compound comprising a modified oligonucleotide consisting of 16 linked nucleosides and having a nucleobase sequence comprising the nucleobase sequence of SEQ ID NO: 13, wherein the modified oligonucleotide comprises at least one modification selected from a modified sugar moiety and a modified internucleoside linkage.

Embodiment 5: An oligomeric compound comprising a modified oligonucleotide consisting of 16 linked nucleosides and having a nucleobase sequence comprising the nucleobase sequence of SEQ ID NO: 14, wherein the modified oligonucleotide comprises at least one modification selected from a modified sugar moiety and a modified internucleoside linkage.

Embodiment 6: An oligomeric compound comprising a modified oligonucleotide consisting of 16 linked nucleosides and having a nucleobase sequence comprising the nucleobase sequence of SEQ ID NO: 15, wherein the modified oligonucleotide comprises at least one modification selected from a modified sugar moiety and a modified internucleoside linkage.

Embodiment 7: The oligomeric compound of any of embodiments 1-6, wherein the modified oligonucleotide has a nucleobase sequence that is at least 80%, at least 85%, at least 90%, at least 95%, or 100% complementary to the nucleobase sequence of any SEQ ID NO: 1 or SEQ ID NO: 2, when measured across the entire nucleobase sequence of the modified oligonucleotide.

Embodiment 8: The oligomeric compound of any of embodiments 1-7, wherein the modified oligonucleotide comprises at least one bicyclic sugar moiety.

Embodiment 9: The oligomeric compound of embodiment 8, wherein the bicyclic sugar moiety has a 4'-2' bridge, wherein the 4'-2' bridge is selected from —CH$_2$—O—; and —CH(CH$_3$)—O—.

Embodiment 10: The oligomeric compound of any of embodiments 1-9, wherein the modified oligonucleotide comprises at least one non-bicyclic modified sugar moiety.

Embodiment 11: The oligomeric compound of embodiment 10, wherein the non-bicyclic modified sugar moiety is a 2'-MOE sugar moiety or a 2'-OMe sugar moiety.

Embodiment 12: The oligomeric compound of any of embodiments 1-11, wherein the modified oligonucleotide comprises at least one sugar surrogate.

Embodiment 13: The oligomeric compound of embodiment 12, wherein the sugar surrogate is any of morpholino, modified morpholino, PNA, THP, and F-HNA.

Embodiment 14: The oligomeric compound of any of embodiments 1-13, wherein the modified oligonucleotide is a gapmer.

Embodiment 15: The oligomeric compound of embodiment 14, wherein the modified oligonucleotide has a sugar motif comprising:
  a 5'-region consisting of 1-6 linked 5'-region nucleosides;
  a central region consisting of 6-10 linked central region nucleosides; and
  a 3'-region consisting of 1-6 linked 3'-region nucleosides;
  wherein
each of the 5'-region nucleosides and each of the 3'-region nucleosides comprises a modified sugar moiety and at least 6 of the central region nucleosides comprises a 2'-β-D-deoxyribosyl sugar moiety.

Embodiment 16: The oligomeric compound of embodiment 14, wherein the modified oligonucleotide has a sugar motif comprising:
  a 5'-region consisting of 1-6 linked 5'-region nucleosides;
  a central region consisting of 6-10 linked central region nucleosides; and
  a 3'-region consisting of 1-6 linked 3'-region nucleosides;
  wherein
each of the 5'-region nucleosides and each of the 3'-region nucleosides comprises a modified sugar moiety and each of the central region nucleosides comprises a 2'-deoxyribosyl sugar moiety Embodiment 17: The oligomeric compound of embodiment 14, wherein the modified oligonucleotide has a sugar motif comprising:
  a 5'-region consisting of 3 linked 5'-region nucleosides;
  a central region consisting of 10 linked central region nucleosides; and
  a 3'-region consisting of 3 linked 3'-region nucleosides;
  wherein
each of the 5'-region nucleosides and each of the 3'-region nucleosides comprises a 2'-MOE sugar moiety or a cEt modified sugar moiety, and each of the central region nucleosides comprises a 2'-β-D-deoxyribosyl sugar moiety.

Embodiment 18: The oligomeric compound of embodiment 14, wherein the modified oligonucleotide has a sugar motif comprising:
  a 5'-region consisting of 3 linked 5'-region nucleosides;
  a central region consisting of 10 linked central region nucleosides; and
  a 3'-region consisting of 3 linked 3'-region nucleosides;
  wherein
each of the 5'-region nucleosides and each of the 3'-region nucleosides comprises a 2'-MOE modified sugar moiety or a cEt modified sugar moiety, and at least 6 of the central region nucleosides comprises a 2'-β-D-deoxyribosyl sugar moiety.

Embodiment 19: The oligomeric compound of any of embodiments 1-18, wherein the modified oligonucleotide has a sugar motif (5' to 3') selected from eekddddddddddkke, ekkddddddddddkke, kkkdyddddddddkkk, kkkddydd-ddddkkk, kkkdddyddddddkkk, kkkdddddddddkkk, or eeeeeddddddddddeeeee; wherein 'e' represents a 2'-MOE sugar moiety, 'k' represents a cEt sugar moiety, 'd' represents a 2'-β-D-deoxyribosyl sugar moiety, and 'y' represents a 2'-OMe sugar moiety.

Embodiment 20: The oligomeric compound of any of embodiments 1-19, wherein the modified oligonucleotide comprises at least one modified internucleoside linkage.

Embodiment 21: The oligomeric compound of embodiment 20, wherein each internucleoside linkage of the modified oligonucleotide is a modified internucleoside linkage.

Embodiment 22: The oligomeric compound of embodiment 20 or embodiment 21, wherein at least one internucleoside linkage is a phosphorothioate internucleoside linkage.

Embodiment 23: The oligomeric compound of any of embodiments 20 and 22, wherein the modified oligonucleotide comprises at least one phosphodiester internucleoside linkage.

Embodiment 24: The oligomeric compound of any of embodiments 20, 22 and 23, wherein each internucleoside linkage is either a phosphodiester internucleoside linkage or a phosphorothioate internucleoside linkage.

Embodiment 25: The oligomeric compound of embodiment 21, wherein each internucleoside linkage is a phosphorothioate internucleoside linkage.

Embodiment 26: The oligomeric compound of any of embodiments 1-20 or 22-24, wherein the modified oligonucleotide has an internucleoside linkage motif of soosssssssssssos; wherein, s=a phosphorothioate internucleoside linkage and o=a phosphodiester internucleoside linkage.

Embodiment 27: The oligomeric compound of any of embodiments 1-26, wherein the modified oligonucleotide comprises at least one modified nucleobase.

Embodiment 28: The oligomeric compound of embodiment 27, wherein the modified nucleobase is a 5-methylcytosine.

Embodiment 29: The oligomeric compound of any of embodiments 1-28, wherein the modified oligonucleotide consists of 12-30, 12-22, 12-20, 14-18, 14-20, 15-17, 15-25, or 16-20 linked nucleosides.

Embodiment 30: The oligomeric compound of any of embodiments 1-28, wherein the modified oligonucleotide consists of 16 linked nucleosides.

Embodiment 31: The oligomeric compound of any of embodiments 1-30, comprising a conjugate group.

Embodiment 32: The oligomeric compound of embodiment 31, wherein the conjugate group comprises a GalNAc cluster comprising 1-3 GalNAc ligands.

Embodiment 33: The oligomeric compound of any one of embodiments 31 and 32, wherein the conjugate group comprises a conjugate linker consisting of a single bond.

Embodiment 34: The oligomeric compound of any one of embodiments 31-33, wherein the conjugate group comprises a cleavable linker.

Embodiment 35: The oligomeric compound of any one of embodiments 31-34, wherein the conjugate group comprises a conjugate linker comprising 1-3 linker-nucleosides.

Embodiment 36: The oligomeric compound of any one of embodiments 31-35, wherein the conjugate group is attached to the modified oligonucleotide at the 5'-end of the modified oligonucleotide.

Embodiment 37: The oligomeric compound of any one of embodiments 31-35, wherein the conjugate group is attached to the modified oligonucleotide at the 3'-end of the modified oligonucleotide.

Embodiment 38: The oligomeric compound of any of embodiments 1-37, wherein the oligomeric compound is a singled-stranded oligomeric compound.

Embodiment 39: The oligomeric compound of any of embodiments 1-30 or 38, consisting of the modified oligonucleotide.

Embodiment 40: An oligomeric duplex comprising an oligomeric compound of any of embodiments 1-37.

Embodiment 41: An antisense compound comprising or consisting of an oligomeric compound of any of embodiments 1-39 or an oligomeric duplex of embodiment 40.

Embodiment 42: A pharmaceutical composition comprising an oligomeric compound of any of embodiments 1-39 or an oligomeric duplex of embodiment 40 and a pharmaceutically acceptable carrier or diluent.

Embodiment 43: A compound according to the following chemical structure:

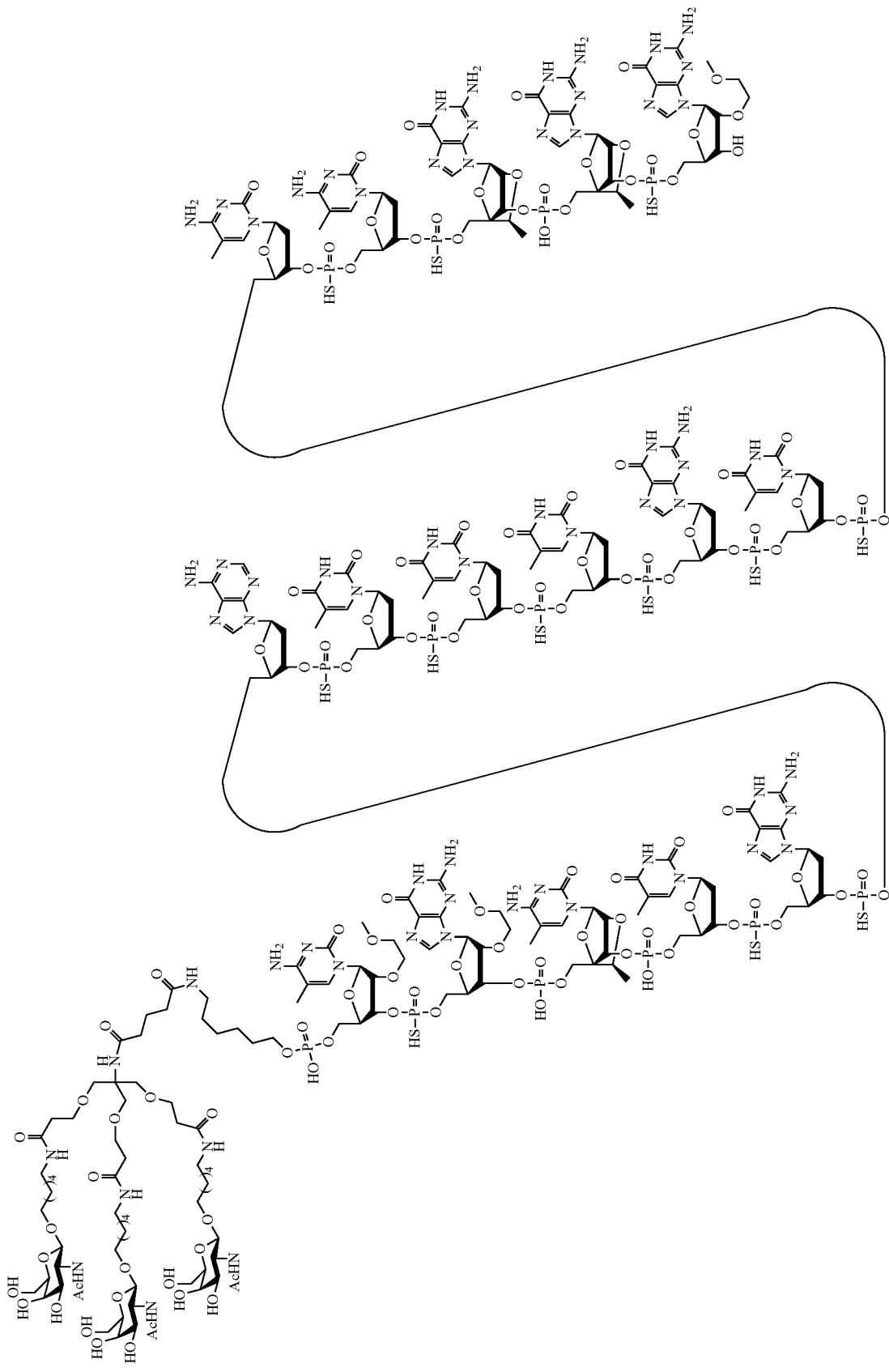

(SEQ ID NO: 12), or a salt thereof.
Embodiment 44: A compound according to the following chemical structure:

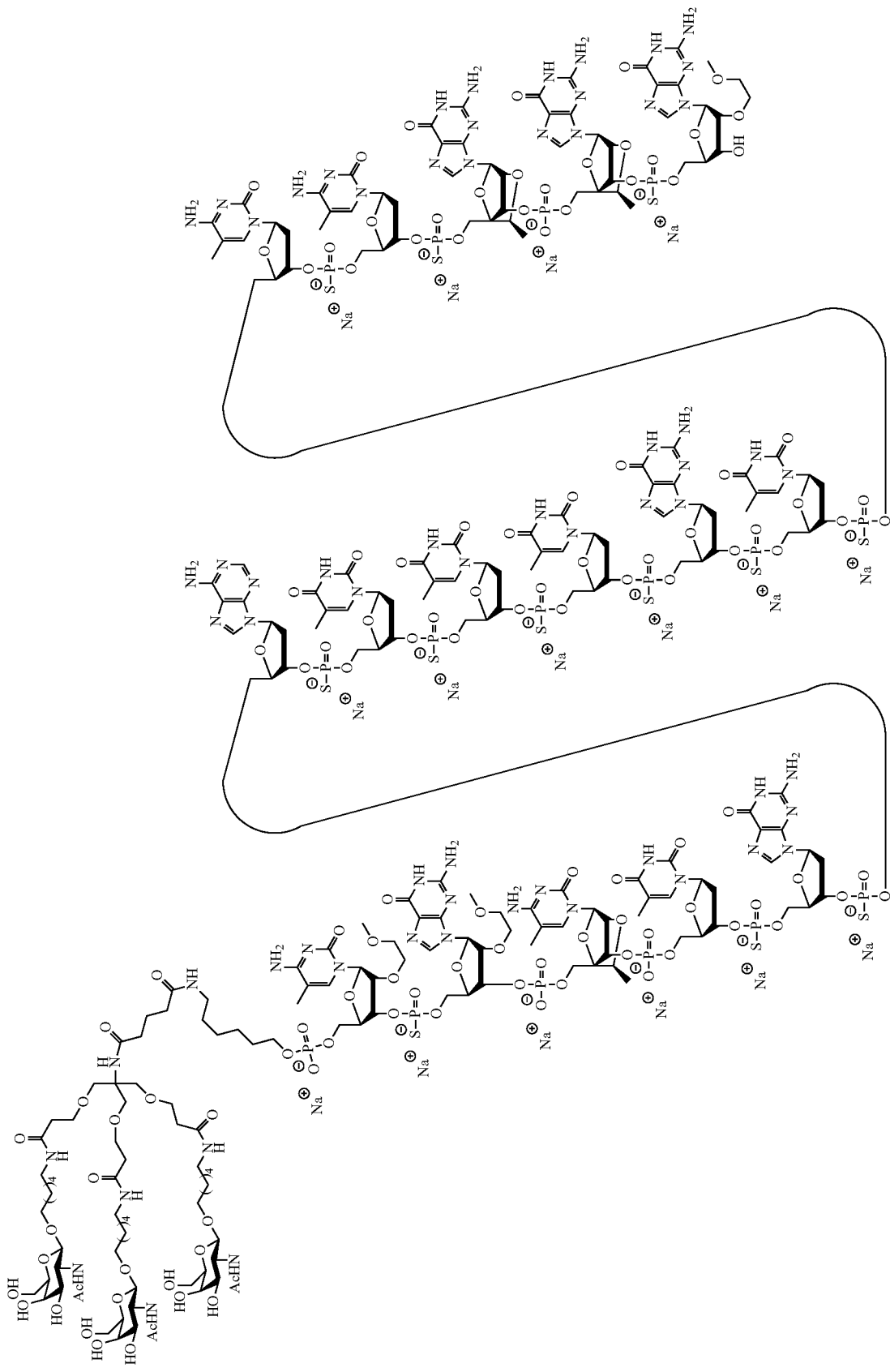

(SEQ ID NO: 12).
Embodiment 45: A compound according to the following chemical structure:


(SEQ ID NO: 13), or a salt thereof.
Embodiment 46: A compound according to the following chemical structure:

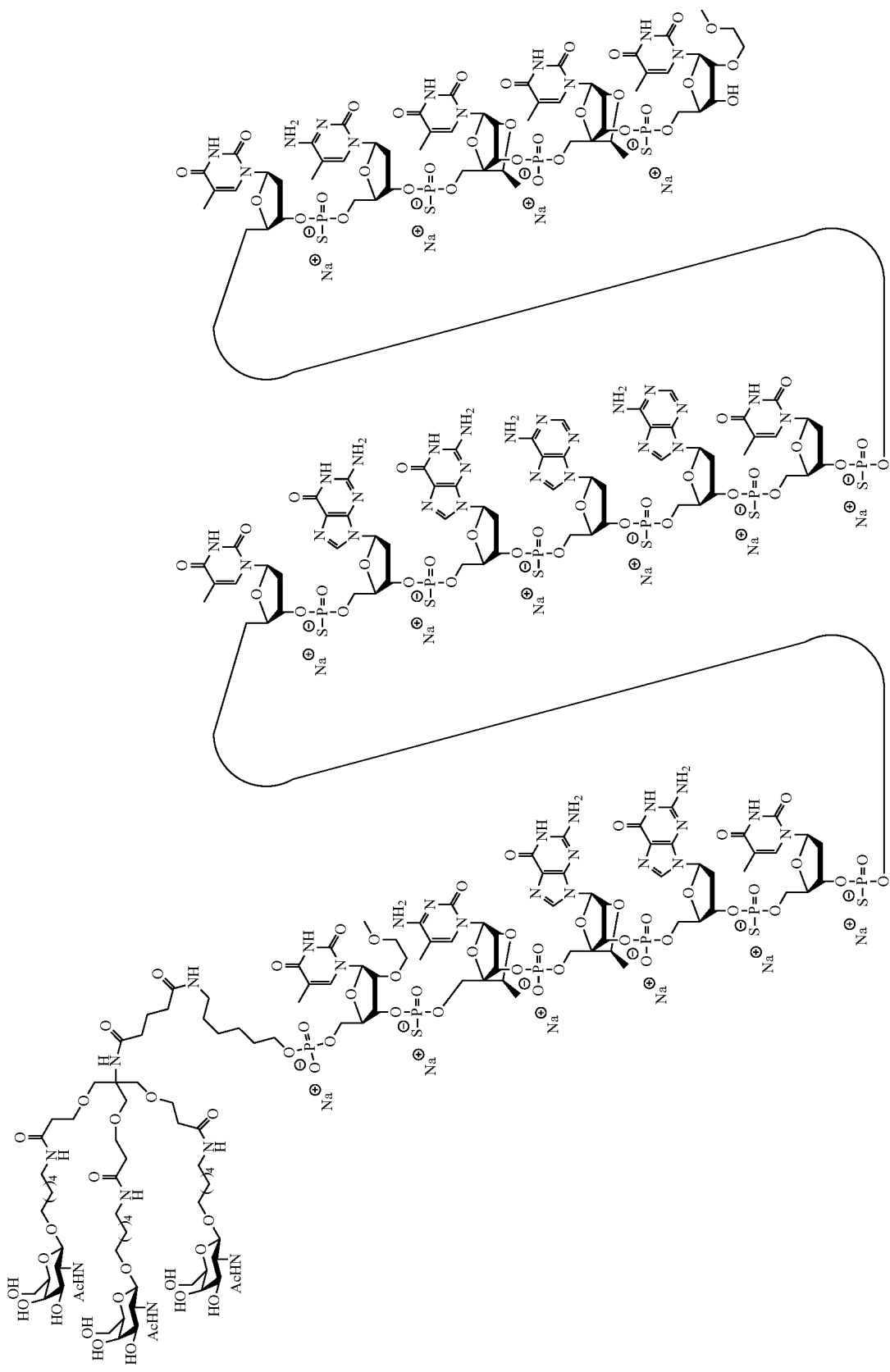

(SEQ ID NO: 13).
Embodiment 47: A compound according to the following chemical structure:

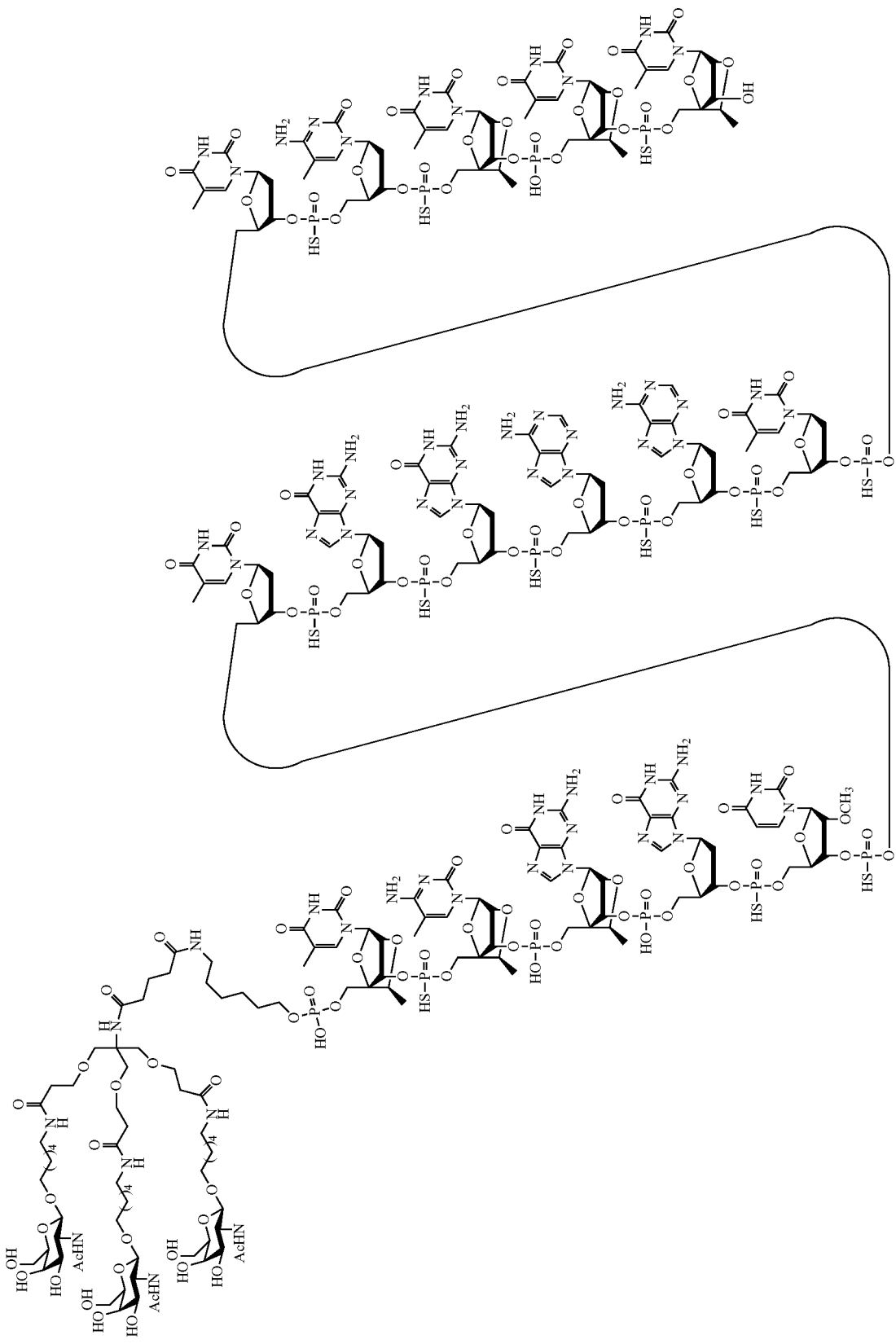

(SEQ ID NO: 14), or a salt thereof.
Embodiment 48: A compound according to the following chemical structure:

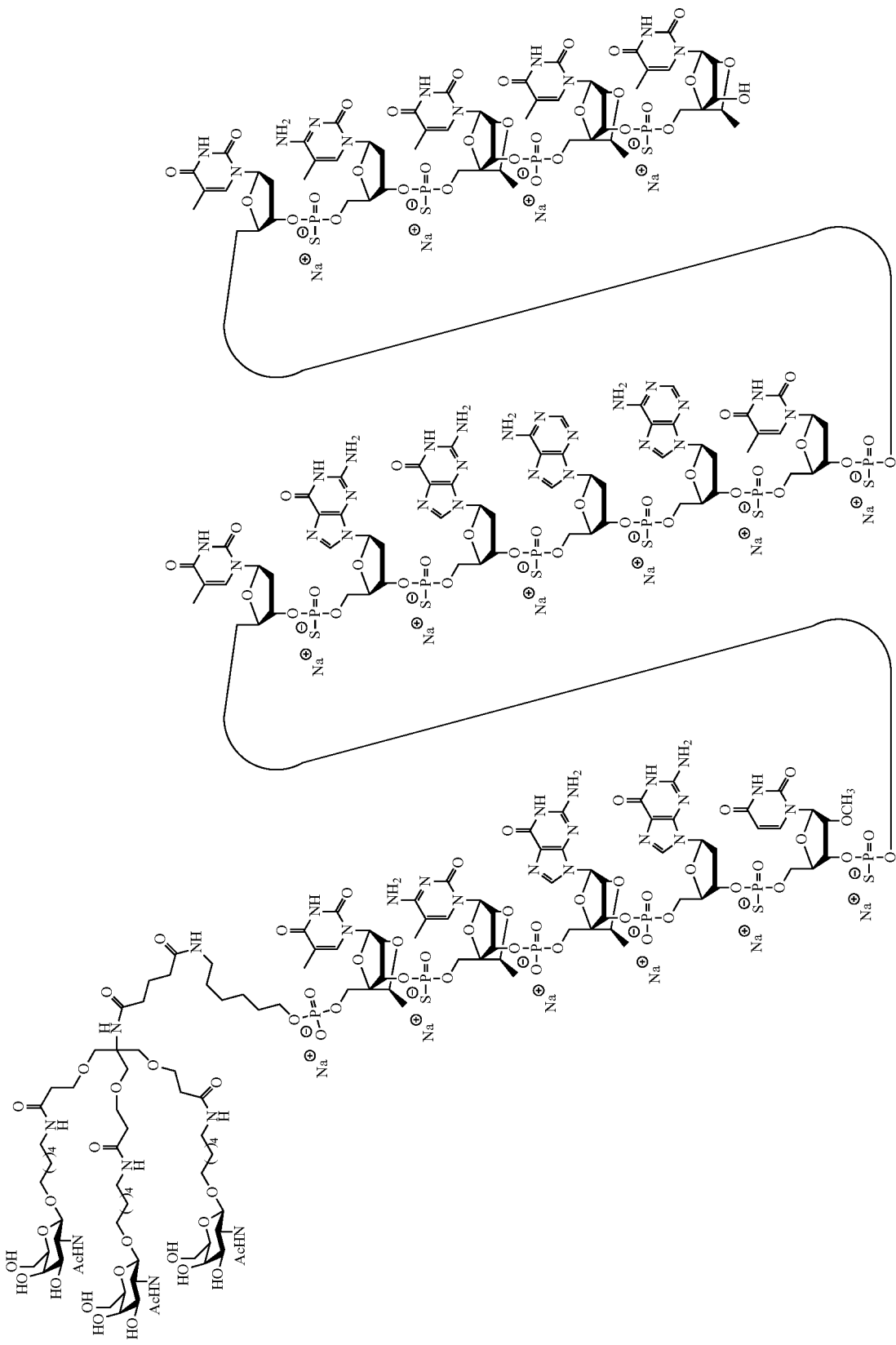

(SEQ ID NO: 14).
Embodiment 49: A compound according to the following chemical structure:

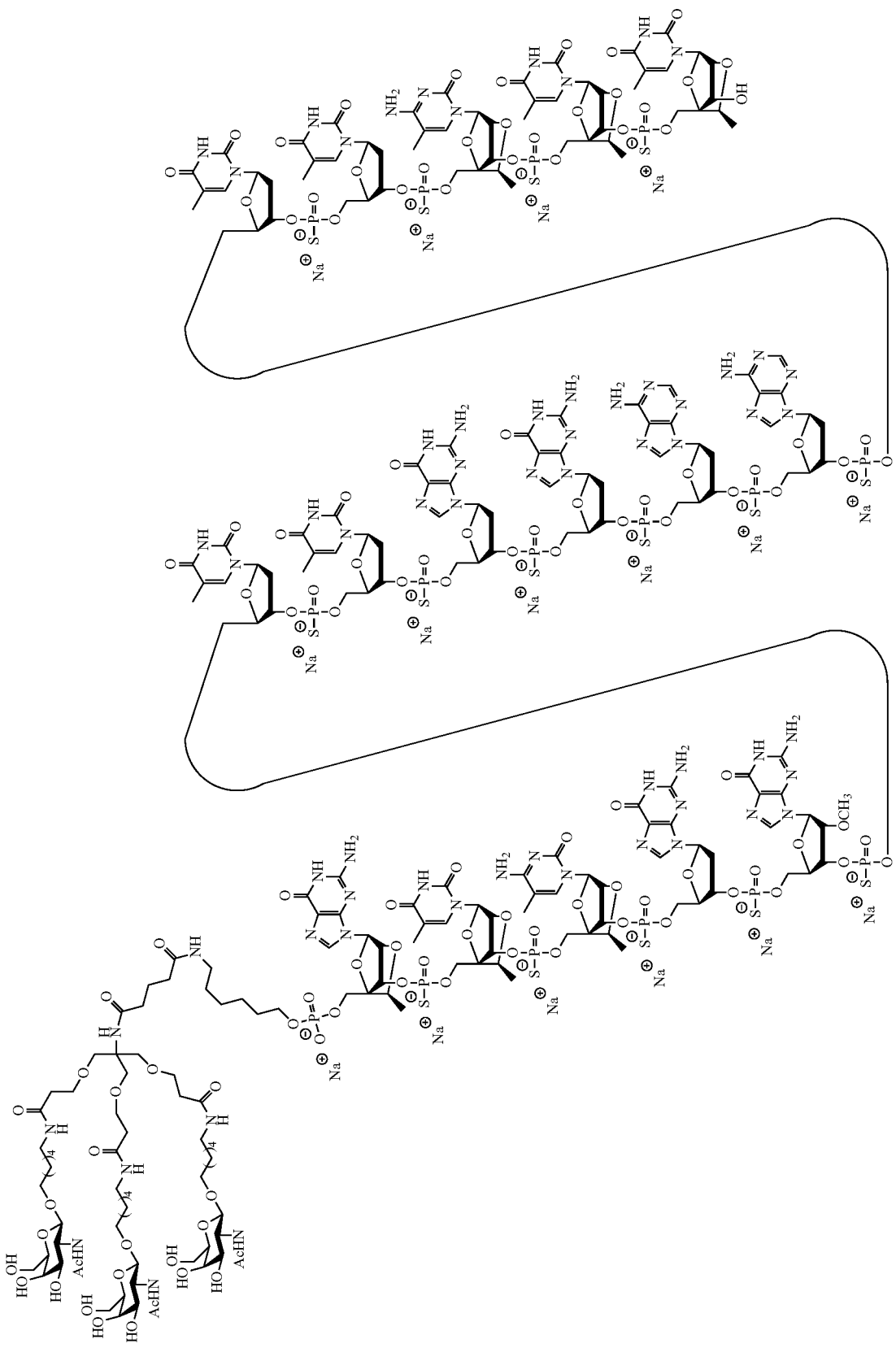

(SEQ ID NO: 15), or salt thereof.
Embodiment 50: A compound according to the following chemical structure:

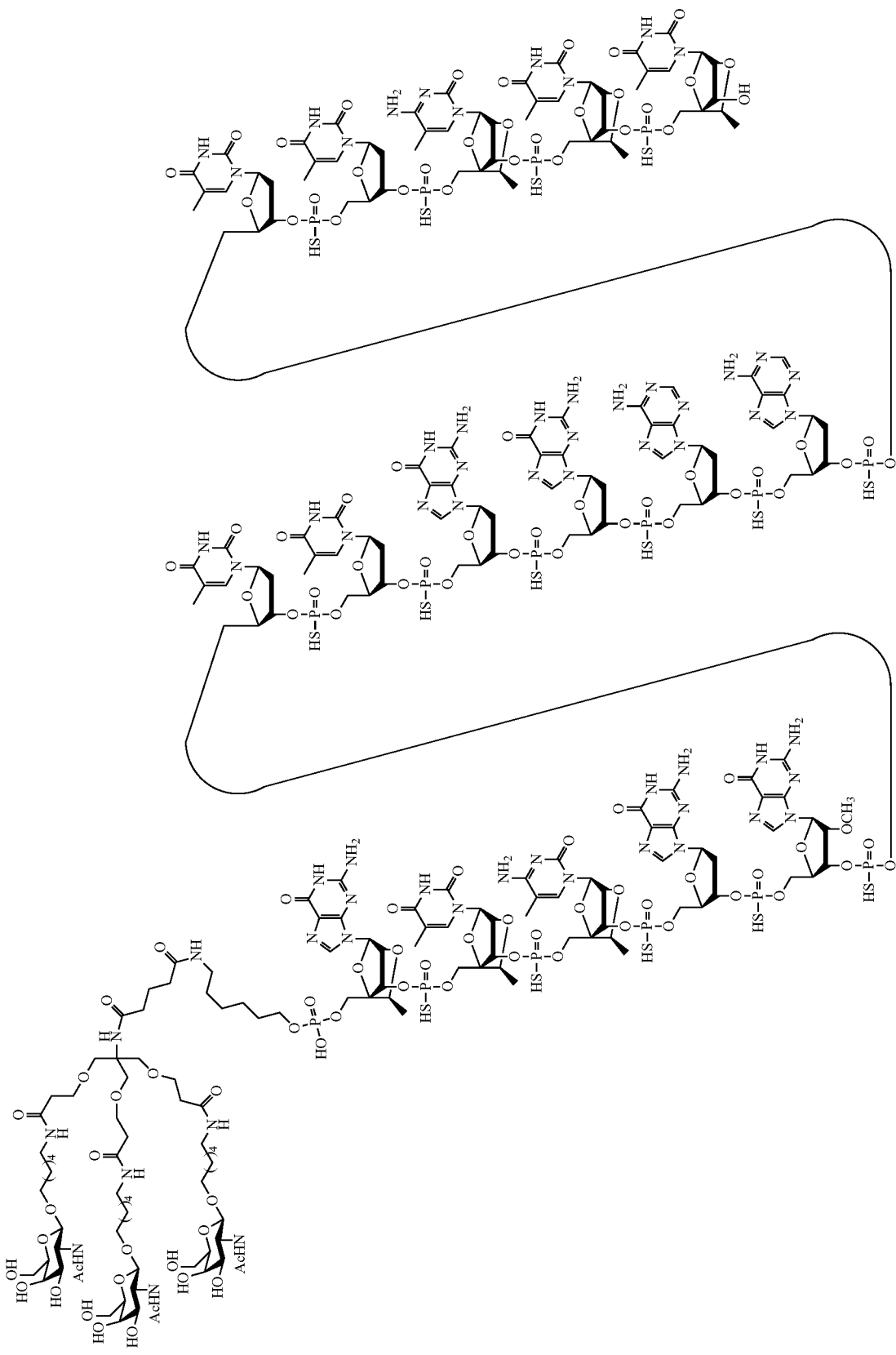

(SEQ ID NO: 15).

Embodiment 51: The modified oligonucleotide of any of embodiments 43, 45, 47, and 49, which is the sodium salt or potassium salt of the chemical structure.

Embodiment 52: A pharmaceutical composition comprising the modified oligonucleotide of any of embodiments 43-51 and a pharmaceutically acceptable carrier or diluent.

Embodiment 53: A compound comprising a modified oligonucleotide according to the following chemical notation:
$^mC_{es}G_{eo}{}^mC_{ko}T_{ds}G_{ds}A_{ds}T_{ds}T_{ds}T_{ds}G_{ds}T_{ds}{}^mC_{ds}{}^mC_{ds}G_{ko}G_{ks}G_e$
(SEQ ID NO: 12), wherein:
- A=an adenine nucleobase,
- $^mC$=a 5-methyl cytosine nucleobase,
- G=a guanine nucleobase,
- T=a thymine nucleobase,
- e=a 2'-β-D-MOE sugar moiety,
- k=a cEt sugar moiety,
- d=a 2'-β-D-deoxyribosyl sugar moiety,
- s=a phosphorothioate internucleoside linkage, and
- o=a phosphodiester internucleoside linkage.

Embodiment 54: A compound comprising a modified oligonucleotide according to the following chemical notation:
$T_{es}{}^mC_{ko}G_{ko}G_{ds}T_{ds}T_{ds}G_{ds}G_{ds}A_{ds}A_{ds}T_{ds}T_{ds}{}^mC_{ds}T_{ko}T_{ks}T_e$
(SEQ ID NO: 13), wherein:
- A=an adenine nucleobase,
- $^mC$=a 5-methyl cytosine nucleobase,
- G=a guanine nucleobase,
- T=a thymine nucleobase,
- e=a 2'-β-D-MOE sugar moiety,
- k=a cEt sugar moiety,
- d=a 2'-β-D-deoxyribosyl sugar moiety,
- s=a phosphorothioate internucleoside linkage, and
- o=a phosphodiester internucleoside linkage.

Embodiment 55: A compound comprising a modified oligonucleotide according to the following chemical notation:
$G_{ks}T_{ks}{}^mC_{ks}G_{ds}G_{ds}T_{ds}T_{ds}G_{ds}G_{ds}A_{ds}A_{ds}T_{ds}T_{ds}{}^mC_{ks}T_{ks}T_k$
(SEQ ID NO: 15), wherein:
- A=an adenine nucleobase,
- $^mC$=a 5-methyl cytosine nucleobase,
- G=a guanine nucleobase,
- T=a thymine nucleobase,
- k=a cEt sugar moiety,
- d=a 2'-β-D-deoxyribosyl sugar moiety,
- y=a 2'-OMe ribose sugar moiety, and
- s=a phosphorothioate internucleoside linkage.

Embodiment 56: A compound comprising a modified oligonucleotide according to the following chemical notation:
$T_{ks}{}^mC_{ko}G_{ko}G_{ds}U_{ys}T_{ds}G_{ds}G_{ds}A_{ds}A_{ds}T_{ds}T_{ds}{}^mC_{ds}T_{ko}T_{ks}T_k$
(SEQ ID NO: 14), wherein:
- A=an adenine nucleobase,
- $^mC$=a 5-methyl cytosine nucleobase,
- G=a guanine nucleobase,
- T=a thymine nucleobase,
- U=a uracil nucleobase,
- k=a cEt sugar moiety,
- d=a 2'-β-D-deoxyribosyl sugar moiety,
- y=a 2'-OMe ribose sugar moiety,
- s=a phosphorothioate internucleoside linkage, and
- o=a phosphodiester internucleoside linkage.

Embodiment 57: The compound of any of embodiments 53-56, comprising the modified oligonucleotide covalently linked to a conjugate group.

Embodiment 58: A pharmaceutical composition of any of embodiments 53-56, and a pharmaceutically acceptable diluent or carrier.

Embodiment 59: A chirally enriched population of modified oligonucleotides of any of embodiments 53-56, wherein the population is enriched for modified oligonucleotides comprising at least one particular phosphorothioate internucleoside linkage having a particular stereochemical configuration.

Embodiment 60: The chirally enriched population of embodiment 59, wherein the population is enriched for modified oligonucleotides comprising at least one particular phosphorothioate internucleoside linkage having the (Sp) configuration.

Embodiment 61: The chirally enriched population of embodiment 59, wherein the population is enriched for modified oligonucleotides comprising at least one particular phosphorothioate internucleoside linkage having the (Rp) configuration.

Embodiment 62: The chirally enriched population of embodiment 59, wherein the population is enriched for modified oligonucleotides having a particular, independently selected stereochemical configuration at each phosphorothioate internucleoside linkage.

Embodiment 63: The chirally enriched population of embodiment 59, wherein the population is enriched for modified oligonucleotides having the (Sp) configuration at each phosphorothioate internucleoside linkage or for modified oligonucleotides having the (Rp) configuration at each phosphorothioate internucleoside linkage.

Embodiment 64: The chirally enriched population of embodiment 59, wherein the population is enriched for modified oligonucleotides having the (Rp) configuration at one particular phosphorothioate internucleoside linkage and the (Sp) configuration at each of the remaining phosphorothioate internucleoside linkages.

Embodiment 65: The chirally enriched population of embodiment 59, wherein the population is enriched for modified oligonucleotides having at least 3 contiguous phosphorothioate internucleoside linkages in the Sp, Sp, and Rp configurations, in the 5' to 3' direction.

Embodiment 66: A population of modified oligonucleotides of any of embodiments 59-65, wherein all the phosphorothioate internucleoside linkages of the modified oligonucleotide are stereorandom.

Embodiment 67: A method comprising administering to an individual the pharmaceutical composition of any preceding embodiment.

Embodiment 68: A method of treating a disease associated with the RAAS pathway, comprising administering to an individual having or at risk of having a disease associated with the RAAS pathway a therapeutically effective amount of a pharmaceutical composition according to any preceding embodiment, thereby treating the disease associated with the RAAS pathway.

Embodiment 69: The method of embodiment 68, wherein the disease is a cardiovascular disease.

Embodiment 70: The method of any of embodiments 68 and 69, wherein the disease is selected from hypertension, resistant hypertension, Marfan syndrome, heart failure, kidney disease, obesity, metabolic syndrome, NASH, and NAFLD.

Embodiment 71: The method of any of embodiments 68-70, wherein at least one symptom or hallmark of the disease is ameliorated.

Embodiment 72: The method of embodiment 71, wherein the symptom or hallmark is any of hypertension, hypertensive emergency (i.e. malignant hypertension), stroke, preeclampsia, aneurysms of the blood vessels, abdominal aneurysm, peripheral artery disease, organ damage, or pulmonary arterial hypertension.

Embodiment 73: The method of any of embodiments 67-72, wherein the pharmaceutical composition is administered systemically.

Embodiment 74: The method of any of embodiments 73, wherein the pharmaceutical composition is administered any of subcutaneously, or intramuscularly.

Embodiment 75: Use of an oligomeric compound of any of embodiments 1-37 or an oligomeric duplex of embodiment 40 for reducing AGT expression in a cell.

Embodiment 76: The use of embodiment 75, wherein the level of AGT RNA is reduced.

Embodiment 77: The use of embodiment 75, wherein the level of AGT protein is reduced.

Embodiment 78. An oligomeric compound comprising a modified oligonucleotide consisting of 14 to 30 linked nucleosides and having a nucleobase sequence comprising at least 14, at least 15, or at least 16 contiguous nucleobases of any of the nucleobase sequences of SEQ ID NOs: 12-15, wherein the modified oligonucleotide comprises at least one modification selected from a modified sugar moiety and a modified internucleoside linkage.

Embodiment 79. An oligomeric compound comprising a modified oligonucleotide consisting of 14 to 30 linked nucleosides and having a nucleobase sequence comprising at least 14, at least 15, or at least 16 contiguous nucleobases complementary to:
 a. an equal length portion of nucleobases 2046-2061 of SEQ ID NO: 1;
 b. an equal length portion of nucleobases 2271-2286 of SEQ ID NO: 1;
 c. an equal length portion of nucleobases 2272-2287 of SEQ ID NO: 1;
wherein the modified oligonucleotide comprises at least one modification selected from a modified sugar moiety and a modified internucleoside linkage.

Embodiment 80. An oligomeric compound comprising a modified oligonucleotide consisting of 16 linked nucleosides and having a nucleobase sequence comprising the nucleobase sequence of SEQ ID NO: 12, wherein the modified oligonucleotide comprises at least one modification selected from a modified sugar moiety and a modified internucleoside linkage.

Embodiment 81. An oligomeric compound comprising a modified oligonucleotide consisting of 16 linked nucleosides and having a nucleobase sequence comprising the nucleobase sequence of SEQ ID NO: 13, wherein the modified oligonucleotide comprises at least one modification selected from a modified sugar moiety and a modified internucleoside linkage.

Embodiment 82. An oligomeric compound comprising a modified oligonucleotide consisting of 16 linked nucleosides and having a nucleobase sequence comprising the nucleobase sequence of SEQ ID NO: 14, wherein the modified oligonucleotide comprises at least one modification selected from a modified sugar moiety and a modified internucleoside linkage.

Embodiment 83. An oligomeric compound comprising a modified oligonucleotide consisting of 16 linked nucleosides and having a nucleobase sequence comprising the nucleobase sequence of SEQ ID NO: 15, wherein the modified oligonucleotide comprises at least one modification selected from a modified sugar moiety and a modified internucleoside linkage.

Embodiment 84. The oligomeric compound of any of embodiments 78-83, wherein the modified oligonucleotide has a nucleobase sequence that is at least 80%, at least 85%, at least 90%, at least 95%, or 100% complementary to the nucleobase sequence of any SEQ ID NO: 1 or SEQ ID NO: 2, when measured across the entire nucleobase sequence of the modified oligonucleotide.

Embodiment 85. The oligomeric compound of any of embodiments 78-84, wherein the modified oligonucleotide comprises at least one bicyclic sugar moiety.

Embodiment 86. The oligomeric compound of embodiment 85, wherein the bicyclic sugar moiety has a 4'-2' bridge, wherein the 4'-2' bridge is selected from —$CH_2$—O—; and —$CH(CH_3)$—O—.

Embodiment 87. The oligomeric compound of any of embodiments 78-86, wherein the modified oligonucleotide comprises at least one non-bicyclic modified sugar moiety.

Embodiment 88. The oligomeric compound of embodiment 87, wherein the non-bicyclic modified sugar moiety is a 2'-MOE sugar moiety or a 2'-OMe sugar moiety.

Embodiment 89. The oligomeric compound of any of embodiments 78-88, wherein the modified oligonucleotide comprises at least one sugar surrogate.

Embodiment 90. The oligomeric compound of embodiment 89, wherein the sugar surrogate is any of morpholino, modified morpholino, PNA, THP, and F-HNA.

Embodiment 91. The oligomeric compound of any of embodiments 78-90, wherein the modified oligonucleotide is a gapmer.

Embodiment 92. The oligomeric compound of any of embodiments 78-91, wherein the modified oligonucleotide has a sugar motif comprising:
 a 5'-region consisting of 1-6 linked 5'-region nucleosides;
 a central region consisting of 6-10 linked central region nucleosides; and
 a 3'-region consisting of 1-6 linked 3'-region nucleosides; wherein
each of the 5'-region nucleosides and each of the 3'-region nucleosides comprises a modified sugar moiety and at least 6 of the central region nucleosides comprises a 2'-β-D-deoxyribosyl sugar moiety.

Embodiment 93. The oligomeric compound of any of embodiments 78-91, wherein the modified oligonucleotide has a sugar motif comprising:
 a 5'-region consisting of 1-6 linked 5'-region nucleosides;
 a central region consisting of 6-10 linked central region nucleosides; and
 a 3'-region consisting of 1-6 linked 3'-region nucleosides; wherein
each of the 5'-region nucleosides and each of the 3'-region nucleosides comprises a modified sugar moiety and each of the central region nucleosides comprises a 2'-deoxyribosyl sugar moiety Embodiment 94. The oligomeric compound of any of embodiments 78-91, wherein the modified oligonucleotide has a sugar motif comprising:
 a 5'-region consisting of 3 linked 5'-region nucleosides;
 a central region consisting of 10 linked central region nucleosides; and
 a 3'-region consisting of 3 linked 3'-region nucleosides; wherein
each of the 5'-region nucleosides and each of the 3'-region nucleosides comprises a 2'-MOE sugar moiety or a cEt sugar moiety, and each of the central region nucleosides comprises a 2'-β-D-deoxyribosyl sugar moiety.

Embodiment 95. The oligomeric compound of any of embodiments 78-91, wherein the modified oligonucleotide has a sugar motif comprising:
a 5'-region consisting of 3 linked 5'-region nucleosides;
a central region consisting of 10 linked central region nucleosides; and
a 3'-region consisting of 43 linked 3'-region nucleosides; wherein
each of the 5'-region nucleosides and each of the 3'-region nucleosides comprises a 2'-MOE sugar moiety or a cEt sugar moiety, and at least 6 of the central region nucleosides comprises a 2'-β-D-deoxyribosyl sugar moiety.

Embodiment 96. The oligomeric compound of any of embodiments 78-95, wherein the modified oligonucleotide has a sugar motif (5' to 3') selected from eekddddddddddkke, ekkddddddddddkke, kkkdyddddddddkkk, kkkddyddddddkkk, kkkdddyddddddkkk, kkkddddddddddkkk, or eeeeeddddddddddeeeee; wherein 'e' represents a 2'-MOE sugar moiety, 'k' represents a cEt sugar moiety, 'd' represents a 2'-β-D-deoxyribosyl sugar moiety, and 'y' represents a 2'-OMe sugar moiety.

Embodiment 97. The oligomeric compound of any of embodiments 78-96, wherein the modified oligonucleotide comprises at least one modified internucleoside linkage.

Embodiment 98. The oligomeric compound of embodiment 97, wherein each internucleoside linkage of the modified oligonucleotide is a modified internucleoside linkage.

Embodiment 99. The oligomeric compound of embodiment 97 or embodiment 98, wherein at least one internucleoside linkage is a phosphorothioate internucleoside linkage.

Embodiment 100. The oligomeric compound of any of embodiments 97 and embodiment 99, wherein the modified oligonucleotide comprises at least one phosphodiester internucleoside linkage.

Embodiment 101. The oligomeric compound of any of embodiments 97, 99, and 100, wherein each internucleoside linkage is either a phosphodiester internucleoside linkage or a phosphorothioate internucleoside linkage.

Embodiment 102. The oligomeric compound of embodiment 98, wherein each internucleoside linkage is a phosphorothioate internucleoside linkage.

Embodiment 103. The oligomeric compound of any of embodiments 78-97 or 99-101, wherein the modified oligonucleotide has an internucleoside linkage motif of sooossssssssssos; wherein,
s=a phosphorothioate internucleoside linkage, and
o=a phosphodiester internucleoside linkage.

Embodiment 104. The oligomeric compound of any of embodiments 78-103, wherein the modified oligonucleotide comprises at least one modified nucleobase.

Embodiment 105. The oligomeric compound of embodiment 104, wherein the modified nucleobase is a 5-methylcytosine.

Embodiment 106. The oligomeric compound of any of embodiments 78-105, wherein the modified oligonucleotide consists of 14-30, 14-22, 14-20, 14-18, 14-20, 15-17, 15-25, or 16-20 linked nucleosides.

Embodiment 107. The oligomeric compound of any of embodiments 78-106, wherein the modified oligonucleotide consists of 16 linked nucleosides.

Embodiment 108. The oligomeric compound of any of embodiments 78-107, comprising a conjugate group.

Embodiment 109. The oligomeric compound of embodiment 108, wherein the conjugate group comprises a GalNAc cluster comprising 1-3 GalNAc ligands.

Embodiment 110. The oligomeric compound of any one of embodiments 108 and 109, wherein the conjugate group comprises a conjugate linker consisting of a single bond.

Embodiment 111. The oligomeric compound of any one of embodiments 108-110, wherein the conjugate group comprises a cleavable linker.

Embodiment 112. The oligomeric compound of any one of embodiments 108-111, wherein the conjugate group comprises a conjugate linker comprising 1-3 linker-nucleosides.

Embodiment 113. The oligomeric compound of any one of embodiments 108-112, wherein the conjugate group is attached to the modified oligonucleotide at the 5'-nucleoside of the modified oligonucleotide.

Embodiment 114. The oligomeric compound of any one of embodiments 108-113, wherein the conjugate group is attached to the modified oligonucleotide at the 3'-nucleoside of the modified oligonucleotide.

Embodiment 115. The oligomeric compound of any of embodiments 78-114, wherein the oligomeric compound is a singled-stranded oligomeric compound.

Embodiment 116. The oligomeric compound of any of embodiments 78-107 or 115, consisting of the modified oligonucleotide.

Embodiment 117. An oligomeric compound according to the following chemical structure:

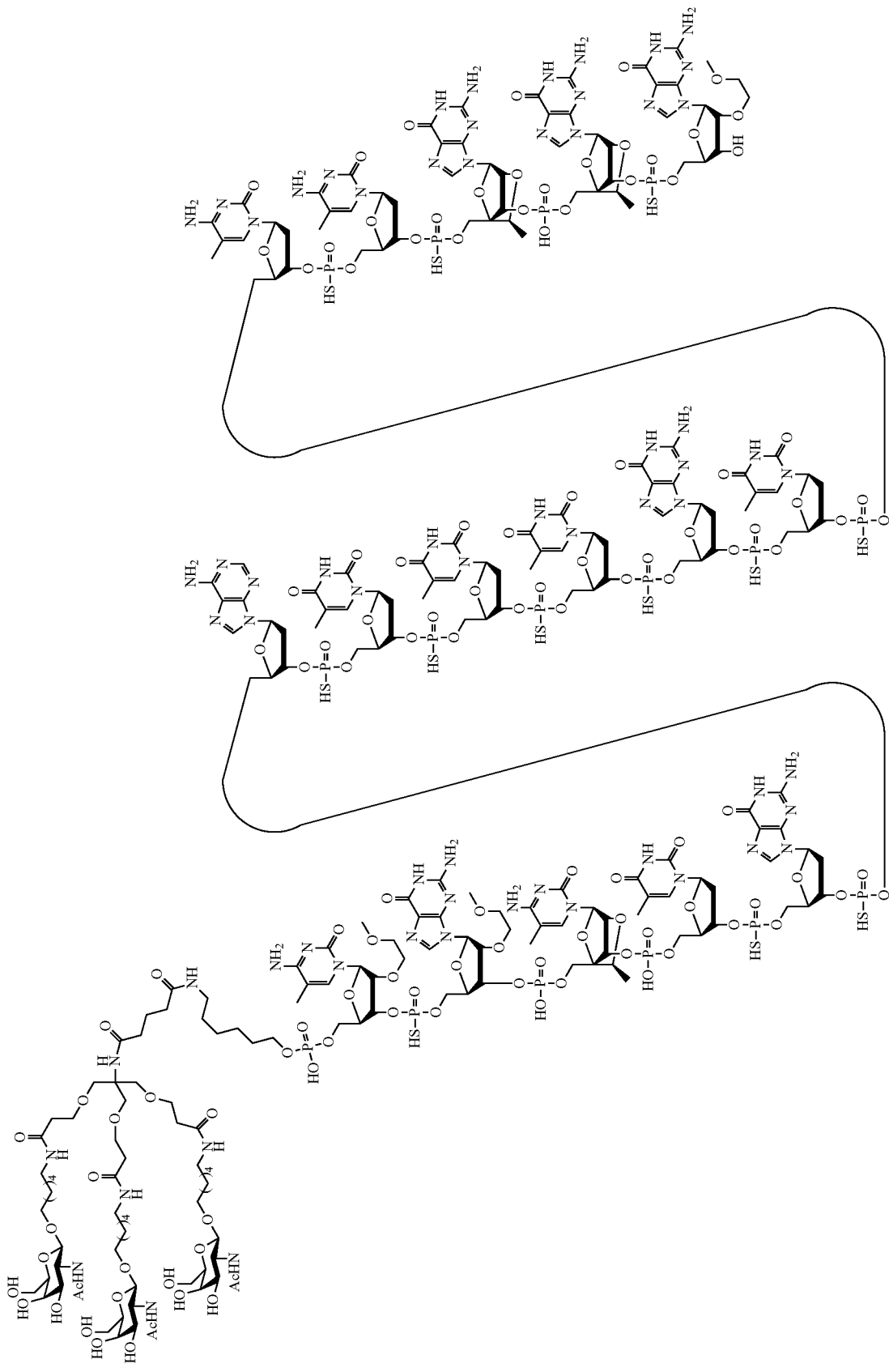

(SEQ ID NO: 12), or a salt thereof

Embodiment 118. An oligomeric compound according to the following chemical structure:

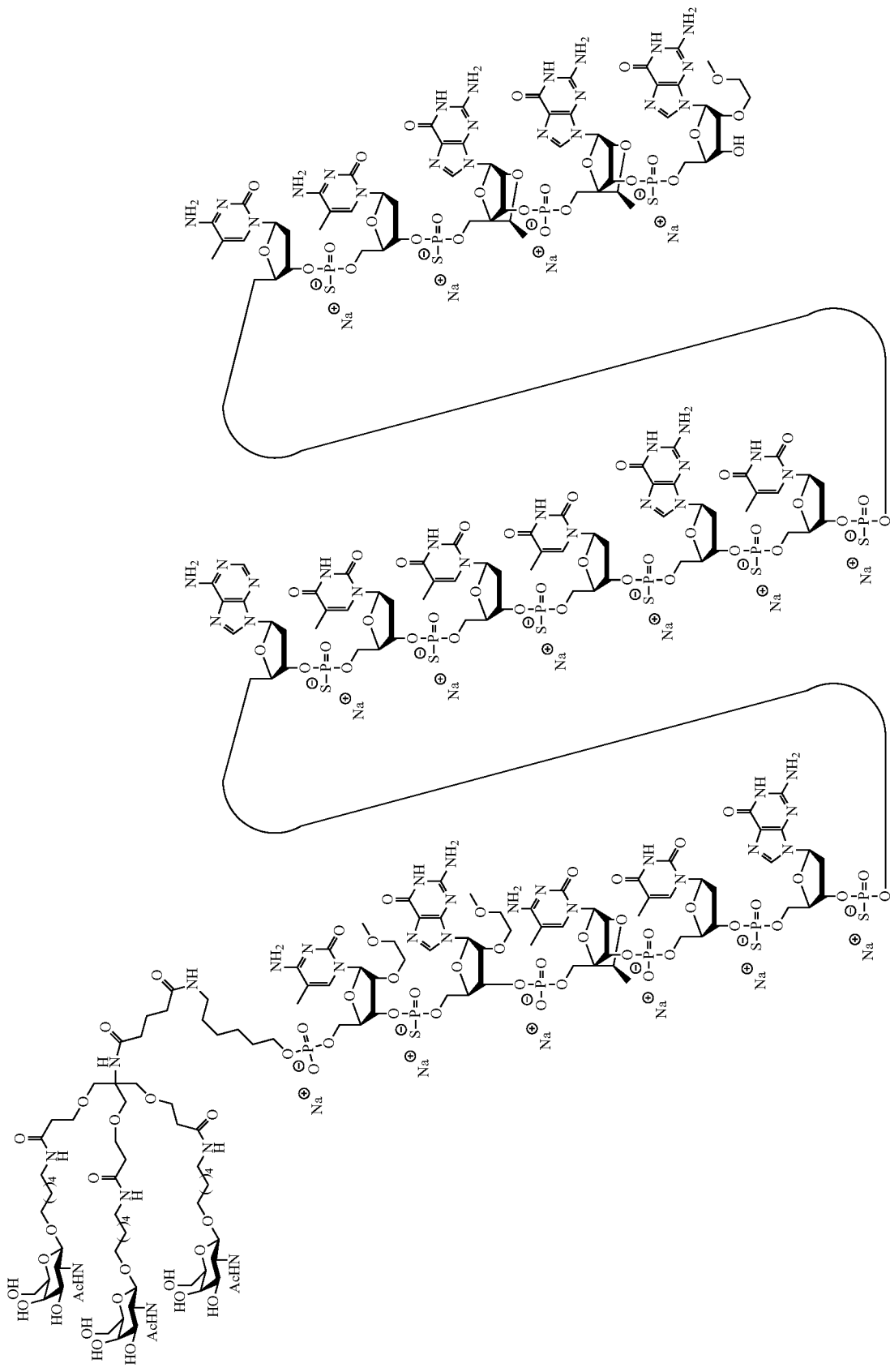

(SEQ ID NO: 12).

Embodiment 119. An oligomeric compound according to the following chemical structure:


(SEQ ID NO: 13), or a salt thereof

Embodiment 120. An oligomeric compound according to the following chemical structure:

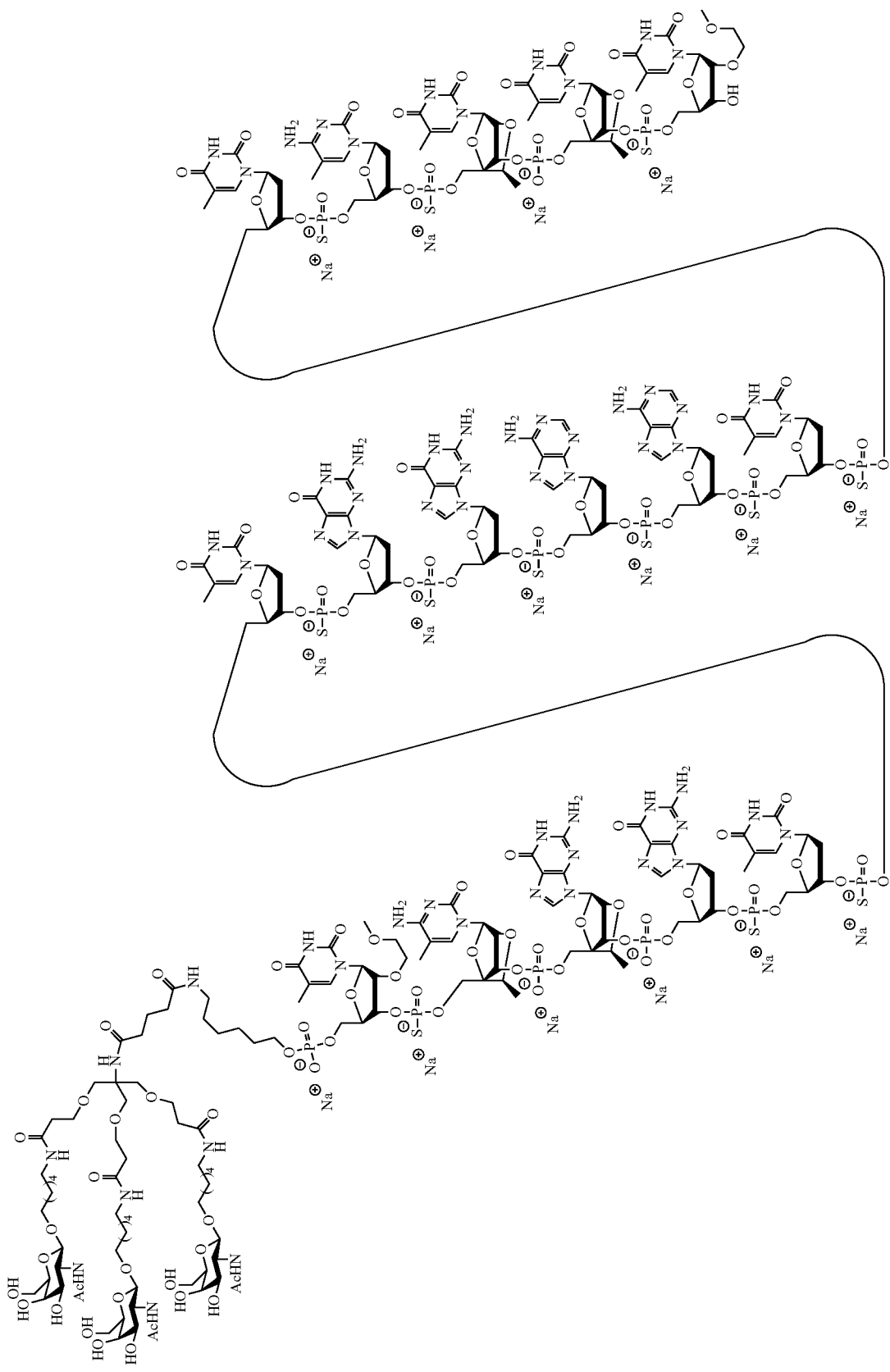

(SEQ ID NO: 13).
Embodiment 121. An oligomeric compound according to the following chemical structure:
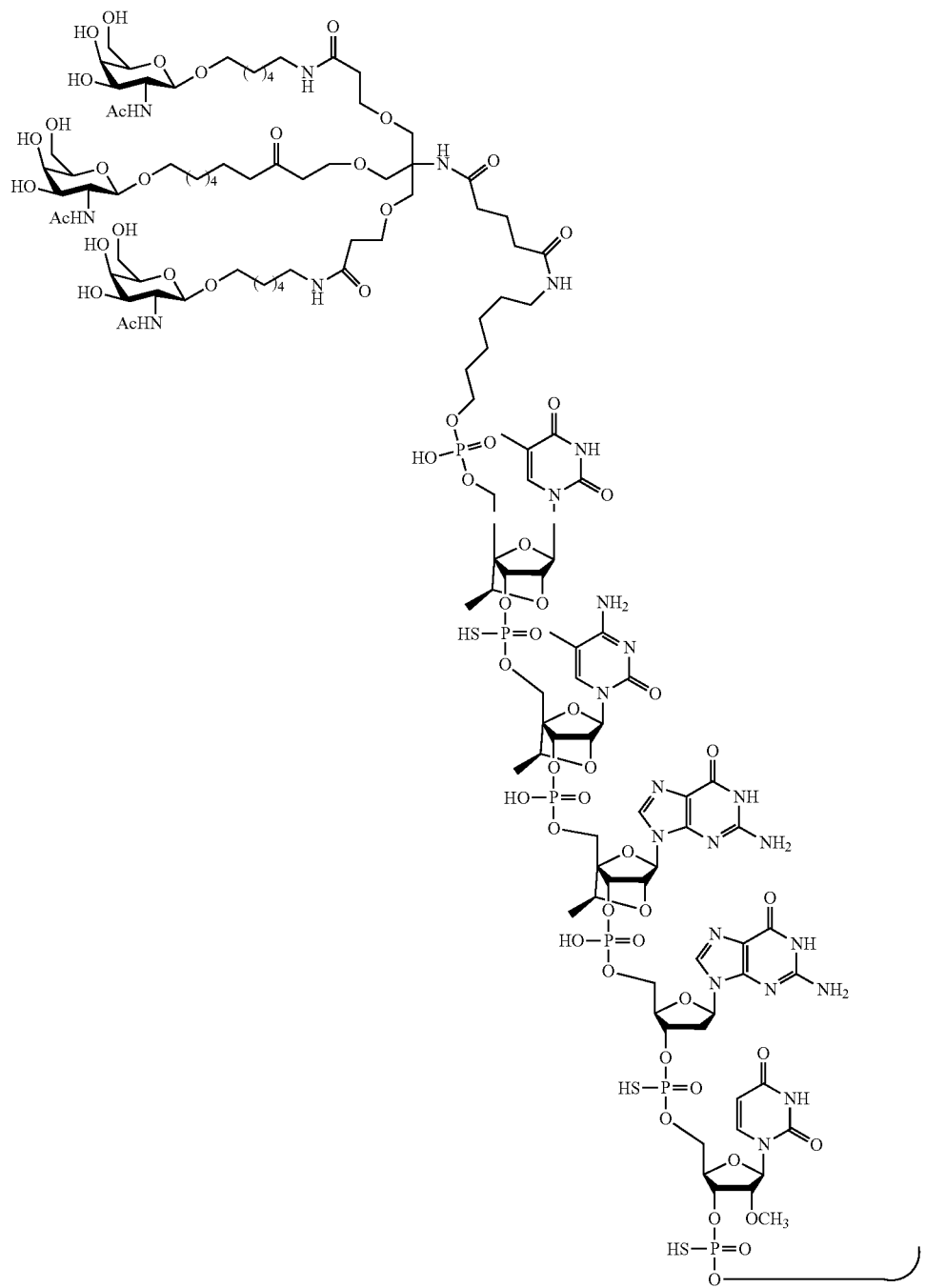

-continued
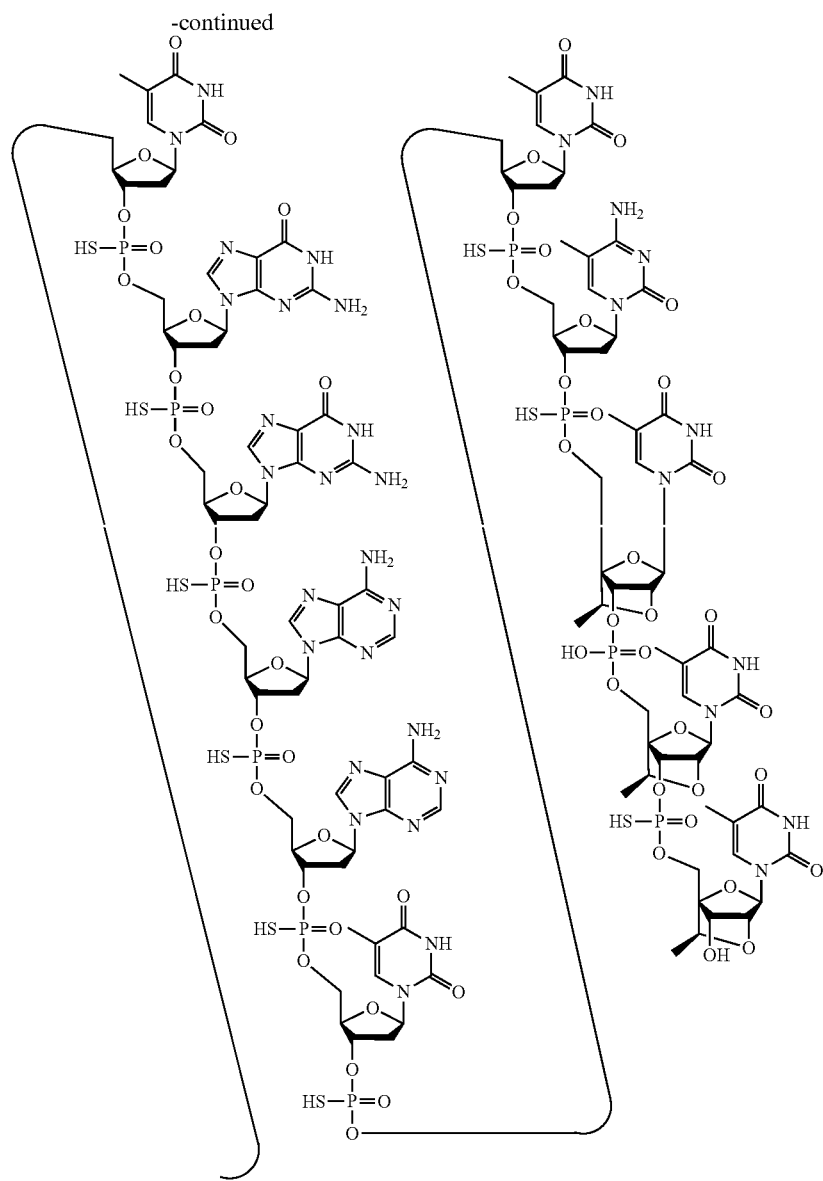
(SEQ ID NO: 14), or a salt thereof
Embodiment 122. An oligomeric compound according to the following chemical structure:

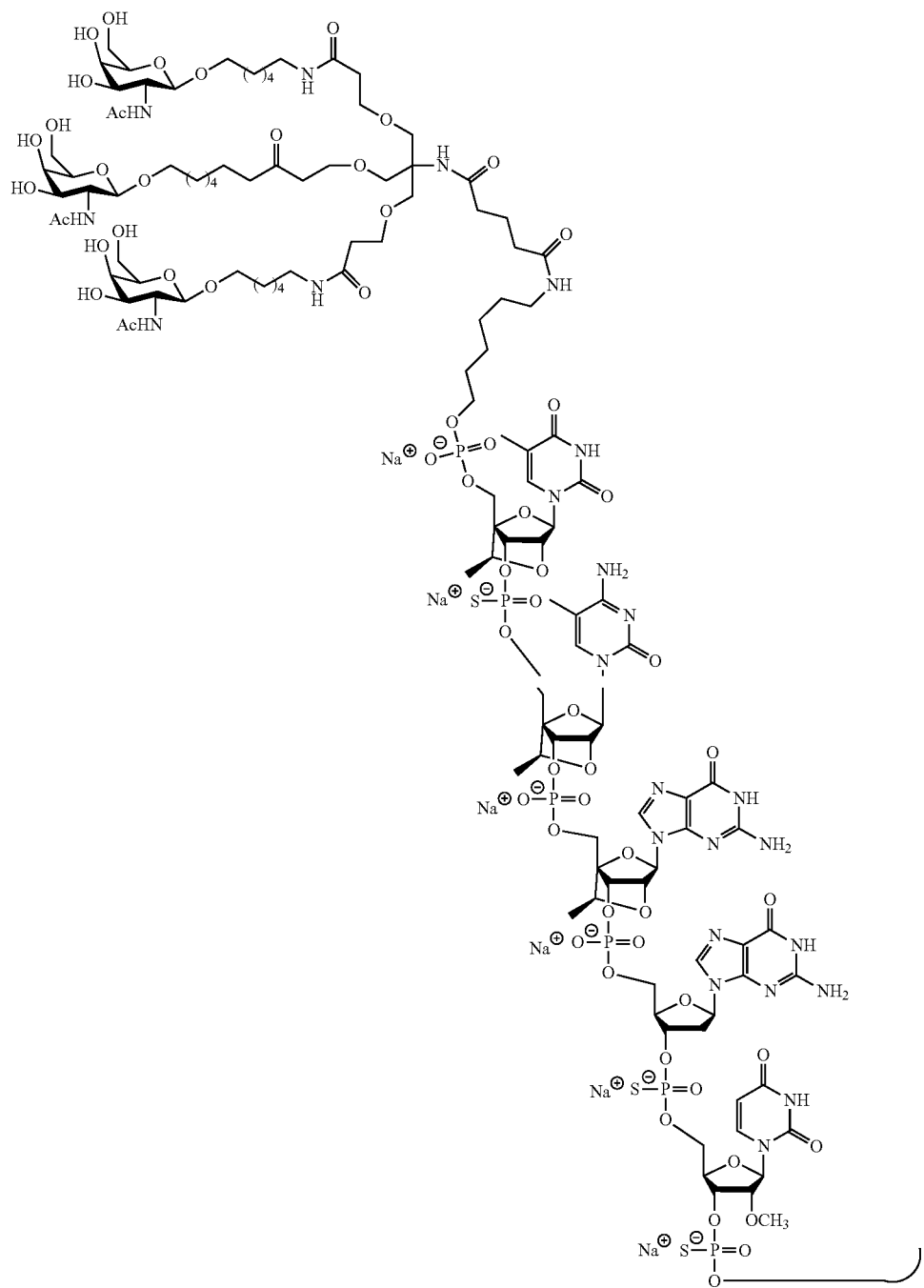

-continued
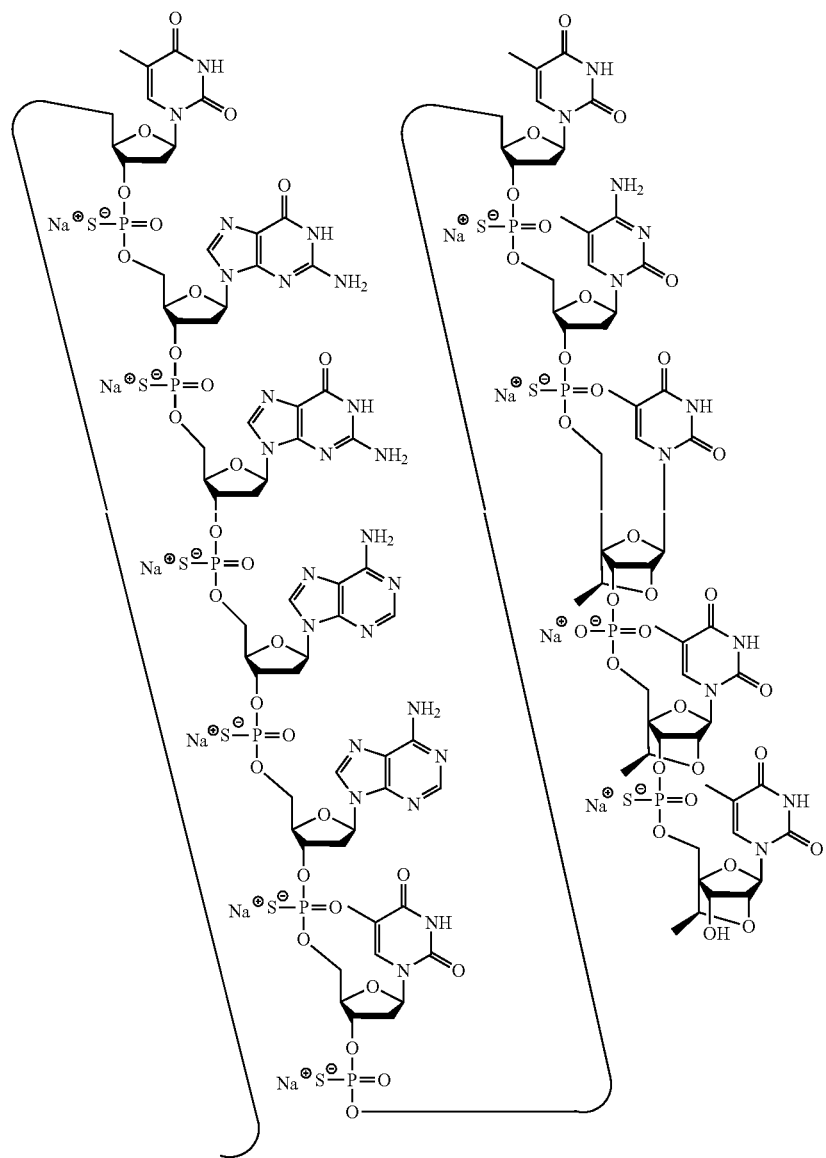
(SEQ ID NO: 14).
Embodiment 123. An oligomeric compound according to the following chemical structure:

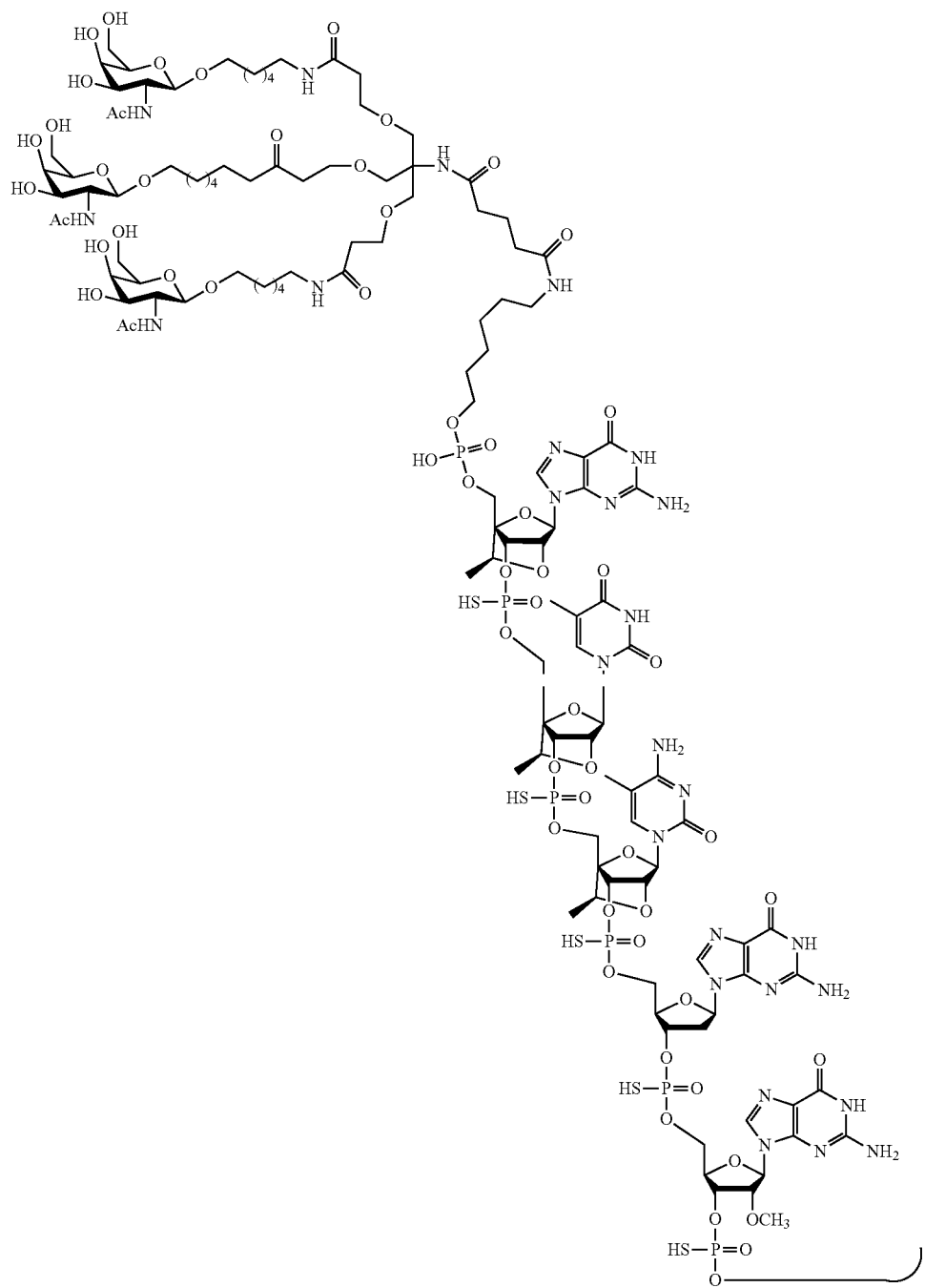

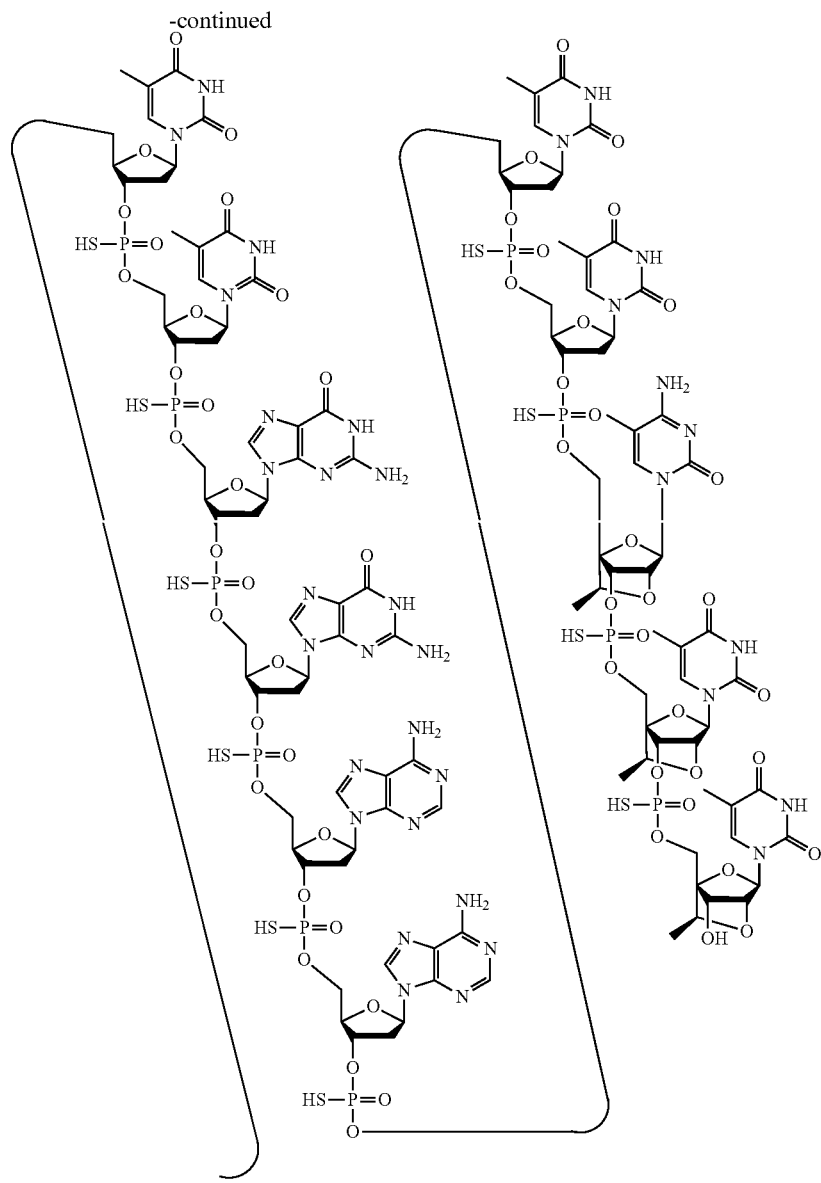
(SEQ ID NO: 15), or salt thereof
Embodiment 124. An oligomeric compound according to the following chemical structure:

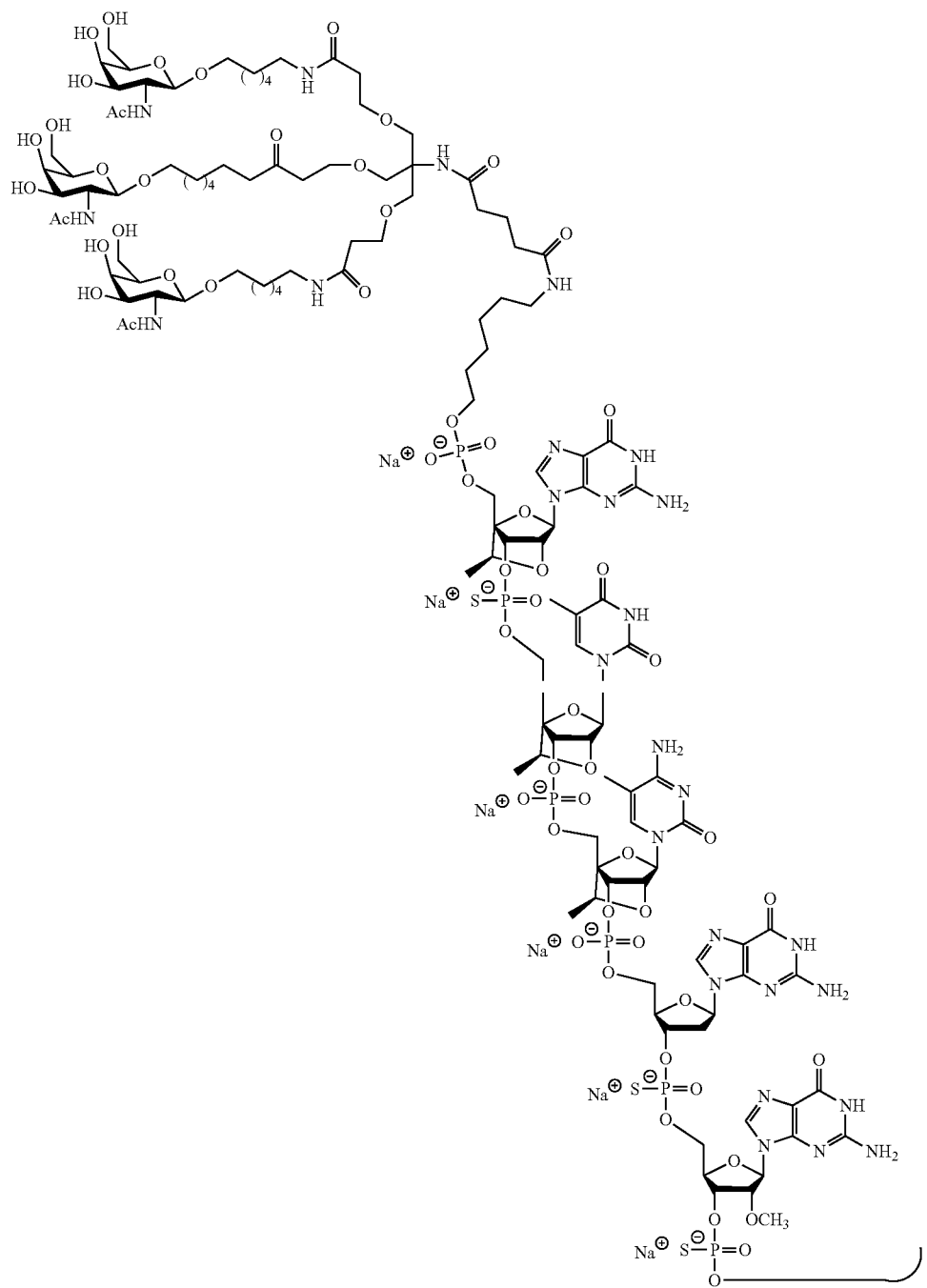

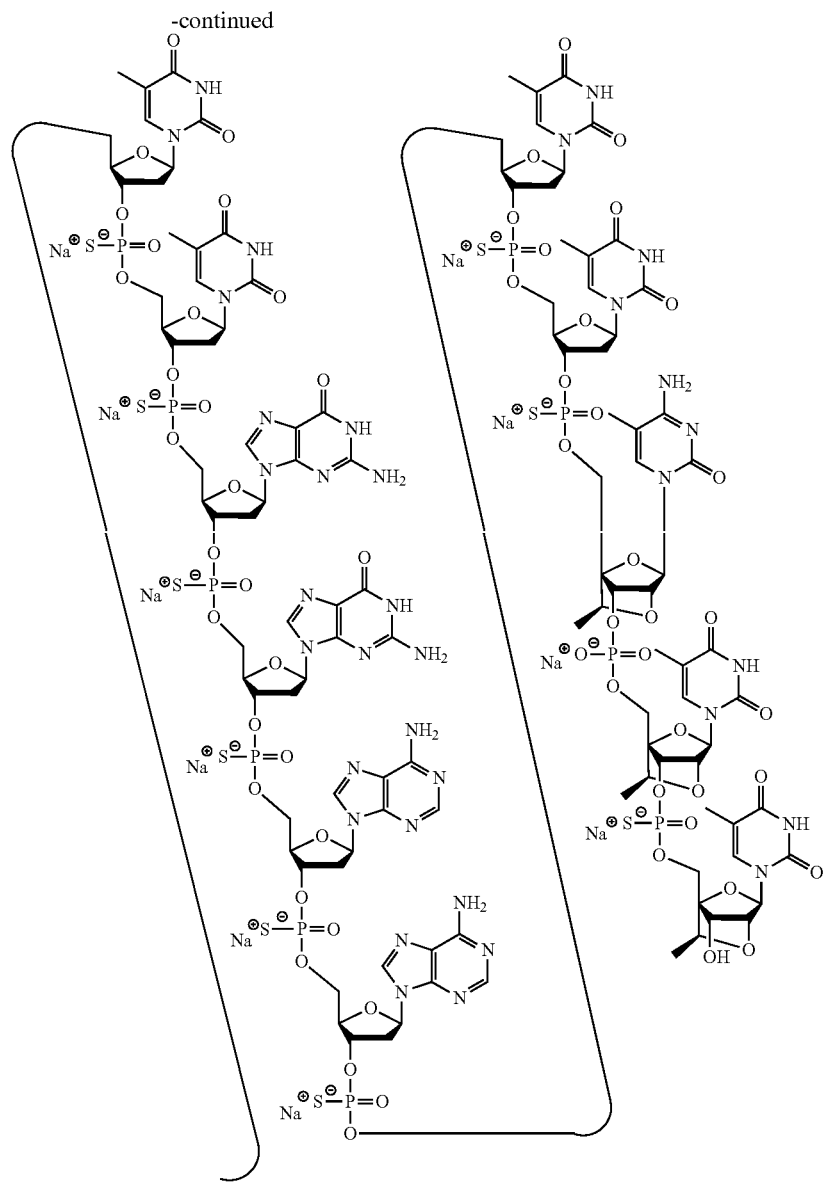

(SEQ ID NO: 15).

Embodiment 125. The oligomeric compound of any of embodiments 117, 119,121, or 123, which is the sodium salt or potassium salt.

Embodiment 126. An oligomeric compound comprising a modified oligonucleotide according to the following chemical notation: $^mC_{es}G_{eo}{}^mC_{ko}T_{ds}G_{ds}A_{ds}T_{ds}T_{ds}T_{ds}G_{ds}T_{ds}{}^mC_{ds}{}^mC_{ds}G_{ko}G_{ks}G_e$ (SEQ ID NO: 12), wherein:
A=an adenine nucleobase,
$^mC$=a 5-methyl cytosine nucleobase,
G=a guanine nucleobase,
T=a thymine nucleobase,
e=a 2'-β-D-MOE sugar moiety,
k=a cEt sugar moiety,
d=a 2'-β-D-deoxyribosyl sugar moiety,
s=a phosphorothioate internucleoside linkage, and
o=a phosphodiester internucleoside linkage.

Embodiment 127. An oligomeric compound comprising a modified oligonucleotide according to the following chemical notation: $T_{es}{}^mC_{ko}G_{ko}G_{ds}T_{ds}T_{ds}G_{ds}G_{ds}A_{ds}A_{ds}T_{ds}T_{ds}{}^mC_{ds}T_{ko}T_{ks}T_e$ (SEQ ID NO: 13), wherein:
A=an adenine nucleobase,
$^mC$=a 5-methyl cytosine nucleobase,
G=a guanine nucleobase,
T=a thymine nucleobase,
e=a 2'-β-D-MOE sugar moiety,
k=a cEt sugar moiety,
d=a 2'-β-D-deoxyribosyl sugar moiety,
s=a phosphorothioate internucleoside linkage, and
o=a phosphodiester internucleoside linkage.

Embodiment 128. An oligomeric compound comprising a modified oligonucleotide according to the following chemical notation: $G_{ks}T_{ks}{}^mC_{ks}G_{ds}G_{ys}T_{ds}T_{ds}G_{ds}G_{ds}A_{d\text{-}s}A_{ds}T_{ds}T_{ds}{}^mC_{ks}T_{ks}T_k$ (SEQ ID NO: 15), wherein:
A=an adenine nucleobase,
$^mC$=a 5-methyl cytosine nucleobase,
G=a guanine nucleobase,
T=a thymine nucleobase,
k=a cEt sugar moiety, d=a 2'-β-D-deoxyribosyl sugar moiety,
y=a 2'-OMe ribose sugar moiety, and
s=a phosphorothioate internucleoside linkage.

Embodiment 129. An oligomeric compound comprising a modified oligonucleotide according to the following chemical notation: $T_{ks}{}^mC_{ko}G_{ko}G_{ds}U_{ys}T_{ds}G_{ds}G_{ds}A_{ds}A_{ds}T_{ds}T_{ds}{}^mC_{ds}T_{ko}T_{ks}T_k$ (SEQ ID NO: 14), wherein:
A=an adenine nucleobase,
$^mC$=a 5-methyl cytosine nucleobase,
G=a guanine nucleobase,
T=a thymine nucleobase,
U=a uracil nucleobase,
k=a cEt sugar moiety,
d=a 2'-β-D-deoxyribosyl sugar moiety,
y=a 2'-OMe ribose sugar moiety,
s=a phosphorothioate internucleoside linkage, and
o=a phosphodiester internucleoside linkage.

Embodiment 130. The oligomeric compound of any of embodiments 126-129, comprising the modified oligonucleotide covalently linked to a conjugate group.

Embodiment 131. An oligomeric duplex comprising an oligomeric compound of any of embodiments 78-130.

Embodiment 132. An antisense compound comprising or consisting of an oligomeric compound of any of embodiments 78-130 or an oligomeric duplex of embodiment 131.

Embodiment 133. A chirally enriched population of oligomeric compounds of any of embodiments 117-130, wherein the population is enriched for compounds comprising at least one particular phosphorothioate internucleoside linkage having a particular stereochemical configuration.

Embodiment 134. The chirally enriched population of embodiment 133, wherein the population is enriched for compounds comprising at least one particular phosphorothioate internucleoside linkage having the (Sp) configuration.

Embodiment 135. The chirally enriched population of embodiment 133, wherein the population is enriched for compounds comprising at least one particular phosphorothioate internucleoside linkage having the (Rp) configuration.

Embodiment 136. The chirally enriched population of embodiment 133, wherein the population is enriched for compounds having a particular, independently selected stereochemical configuration at each phosphorothioate internucleoside linkage.

Embodiment 137. The chirally enriched population of embodiment 133, wherein the population is enriched for compounds having the (Sp) configuration at each phosphorothioate internucleoside linkage or for modified oligonucleotides having the (Rp) configuration at each phosphorothioate internucleoside linkage.

Embodiment 138. The chirally enriched population of embodiment 133, wherein the population is enriched for compounds having the (Rp) configuration at one particular phosphorothioate internucleoside linkage and the (Sp) configuration at each of the remaining phosphorothioate internucleoside linkages.

Embodiment 139. The chirally enriched population of embodiment 133, wherein the population is enriched for compounds having at least 3 contiguous phosphorothioate internucleoside linkages in the Sp, Sp, and Rp configurations, in the 5' to 3' direction.

Embodiment 140. A population of oligomeric compounds of any of embodiments 117-130, in which all phosphorothioate internucleoside linkages of the oligomeric compound are stereorandom.

Embodiment 141. A pharmaceutical composition comprising the oligomeric compound of any of embodiments 78-130, the oligomeric duplex of embodiment 131, the antisense compound of embodiment 132, or the population of any of embodiments 133-140 and a pharmaceutically acceptable carrier or diluent.

Embodiment 142. A method comprising administering to an individual the pharmaceutical composition of embodiment 141.

Embodiment 143. A method of treating a disease associated with the RAAS pathway, comprising administering to an individual having or at risk of having a disease associated with the RAAS pathway a therapeutically effective amount of the pharmaceutical composition according to embodiment 142, thereby treating the disease associated with the RAAS pathway.

Embodiment 144. The method of embodiment 143, wherein the disease is a cardiovascular disease.

Embodiment 145. The method of any of embodiments 143 and 144, wherein the disease is selected from hypertension, resistant hypertension, Marfan syndrome, heart failure, kidney disease, obesity, metabolic syndrome, NASH, and NAFLD.

Embodiment 146. The method of any of embodiments 143-145, wherein at least one symptom or hallmark of the disease is ameliorated.

Embodiment 147. The method of embodiment 146, wherein the symptom or hallmark is any of hypertension, hypertensive emergency (i.e. malignant hypertension), stroke, pre-eclampsia, aneurysms of the blood vessels, abdominal aneurysm, peripheral artery disease, organ damage, or pulmonary arterial hypertension.

Embodiment 148. The method of any of embodiments 142-147, wherein the pharmaceutical composition is administered systemically.

Embodiment 149. The method of any of embodiments 142-148, wherein the pharmaceutical composition is administered subcutaneously or intramuscularly.

Embodiment 150. Use of the oligomeric compound of any of embodiments 78-130, the oligomeric duplex of embodiment 131, the antisense compound of embodiment 132, or the population of any of embodiments 133-140 for reducing AGT expression in a cell.

Embodiment 151. The use of embodiment 150, wherein the level of AGT RNA is reduced.

Embodiment 152. The use of embodiment 150, wherein the level of AGT protein is reduced.

I. Certain Oligonucleotides

In certain embodiments, provided herein are oligomeric compounds comprising oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA. That is, modified oligonucleotides comprise at least one modified nucleoside (comprising a modified sugar moiety and/or a modified nucleobase) and/or at least one modified internucleoside linkage.

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more substituent groups none of which bridges two atoms of the furanosyl ring to form a bicyclic structure. Such non bridging substituents may be at any position of the furanosyl, including but not limited to substituents at the 2', 4', and/or 5' positions. In certain embodiments one or more non-bridging substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE" or "O-methoxyethyl"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$O N(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugar moieties comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.

In certain embodiments, a 2'-substituted non-bicyclic modified nucleoside comprises a sugar moiety comprising a non-bridging 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted non-bicyclic modified nucleoside comprises a sugar moiety comprising a non-bridging 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted non-bicyclic modified nucleoside comprises a sugar moiety comprising a non-bridging 2'-substituent group selected from: F, OCH$_3$, and OCH$_2$CH$_2$OCH$_3$.

In certain embodiments, modified furanosyl sugar moieties and nucleosides incorporating such modified furanosyl sugar moieties are further defined by isomeric configuration. For example, a 2'-deoxyfuranosyl sugar moiety may be in seven isomeric configurations other than the naturally occurring β-D-deoxyribosyl configuration. Such modified sugar moieties are described in, e.g., WO 2019/157531, incorporated by reference herein. A 2'-modified sugar moiety has an additional stereocenter at the 2'-position relative to a 2'-deoxyfuranosyl sugar moiety; therefore, such sugar moieties have a total of sixteen possible isomeric configurations. 2'-modified sugar moieties described herein are in the β-D-ribosyl isomeric configuration unless otherwise specified.

Certain modified sugar moieties comprise a substituent that bridges two atoms of the furanosyl ring to form a second ring, resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-CH$_2$-2', 4'-(CH$_2$)$_2$-2', 4'-(CH$_2$)$_3$-2', 4'-CH$_2$—O—2' ("LNA"), 4'-CH$_2$—S-2', 4'-(CH$_2$)$_2$—O—2' ("ENA"), 4'-CH(CH$_3$)—O-2' (referred to as "constrained ethyl" or "cEt"), O—CH$_2$-2', 4'-CH$_2$—N(R)-2', 4'-CH(CH$_2$OCH$_3$)—O—2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O—2' and analogs thereof (see, e.g., Seth et al., U.S. Pat. No. 8,278,283), 4'-CH$_2$—N(OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., *J. Org. Chem.*, 2009, 74, 118-134), 4'-CH$_2$—C(=CH$_2$)-2' and analogs thereof (see e.g., Seth et al., U.S. Pat. No. 8,278, 426), 4'-C(R$_a$R$_b$)—N(R)—O—2', 4'-C(R$_a$R$_b$)—O—N(R)-2', 4'-CH$_2$—O—N(R)-2', and 4'-CH$_2$—N(R)—O—2', wherein each R, R$_a$, and R$_b$ is, independently, H, a protecting group, or C$_1$-C$_{12}$ alkyl (see, e.g. Imanishi et al., U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COM, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129, 8362-8379; Wengel et a., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

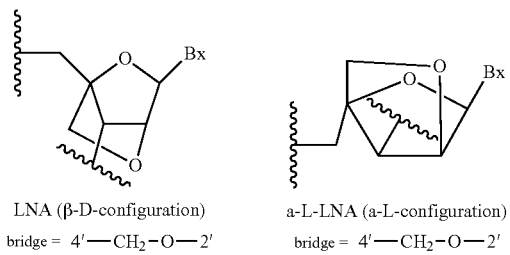

LNA (β-D-configuration)
bridge = 4'—CH$_2$—O—2' a-L-LNA (a-L-configuration)
bridge = 4'—CH$_2$-O—2'

α-L-methyleneoxy (4'-CH$_2$—O—2') or α-L-LNA bicyclic nucleosides have been incorporated into oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, C J. *Bioorg. & Med. Chem.* 2002, 10, 841-854), fluoro HNA:

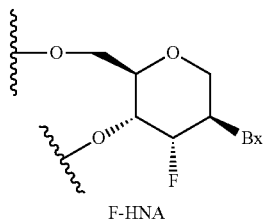

F-HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

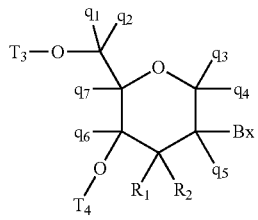

wherein, independently, for each of the modified THP nucleosides:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)$ $NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

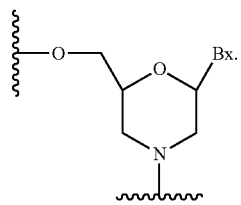

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., Org. Biomol. Chem., 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides.

2. Certain Modified Nucleobases

In certain embodiments, modified oligonucleotides comprise one or more nucleosides comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and 0-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et at, *Angewandte Chemie, International Edition*, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., 6,166,199; and Matteucci et al., U.S. Pat. No. 6,005,096.

3. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphodiesters, which contain a phosphodiester bond ("P(O$_2$)═O") (also referred to as unmodified or naturally occurring linkages), phosphotriesters, methylphosphonates, phosphoramidates, phosphorothioates ("P(O$_2$)═S"), and phosphorodithioates ("HS—P═S"). Representative non-phosphorus containing internucleoside linking groups include but are not limited to methylenemethylimino (—CH$_2$—N(CH$_3$)—O—CH$_2$—), thiodiester, thionocarbamate (—O—C(═O) (NH)—S—); siloxane (—O—SiH$_2$—O—); and N,N'-dimethylhydrazine (—CH$_2$—N(CH$_3$)—N(CH$_3$)—). Modified internucleoside linkages, compared to naturally occurring phosphodiester internucleoside linkages, can be used to alter, typically increase, nuclease resistance of the oligonucleotide. In certain embodiments, internucleoside linkages having a chiral atom can be prepared as a racemic mixture, or as separate enantiomers. Methods of preparation of phosphorous-containing and non-phosphorous-containing internucleoside linkages are well known to those skilled in the art.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate internucleoside linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate internucleoside linkage. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkage in a particular, independently selected stereochemical configuration. In certain embodiments, the particular configuration of the particular phosphorothioate internucleoside linkage is present in at least 65% of the molecules in the population. In certain embodiments, the particular configuration of the particular phosphorothioate internucleoside linkage is present in at least 70% of the molecules in the population. In certain embodiments, the particular configuration of the particular phosphorothioate internucleoside linkage is present in at least 80% of the molecules in the population. In certain embodiments, the particular configuration of the particular phosphorothioate internucleoside linkage is present in at least 90% of the molecules in the population. In certain embodiments, the particular configuration of the particular phosphorothioate internucleoside linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

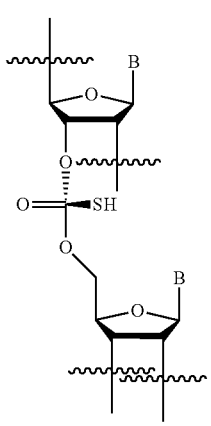

(Rp)

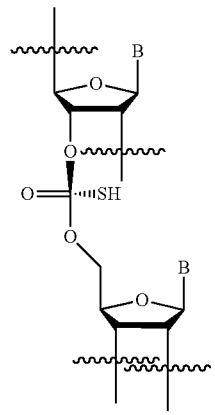

(Sp)

Unless otherwise indicated, chiral internucleoside linkages of modified oligonucleotides described herein can be stereorandom or in a particular stereochemical configuration.

Neutral internucleoside linkages include, without limitation, phosphotriesters, methylphosphonates, MMI (3'-CH$_2$—N(CH$_3$)—O—5'), amide-3 (3'-CH$_2$—C(=O)—N(H)-5'), amide-4 (3'-CH$_2$—N(H)—C(=O)-5'), formacetal (3'-O—CH$_2$—O—5'), methoxypropyl (MOP), and thioformacetal (3'-S—CH$_2$—O—5'). Further neutral internucleoside linkages include nonionic linkages comprising siloxane (dialkylsiloxane), carboxylate ester, carboxamide, sulfide, sulfonate ester and amides (see, e.g., *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

B. Certain Motifs

In certain embodiments, modified oligonucleotides comprise one or more modified nucleosides comprising a modified sugar moiety. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or portion thereof in a defined pattern or sugar motif. In certain instances, such sugar motifs include but are not limited to any of the sugar modifications discussed herein.

In certain embodiments, modified oligonucleotides have a gapmer motif, which is defined by two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-6 nucleosides. In certain embodiments, each nucleoside of each wing of a gapmer comprises a modified sugar moiety. In certain embodiments, at least one nucleoside of each wing of a gapmer comprises a modified sugar moiety. In certain embodiments, at least two nucleosides of each wing of a gapmer comprises a modified sugar moiety. In certain embodiments, at least three nucleosides of each wing of a gapmer comprises a modified sugar moiety. In certain embodiments, at least four nucleosides of each wing of a gapmer comprises a modified sugar moiety. In certain embodiments, at least five nucleosides of each wing of a gapmer comprises a modified sugar moiety.

In certain embodiments, the gap of a gapmer comprises 7-12 nucleosides. In certain embodiments, at least six nucleosides of the gap of a gapmer comprise a 2'-β-D-deoxyribosyl sugar moiety. In certain embodiments, each nucleoside of the gap of a gapmer comprises a 2'-deoxyribosyl sugar moiety. In certain embodiments, each nucleoside of the gap of a gapmer comprises a 2'-β-D-deoxyribosyl sugar moiety. In certain embodiments, at least one nucleoside of the gap of a gapmer comprises a modified sugar moiety. In certain embodiments, at least one nucleoside of the gap of a gapmer comprises a 2'-OMe sugar moiety.

In certain embodiments, the gapmer is a deoxy gapmer. In certain embodiments, the nucleosides on the gap side of each wing/gap junction comprise 2'-deoxyribosyl sugar moieties and the nucleosides on the wing sides of each wing/gap junction comprise modified sugar moieties. In certain embodiments, at least six nucleosides of the gap of a gapmer comprise a 2'-β-D-deoxyribosyl sugar moiety. In certain embodiments, each nucleoside of the gap comprises a 2'-deoxyribosyl sugar moiety. In certain embodiments, each nucleoside of each wing of a gapmer comprises a modified sugar moiety. In certain embodiments, one nucleoside of the gap comprises a modified sugar moiety and each remaining nucleoside of the gap comprises a 2'-deoxyribosyl sugar moiety.

In certain embodiments, modified oligonucleotides comprise or consist of a portion having a fully modified sugar motif. In such embodiments, each nucleoside of the fully modified portion of the modified oligonucleotide comprises a modified sugar moiety. In certain embodiments, each nucleoside of the entire modified oligonucleotide comprises a modified sugar moiety. In certain embodiments, modified oligonucleotides comprise or consist of a portion having a fully modified sugar motif, wherein each nucleoside within the fully modified portion comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified oligonucleotide comprises the same 2'-modification.

Herein, the lengths (number of nucleosides) of the three regions of a gapmer may be provided using the notation [# of nucleosides in the 5'-wing]–[# of nucleosides in the gap]–[# of nucleosides in the 3'-wing]. Thus, a 5-10-5 gapmer consists of 5 linked nucleosides in each wing and 10 linked nucleosides in the gap. Where such nomenclature is followed by a specific modification, that modification is the modification in each sugar moiety of each wing and the gap nucleosides comprises a 2'-β-D-deoxyribosyl sugar moiety. Thus, a 5-10-5 MOE gapmer consists of 5 linked 2'-MOE nucleosides in the 5'-wing, 10 linked 2'-β-D-deoxynucleosides in the gap, and 5 linked 2'-MOE nucleosides in the 3'-wing. A 3-10-3 cEt gapmer consists of 3 linked cEt nucleosides in the 5'-wing, 10 linked 2'-β-D-deoxynucleosides in the gap, and 3 linked cEt nucleosides in the 3'-wing. A 5-8-5 gapmer consists of 5 linked nucleosides comprising a modified sugar moiety in the 5'-wing, 8 linked 2'-deoxynucleosides in the gap, and 5 linked nucleosides comprising a modified sugar moiety in the 3'-wing. A mixed wing gapmer has at least two different modified sugars in the 5' and/or 3' wing. A 5-8-5 or 5-8-4 mixed wing gapmer has at least two different modified sugar moieties in the 5'- and/or the 3'-wing.

In certain embodiments, modified oligonucleotides are 5-10-5 MOE gapmers. In certain embodiments, modified oligonucleotides are 4-10-6 MOE gapmers. In certain embodiments, modified oligonucleotides are 6-10-4 MOE gapmers. In certain embodiments, modified oligonucleotides are 5-8-5 MOE gapmers. In certain embodiments, modified oligonucleotides are X—Y—Z MOE gapmers, wherein X and Z are independently selected from 1, 2, 3, 4, 5, or 6 linked 2'-MOE nucleosides and Y is 7, 8, 9, 10, or 11 linked deoxynucleosides.

In certain embodiments, modified oligonucleotides have a sugar motif selected from the following (5' to 3'): meeeemdddddddddmmmmm, wherein 'd' represents a 2'-deoxyribosyl sugar moiety, 'e' represents a 2'-MOE sugar moiety, and 'm' represents a 2'-OMe sugar moiety.

2. Certain Nucleobase Motifs

In certain embodiments, oligonucleotides comprise modified and/or unmodified nucleobases arranged along the oligonucleotide or portion thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methyl cytosines. In certain embodiments, all of the cytosine nucleobases are 5-methyl cytosines and all of the other nucleobases of the modified oligonucleotide are unmodified nucleobases.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of the nucleoside is a 2'-deoxyribosyl sugar moiety. In certain embodiments, the modified nucleobase is selected from: a 2-thiopyrimidine and a 5-propynepyrimidine.

3. Certain Internucleoside Linkage Motifs

In certain embodiments, oligonucleotides comprise modified and/or unmodified internucleoside linkages arranged along the oligonucleotide or portion thereof in a defined pattern or motif. In certain embodiments, each internucleoside linking group is a phosphodiester internucleoside linkage (P(O$_2$)=O). In certain embodiments, each internucleoside linking group of a modified oligonucleotide is a phosphorothioate internucleoside linkage (P(O$_2$)=S). In certain embodiments, each internucleoside linkage of a modified oligonucleotide is independently selected from a phosphorothioate internucleoside linkage and phosphodiester internucleoside linkage. In certain embodiments, each phosphorothioate internucleoside linkage is independently selected from a stereorandom phosphorothioate, a (Sp) phosphorothioate, and a (Rp) phosphorothioate. In certain embodiments, the sugar motif of a modified oligonucleotide is a gapmer and the internucleoside linkages within the gap are all modified. In certain such embodiments, some or all of the internucleoside linkages in the wings are unmodified phosphodiester internucleoside linkages. In certain embodiments, the terminal internucleoside linkages are modified. In certain embodiments, the sugar motif of a modified oligonucleotide is a gapmer, and the internucleoside linkage motif comprises at least one phosphodiester internucleoside linkage in at least one wing, wherein the at least one phosphodiester internucleoside linkage is not a terminal internucleoside linkage, and the remaining internucleoside linkages are phosphorothioate internucleoside linkages. In certain such embodiments, all of the phosphorothioate internucleoside linkages are stereorandom. In certain embodiments, all of the phosphorothioate internucleoside linkages in the wings are (Sp) phosphorothioates, and the gap comprises at least one Sp, Sp, Rp motif. In certain embodiments, populations of modified oligonucleotides are enriched for modified oligonucleotides comprising such internucleoside linkage motifs.

In certain embodiments, all of the internucleoside linkages are either phosphodiester internucleoside linkages or phosphorothioate internucleoside linkages, and the chiral motif is (5' to 3'): Sp-o-o-o-Sp-Sp-Sp-Rp-Sp-Sp-Rp-Sp-Sp-Sp-Sp-Sp-Sp-Sp-Sp or Sp-o-o-o-Sp-Sp-Sp-Rp-Sp-Sp-Sp-Sp-Sp-Sp-Sp-Sp-Sp-Sp, wherein each 'Sp' represents a (Sp) phosphorothioate internucleoside linkage, each 'Rp' is a Rp internucleoside linkage, and each 'o' represents a phosphodiester internucleoside linkage. In certain embodiments, populations of modified oligonucleotides are enriched for modified oligonucleotides comprising such internucleoside linkage motifs.

In certain embodiments, modified oligonucleotides have an internucleoside linkage motif of sooosssssssssssooss, wherein each "s" represents a phosphorothioate internucleoside linkage and each "o" represents a phosphodiester internucleoside linkage. In certain embodiments, modified oligonucleotides have an internucleoside linkage motif of (5' to 3'): sooooosssssssssssoss, wherein each "s" represents a phosphorothioate internucleoside linkage and each "o" represents a phosphodiester internucleoside linkage. In certain embodiments, modified oligonucleotides have an internucleoside linkage motif of (5' to 3'): sooosssssssssssooss, wherein each "s" represents a phosphorothioate internucleoside linkage and each "o" represents a phosphodiester internucleoside linkage. In certain embodiments, modified oligonucleotides have an internucleoside linkage motif of (5' to 3'):sooosssssssssssooss, wherein each "s" represents a phosphorothioate internucleoside linkage and each "o" represents a phosphodiester internucleoside linkage. In certain embodiments, modified oligonucleotides have an internucleoside linkage motif of (5' to 3'): sooossssssssssssoooss, wherein each "s" represents a phosphorothioate internucleoside linkage and each "o" represents a phosphodiester internucleoside linkage. In certain embodiments, modified oligonucleotides have an internucleoside linkage motif of (5' to 3'): soooosssssssssssssss, wherein each "s" represents a phosphorothioate internucleoside linkage and each "o" represents a phosphodiester internucleoside linkage.

C. Certain Lengths

It is possible to increase or decrease the length of an oligonucleotide without eliminating activity. For example, in Woolf et al. Proc. Natl. Acad. Sci. USA 89:7305-7309, 1992) a series of oligonucleotides 13-25 nucleobases in length were tested for their ability to induce cleavage of a target nucleic acid in an oocyte injection model. Oligonucleotides 25 nucleobases in length with 8 or 11 mismatch bases near the ends of the oligonucleotides were able to direct specific cleavage of the target nucleic acid, albeit to a lesser extent than the oligonucleotides that contained no mismatches. Similarly, target specific cleavage was achieved using 13 nucleobase oligonucleotides, including those with 1 or 3 mismatches.

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides.

D. Certain Modified Oligonucleotides

In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Unless otherwise indicated, all modifications are independent of nucleobase sequence.

E. Certain Populations of Modified Oligonucleotides

Populations of modified oligonucleotides in which all of the modified oligonucleotides of the population have the same molecular formula can be stereorandom populations or chirally enriched populations. All of the chiral centers of all of the modified oligonucleotides are stereorandom in a stereorandom population. In a chirally enriched population, at least one particular chiral center is not stereorandom in the modified oligonucleotides of the population. In certain embodiments, the modified oligonucleotides of a chirally enriched population are enriched for β-D ribosyl sugar moieties, and all of the phosphorothioate internucleoside linkages are stereorandom. In certain embodiments, the modified oligonucleotides of a chirally enriched population are enriched for both β-D ribosyl sugar moieties and at least one, particular phosphorothioate internucleoside linkage in a particular stereochemical configuration.

F. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a portion of an oligonucleotide has a nucleobase sequence that is complementary to a second oligonucleotide or an identified reference nucleic acid, such as a target nucleic acid. In certain embodiments, the nucleobase sequence of a portion or entire length of an oligonucleotide is at least 50%, at least 60%, at least 70%, at least 80%, at least 85%, at least 90%, at least 95%, or 100% complementary to the second oligonucleotide or nucleic acid, such as a target nucleic acid.

II. Certain Oligomeric Compounds

In certain embodiments, provided herein are oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, abasic nucleosides, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., *Proc. Natl. Acad. Sci. USA,* 1989, 86, 6553-6556), cholic acid (Manoharan et al., *Bioorg. Med. Chem. Lett.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO 1,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid a palmityl moiety (Mishra et al., *Biochim. Biophys. Acta,* 1995, 1264, 229-237), an octadecylamine or hexylamino-carbonyl-oxycholesterol moiety (Crooke et al., *J. Pharmacol. Exp. Ther.,* 1996, 277, 923-937), a tocopherol group (Nishina et al., *Molecular Therapy Nucleic Acids,* 2015, 4, e220; and Nishina et al., *Molecular Therapy,* 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, lipophilic groups, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain oligomeric compounds, a conjugate moiety is attached to an oligonucleotide via a more complex conjugate linker comprising one or more conjugate linker moieties, which are sub-units making up a conjugate linker. In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methyl cytosine, 4-N-benzoyl-5-methyl cytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate or phosphodiester linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxynucleoside that is attached to either the 3' or 5'-terminal nucleoside of an oligonucleotide by a phosphodiester internucleoside linkage and covalently attached to the remainder of the conjugate linker or conjugate moiety by a phosphate or phosphorothioate internucleoside linkage. In certain such embodiments, the cleavable moiety is 2'-deoxyadenosine.

3. Cell-Targeting Moieties

In certain embodiments, a conjugate group comprises a cell-targeting moiety. In certain embodiments, a conjugate group has the general formula:

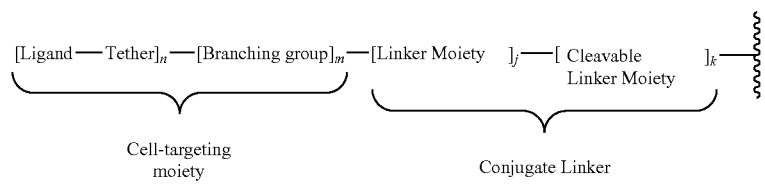

wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group. In certain embodiments, cell-targeting moieties comprise three tethered ligands covalently attached to a branching group.

B. Certain Terminal Groups

In certain embodiments, oligomeric compounds comprise one or more terminal groups. In certain such embodiments, oligomeric compounds comprise a stabilized 5'-phosphate. Stabilized 5'-phosphates include, but are not limited to 5'-phosphonates, including, but not limited to 5'-vinylphosphonates. In certain embodiments, terminal groups comprise one or more abasic nucleosides and/or inverted nucleosides. In certain embodiments, terminal groups comprise one or more 2'-linked nucleosides. In certain such embodiments, the 2'-linked nucleoside is an abasic nucleoside.

III. Oligomeric Duplexes

In certain embodiments, oligomeric compounds described herein comprise an oligonucleotide, having a nucleobase sequence complementary to that of a target nucleic acid. In certain embodiments, an oligomeric compound is paired with a second oligomeric compound to form an oligomeric duplex. Such oligomeric duplexes comprise a first oligomeric compound having a portion complementary to a target nucleic acid and a second oligomeric compound having a portion complementary to the first oligomeric compound. In certain embodiments, the first oligomeric compound of an oligomeric duplex comprises or consists of (1) a modified or unmodified oligonucleotide and optionally a conjugate group and (2) a second modified or unmodified oligonucleotide and optionally a conjugate group. Either or both oligomeric compounds of an oligomeric duplex may comprise a conjugate group. The oligonucleotides of each oligomeric compound of an oligomeric duplex may include non-complementary overhanging nucleosides.

IV. Antisense Activity

In certain embodiments, oligomeric compounds and oligomeric duplexes are capable of hybridizing to a target nucleic acid, resulting in at least one antisense activity; such oligomeric compounds and oligomeric duplexes are antisense compounds. In certain embodiments, antisense compounds have antisense activity when they reduce the amount or activity of a target nucleic acid by 25% or more in the standard cell assay. In certain embodiments, antisense compounds selectively affect one or more target nucleic acid. Such antisense compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an antisense compound to a target nucleic acid results in recruitment of a protein that cleaves the target nucleic acid. For example, certain antisense compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, described herein are antisense compounds that are sufficiently "DNA-like" to elicit RNase H activity. In certain embodiments, one or more non-DNA-like nucleoside in the gap of a gapmer is tolerated.

In certain antisense activities, an antisense compound or a portion of an antisense compound is loaded into an RNA-induced silencing complex (RISC), ultimately resulting in cleavage of the target nucleic acid. For example, certain antisense compounds result in cleavage of the target nucleic acid by Argonaute. Antisense compounds that are loaded into RISC are RNAi compounds. RNAi compounds may be double-stranded (siRNA) or single-stranded (ssRNA).

In certain embodiments, hybridization of an antisense compound to a target nucleic acid does not result in recruitment of a protein that cleaves that target nucleic acid. In certain embodiments, hybridization of the antisense compound to the target nucleic acid results in alteration of splicing of the target nucleic acid. In certain embodiments, hybridization of an antisense compound to a target nucleic acid results in inhibition of a binding interaction between the target nucleic acid and a protein or other nucleic acid. In certain embodiments, hybridization of an antisense compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein and/or a phenotypic change in a cell or subject.

V. Certain Target Nucleic Acids

In certain embodiments, oligomeric compounds comprise or consist of an oligonucleotide comprising a portion that is complementary to a target nucleic acid. In certain embodiments, the target nucleic acid is an endogenous RNA molecule. In certain embodiments, the target nucleic acid encodes a protein. In certain such embodiments, the target nucleic acid is selected from: a mature mRNA and a pre-mRNA, including intronic, exonic and untranslated regions. In certain embodiments, the target nucleic acid is a mature mRNA. In certain embodiments, the target nucleic acid is a pre-mRNA. In certain embodiments, the target region is entirely within an intron. In certain embodiments, the target region spans an intron/exon junction. In certain embodiments, the target region is at least 50% within an intron.

A. Complementarity/Mismatches to the Target Nucleic Acid

It is possible to introduce mismatch bases without eliminating activity. For example, Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo. Maher and Dolnick (Nuc. Acid. Res. 16:3341-3358, 1988) tested a series of tandem 14 nucleobase oligonucleotides, and a 28- and 42-nucleobase oligonucleotides comprised of the sequence of two or three of the tandem oligonucleotides, respectively, for their ability to arrest translation of human DHFR in a rabbit reticulocyte assay. Each of the three 14 nucleobase oligonucleotides alone was able to inhibit translation, albeit at a more modest level than the 28 or 42 nucleobase oligonucleotides.

In certain embodiments, oligonucleotides are complementary to the target nucleic acid over the entire length of the oligonucleotide. In certain embodiments, oligonucleotides are 99%, 95%, 90%, 85%, or 80% complementary to the target nucleic acid. In certain embodiments, oligonucleotides are at least 80% complementary to the target nucleic acid over the entire length of the oligonucleotide and comprise a portion that is 100% or fully complementary to a target nucleic acid. In certain embodiments, the portion of full complementarity is 6, 7, 8, 9, 10, 11, 12, 13, 14, 15, 16, 17, 18, 19, 20, 21, 22, 23, or 24 nucleobases in length.

In certain embodiments, oligonucleotides comprise one or more mismatched nucleobases relative to the target nucleic acid. In certain embodiments, antisense activity against the target is reduced by such mismatch, but activity against a non-target is reduced by a greater amount. Thus, in certain embodiments selectivity of the oligonucleotide is improved. In certain embodiments, the mismatch is specifically positioned within an oligonucleotide having a gapmer motif. In certain embodiments, the mismatch is at position 1, 2, 3, 4, 5, 6, 7, 8, 9, 10, or 11 from the 5'-end of the gap region. In certain embodiments, the mismatch is at position 1, 2, 3, 4, 5, or 6 from the 5'-end of the 5' wing region or the 3' wing region.

B. AGT

In certain embodiments, oligomeric compounds comprise or consist of an oligonucleotide that is complementary to a target nucleic acid, wherein the target nucleic acid is an AGT nucleic acid. In certain embodiments, AGT nucleic acid has the sequence set forth in SEQ ID NO: 1 (GENBANK Accession No. NM_000029.3) or SEQ ID NO: 2 (the complement of GENBANK Accession No. NC_000001.11 truncated from nucleotides 230700001 to 230718000).

In certain embodiments, contacting a cell with an oligomeric compound complementary to any of SEQ ID NO: 1 and 2 reduces the amount of AGT RNA and in certain embodiments reduces the amount of AGT protein. In certain embodiments, the oligomeric compound consists of a modified oligonucleotide. In certain embodiments, contacting a cell with an oligomeric compound complementary to any of SEQ ID NO: 1 and 2 reduces the amount of AGT RNA in a cell, and in certain embodiments reduces the amount of AGT protein in a cell. In certain embodiments, the cell is in vitro. In certain embodiments, the cell is in a subject. In certain embodiments, the oligomeric compound consists of a modified oligonucleotide. In certain embodiments, contacting a cell in a subject with an oligomeric compound complementary to any of SEQ ID NO: 1 and 2 ameliorates one or more symptom or hallmark of a cardiovascular disease. In certain embodiments, the disease is hypertension. In certain embodiments, the disease is resistant hypertension. In certain embodiments, the disease is Marfan syndrome. In certain embodiments, the disease is heart failure. In certain embodiments, the symptom or hallmark is selected from hypertension, chronic kidney disease, stroke, myocardial infarction, heart failure, valvular heart disease, aneurysms of the blood vessels, peripheral artery disease, and organ damage.

In certain embodiments, an oligomeric compound complementary to any of SEQ ID NO: 1 and 2 is capable of reducing the detectable amount of AGT RNA in vitro by at least 10%, at least 20%, at least 30%, at least 40%, at least 50%, at least 60%, at least 70%, at least 80%, or at least 90% when administered according to the standard cell assay. In certain embodiments, an oligomeric compound complementary to SEQ ID NO: 1 or 2 is capable of decreasing the amount of AGT in vitro by at least 10%, at least 20%, at least 30%, at least 40%, at least 50%, at least 60%, at least 70%, at least 80%, or at least 90% when administered according to the standard in vitro assay. In certain embodiments, an oligomeric compound complementary to SEQ ID NO: 1 or SEQ ID NO: 2 is capable of reducing the detectable amount of AGT RNA in a subject by at least 10%, at least 20%, at least 30%, at least 40%, at least 50%, at least 60%, at least 70%, at least 80%, or at least 90%.

VI. Certain Conjugated Compounds

In certain embodiments, the oligomeric compounds described herein comprise or consist of an oligonucleotide (modified or unmodified) and, optionally, one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

In certain embodiments, the oligonucleotide is modified. In certain embodiments, the oligonucleotide of a compound has a nucleobase sequence that is complementary to a target nucleic acid. In certain embodiments, oligonucleotides are complementary to a messenger RNA (mRNA). In certain embodiments, oligonucleotides are complementary to a pre-mRNA. In certain embodiments, oligonucleotides are complementary to a sense transcript.

Examples of terminal groups include but are not limited to conjugate groups, capping groups, phosphate moieties, protecting groups, modified or unmodified nucleosides, and two or more nucleosides that are independently modified or unmodified.

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., *Proc. Natl. Acad. Sci. USA,* 1989, 86, 6553-6556), cholic acid (Manoharan et al., *Bioorg. Med. Chem. Lett.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid a palmityl moiety (Mishra et al., *Biochim. Biophys. Acta,* 1995, 1264, 229-237), an octadecylamine or hexylamino-carbonyl-oxycholesterol moiety (Crooke et al., *J. Pharmacol. Exp. Ther.,* 1996, 277, 923-937), a tocopherol group (Nishina et al., *Molecular Therapy Nucleic Acids,* 2015, 4, e220; and Nishina et al., *Molecular Therapy,* 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain compounds, the conjugate linker is a single chemical bond (i.e., the conjugate moiety is attached directly to an oligonucleotide through a single bond). In certain compounds, a conjugate moiety is attached to an oligonucleotide via a more complex conjugate linker comprising one or more conjugate linker moieities, which are sub-units making up a conjugate linker. In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N- isobutyrylguanine. It is typically desirable for linker-nucleosides to be cleaved from the compound after it reaches a target tissue. Accordingly, linker-nucleosides are typically linked to one another and to the remainder of the compound through cleavable bonds. In certain embodiments, such cleavable bonds are phosphodiester bonds.

Herein, linker-nucleosides are not considered to be part of the oligonucleotide. Accordingly, in embodiments in which an compound comprises an oligonucleotide consisting of a specified number or range of linked nucleosides and/or a specified percent complementarity to a reference nucleic acid and the compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, a compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such a compound is more than 30. Alternatively, a compound may comprise a modified oligonucleotide consisting of 8-30 nucleosides and no conjugate group. The total number of contiguous linked nucleosides in such a compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances compounds comprising a particular conjugate moiety are better taken up by a particular cell type, but once the compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

3. Certain Cell-Targeting Conjugate Moieties

In certain embodiments, a conjugate group comprises a cell-targeting conjugate moiety. In certain embodiments, a conjugate group has the general formula:

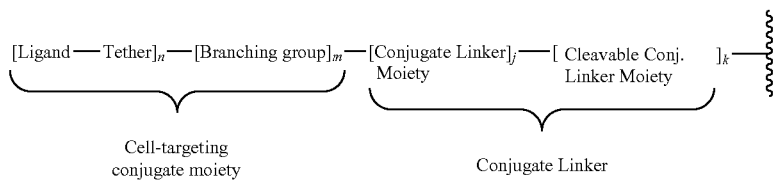

wherein n is from 1 to about 3, m is 0 when n is 1, m is 1 when n is 2 or greater, j is 1 or 0, and k is 1 or 0.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group. In certain embodiments, cell-targeting moieties comprise three tethered ligands covalently attached to a branching group.

In certain embodiments, the cell-targeting moiety comprises a branching group comprising one or more groups selected from alkyl, amino, oxo, amide, disulfide, polyethylene glycol, ether, thioether and hydroxylamino groups. In certain embodiments, the branching group comprises a branched aliphatic group comprising groups selected from alkyl, amino, oxo, amide, disulfide, polyethylene glycol, ether, thioether and hydroxylamino groups. In certain such embodiments, the branched aliphatic group comprises groups selected from alkyl, amino, oxo, amide and ether groups. In certain such embodiments, the branched aliphatic group comprises groups selected from alkyl, amino and ether groups. In certain such embodiments, the branched aliphatic group comprises groups selected from alkyl and ether groups. In certain embodiments, the branching group comprises a mono or polycyclic ring system.

In certain embodiments, each tether of a cell-targeting moiety comprises one or more groups selected from alkyl, substituted alkyl, ether, thioether, disulfide, amino, oxo, amide, phosphodiester, and polyethylene glycol, in any combination. In certain embodiments, each tether is a linear aliphatic group comprising one or more groups selected from alkyl, ether, thioether, disulfide, amino, oxo, amide, and polyethylene glycol, in any combination. In certain embodiments, each tether is a linear aliphatic group comprising one or more groups selected from alkyl, phosphodiester, ether, amino, oxo, and amide, in any combination. In certain embodiments, each tether is a linear aliphatic group comprising one or more groups selected from alkyl, ether, amino, oxo, and amid, in any combination. In certain embodiments, each tether is a linear aliphatic group comprising one or more groups selected from alkyl, amino, and oxo, in any combination. In certain embodiments, each tether is a linear aliphatic group comprising one or more groups selected from alkyl and oxo, in any combination. In certain embodiments, each tether is a linear aliphatic group comprising one or more groups selected from alkyl and phosphodiester, in any combination. In certain embodiments, each tether comprises at least one phosphorus linking group or neutral linking group. In certain embodiments, each tether comprises a chain from about 6 to about 20 atoms in length. In certain embodiments, each tether comprises a chain from about 10 to about 18 atoms in length. In certain embodiments, each tether comprises about 10 atoms in chain length.

In certain embodiments, each ligand of a cell-targeting moiety has an affinity for at least one type of receptor on a target cell. In certain embodiments, each ligand has an affinity for at least one type of receptor on the surface of a mammalian liver cell. In certain embodiments, each ligand has an affinity for the hepatic asialoglycoprotein receptor (ASGP-R). In certain embodiments, each ligand is a carbohydrate. In certain embodiments, each ligand is, independently selected from galactose, N-acetyl galactoseamine (GalNAc), mannose, glucose, glucoseamine and fucose. In certain embodiments, each ligand is N-acetyl galactoseamine (GalNAc). In certain embodiments, the cell-targeting moiety comprises 3 GalNAc ligands. In certain embodiments, the cell-targeting moiety comprises 2 GalNAc ligands. In certain embodiments, the cell-targeting moiety comprises 1 GalNAc ligand.

In certain embodiments, each ligand of a cell-targeting moiety is a carbohydrate, carbohydrate derivative, modified carbohydrate, polysaccharide, modified polysaccharide, or polysaccharide derivative. In certain such embodiments, the conjugate group comprises a carbohydrate cluster (see, e.g., Maier et al., "Synthesis of Antisense Oligonucleotides Conjugated to a Multivalent Carbohydrate Cluster for Cellular Targeting," Bioconjugate Chemistry, 2003, 14, 18-29 or Rensen et al., "Design and Synthesis of Novel N-Acetylgalactosamine-Terminated Glycolipids for Targeting of Lipoproteins to the Hepatic Asiaglycoprotein Receptor," J. Med. Chem. 2004, 47, 5798-5808). In certain such embodiments, each ligand is an amino sugar or a thio sugar. For example, amino sugars may be selected from any number of compounds known in the art, such as sialic acid, α-D-galactosamine, β-muramic acid, 2-deoxy-2-methylamino-L-glucopyranose, 4,6-dideoxy-4-formamido-2,3-di-O-methyl-D-mannopyranose, 2-deoxy-2-sulfoamino-D-glucopyranose and N-sulfo-D-glucosamine, and N-glycoloyl-α-neuraminic acid. For example, thio sugars may be selected from 5-Thio-β-D-glucopyranose, methyl 2,3,4-tri-O-acetyl-1-thio-6-O-trityl-α-D-glucopyranoside, 4-thio-β-D-galactopyranose, and ethyl 3,4,6,7-tetra-O-acetyl-2-deoxy-1,5-dithio-α-D-gluco-heptopyranoside.

In certain embodiments, conjugate groups comprise a cell-targeting moiety having the formula:

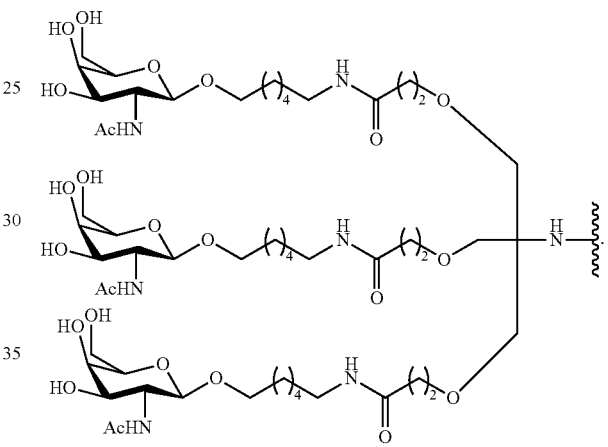

In certain embodiments, conjugate groups comprise a cell-targeting moiety having the formula:

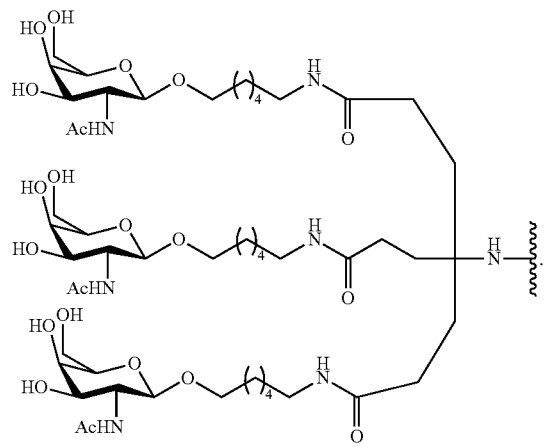

In certain embodiments, conjugate groups comprise a cell-targeting moiety having the formula:

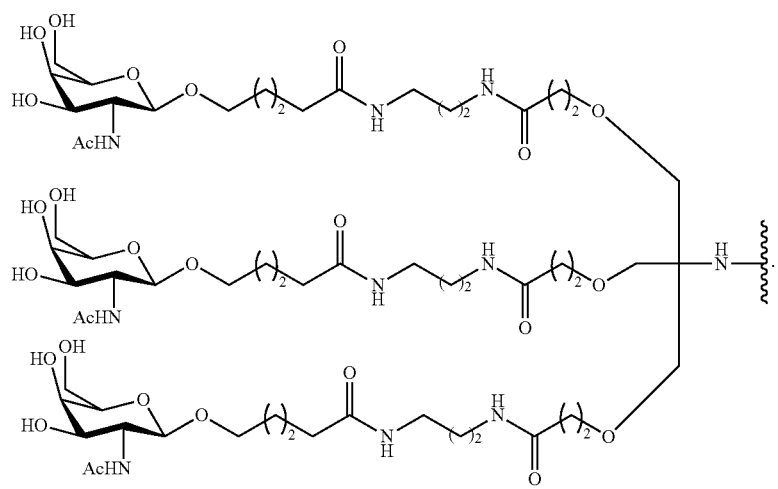
In certain embodiments, conjugate groups comprise a cell-targeting moiety having the formula:
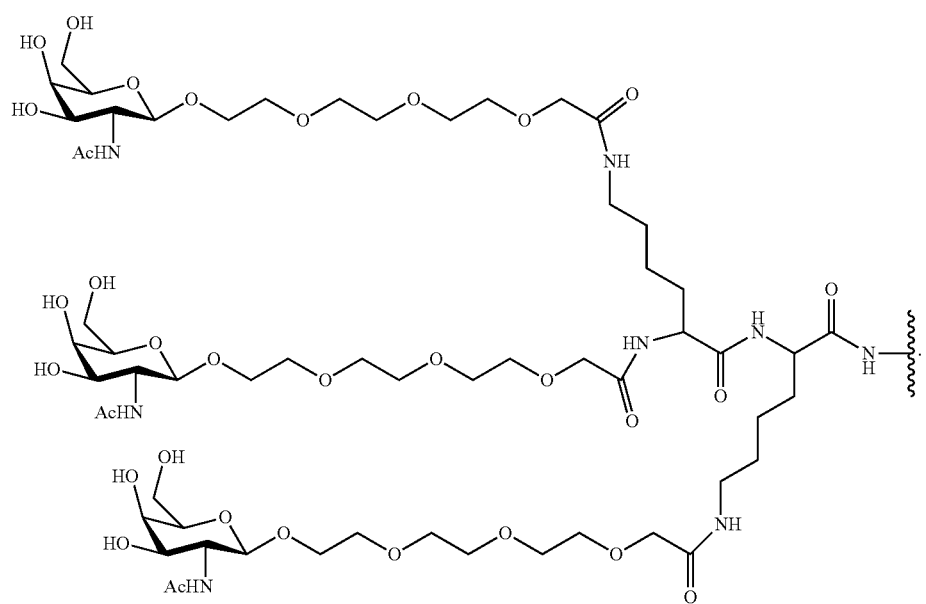
In certain embodiments, conjugate groups comprise a cell-targeting moiety having the formula:

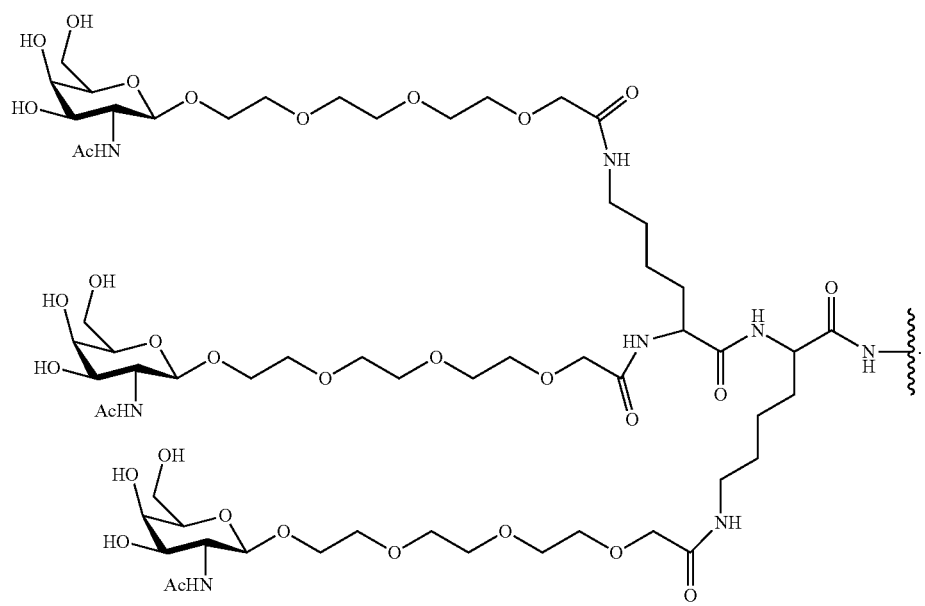
In certain embodiments, compounds comprise a conjugate group described herein as "LICA-1". LICA-1 has the formula:
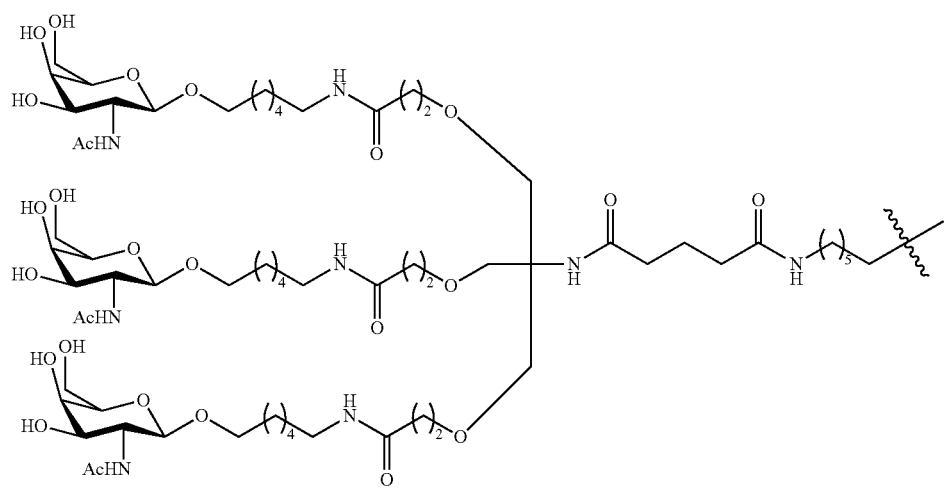
In certain embodiments, compounds described herein comprise LICA-1 and a cleavable moiety within the conjugate linker have the formula:

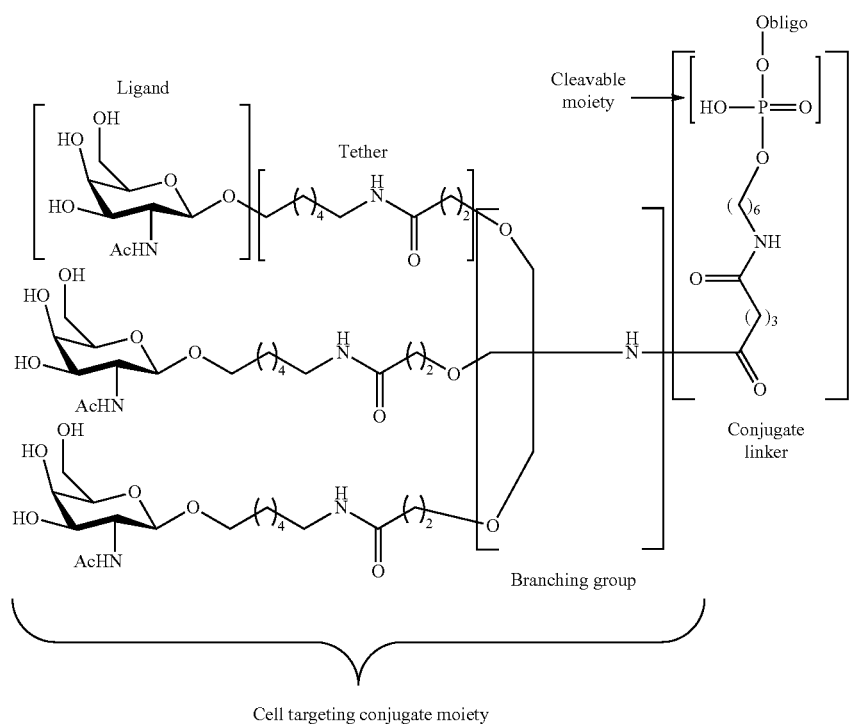

wherein oligo is an oligonucleotide.

Representative United States patents, United States patent application publications, international patent application publications, and other publications that teach the preparation of certain of the above noted conjugate groups, compounds comprising conjugate groups, tethers, conjugate linkers, branching groups, ligands, cleavable moieties as well as other modifications include without limitation, U.S. Pat. Nos. 5,994,517, 6,300,319, 6,660,720, 6,906,182, 7,262,177, 7,491,805, 8,106,022, 7,723,509, US 2006/0148740, US 2011/0123520, WO 2013/033230 and WO 2012/037254, Biessen et al., *J. Med. Chem.* 1995, 38, 1846-1852, Lee et al., *Bioorganic & Medicinal Chemistry* 2011, 19, 2494-2500, Rensen et al., *J. Biol. Chem.* 2001, 276, 37577-37584, Rensen et al., *J. Med. Chem.* 2004, 47, 5798-5808, Sliedregt et al., *J. Med. Chem.* 1999, 42, 609-618, and Valentijn et al., *Tetrahedron*, 1997, 53, 759-770.

In certain embodiments, modified oligonucleotides comprise a gapmer or fully modified sugar motif and a conjugate group comprising at least one, two, or three GalNAc ligands. In certain embodiments, compounds comprise a conjugate group found in any of the following references: Lee, *Carbohydr Res*, 1978, 67, 509-514; Connolly et al., *J Biol Chem*, 1982, 257, 939-945; Pavia et al., *Int J Pep Protein Res*, 1983, 22, 539-548; Lee et al., *Biochem*, 1984, 23, 4255-4261; Lee et al., *Glycoconjugate J*, 1987, 4, 317-328; Toyokuni et al., *Tetrahedron Lett*, 1990, 31, 2673-2676; Biessen et al., *J Med Chem*, 1995, 38, 1538-1546; Valentijn et al., *Tetrahedron*, 1997, 53, 759-770; Kim et al., *Tetrahedron Lett*, 1997, 38, 3487-3490; Lee et al., *Bioconjug Chem*, 1997, 8, 762-765; Kato et al., *Glycobiol*, 2001, 11, 821-829; Rensen et al., *J Biol Chem*, 2001, 276, 37577-37584; Lee et al., *Methods Enzymol*, 2003, 362, 38-43; Westerlind et al., *Glycoconj J*, 2004, 21, 227-241; Lee et al., *Bioorg Med Chem Lett*, 2006, 16(19), 5132-5135; Maierhofer et al., *Bioorg Med Chem*, 2007, 15, 7661-7676; Khorev et al., *Bioorg Med Chem*, 2008, 16, 5216-5231; Lee et al., *Bioorg Med Chem*, 2011, 19, 2494-2500; Kornilova et al., *Analyt Biochem*, 2012, 425, 43-46; Pujol et al., *Angew Chemie Int Ed Engl*, 2012, 51, 7445-7448; Biessen et al., *J Med Chem*, 1995, 38, 1846-1852; Sliedregt et al., *J Med Chem*, 1999, 42, 609-618; Rensen et al., *J Med Chem*, 2004, 47, 5798-5808; Rensen et al., *Arterioscler Thromb Vasc Biol*, 2006, 26, 169-175; van Rossenberg et al., *Gene Ther*, 2004, 11, 457-464; Sato et al., *J Am Chem Soc*, 2004, 126, 14013-14022; Lee et al., *J Org Chem*, 2012, 77, 7564-7571; Biessen et al., *FASEB J*, 2000, 14, 1784-1792; Rajur et al., *Bioconjug Chem*, 1997, 8, 935-940; Duff et al., *Methods Enzymol*, 2000, 313, 297-321; Maier et al., *Bioconjug Chem*, 2003, 14, 18-29; Jayaprakash et al., *Org Lett*, 2010, 12, 5410-5413; Manoharan, *Antisense Nucleic Acid Drug Dev*, 2002, 12, 103-128; Merwin et al., *Bioconjug Chem*, 1994, 5, 612-620; Tomiya et al., *Bioorg Med Chem*, 2013, 21, 5275-5281; International applications WO1998/013381; WO2011/038356; WO1997/046098; WO2008/098788; WO2004/101619; WO2012/037254; WO2011/120053; WO2011/100131; WO2011/163121; WO2012/177947; WO2013/033230; WO2013/075035; WO2012/083185; WO2012/083046; WO2009/082607; WO2009/134487; WO2010/144740; WO2010/148013; WO1997/020563; WO2010/088537; WO2002/043771; WO2010/129709; WO2012/068187; WO2009/126933; WO2004/024757; WO2010/054406; WO2012/089352; WO2012/089602; WO2013/166121; WO2013/165816; U.S. Pat. Nos. 4,751,219; 8,552,163; 6,908,903; 7,262,177; 5,994,517; 6,300,319; 8,106,022; 7,491,805; 7,491,805; 7,582,744; 8,137,695; 6,383,812; 6,525,031; 6,660,720; 7,723,509; 8,541,548; 8,344,125; 8,313,772; 8,349,308; 8,450,467; 8,501,930; 8,158,601; 7,262,177; 6,906,182; 6,620,916; 8,435,491; 8,404,862; 7,851,615; Published U.S. Patent Application Publications US2011/0097264; US2011/0097265; US2013/0004427; US2005/0164235; US2006/0148740; US2008/0281044; US2010/0240730; US2003/

0119724; US2006/0183886; US2008/0206869; US2011/ 0269814; US2009/0286973; US2011/0207799; US2012/ 0136042; US2012/0165393; US2008/0281041; US2009/ 0203135; US2012/0035115; US2012/0095075; US2012/ 0101148; US2012/0128760; US2012/0157509; US2012/ 0230938; US2013/0109817; US2013/0121954; US2013/ 0178512; US2013/0236968; US2011/0123520; US2003/ 0077829; US2008/0108801; and US2009/0203132.

VII. Certain Pharmaceutical Compositions

In certain embodiments, described herein are pharmaceutical compositions comprising one or more oligomeric compounds. In certain embodiments, the one or more oligomeric compounds each consists of a modified oligonucleotide. In certain embodiments, the pharmaceutical composition comprises a pharmaceutically acceptable diluent or carrier. In certain embodiments, a pharmaceutical composition comprises or consists of a saline solution and one or more oligomeric compound. In certain embodiments, a pharmaceutical composition comprises or consists of a sterile saline solution and one or more oligomeric compound. In certain embodiments, the sterile saline is pharmaceutical grade saline. In certain embodiments, a pharmaceutical composition comprises or consists of one or more oligomeric compound and water. In certain embodiments, a pharmaceutical composition comprises or consists of one or more oligomeric compound and sterile water. In certain embodiments, the sterile water is pharmaceutical grade water. In certain embodiments, a pharmaceutical composition comprises or consists of one or more oligomeric compound and phosphate-buffered saline (PBS). In certain embodiments, the sterile PBS is pharmaceutical grade PBS.

In certain embodiments, pharmaceutical compositions comprise one or more oligomeric compound and one or more excipients. In certain embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, oligomeric compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an oligomeric compound encompass any pharmaceutically acceptable salts of the oligomeric compound, esters of the oligomeric compound, or salts of such esters. In certain embodiments, pharmaceutical compositions comprising oligomeric compounds comprising one or more oligonucleotide, upon administration to a subject, including a human, are capable of providing (directly or indirectly) the biologically active metabolite or residue thereof. Accordingly, for example, the disclosure is also drawn to pharmaceutically acceptable salts of oligomeric compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an oligomeric compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents comprising an oligomeric compound provided herein to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, intrathecal (IT), intracerebroventricular (ICV), intraneural, perineural, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes.

Under certain conditions, certain compounds disclosed herein act as acids. Although such compounds may be drawn or described in protonated (free acid) form, or ionized and in association with a cation (salt) form, aqueous solutions of such compounds exist in equilibrium among such forms. For example, a phosphate linkage of an oligonucleotide in aqueous solution exists in equilibrium among free acid, anion and salt forms. Unless otherwise indicated, compounds described herein are intended to include all such forms. Moreover, certain oligonucleotides have several such linkages, each of which is in equilibrium. Thus, oligonucleotides in solution exist in an ensemble of forms at multiple positions all at equilibrium. The term "oligonucleotide" is intended to include all such forms. Drawn structures necessarily depict a single form. Nevertheless, unless otherwise indicated, such drawings are likewise intended to include corresponding forms. Herein, a structure depicting the free acid of a compound followed by the term "or salt thereof" expressly includes all such forms that may be fully or partially protonated/de-protonated/in association with a cation. In certain instances, one or more specific cation is identified.

In certain embodiments, modified oligonucleotides or oligomeric compounds are in aqueous solution with sodium. In certain embodiments, modified oligonucleotides or oligomeric compounds are in aqueous solution with potassium. In certain embodiments, modified oligonucleotides or oligomeric compounds are in PBS. In certain embodiments, modified oligonucleotides or oligomeric compounds are in water. In certain such embodiments, the pH of the solution is adjusted with NaOH and/or HCl to achieve a desired pH.

Herein, certain specific doses are described. A dose may be in the form of a dosage unit. For clarity, a dose (or dosage unit) of a modified oligonucleotide or an oligomeric compound in milligrams indicates the mass of the free acid form of the modified oligonucleotide or oligomeric compound. As described above, in aqueous solution, the free acid is in equilibrium with anionic and salt forms. However, for the purpose of calculating dose, it is assumed that the modified oligonucleotide or oligomeric compound exists as a solvent-free, sodium-acetate free, anhydrous, free acid. For example, where a modified oligonucleotide or an oligomeric compound is in solution comprising sodium (e.g., saline), the modified oligonucleotide or oligomeric compound may be partially or fully de-protonated and in association with Na+ ions. However, the mass of the protons are nevertheless counted toward the weight of the dose, and the mass of the Na+ ions are not counted toward the weight of the dose. When an oligomeric compound comprises a conjugate group, the mass of the conjugate group is included in calculating the dose of such oligomeric compound. If the conjugate group also has an acid, the conjugate group is likewise assumed to be fully protonated for the purpose of calculating dose.

VIII. Certain Compositions

1. Compound No. 1205407

In certain embodiments, Compound No. 1205407 is characterized as a 3-10-3 MOE/cEt mixed wing gapmer conjugated at the 5'-end to a conjugate group. Compound 1205407 has a sequence (from 5' to 3') of CGCTGATTTGTCCGGG (SEQ ID NO: 12), wherein nucleosides 1-3 have sugar modifications of e-e-k (from 5' to 3'), wherein nucleosides 14-16 have sugar modifications of k-k-e, wherein each 'e' represents a 2'-MOE sugar moiety, and each 'k' refers to a cEt sugar moiety; and each of nucleosides 4-13 are 2'-β-D-deoxynucleosides; wherein the internucleoside linkages between nucleosides 2 to 3, 3 to 4, and 14 to 15 are phosphodiester internucleoside linkages and the internucleoside linkages between nucleosides 1 to 2, 4 to 5, 5 to 6, 6 to 7, 7 to 8, 8 to 9, 9 to 10, 10 to 11, 11 to 12, 12 to 13, 13 to 14, and 15 to 16 are phosphorothioate internucleoside linkages, and wherein each cytosine is a 5-methylcytosine. Compound No. 1205407 has a 5'-trishexylamino-(THA)-$C_6$GalNAc$_3$ endcap, represented by the structure below, wherein the phosphate group is attached to the 5'-oxygen atom of the 5'-nucleoside:

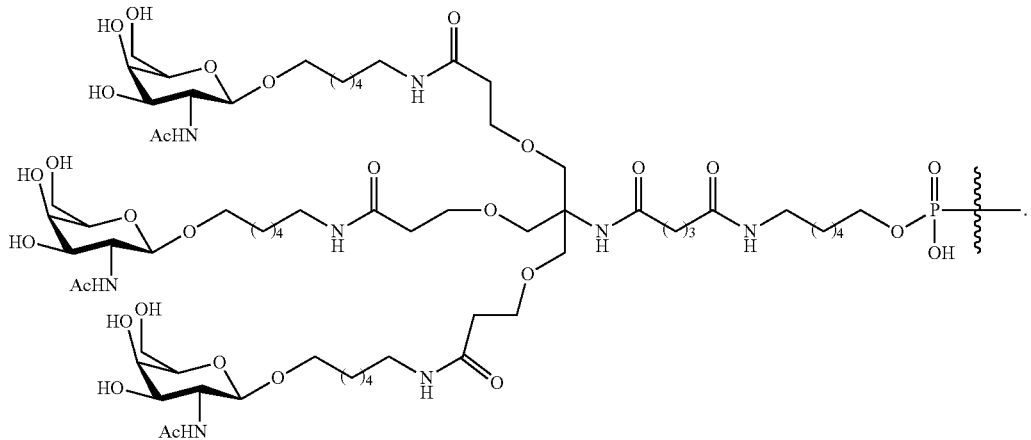

In certain embodiments, Compound No. 1205407 is represented by the following chemical notation: THA-$C_6$-GalNAc$_3$-$^mC_{es}G_{eo}{}^mC_{ko}T_{ds}G_{ds}A_{ds}T_{ds}T_{ds}T_{ds}G_{ds}T_{ds}{}^mC_{ds}{}^mC_{ds}G_{ko}G_{ks}G_e$ (SEQ ID NO: 12), wherein:
  A=an adenine nucleobase,
  $^mC$=a 5-methyl cytosine nucleobase,
  G=a guanine nucleobase,
  T=a thymine nucleobase,
  e=a 2'-β-D-MOE sugar moiety,
  k=a cEt sugar moiety,
  d=a 2'-β-D-deoxyribosyl sugar moiety,
  s=a phosphorothioate internucleoside linkage, and
  o=a phosphodiester internucleoside linkage.

In certain embodiments, Compound No. 1205407 is represented by the following chemical structure:
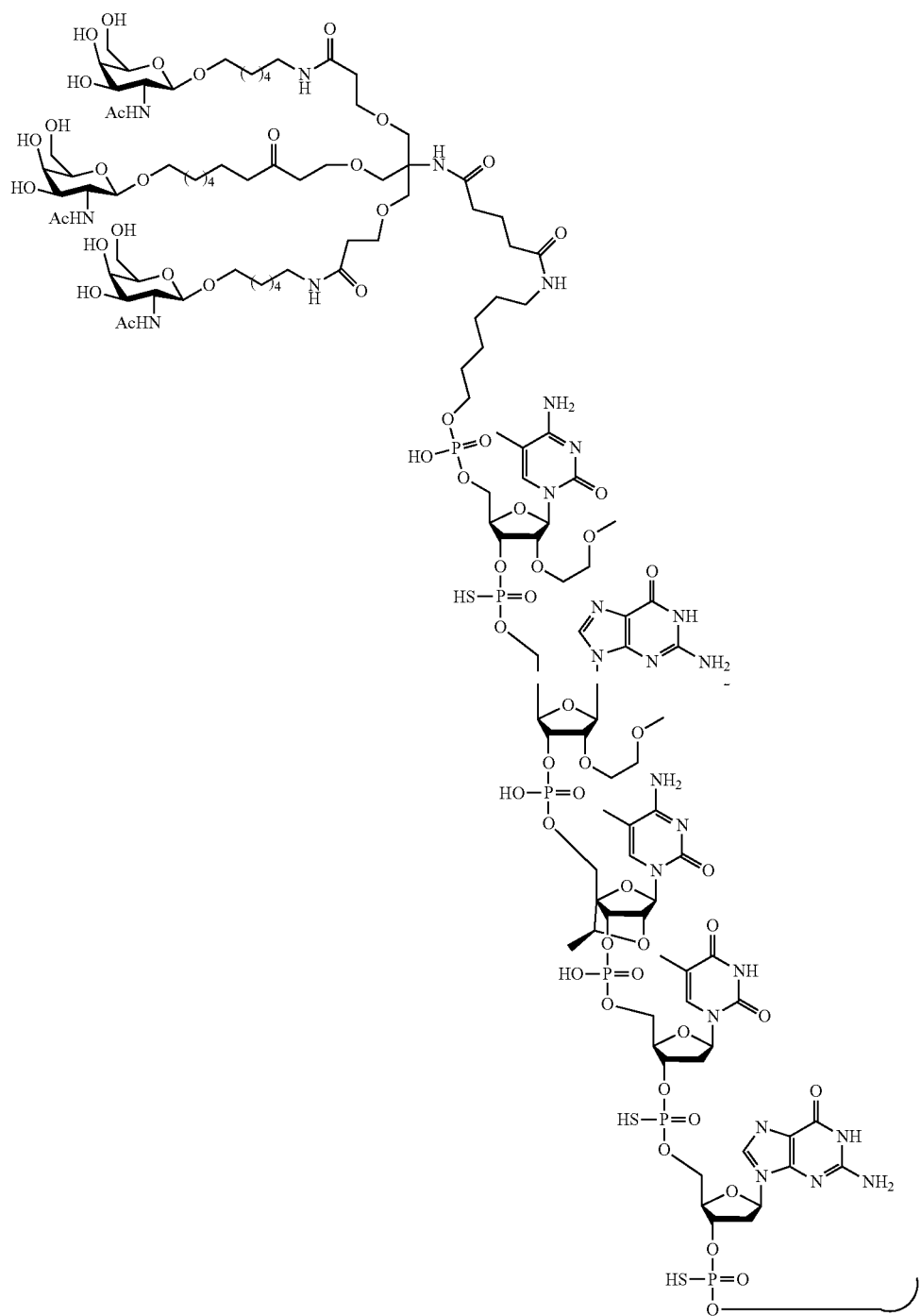

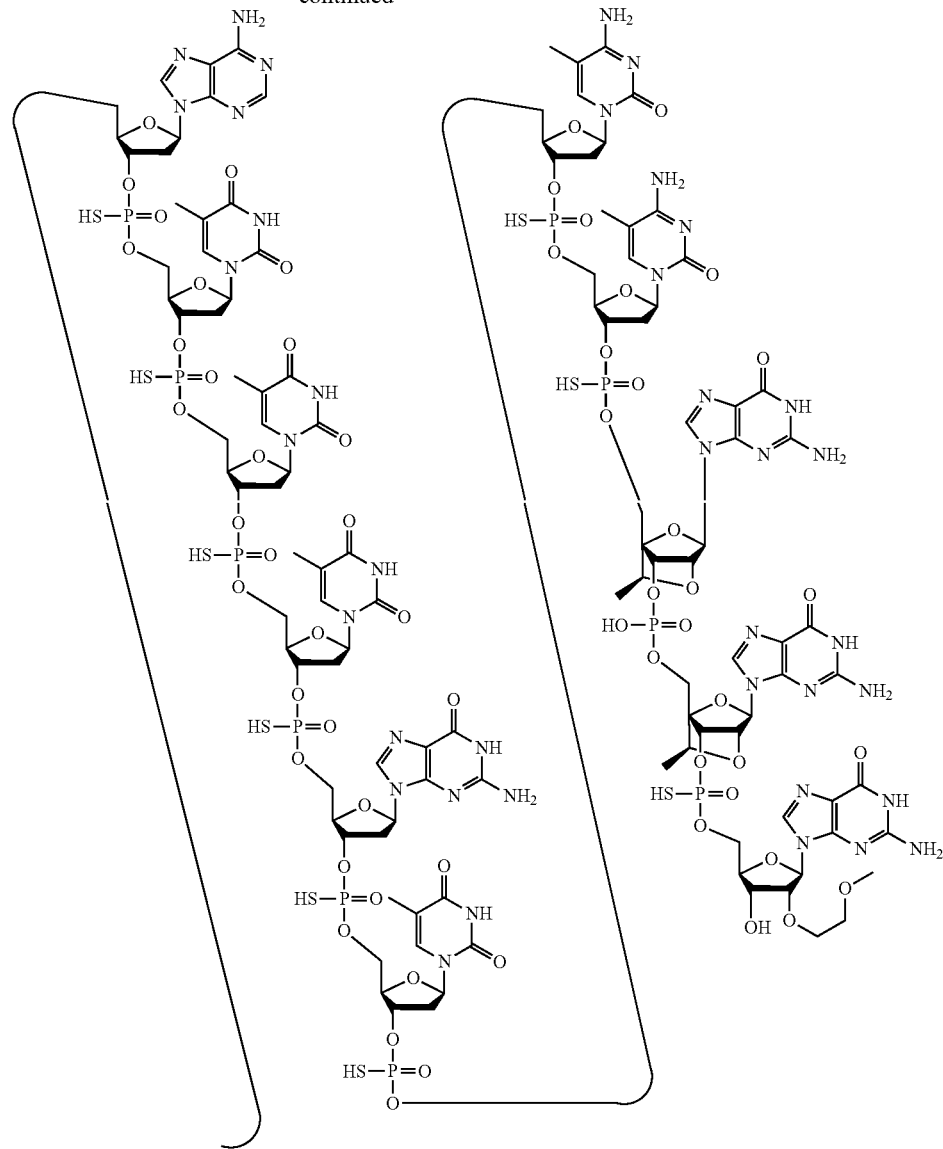
(SEQ ID NO: 12) or a salt thereof.
In certain embodiments, the sodium salt of Compound No. 1205407 is represented by the following chemical structure:

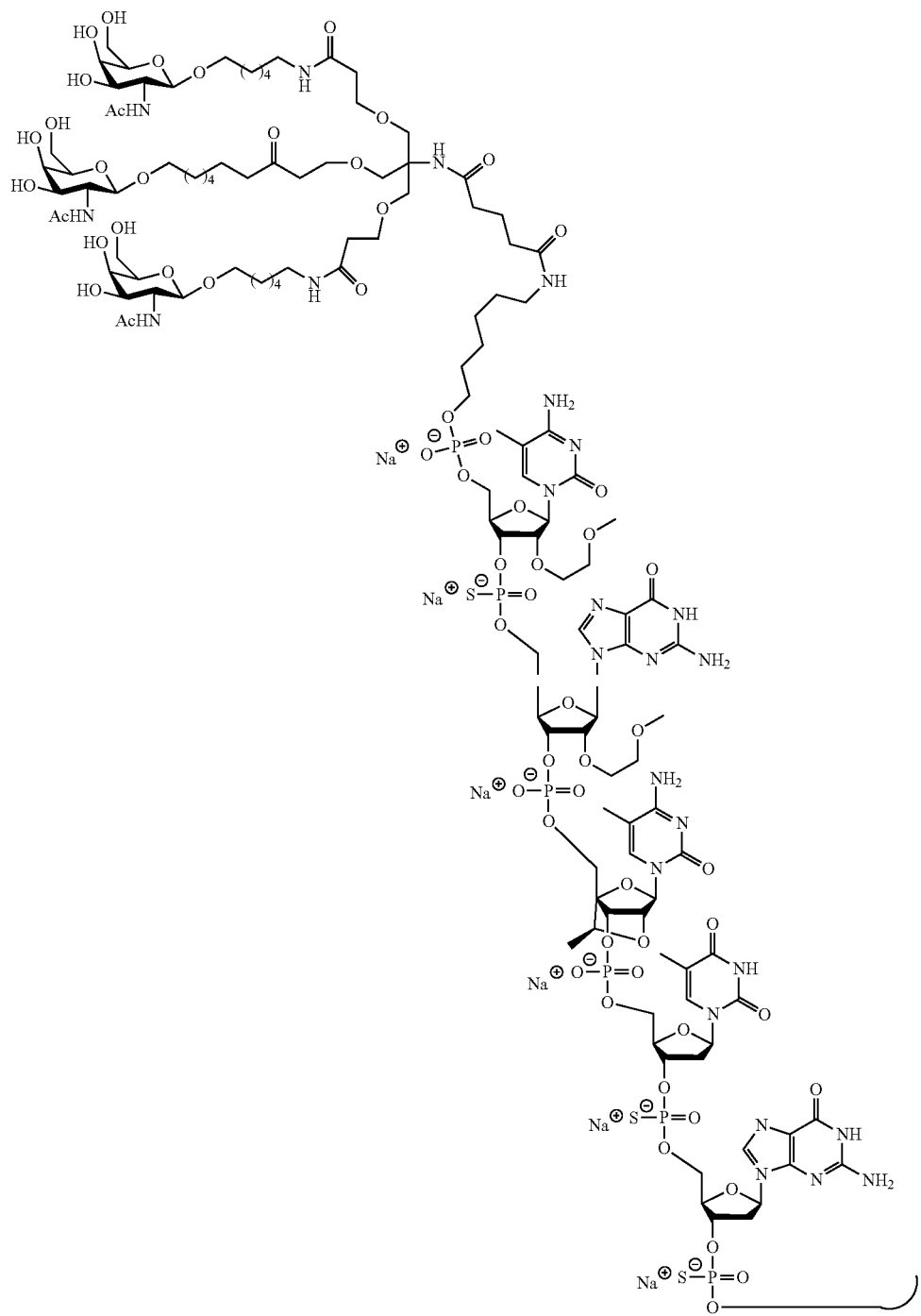

-continued

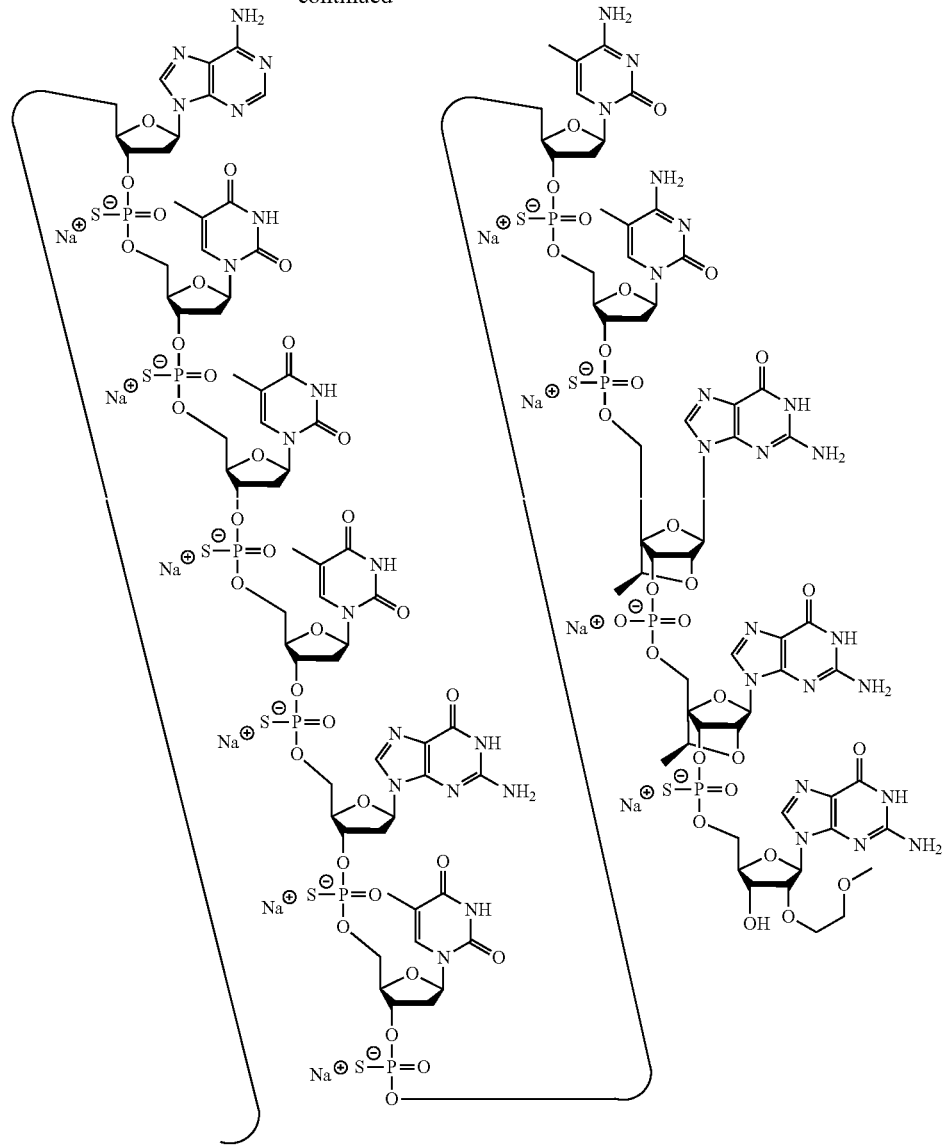

(SEQ ID NO: 12).

In certain embodiments, Compound No. 1205407 is in anionic form.

2. Compound No. 1205408

In certain embodiments, Compound No. 1205408 is characterized as a 3-10-3 MOE/cEt mixed wing gapmer conjugated at the 5'-end to a conjugate group. Compound 1205408 has a sequence (from 5' to 3') of TCGGTTGGAATTCTTT (SEQ ID NO: 13), wherein nucleosides 1-3 have sugar modifications of e-k-k (from 5' to 3') and wherein nucleosides 14-16 have sugar modifications of k-k-e; wherein each 'e' represents a 2'-MOE sugar moiety, and each 'l' refers to a cEt sugar moiety; and each of nucleosides 4-13 are 2'-β-D-deoxynucleosides; wherein the internucleoside linkages between nucleosides 2 to 3, 3 to 4, and 14 to 15 are phosphodiester internucleoside linkages and the internucleoside linkages between nucleosides 1 to 2, 4 to 5, 5 to 6, 6 to 7, 7 to 8, 8 to 9, 9 to 10, 10 to 11, 11 to 12, 12 to 13, 13 to 14, and 15 to 16 are phosphorothioate internucleoside linkages, and wherein each cytosine is a 5-methyl cytosine. Compound No. 1205408 has a 5'-trishexylamino-(THA)-C₆GalNAc₃ endcap, represented by the structure below, wherein the phosphate group is attached to the 5'-oxygen atom of the 5'-nucleoside:

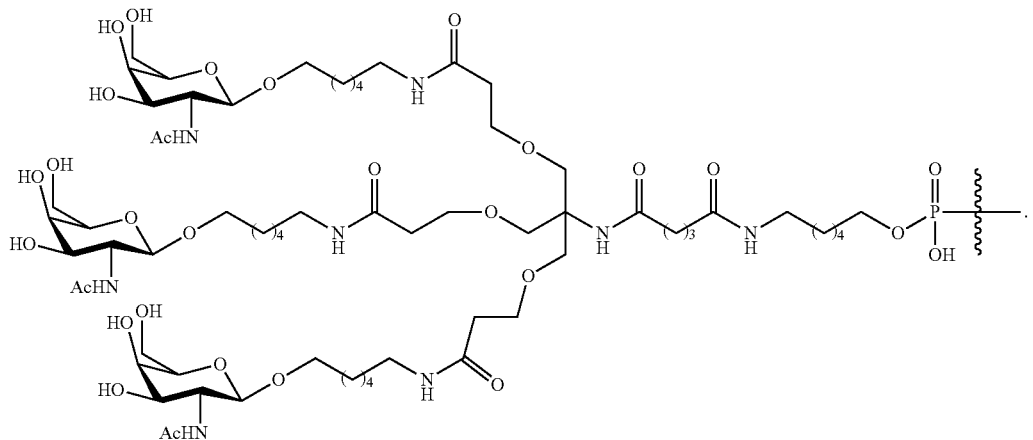

In certain embodiments, Compound No. 1205408 is represented by the following chemical notation: THA-C$_6$-Gal-NAc$_3$-T$_{es}$$^m$C$_{ko}$G$_{ko}$G$_{ds}$T$_{ds}$T$_{ds}$G$_{ds}$G$_{ds}$A$_{ds}$A$_{ds}$T$_{ds}$T$_{ds}$$^m$C$_{ds}$T$_{ko}$T$_{ks}$T$_e$ (SEQ ID NO: 13), wherein:
- A=an adenine nucleobase,
- $^m$C=a 5-methyl cytosine nucleobase,
- G=a guanine nucleobase,
- T=a thymine nucleobase,
- e=a 2'-β-D-MOE sugar moiety,
- k=a cEt sugar moiety,
- d=a 2'-β-D-deoxyribosyl sugar moiety,
- s=a phosphorothioate internucleoside linkage, and
- o=a phosphodiester internucleoside linkage.

In certain embodiments, Compound No. 1205408 is represented by the following chemical structure:

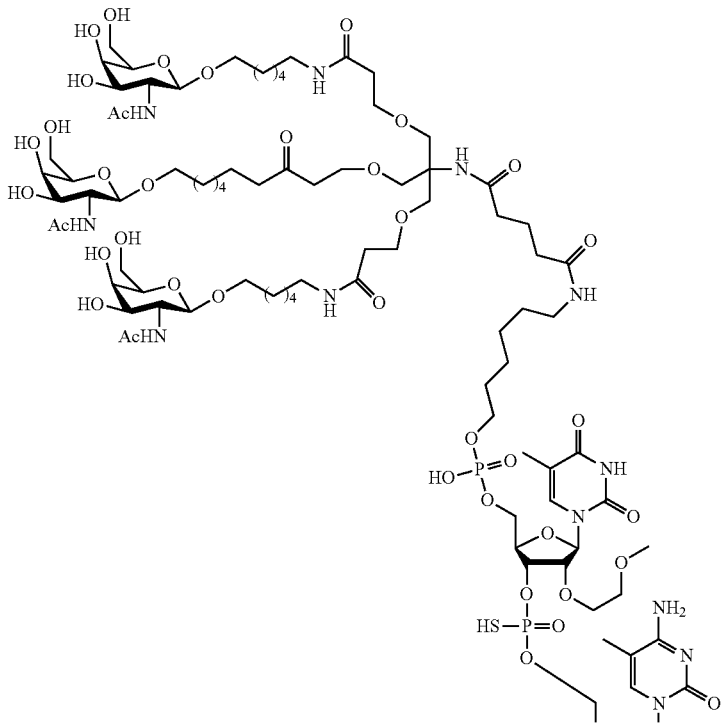

-continued
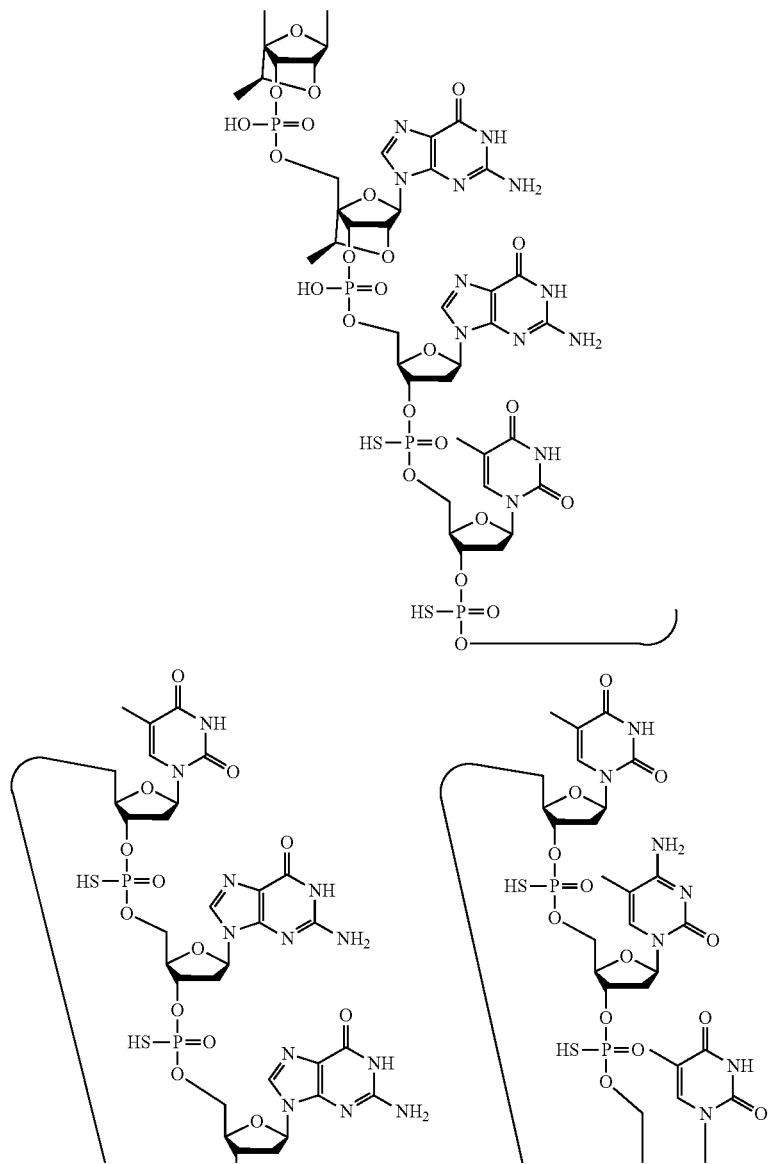

-continued
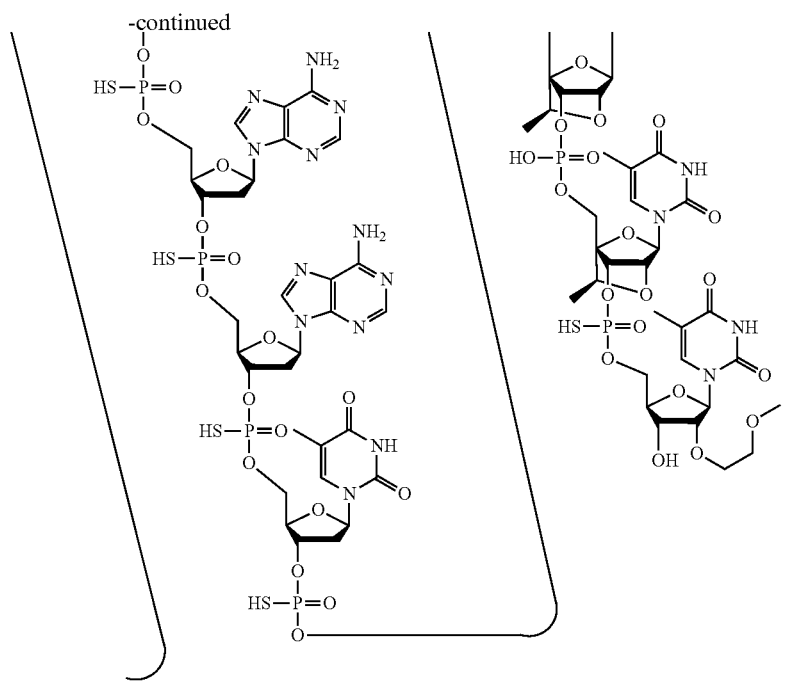
(SEQ ID NO: 13) or salt thereof.
In certain embodiments, the sodium salt of Compound No. 1205408 is represented by the following chemical structure:
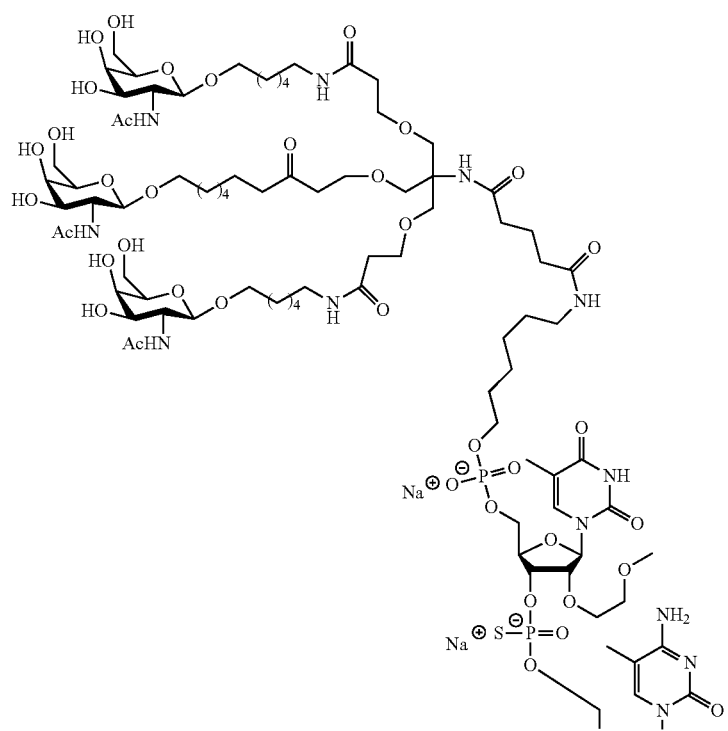

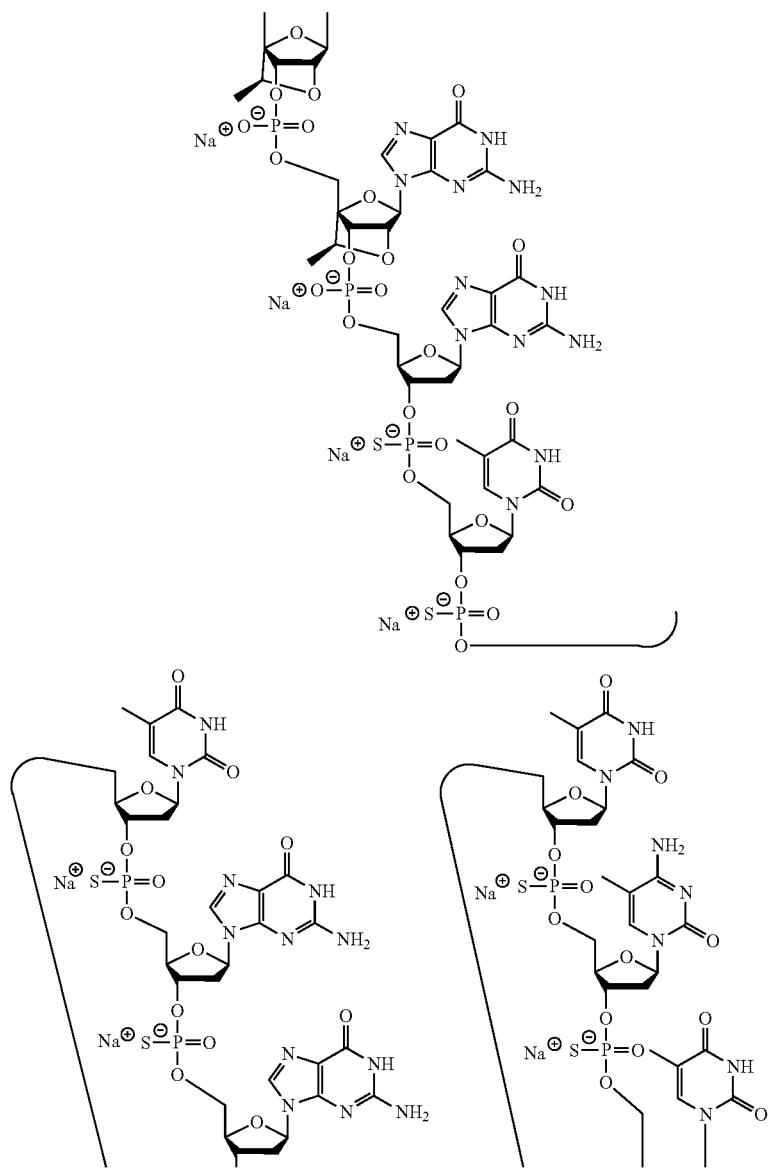

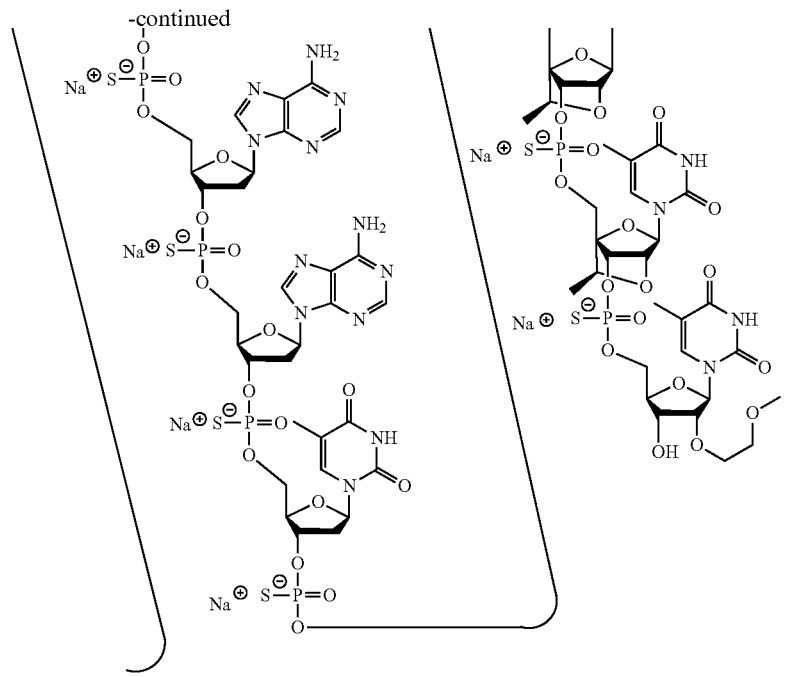

(SEQ ID NO: 13).

In certain embodiments, Compound No. 1205408 is in anionic form.

3. Compound No. 1250837

In certain embodiments, Compound No. 1250837 is characterized as a 3-10-3 gapmer conjugated at the 5'-end to a conjugate group. Compound 1250837 has a sequence (from 5' to 3') of GTCGGTTGGAATTCTT (SEQ ID NO: 15), wherein nucleosides 1-3 and 14-16 have cEt sugar modifications, wherein nucleoside 5 has a 2'-OMe ribose sugar, and wherein each of nucleosides 4 and 6-13 are 2'-β-D-deoxynucleosides; wherein each internucleoside linkage between the nucleosides is a phosphorothioate internucleoside linkage, and wherein each cytosine is a 5-methyl cytosine. Compound No. 1250837 has a 5'-trishexylamino-(THA)-$C_6$GalNAc$_3$ endcap, represented by the structure below, wherein the phosphate group is attached to the 5'-oxygen atom of the 5'-nucleoside:

In certain embodiments, Compound No. 1250837 is represented by the following chemical notation: THA-$C_6$-GalNAc$_3$-$G_{ks}T_{ks}{}^mC_{ks}G_{ds}G_{ys}T_{ds}T_{ds}G_{ds}G_{ds}A_dA_{ds}T_{ds}T_{ds}{}^mC_{ks}T_{ks}T_k$ (SEQ ID NO: 15), wherein:

A = an adenine nucleobase, $^m$C = a 5-methyl cytosine nucleobase,

G = a guanine nucleobase,

T = a thymine nucleobase, k = a cEt sugar moiety, d = a 2'-β-D-deoxyribosyl sugar moiety, y = a 2'-OMe ribose sugar moiety, and s = a phosphorothioate internucleoside linkage.

In certain embodiments, Compound No. 1250837 is represented by the following chemical structure:

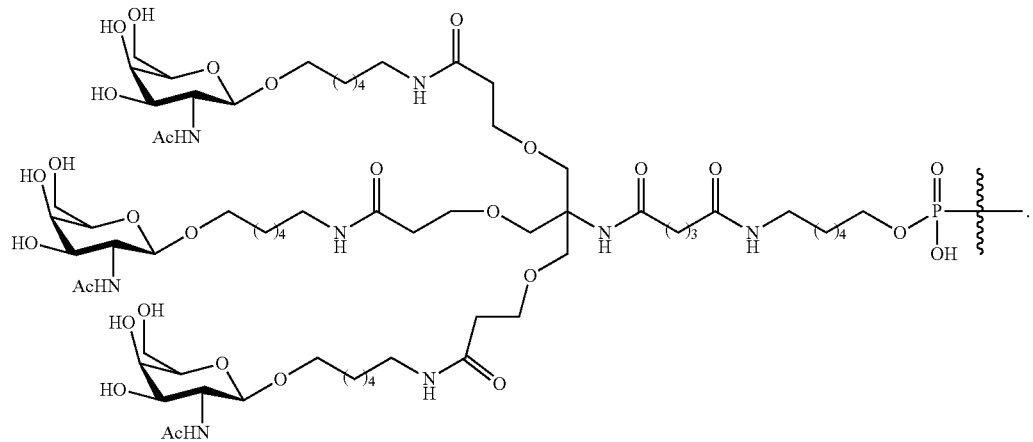

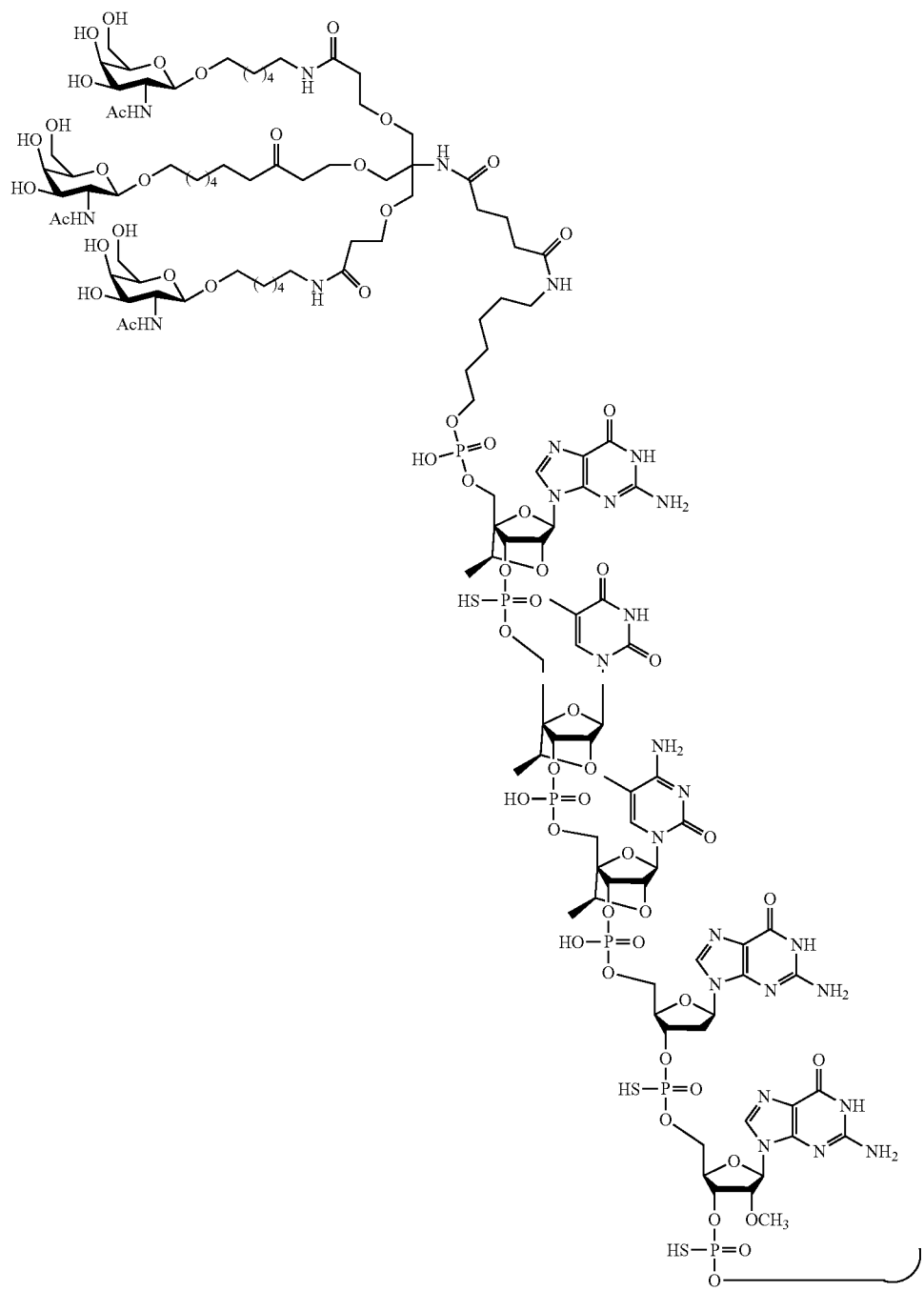

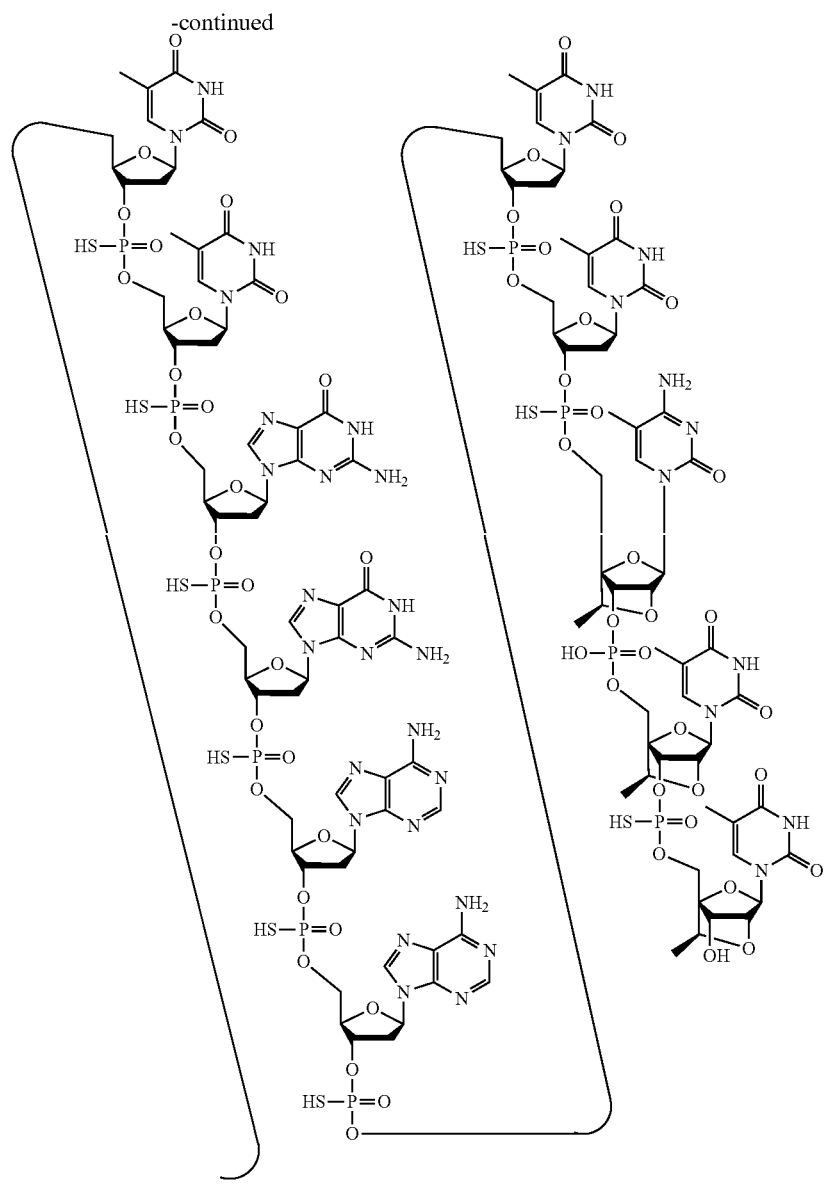
(SEQ ID NO: 15) or a salt thereof.
In certain embodiments, the sodium salt of Compound No. 1250837 is represented by the following chemical structure:

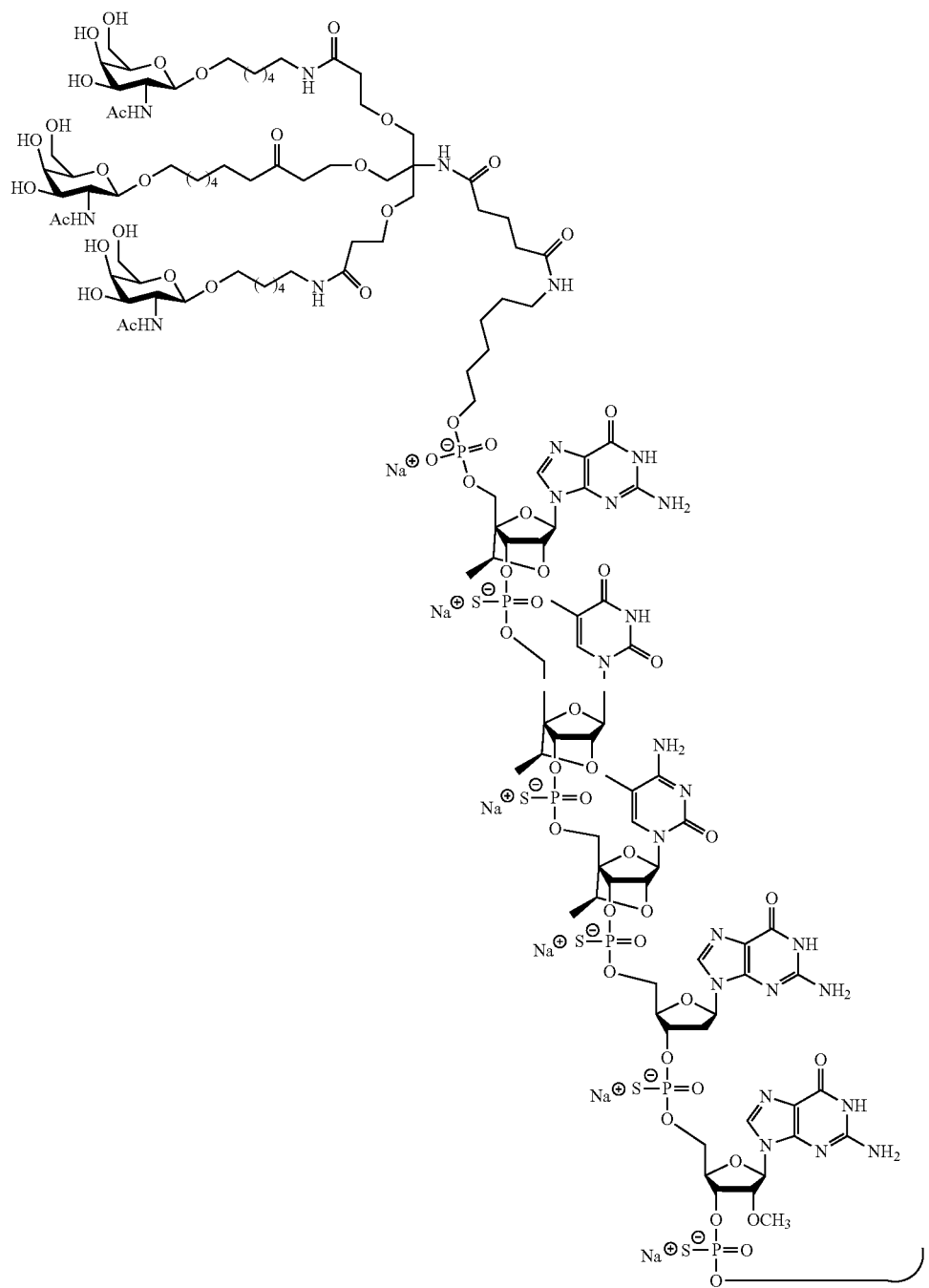

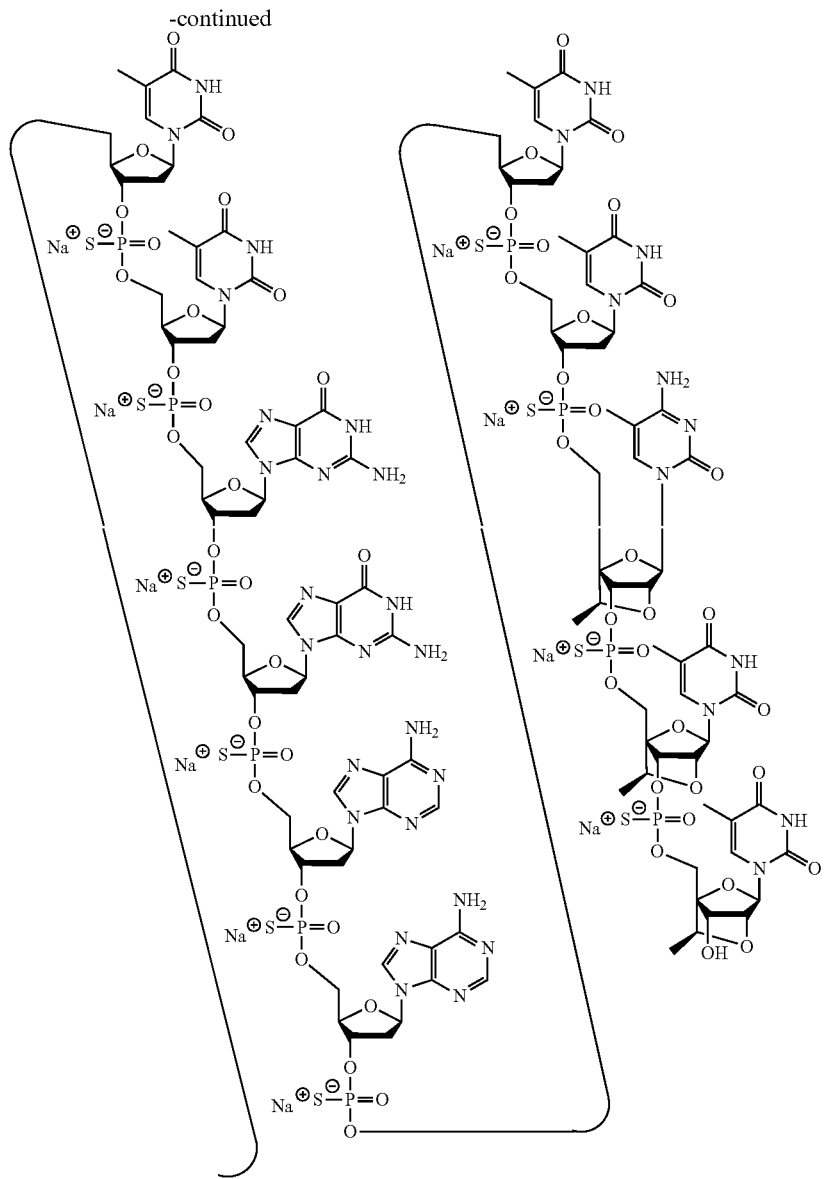

(SEQ ID NO: 15).

In certain embodiments, Compound No. 1250837 is in anionic form.

4. Compound No. 1250851

In certain embodiments, Compound No. 1250851 is characterized as a 3-10-3 gapmer conjugated at the 5'-end to a conjugate group. Compound 1250851 has a sequence (from 5' to 3') of TCGGUTGGAATTCTTT (SEQ ID NO: 14), wherein nucleosides 1-3 and 14-16 have cEt sugar modifications, wherein nucleoside 5 has a 2'-OMe ribose sugar, and wherein each of nucleosides 4 and 6-13 are 2'-β-D-deoxy-nucleosides; wherein the internucleoside linkages between nucleosides 2 to 3, 3 to 4, and 14 to 15 are phosphodiester internucleoside linkages and the internucleoside linkages between nucleosides 1 to 2, 4 to 5, 5 to 6, 6 to 7, 7 to 8, 8 to 9, 9 to 10, 10 to 11, 11 to 12, 12 to 13, 13 to 14, and 15 to 16 are phosphorothioate internucleoside linkages, and wherein each cytosine is a 5-methyl cytosine. Compound No. 1250851 has a 5'-trishexylamino-(THA)-C$_6$GalNAc$_3$ endcap, represented by the structure below, wherein the phosphate group is attached to the 5'-oxygen atom of the 5'-nucleoside:

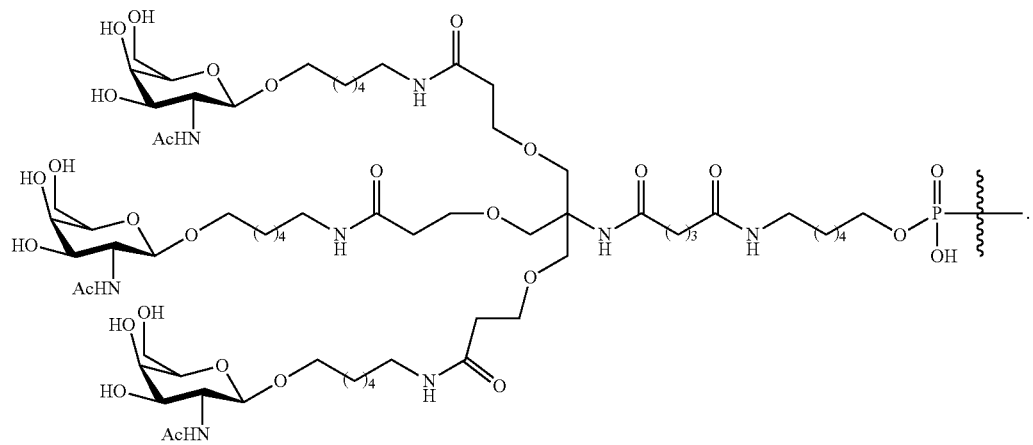

In certain embodiments, Compound No. 1250851 is represented by the following chemical notation: THA-C$_6$-Gal-NAc$_3$-T$_{ks}$$^m$C$_{ko}$G$_{ko}$G$_{ds}$U$_{ys}$T$_{ds}$G$_{ds}$G$_{ds}$A$_{ds}$A$_{ds}$T$_{ds}$T$_{ds}$$^m$C$_{ds}$T$_{ko}$T$_{ks}$T$_k$ (SEQ ID NO: 14), wherein:

A=an adenine nucleobase,
$^m$C=a 5-methyl cytosine nucleobase,
G=a guanine nucleobase,
T=a thymine nucleobase,
U=a uracil nucleobase,
k=a cEt sugar moiety,
d=a 2'-β-D-deoxyribosyl sugar moiety,
y=a 2'-OMe ribose sugar moiety,
s=a phosphorothioate internucleoside linkage, and
o=a phosphodiester internucleoside linkage.

In certain embodiments, Compound No. 1250851 is represented by the following chemical structure:

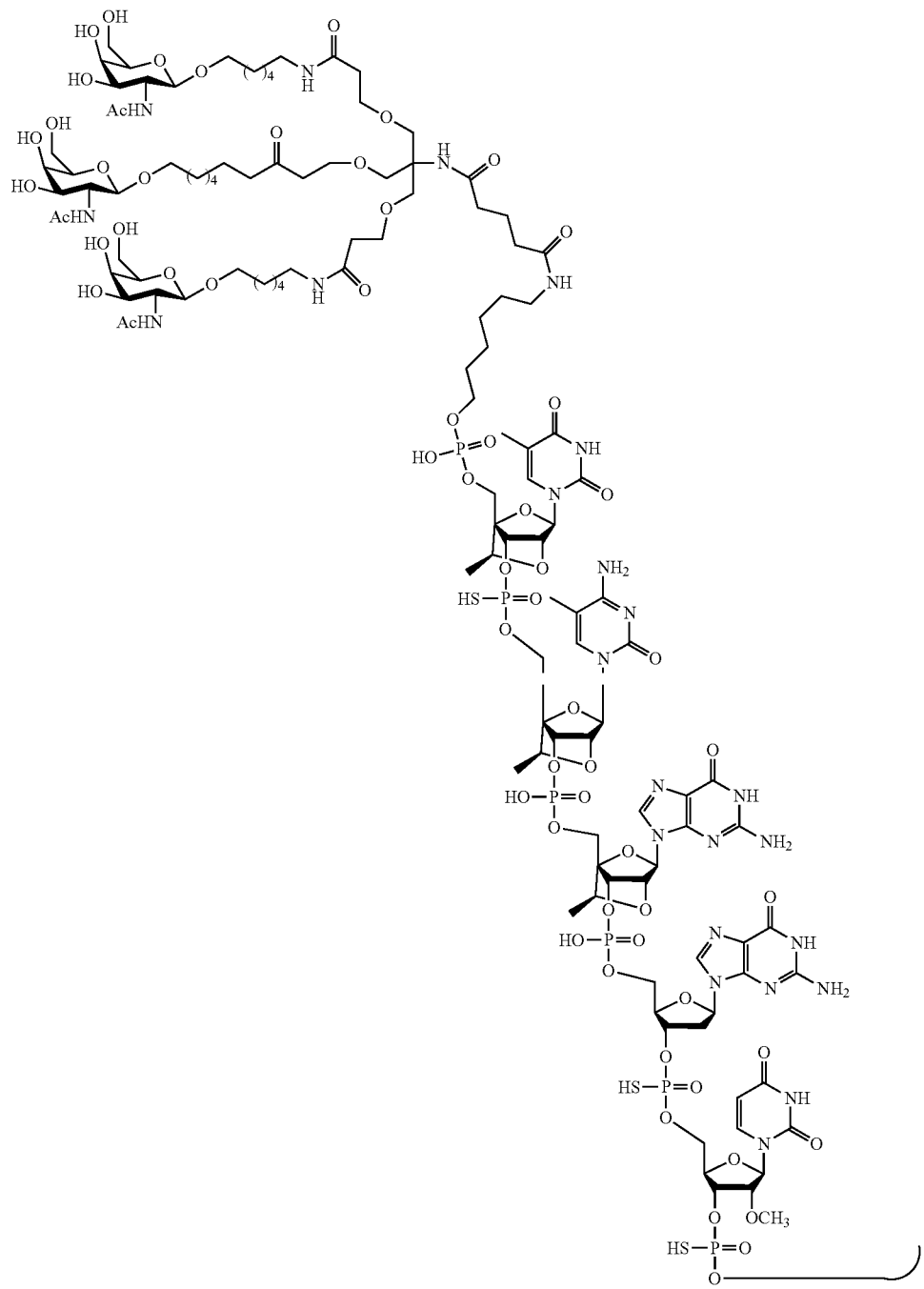

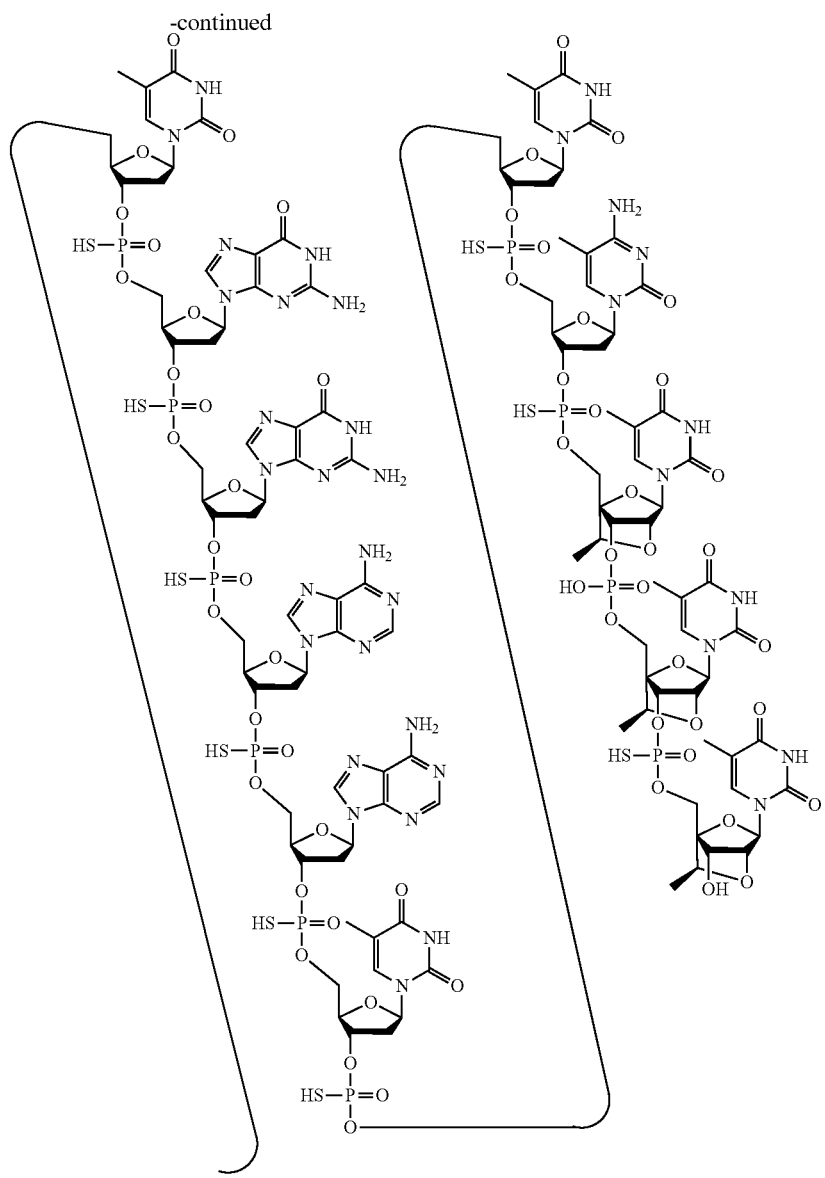
(SEQ ID NO: 14) or a salt thereof.
In certain embodiments, the sodium salt of Compound No. 1250851 is represented by the following chemical structure:

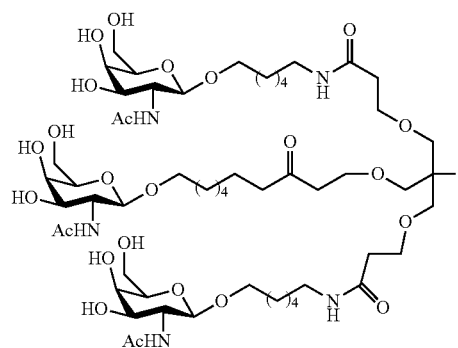
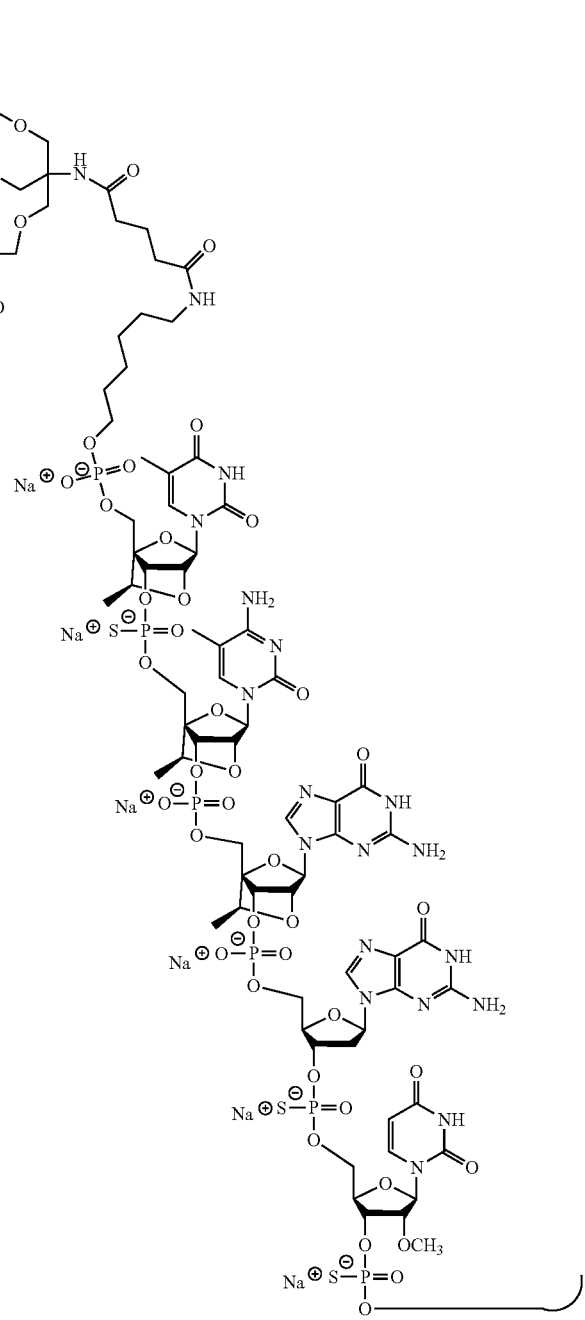

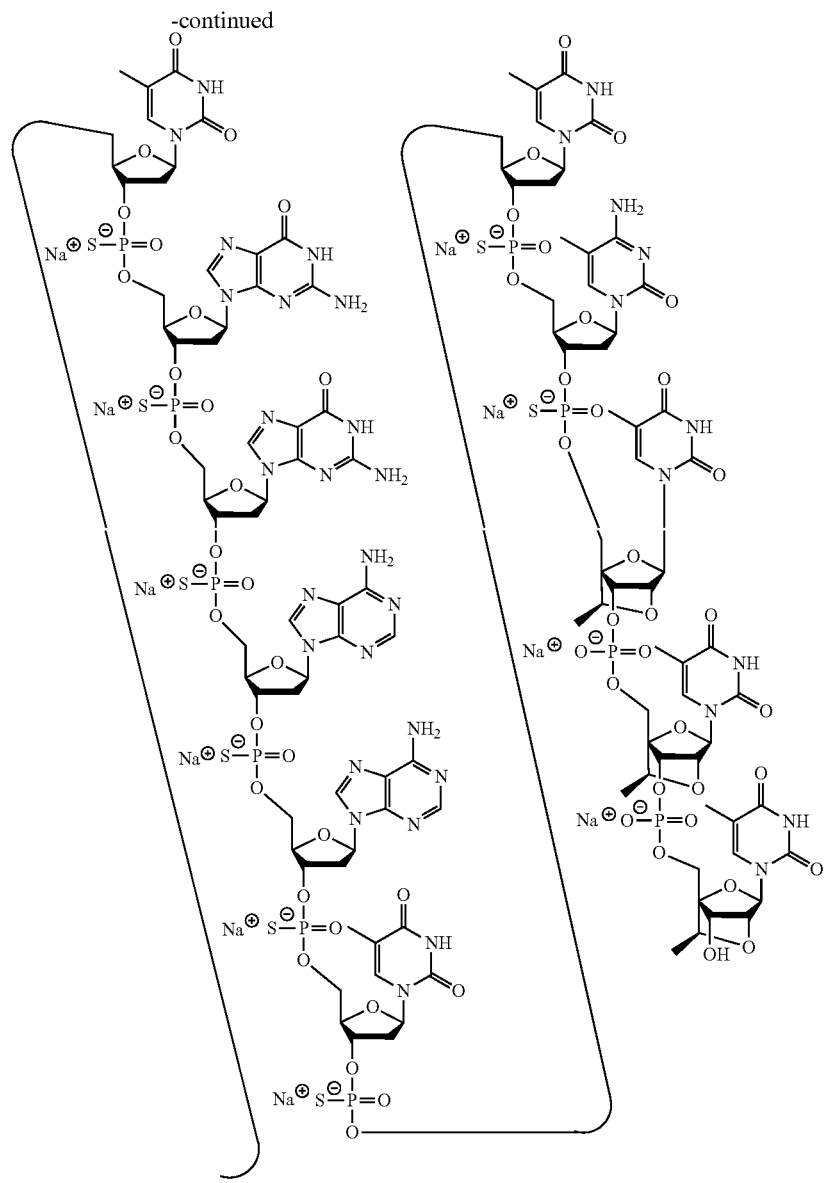

(SEQ ID NO: 14).

In certain embodiments, Compound No. 1250851 is in anionic form.

VI. Certain Comparator Compositions

In certain embodiments, Compound No. 757456 is a comparator compound. Compound No. 757456 was previously described in WO2017062816, incorporated herein by reference, and has a sequence (from 5' to 3') of CACAAACAAGCTGGTCGGTT (SEQ ID NO: 28), wherein the compound comprises a conjugate group and a modified oligonucleotide; wherein the modified oligonucleotide is a 5-10-5 MOE gapmer, wherein the central gap segment consists of ten 2'-β-D-deoxynucleosides and the 5' and 3' wing segments each consists of five 2'-MOE modified nucleosides. Each internucleoside linkage is a phosphorothioate internucleoside linkage. All cytosine residues are 5-methylcytosines. Compound No. 757456 has a 5'-trishexylamino-(THA)-C$_6$GalNAc$_3$ endcap, represented by the structure below, wherein the phosphate group is attached to the 5'-oxygen atom of the 5'-nucleoside:

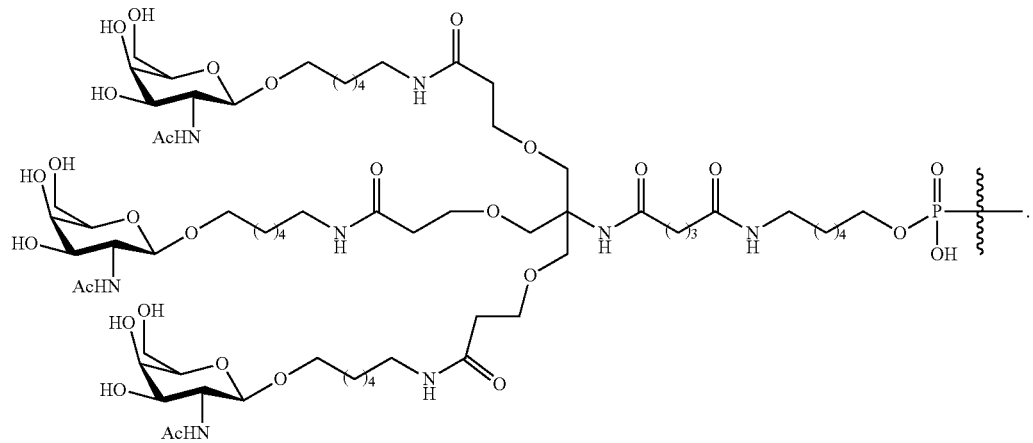

In certain embodiments, Compound No. 568637 is a comparator compound. Compound No. 568637 was previously described in WO2017062816, incorporated herein by reference, and has a sequence (from 5' to 3') of CGCTGATTTGTCCGGG (SEQ ID NO: 12), wherein the compound consists a modified oligonucleotide; wherein the modified oligonucleotide is 16 nucleosides in length with mixed sugar moieties, as described by the sugar motif eekddddddddddkke; wherein each represents a 2'-β-D-deoxyribosyl sugar moiety, each 'e' represents a 2'-MOE sugar moiety, and each 'k' represents a cEt sugar moiety. Each internucleoside linkage is a phosphorothioate internucleoside linkage. All cytosine residues are 5-methylcytosines.

In certain embodiments, Compound No. 1176644 is a comparator compound. Compound No. 1176644 is Compound No. 568637 that has a 5'-trishexylamino-(THA)-$C_6GalNAc_3$ endcap. Compound No. 1176644, similar to Compound No. 568637, has a sequence (from 5' to 3') of CGCTGATTTGTCCGGG (SEQ ID NO: 12), wherein the compound comprises a modified oligonucleotide; wherein the modified oligonucleotide is 16 nucleosides in length with mixed sugar moieties, as described by the sugar motif eekddddddddddkke; wherein each represents a 2'-β-D-deoxyribosyl sugar moiety, each 'e' represents a 2'-MOE sugar moiety, and each 1' represents a cEt sugar moiety. Each internucleoside linkage is a phosphorothioate internucleoside linkage. All cytosine residues are 5-methylcytosines.

In certain embodiments, compounds described herein are superior relative to compounds described in WO2017062816 because they demonstrate one or more improved properties, such as potency.

For example, Compound No. 1205407 demonstrated improved potency in vivo as compared to Compound No. 757456. As shown in Example 5, Compound No. 1205407 achieved 93% and 90% inhibition of AGT RNA and protein respectively at a dose of 2.7 mg/kg. In comparison, Compound No. 757456 achieved 65% and 60% inhibition of AGT RNA and protein respectively at a dose of 3.3 mg/kg. Therefore, Compound No. 1205407 is more potent than Compound No. 757456 in this assay. For example, as shown in Study 1 of Example 6, Compound No. 1205407 achieved an $ED_{50}$ of 0.1 in the liver and plasma. In comparison, Compound No. 757456 achieved an $ED_{50}$ of 1.3 in the liver and plasma. Therefore, Compound No. 1205407 is more potent than Compound No. 757456 in this assay.

For example, Compound No. 1205407 demonstrated improved potency ex-vivo as compared to Compound No. 757456. As shown in Example 8, Compound No. 1205407 achieved an $IC_{50}$ of 0.04 nM ex vivo using the Hepatopac system. In comparison, Compound No. 757456 had an $IC_{50}$ of >20 µM ex vivo. Therefore, Compound No. 1205407 is more potent than Compound No. 757456 in this assay.

For example, Compound No. 1205407 demonstrated improved potency in vitro as compared to Compound No. 757456 or Compound No. 1176644. As shown in Example 7, Compound No. 1205407 achieved an $IC_{50}$ of 8 nM and 12 nM when tested with two different primer probe sets in vitro. In comparison, Compound No. 757456 achieved an $IC_{50}$ of 868 nM and 709 nM under the same culture conditions in vitro. In comparison, Compound No. 1176644 achieved an $IC_{50}$ of 35 nM and 43 nM under the same culture conditions in vitro. Therefore, Compound No. 1205407 is more potent than Compound No. 757456 or Compound No. 1176644 in this assay.

For example, Compound No. 1205407 demonstrated improved potency in vivo as compared to Compound No. 757456 or Compound No. 1176644. As shown in Study 2 of Example 6, Compound No. 1205407 achieved an $ED_{50}$ of 0.11 and an $ED_{75}$ of 0.38 in a transgenic mouse study. In comparison, Compound No. 757456 achieved an $ED_{50}$ of 2.1 and an $ED_{75}$ of 2.68. In comparison, Compound No. 1176644 achieved an $ED_{50}$ of 0.38 and an $ED_{75}$ of 0.61. Therefore, Compound No. 1205407 is more potent than Compound No. 757456 or Compound No. 1176644 in this assay.

Nonlimiting Disclosure and Incorporation by Reference

Each of the literature and patent publications listed herein is incorporated by reference in its entirety.

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar moiety (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "ATmCGAUCG," wherein mC indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as a or 13 such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms, unless specified otherwise. Likewise, all cis- and trans-isomers and tautomeric forms of the compounds herein are also included unless otherwise indicated. Oligomeric compounds described herein include chirally pure or enriched mixtures as well as racemic mixtures. For example, oligomeric compounds having a plurality of phosphorothioate internucleoside linkages include such compounds in which chirality of the phosphorothioate internucleoside linkages is controlled or is random. Unless otherwise indicated, compounds described herein are intended to include corresponding salt forms.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^1$H hydrogen atoms. Isotopic substitutions encompassed by the compounds herein include but are not limited to: $^2$H or $^3$H in place of $^1$H, $^{13}$C or $^{14}$C in place of $^{12}$C, $^{15}$N in place of $^{14}$N, $^{17}$O or $^{18}$O in place of $^{16}$O, and $^{33}$S, $^{34}$S, $^{35}$S, or $^{36}$S in place of $^{32}$S. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

The following examples illustrate certain embodiments of the present disclosure and are not limiting. Moreover, where specific embodiments are provided, the inventors have contemplated generic application of those specific embodiments.

Example 1: Design of Modified Oligonucleotides Complementary to a Human AGT Nucleic Acid Modified oligonucleotides complementary to a human AGT nucleic acid were designed, as described in the tables below. "Start site" in all the tables below indicates the 5'-most nucleoside to which the modified oligonucleotide is complementary in the target nucleic acid sequence. "Stop site" indicates the 3'-most nucleoside to which the modified oligonucleotide is complementary in the target nucleic acid sequence. Each modified oligonucleotide listed in the tables below is 100% complementary to SEQ ID NO: 1 (GENBANK Accession No. NM_000029.3), or to SEQ ID NO: 2 (the complement of GENBANK Accession No. NC_000001.11 truncated from nucleotides 230700001 to 230718000), or to both.

The modified oligonucleotide in Table 1 is 16 nucleosides in length with mixed sugar moieties as indicated in the table below, wherein each 'd' represents a 2'-β-D-deoxyribosyl sugar moiety, each 'e' represents a 2'-MOE sugar moiety, and each 'k' represents a cEt sugar moiety. Each internucleoside linkage is a phosphorothioate internucleoside linkage. All cytosine residues are 5-methylcytosines. 568637 is a comparator compound previously described in WO 2017/062816.

TABLE 1

3-10-3 MOE/cEt mixed wing gapmers with uniform PS internucleoside linkages complementary to human AGT RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | Sugar Motif (5' to 3') | SEQ ID NO |
|---|---|---|---|---|---|---|---|
| 568637 | 2046 | 2061 | 14940 | 14955 | CGCTGATTTGTCCGGG | eekddddddddddkke | 12 |

The modified oligonucleotides in Tables 2-6 all have a 5'-trishexylamino-(THA)-C$_6$GalNAc$_3$ endcap, represented by the structure below, wherein the phosphate group is attached to the 5'-oxygen atom of the 5'-nucleoside:

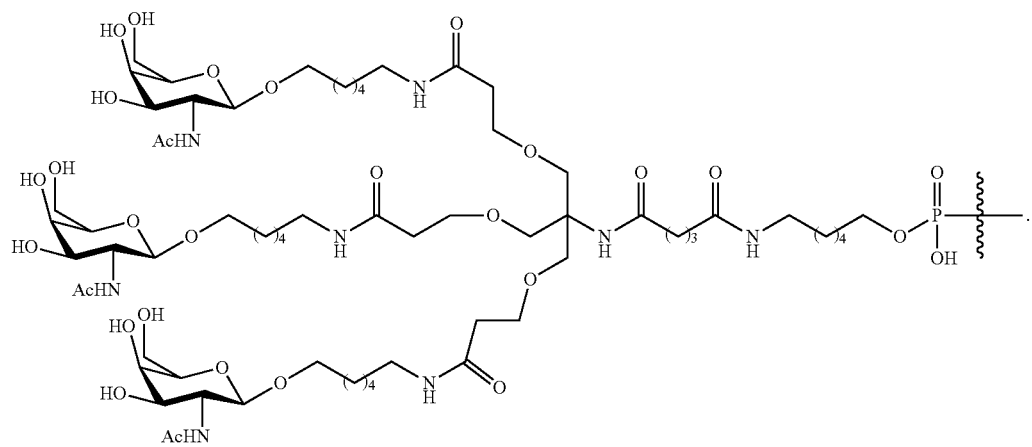

The modified oligonucleotides in Table 2 are 16 nucleosides in length with mixed sugar moieties as indicated, wherein each 'd' represents a 2'-β-D-deoxyribosyl sugar moiety, each 'e' represents a 2'-MOE sugar moiety, and each 'k' refers to a cEt sugar moiety. The internucleoside motif for the gapmers is (from 5' to 3'): soossssssssssos; wherein each 'o' represents a phosphodiester internucleoside linkage and each 's' represents a phosphorothioate internucleoside linkage. All cytosine residues are 5-methylcytosines.

wherein each 'd' represents a 2'-β-D-deoxyribosyl sugar moiety, each 'e' represents a 2'-MOE sugar moiety, each 'k' refers to a cEt sugar moiety, and each 'y' refers to a 2'-OMe ribose sugar. The internucleoside motif for the gapmers is (from 5' to 3'): soossssssssssos; wherein each 'o' represents a phosphodiester internucleoside linkage and each 's' represents a phosphorothioate internucleoside linkage. All cytosine residues are 5-methylcytosines, unless indicated by a bold underlined 'C', in which case, the cytosine is not methylated.

TABLE 2

GalNAc-conjugated 3-10-3 MOE/cEt mixed wing gapmers with mixed PO/PS internucleoside linkages complementary to human AGT RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | Sugar Motif (5' to 3') | SEQ ID NO |
|---|---|---|---|---|---|---|---|
| 1205407 | 2046 | 2061 | 14940 | 14955 | THA-GalNAc-CGCTGATTTGTCCGGG | eekddddddddddkke | 12 |
| 1205408 | 2271 | 2286 | 15165 | 15180 | THA-GalNAc-TCGGTTGGAATTCTTT | ekkddddddddddkke | 13 |
| 1205410 | 2046 | 2061 | 14940 | 14955 | THA-GalNAc-CGCTGATTTGTCCGGG | ekkddddddddddkke | 12 |

The modified oligonucleotides in Table 3 are 16 nucleosides in length with mixed sugar moieties as indicated,

TABLE 3

GalNAc-conjugated 3-10-3 cEt gapmers having a 2'-OMe in the gap with mixed PO/PS internucleoside linkages complementary to human AGT RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | Sugar Motif (5' to 3') | SEQ ID NO |
|---|---|---|---|---|---|---|---|
| 1299239 | 637 | 652 | 7279 | 7294 | THA-GalNAc-CTCATUGTGGATGACG | kkkddyddddddkkk | 16 |
| 1299240 | 637 | 652 | 7279 | 7294 | THA-GalNAc-CTCATTGTGGATGACG | kkkdddyddddddkkk | 17 |
| 1299247 | 711 | 726 | 7353 | 7368 | THA-GalNAc-TGAATGGAGCAGGTA | kkkddydddddddkkk | 18 |

TABLE 3-continued

GalNAc-conjugated 3-10-3 cEt gapmers having a 2'-OMe in the gap with mixed PO/PS internucleoside linkages complementary to human AGT RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | Sugar Motif (5' to 3') | SEQ ID NO |
|---|---|---|---|---|---|---|---|
| 1299248 | 711 | 726 | 7353 | 7368 | THA-GalNAc-TGAATTGGAGCAGGTA | kkkdddydddddddkkk | 19 |
| 1251199 | 785 | 800 | 7427 | 7442 | THA-GalNAc-CGGTGTCAAGTTTTGC | kkkdyddddddddkkk | 20 |
| 1251204 | 1826 | 1841 | 14720 | 14735 | THA-GalNAc-GTTGGGTAGACTCTGT | kkkdyddddddddkkk | 21 |
| 1250850 | 2046 | 2061 | 14940 | 14955 | THA-GalNAc-CGCTGATTTGTCCGGG | kkkdyddddddddkkk | 12 |
| 1251213 | 2268 | 2283 | 15162 | 15177 | THA-GalNAc-GTTGGAATTCTTTTG | kkkdyddddddddkkk | 22 |
| 1250851 | 2271 | 2286 | 15165 | 15180 | THA-GalNAc-TCGGUTGGAATTCTTT | kkkdyddddddddkkk | 14 |

The modified oligonucleotides in Table 4 are 16 nucleosides in length with mixed sugar motifs as indicated, wherein 'd' represents a 2'-β-D-deoxyribosyl sugar moiety, 'e' represents a 2'-MOE sugar moiety, and 'k' refers to a cEt sugar moiety. Each internucleoside linkage is a phosphorothioate internucleoside linkage. All cytosine residues are 5-methylcytosines.

TABLE 4

GalNAc-conjugated 3-10-3 MOE/cEt mixed wing gapmers with uniform PS internucleoside linkages complementary to human AGT RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | Sugar Motif (5' to 3') | SEQ ID NO |
|---|---|---|---|---|---|---|---|
| 1176644 | 2046 | 2061 | 14940 | 14955 | THA-GalNAc-CGCTGATTTGTCCGGG | eekddddddddddkke | 12 |
| 1176648 | 2271 | 2286 | 15165 | 15180 | THA-GalNAc-TCGGTTGGAATTCTTT | ekkddddddddddkke | 13 |
| 1176649 | 2272 | 2287 | 15166 | 15181 | THA-GalNAc-GTCGGTTGGAATTCTT | ekkddddddddddkke | 15 |
| 1176653 | 2046 | 2061 | 14940 | 14955 | THA-GalNAc-CGCTGATTTGTCCGGG | ekkddddddddddkke | 12 |
| 1231463 | 1834 | 1849 | 14728 | 14743 | THA-GalNAc-GTTAAGCTGTTGGGTA | kkkddddddddddkkk | 23 |

The modified oligonucleotides in Table 5 are 16 nucleosides in length with mixed sugar motifs as indicated, wherein 'd' represents a 2'-β-D-deoxyribosyl sugar moiety, 'e' represents a 2'-MOE sugar moiety, 'k' refers to a cEt sugar moiety, and 'y' refers to a 2'-OMe ribose sugar. Each internucleoside linkage is a phosphorothioate internucleoside linkage. All cytosine residues are 5-methylcytosines, unless indicated by a bold underlined 'C', in which case, the cytosine is not methylated.

TABLE 5

GalNAc-conjugated 3-10-3 cEt gapmers having a 2'-OMe in the gap with uniform PS internucleoside linkages complementary to human AGT RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | Sugar Motif (5' to 3') | SEQ ID NO |
|---|---|---|---|---|---|---|---|
| 1250835 | 2046 | 2061 | 14940 | 14955 | THA-GalNAc-CGCTGATTTGTCCGGG | kkkdyddddddddkkk | 12 |
| 1250836 | 2271 | 2286 | 15165 | 15180 | THA-GalNAc-TCGGUTGGAATTCTTT | kkkdyddddddddkkk | 14 |
| 1250837 | 2272 | 2287 | 15166 | 15181 | THA-GalNAc-GTCGGTTGGAATTCTT | kkkdyddddddddkkk | 15 |
| 1250840 | 711 | 726 | 7353 | 7368 | THA-GalNAc-TGAAUTGGAGCAGGTA | kkkdyddddddddkkk | 24 |
| 1250842 | 1729 | 1744 | 13760 | 13775 | THA-GalNAc-TTGCAGGTTCAGCTCG | kkkdyddddddddkkk | 25 |
| 1251216 | 1822 | 1837 | 14716 | 14731 | THA-GalNAc-GGTAGACTCTGTGGGC | kkkdyddddddddkkk | 26 |
| 1251228 | 2268 | 2283 | 15162 | 15177 | THA-GalNAc-GTTGGAATTCTTTTTG | kkkdyddddddddkkk | 27 |

The modified oligonucleotide in Table 6 is a 5-10-5 MOE gapmer with uniform phosphorothioate internucleoside linkages. The compound is 20 nucleosides in length, wherein the central gap segment consists of ten 2'-β-D-deoxynucleosides and the 5' and 3' wing segments each consists of five 2'-MOE modified nucleosides. Each internucleoside linkage is a phosphorothioate internucleoside linkage. All cytosine residues are 5-methylcytosines. 757456 is comparator compound previously described in WO 2017/062816.

sequence GAAGATGGTGATGGGATTTC, designated herein as SEQ ID NO: 10; probe sequence CAAGCTTCCCGTTCTCAGCC, designated herein as SEQ ID NO: 11). Results are presented in the tables below as percent inhibition of AGT, relative to untreated control cells. As used herein, a value of '0' indicates that treatment with the modified oligonucleotide did not inhibit AGT mRNA levels.

TABLE 6

GalNAc-conjugated 5-10-5 MOE gapmer with uniform PS internucleoside linkages complementary to human AGT RNA

| Compound ID | SEQ ID NO: 1 Start Site | SEQ ID NO: 1 Stop Site | SEQ ID NO: 2 Start Site | SEQ ID NO: 2 Stop Site | Sequence (5' to 3') | Sugar Motif (5' to 3') | SEQ ID NO |
|---|---|---|---|---|---|---|---|
| 757456 | 2281 | 2300 | 15175 | 15194 | THA-GalNAc-CACAAACAAGCTGGTCGGTT | eeeeeddddddddddeeeee | 28 |

Example 2: Dose-Dependent In Vitro Inhibition of Human AGT in HepG2 Cells

Cultured HepG2 cells at a density of 10,000 cells per well treated by electroporation with modified oligonucleotides diluted to different concentrations as specified in the tables below. After a treatment period of approximately 24 hours, AGT RNA levels were measured as previously described using the Human AGT primer-probe set RTS3721 (described herein above). AGT RNA levels were normalized to Human GAPDH expression level using the primer probe set RTS104 (forward sequence GAAGGTGAAGGTCG-GAGTC, designated herein as SEQ ID NO: 9; reverse

TABLE 7

Multi-dose assay of modified oligonucleotides in HepG2 cells

| Compound No. | % Inhibition | | | | | $IC_{50}$ (μM) |
|---|---|---|---|---|---|---|
| | 23 nM | 94 nM | 375 nM | 1500 nM | 6000 nM | |
| 1250840 | 0 | 0 | 5 | 25 | 51 | 5.3 |
| 1231463 | 0 | 8 | 14 | 47 | 77 | 1.8 |
| 1205407 | 0 | 19 | 52 | 81 | 91 | 0.4 |
| 1250850 | 12 | 25 | 49 | 74 | 93 | 0.4 |
| 1251213 | 0 | 6 | 3 | 33 | 71 | 2.8 |
| 1251228 | 0 | 0 | 4 | 34 | 58 | 3.9 |
| 1205408 | 3 | 5 | 15 | 47 | 77 | 1.8 |

TABLE 7-continued

Multi-dose assay of modified oligonucleotides in HepG2 cells

| Compound No. | % Inhibition | | | | | IC$_{50}$ (µM) |
|---|---|---|---|---|---|---|
| | 23 nM | 94 nM | 375 nM | 1500 nM | 6000 nM | |
| 1250836 | 0 | 9 | 22 | 48 | 75 | 1.7 |
| 1250851 | 11 | 7 | 24 | 61 | 80 | 1.1 |
| 1250837 | 11 | 4 | 29 | 61 | 83 | 1.0 |
| 1299239 | 13 | 37 | 65 | 92 | 97 | 0.8 |
| 1299240 | 23 | 56 | 85 | 97 | 96 | 1.9 |
| 1205410 | 6 | 16 | 31 | 68 | 98 | 0.2 |
| 1250835 | 10 | 20 | 50 | 87 | 86 | 0.4 |

Example 3: Tolerability of Modified Oligonucleotides Targeting Human AGT in CD-1 Mice CD1 mice are a multipurpose mouse model frequently utilized for safety and efficacy testing. The mice were treated with modified oligonucleotides selected from studies described above and evaluated for changes in the levels of various plasma chemistry markers.

Treatment

Groups of 6- to 8-week-old male CD-1 mice were injected subcutaneously once a week for six weeks (for a total of 7 treatments) with 15 mg/kg of modified oligonucleotides. One group of male CD-1 mice was injected with saline. Mice were euthanized 72 hours following the final administration.

Plasma Chemistry Markers

To evaluate the effect of modified oligonucleotides on liver function, plasma levels of blood urea nitrogen (BUN), albumin, alanine aminotransferase (ALT), aspartate aminotransferase (AST), creatinine (CREA) and total bilirubin (TBIL) were measured using an automated clinical chemistry analyzer (Hitachi Olympus AU400c, Melville, N.Y.). The results are presented in the table below.

TABLE 8

Plasma chemistry markers in male CD-1 mice

| Compound No. | BUN (mg/dL) | Albumin (g/dL) | ALT (IU/L) | AST (IU/L) | TBIL (mg/dL) | CREA (mg/dL) |
|---|---|---|---|---|---|---|
| Saline | 23 | 3 | 31 | 49 | 0.14 | 0.08 |
| 1176644 | 24 | 3 | 52 | 56 | 0.13 | 0.11 |
| 1176648 | 25 | 3 | 70 | 51 | 0.12 | 0.11 |
| 1176653 | 22 | 3 | 309 | 330 | 0.12 | 0.09 |
| 1205407 | 21 | 3 | 123 | 83 | 0.12 | 0.09 |
| 1205408 | 24 | 3 | 64 | 78 | 0.12 | 0.13 |
| 1205410 | 26 | 3 | 161 | 121 | 0.13 | 0.11 |
| 1231463 | 27 | 3 | 132 | 188 | 0.19 | 0.13 |

Blood obtained from mouse groups at week 6 were sent to IDEXX BioResearch for measurement of blood cell counts. Counts taken include red blood cell (RBC) count, white blood cell (WBC) count, hemoglobin (HGB), hematocrit (HCT), Mean corpuscular volume (MCV), mean corpuscular hemoglobin (MCH), mean corpuscular hemoglobin concentration (MCHC), and individual white blood cell counts, such as that of monocytes (MON), neutrophils (NEU), lymphocytes (LYM), and platelets (PLT). The results are presented in the tables below.

TABLE 9

Blood Cell Count in male CD-1 mice

| Compound No. | WBC (K/uL) | RBC (M/uL) | HGB (g/dL) | HCT (%) | MCV (fL) | MCH (pg) | MCHC (g/dL) | NEU (/uL) | LYM (/uL) | MON (/uL) | PLT (K/uL) |
|---|---|---|---|---|---|---|---|---|---|---|---|
| Saline | 8 | 9 | 14 | 47 | 52 | 16 | 31 | 1133 | 6142 | 390 | 1290 |
| 1176644 | 6 | 9 | 14 | 46 | 50 | 16 | 31 | 919 | 4533 | 231 | 1182 |
| 1176648 | 4 | 9 | 14 | 44 | 50 | 16 | 31 | 703 | 3370 | 227 | 1186 |
| 1176653 | 8 | 10 | 15 | 48 | 48 | 15 | 32 | 989 | 6505 | 361 | 829 |
| 1205407 | 9 | 10 | 15 | 47 | 47 | 15 | 33 | 901 | 7171 | 355 | 1228 |
| 1205408 | 9 | 9 | 15 | 46 | 48 | 15 | 32 | 1633 | 6745 | 501 | 1446 |
| 1205410 | 6 | 9 | 14 | 45 | 50 | 16 | 32 | 714 | 5112 | 227 | 994 |
| 1231463 | 8 | 10 | 15 | 46 | 48 | 16 | 32 | 872 | 6365 | 481 | 1260 |

Body weights of mice were measured at days 1 and 35, and the average body weight for each group is presented in the table below. Liver, spleen and kidney weights were measured at the end of the study and are presented in the table below. Modified oligonucleotides that caused any changes in organ weights outside the expected range for modified oligonucleotides were excluded from further studies

TABLE 10

Body and organ weights (g)

| Compound No. | Body Weight (g) | | Liver Weight (g) | Kidney Weight (g) | Spleen Weight (g) |
|---|---|---|---|---|---|
| | Day 1 | Day 35 | | | |
| PBS | 31.7 | 37.7 | 2.1 | 0.7 | 0.2 |
| 1176644 | 31.0 | 37.7 | 2.5 | 0.5 | 0.1 |
| 1176648 | 32.4 | 40.0 | 2.5 | 0.6 | 0.1 |
| 1176653 | 32.0 | 40.7 | 2.8 | 0.7 | 0.1 |
| 1205407 | 31.7 | 39.2 | 2.7 | 0.6 | 0.1 |
| 1205408 | 30.5 | 38.3 | 2.2 | 0.5 | 0.1 |
| 1205410 | 29.8 | 35.2 | 2.4 | 0.5 | 0.1 |
| 1231463 | 32.5 | 39.6 | 2.5 | 0.5 | 0.1 |

Example 4: Tolerability of Modified Oligonucleotides Targeting Human AGT in Sprague-Dawley Rats Sprague-Dawley rats are a multipurpose model used for safety and efficacy evaluations. The rats were treated with Ionis modified oligonucleotides from the studies described in the Examples above and evaluated for changes in the levels of various plasma chemistry markers.

Study 1

Treatment

Male Sprague-Dawley rats were maintained on a 12-hour light/dark cycle and fed ad libitum with Purina normal rat chow. Groups of 4 Sprague-Dawley rats each were weekly injected subcutaneously with 15 mg/kg of Ionis oligonucleotide for 6 weeks (total 6 doses). 72 hours after the last dose, rats were euthanized; and organs, urine and plasma were harvested for further analysis.

Plasma Chemistry Markers

To evaluate the effect of Ionis oligonucleotides on hepatic function, plasma levels of transaminases were measured using an automated clinical chemistry analyzer (Hitachi Olympus AU400c, Melville, N.Y.). Plasma levels of ALT (alanine transaminase) and AST (aspartate transaminase) were measured and the results are presented in the Table below expressed in IU/L. Plasma levels of total bilirubin (TBIL), creatinine, albumin, and Blood Urea Nitrogen (BUN) were also measured using the same clinical chemistry analyzer and the results are also presented in the table below.

TABLE 11

Plasma chemistry markers in Sprague-Dawley rats

| Compound No. | BUN (mg/dL) | Albumin (g/dL) | ALT (IU/L) | AST (IU/L) | TBIL (mg/dL) | CREA (mg/dL) |
|---|---|---|---|---|---|---|
| Saline | 17 | 3 | 27 | 78 | 0.13 | 0.23 |
| 1205407 | 15 | 3 | 69 | 182 | 0.15 | 0.25 |
| 1205408 | 20 | 3 | 34 | 151 | 0.36 | 0.25 |

Organ Weights

Liver, heart, spleen and kidney weights were measured at the end of the study and are presented in the Table below.

TABLE 12

Organ weights (g)

| Compound No. | Liver (g) | Kidney (g) | Spleen (g) |
|---|---|---|---|
| Saline | 13.7 | 3.4 | 0.8 |
| 1205407 | 15.2 | 3.6 | 1.2 |
| 1205408 | 18.3 | 4.0 | 1.2 |

Kidney Function

To evaluate the effect of Ionis modified oligonucleotides on kidney function, urinary levels of total protein and creatinine were measured using an automated clinical chemistry analyzer (Hitachi Olympus AU400c, Melville, N.Y.). The ratios of total protein to creatinine (P/C ratio) are presented in the Table below.

TABLE 13

Total protein to creatinine ratio in Sprague-Dawley rats

| Compound No. | P/C Ratio |
|---|---|
| Saline | 1.1 |
| 1205407 | 2.1 |
| 1205408 | 0.7 |

Study 2

Treatment

Male Sprague-Dawley rats were maintained on a 12-hour light/dark cycle and fed ad libitum with Purina normal rat chow. Groups of 4 Sprague-Dawley rats each were weekly injected subcutaneously with 15 mg/kg of Ionis oligonucleotide for 6 weeks (total 6 doses). 72 hours after the last dose, rats were euthanized; and organs, urine and plasma were harvested for further analysis.

Plasma Chemistry Markers

To evaluate the effect of Ionis oligonucleotides on hepatic function, plasma levels of transaminases were measured using an automated clinical chemistry analyzer (Hitachi Olympus AU400c, Melville, N.Y.). Plasma levels of ALT (alanine transaminase) and AST (aspartate transaminase) were measured and the results are presented in the Table below expressed in IU/L. Plasma levels of total bilirubin (TBIL), creatinine, albumin, and Blood Urea Nitrogen (BUN) were also measured using the same clinical chemistry analyzer and the results are also presented in the Table below.

TABLE 14

Plasma chemistry markers in Sprague-Dawley rats

| Compound No. | BUN (mg/dL) | Albumin (g/dL) | ALT (IU/L) | AST (IU/L) | TBIL (mg/dL) | CREA (mg/dL) |
|---|---|---|---|---|---|---|
| Saline | 16 | 3 | 28 | 112 | 0.11 | 0.27 |
| 1250837 | 18 | 4 | 32 | 129 | 0.14 | 0.23 |
| 1250851 | 18 | 3 | 119 | 641 | 0.41 | 0.25 |

Organ Weights

Liver, heart, spleen and kidney weights were measured at the end of the study and are presented in the Table below.

TABLE 15

Organ weights (g)

| Compound No. | Liver (g) | Kidney (g) | Spleen (g) |
|---|---|---|---|
| Saline | 12.242 | 3.388 | 1.051 |
| 1250837 | 13.771 | 3.580 | 1.184 |
| 1250851 | 14.850 | 3.756 | 1.166 |

Kidney Function

To evaluate the effect of Ionis modified oligonucleotides on kidney function, urinary levels of total protein and creatinine were measured using an automated clinical chemistry analyzer (Hitachi Olympus AU400c, Melville, N.Y.). The ratios of total protein to creatinine (P/C ratio) are presented in the Table below.

TABLE 16

Total protein to creatinine ratio in Sprague-Dawley rats

| Compound No. | P/C Ratio |
|---|---|
| Saline | 0.9 |
| 1250837 | 1.1 |
| 1250851 | 0.8 |

Example 5: Activity of Modified Oligonucleotides Complementary to Human AGT in Transgenic Mice A transgenic AGT mouse model was developed in Dr. Curt Sigmund's lab by insertion of a 14 kb transgenic construct containing the entire human angiotensinogen gene (approximately 11.5 kb) and 5' (1.2 kb) and 3' (1.4 kb) flanking sequence (Yang G; et al. 1994. J Biol Chem 269(51):32497-502) and used for further testing of the modified oligonucleotides described above.

Treatment

The AGT transgenic mice were divided into groups of 2 mice each. Each mouse was injected subcutaneously weekly with 2.7 mg/kg of modified oligonucleotides (total of 2 doses on Days 0 and 7). A group of 2 mice received saline as a negative control. In addition, a group of 2 mice received 3.3 mg/kg of comparator modified oligonucleotide 757456 (total of 2 doses on Days 0 and 7). The mice were sacrificed three days after the last dose (Day 10). Liver and plasma were collected for analysis.

RNA and Protein Analysis

RNA was extracted from liver tissue for real-time PCR analysis to measure the amount of AGT RNA using Human primer probe set RTS3721 (described herein above). Results are presented as percent inhibition of AGT RNA relative to saline control, normalized to total RNA content, as measured by RIBOGREEN®. In addition, plasma was extracted to measure human AGT protein levels in plasma using an ELISA kit (Human Total Angiotensinogen Assay Kit, IBL, Cat #27412). Results are presented as percent inhibition of AGT protein relative to saline control.

TABLE 17

Reduction of human AGT RNA and protein in transgenic mice

| Compound No. | Dose (mg/kg) | % inhibition (AGT RNA) in liver | % inhibition (AGT protein) in plasma |
|---|---|---|---|
| 757456 | 3.3 | 65 | 60 |
| 1231463 | 2.7 | 93 | 87 |
| 1176644 | 2.7 | 90 | 91 |
| 1176648 | 2.7 | 93 | 90 |
| 1176653 | 2.7 | 96 | 93 |
| 1205407 | 2.7 | 93 | 90 |
| 1205408 | 2.7 | 94 | 91 |
| 1205410 | 2.7 | 96 | 92 |
| 1250842 | 2.7 | 88 | 65 |
| 1251204 | 2.7 | 44 | 47 |

Example 6: Potency of Modified Oligonucleotides Complementary to Human AGT RNA in Transgenic Mice, Multiple Dose Modified oligonucleotides were further tested in a dose-dependent manner in the transgenic mouse model described above.

Treatment

The AGT transgenic mice were divided into groups of 2 mice each. Each mouse was injected subcutaneously with two doses (on Days 0 and 7) of modified oligonucleotide at the concentrations indicated in the table below. A group of 4 mice received PBS as a negative control. Seventy-two hours after the last dose (Day 10), the mice were euthanized. Liver and plasma were collected for analysis. Compound No. 757456 was added as a comparator compound in some studies.

Study 1

RNA and Protein Analysis

RNA was extracted from liver tissue for real-time PCR analysis to measure the amount of AGT RNA using Human primer probe set RTS3721 (described herein above). Results are presented as percent inhibition of AGT RNA relative to saline control, normalized to total RNA content, as measured by RIBOGREEN®. In addition, plasma was extracted to measure human AGT protein levels in plasma using an ELISA kit (Human Total Angiotensinogen Assay Kit, IBL, Cat #27412). Results are presented as percent inhibition of AGT protein relative to saline control.

TABLE 18

Reduction (%) of human AGT RNA and protein in transgenic mice

| Compound No. | Dose (mg/kg) | % inhibition (AGT RNA) in liver | $ED_{50}$ (mg/kg) | % inhibition (AGT protein) in plasma |
|---|---|---|---|---|
| 757456 | 4.5 | 81 | 1.3 | 81 |
|  | 1.5 | 41 |  | 49 |
|  | 0.5 | 39 |  | 31 |
| 1205407 | 4.5 | 97 | 0.1 | 97 |
|  | 1.5 | 95 |  | 94 |
|  | 0.5 | 75 |  | 79 |
| 1205408 | 4.5 | 97 | 0.2 | 95 |
|  | 1.5 | 91 |  | 90 |
|  | 0.5 | 75 |  | 74 |
| 1205410 | 4.5 | 98 | 0.1 | 98 |
|  | 1.5 | 97 |  | 96 |
|  | 0.5 | 83 |  | 85 |
| 1231463 | 4.5 | 97 | 0.3 | 94 |
|  | 1.5 | 90 |  | 87 |
|  | 0.5 | 70 |  | 65 |
| 1250835 | 4.5 | 88 | 0.2 | 91 |
|  | 1.5 | 86 |  | 84 |
|  | 0.5 | 72 |  | 73 |
| 1250836 | 4.5 | 95 | 0.1 | 96 |
|  | 1.5 | 93 |  | 93 |
|  | 0.5 | 82 |  | 77 |
| 1250837 | 4.5 | 96 | 0.2 | 94 |
|  | 1.5 | 89 |  | 88 |
|  | 0.5 | 62 |  | 69 |
| 1250840 | 4.5 | 96 | 0.3 | 95 |
|  | 1.5 | 81 |  | 85 |
|  | 0.5 | 47 |  | 64 |
| 1250850 | 4.5 | 91 | 0.2 | 93 |
|  | 1.5 | 78 |  | 84 |
|  | 0.5 | 74 |  | 78 |
| 1250851 | 4.5 | 96 | 0.1 | 96 |
|  | 1.5 | 94 |  | 95 |
|  | 0.5 | 77 |  | 81 |
| 1251199 | 4.5 | 92 | 0.2 | 91 |
|  | 1.5 | 84 |  | 83 |
|  | 0.5 | 69 |  | 69 |
| 1251213 | 4.5 | 91 | 0.2 | 93 |
|  | 1.5 | 84 |  | 86 |
|  | 0.5 | 74 |  | 75 |
| 1251216 | 4.5 | 90 | 0.3 | 91 |
|  | 1.5 | 79 |  | 80 |
|  | 0.5 | 46 |  | 68 |

TABLE 18-continued

Reduction (%) of human AGT RNA and protein in transgenic mice

| Compound No. | Dose (mg/kg) | % inhibition (AGT RNA) in liver | ED$_{50}$ (mg/kg) | % inhibition (AGT protein) in plasma |
|---|---|---|---|---|
| 1251228 | 4.5 | 94 | 0.2 | 95 |
|  | 1.5 | 83 |  | 88 |
|  | 0.5 | 58 |  | 67 |
| 1299247 | 4.5 | 99 | 0.1 | 98 |
|  | 1.5 | 98 |  | 97 |
|  | 0.5 | 83 |  | 84 |
| 1299248 | 4.5 | 89 | 0.3 | 91 |
|  | 1.5 | 74 |  | 84 |
|  | 0.5 | 49 |  | 61 |

Study 2
RNA and Protein Analysis

RNA was extracted from liver tissue for real-time PCR analysis to measure the amount of AGT RNA using Human primer probe set RTS3721 (described herein above). Results are presented as percent inhibition of AGT RNA relative to saline control, normalized to total RNA content, as measured by RIBOGREEN®. In addition, plasma was extracted to measure human AGT protein levels in plasma using an ELISA kit (Human Total Angiotensinogen Assay Kit, IBL, Cat #27412). Results are presented as percent inhibition of AGT protein relative to saline control.

TABLE 19

Reduction of human AGT RNA and protein in transgenic mice

| Compound No. | Dose (mg/kg) | % inhibition (AGT RNA) in liver | ED50 (mg/kg) | % inhibition (AGT protein) in plasma |
|---|---|---|---|---|
| 1205407 | 5.0 | 98 | 0.14 | 96 |
|  | 1.7 | 93 |  | 90 |
|  | 0.6 | 85 |  | 80 |
|  | 0.2 | 56 |  | 37 |
|  | 0.1 | 30 |  | 29 |
| 1205408 | 5.0 | 98 | 0.27 | 95 |
|  | 1.7 | 93 |  | 88 |
|  | 0.6 | 73 |  | 76 |
|  | 0.2 | 37 |  | 23 |
|  | 0.1 | 9 |  | 0 |
| 1250837 | 5.0 | 85 | 0.53 | 83 |
|  | 1.7 | 84 |  | 84 |
|  | 0.6 | 57 |  | 64 |
|  | 0.2 | 26 |  | 40 |
|  | 0.1 | 0 |  | 46 |
| 1250851 | 5.0 | 94 | 0.23 | 91 |
|  | 0.6 | 76 |  | 76 |
|  | 0.2 | 32 |  | 49 |
|  | 0.1 | 32 |  | 37 |

Study 3
RNA and Protein Analysis

RNA was extracted from liver tissue for real-time PCR analysis to measure the amount of AGT RNA using Human primer probe set RTS3721 (described herein above). Results are presented as percent inhibition of AGT RNA relative to saline control, normalized to total RNA content, as measured by RIBOGREEN®. In addition, plasma was extracted to measure human AGT protein levels in plasma using an ELISA kit (Human Total Angiotensinogen Assay Kit, IBL, Cat #27412). Results are presented as percent inhibition of AGT protein relative to saline control. As used herein, a value of '0' indicates that treatment with the modified oligonucleotide did not inhibit AGT levels.

TABLE 20

Reduction of human AGT RNA and protein in transgenic mice

| Compound No. | Dose (mg/kg) | % inhibition (AGT RNA) in liver | ED50 (mg/kg) | ED75 (mg/kg) | % inhibition (AGT protein) in plasma |
|---|---|---|---|---|---|
| 757456 | 10 | 88 | 2.1 | 2.68 | 88 |
|  | 3.3 | 74 |  |  | 72 |
|  | 0.1 | 0 |  |  | 0 |
|  | 0.04 | 0 |  |  | 0 |
| 1205407 | 1.5 | 86 | 0.11 | 0.38 | 87 |
|  | 0.5 | 68 |  |  | 62 |
|  | 0.17 | 38 |  |  | 29 |
|  | 0.06 | 35 |  |  | 11 |
| 1176644 | 1.5 | 76 | 0.38 | 0.61 | 71 |
|  | 0.5 | 62 |  |  | 51 |
|  | 0.17 | 0 |  |  | 5 |
|  | 0.06 | 0 |  |  | 0 |
| 1250837 | 1.5 | 74 | 0.22 | 0.67 | 67 |
|  | 0.5 | 60 |  |  | 52 |
|  | 0.17 | 38 |  |  | 28 |
|  | 0.06 | 0 |  |  | 0 |
| 1176649 | 1.5 | 83 | 0.20 | 0.59 | 82 |
|  | 0.5 | 50 |  |  | 56 |
|  | 0.17 | 17 |  |  | 17 |
|  | 0.06 | 0 |  |  | 0 |

Example 7: Dose-Dependent In Vitro Inhibition of Human AGT in Transgenic Mouse Hepatocytes The transgenic AGT mouse model described above was used in this study. Modified oligonucleotides described in the studies above were tested for inhibition of AGT RNA at various doses in primary mouse hepatocytes extracted from these transgenic mice.

Primary mouse transgenic hepatocytes were plated at a density of 20,000 cells per well and were treated by free uptake with modified oligonucleotides diluted to different concentrations as specified in the tables below. After an overnight incubation, AGT RNA levels were measured using the Human AGT primer-probe set RTS3721 (forward sequence CCCTGATGGGAGCCAGTGT, designated herein as SEQ ID NO: 3; reverse sequence AGCAGG-GAGAAGCCCTTCA, designated herein as SEQ ID NO: 4; probe sequence CCCTGGCTTTCAACACCTACGTC-CACT, designated herein as SEQ ID NO: 5). In addition, data was confirmed a second human AGT primer probe set RTS4039 (forward sequence GGACAAGGTG-GAGGGTCTCA, designated herein as SEQ ID NO: 6; reverse sequence AGATCCTTGCAGCACCAGTTG, designated herein as SEQ ID NO: 7; probe sequence ATGAAGAAACTATCTCCCCGGACCATCCA, designated herein as SEQ ID NO: 8) to measure human AGT RNA levels. AGT RNA levels were normalized to total RNA content, as measured by RIBOGREEN®. Results are presented in the tables below as percent inhibition of AGT, relative to untreated control cells. As used herein, a value of '0' indicates that treatment with the modified oligonucleotide did not inhibit AGT mRNA levels. The half maximal inhibitory concentration (IC$_{50}$) of each modified oligonucleotide is also presented. IC$_{50}$ was calculated using a nonlinear regression using 4 parameter variable slope method of log(inhibitor) vs. response with the bottom and top fixed to 0 and 100, respectively (Prism).

TABLE 21

Multi-dose assay of modified oligonucleotides in primary mouse hepatocytes

| Compound | % Inhibition (RTS3721) | | | | | | | | $IC_{50}$ |
| --- | --- | --- | --- | --- | --- | --- | --- | --- | --- |
| No. | 0.61 nM | 2.44 nM | 9.77 nM | 39.06 nM | 156.25 nM | 625 nM | 2500 nM | 10000 nM | (µM) |
| 757456 | 0 | 0 | 0 | 0 | 39 | 52 | 32 | 20 | 868 |
| 1205407 | 36 | 19 | 51 | 74 | 86 | 94 | 88 | 77 | 8 |
| 1176644 | 0 | 8 | 25 | 51 | 79 | 88 | 86 | 88 | 35 |
| 1176649 | 0 | 0 | 25 | 33 | 60 | 74 | 72 | 53 | 95 |
| 1250837 | 0 | 0 | 12 | 27 | 61 | 67 | 72 | 73 | 145 |

TABLE 22

Multi-dose assay of modified oligonucleotides in primary mouse hepatocytes

| Compound | % Inhibition (RTS4039) | | | | | | | | $IC_{50}$ |
| --- | --- | --- | --- | --- | --- | --- | --- | --- | --- |
| No. | 0.61 nM | 2.44 nM | 9.77 nM | 39.06 nM | 156.25 nM | 625 nM | 2500 nM | 10000 nM | (µM) |
| 757456 | 0 | 0 | 0 | 3 | 43 | 50 | 37 | 7 | 709 |
| 1205407 | 27 | 21 | 44 | 69 | 84 | 89 | 87 | 83 | 12 |
| 1176644 | 0 | 16 | 16 | 48 | 74 | 85 | 82 | 82 | 43 |
| 1176649 | 0 | 0 | 13 | 35 | 55 | 74 | 73 | 65 | 116 |
| 1250837 | 2 | 0 | 14 | 28 | 57 | 66 | 70 | 67 | 169 |

Example 8: Dose-Dependent Ex-Vivo Inhibition of Human AGT in HepatoPac®

The HepatoPac® kit is a commercially available liver model system available from BIOIVT that consists of micropatterned hepatocyte "islands" co-cultured with supportive stromal cells. A 96-well HepatoPac plate was equilibrated for 48 hrs at 37° C. and 10% $CO_2$ in fresh Maintenance medium prior to treatment. Modified oligonucleotides were diluted into maintenance medium at the concentrations described in the table below for 48 hours. After 48 hours, medium was replaced with fresh maintenance medium without additional oligonucleotide. Cell lysates were collected at 96 hours post oligonucleotide addition and analyzed by RT-PCR using primer probe set RTS3721 (described herein above). Results are presented in the tables below as percent inhibition of AGT, relative to untreated control cells. As used herein, a value of '0' indicates that treatment with the modified oligonucleotide did not inhibit AGT mRNA levels. $IC_{50}$s were calculated using variable slope 4 parameter logistic regression in Prism with the bottom and top of the curves set to 5 and 100, respectively.

TABLE 23

Multi-dose assay of modified oligonucleotides in Hepatopac ® cells

| Compound No. | % Inhibition | | | | | | $IC_{50}$ (µM) |
| --- | --- | --- | --- | --- | --- | --- | --- |
| | 6.4 nM | 32 nM | 160 nM | 800 nM | 4000 nM | 20000 nM | |
| 57456 | 31 | 31 | 21 | 16 | 29 | 16 | >20 |
| 1250850 | 0 | 3 | 18 | 61 | 78 | 86 | 0.85 |
| 1205407 | 27 | 52 | 70 | 84 | 93 | 92 | 0.04 |
| 1205410 | 9 | 46 | 63 | 89 | 95 | 99 | 0.06 |

Example 9: Effect of Modified Oligonucleotides Targeting Human AGT in Cynomolgus Monkeys Cynomolgus monkeys were treated with modified oligonucleotides selected from studies described in the Examples above.

Treatment

Prior to the study, the monkeys were kept in quarantine, followed by an acclimation period during which the animals were observed daily for general health. The monkeys were 2-4 years old and weighed 2-4 kg. Nine groups of 4 randomly assigned male cynomolgus monkeys each were injected subcutaneously with Ionis oligonucleotide or saline in a clockwise rotation between four different sites on the back. Following loading doses on days 1, 4 and 8, the monkeys were dosed once per week (on days 15, 22, 29, 36, 43, 50, 57, 64, 71, 78 and 85) with 20 mg/kg of Ionis oligonucleotide. A control group of 4 cynomolgus monkeys was injected with 0.9% saline in a similar manner and served as the control group.

During the study period, the monkeys were observed at least once daily for signs of illness or distress. Any animal showing signs of severe debility or toxicity, particularly if death appeared imminent, was euthanized for humane reasons as soon as possible with attending veterinarian consultation. Scheduled euthanasia of the animals was conducted on day 87 approximately 48 hours after the last dose by exsanguination while under deep anesthesia. The protocols described in the Example were approved by the Institutional Animal Care and Use Committee (IACUC).

Body and Organ Weight Measurements

To evaluate the effect of Ionis oligonucleotides on the overall health of the animals, body and organ weights were measured. Terminal body weight was measured prior to necropsy. Organ weights were measured as well, and all weight measurements are presented in the table below.

TABLE 24

Body and Organ weights (g)

| Compound No. | Terminal Body Weight | Liver with gallbladder | Kidneys | Spleen |
|---|---|---|---|---|
| saline | 2967 | 60 | 13 | 3 |
| 1205407 | 2956 | 96 | 15 | 5 |
| 1205408 | 2971 | 72 | 13 | 3 |
| 1205410 | 2868 | 101 | 14 | 4 |
| 1231463 | 2923 | 69 | 13 | 5 |
| 1250835 | 2949 | 93 | 16 | 6 |
| 1250836 | 2973 | 71 | 14 | 6 |
| 1250837 | 2712 | 63 | 15 | 3 |
| 1250850 | 3044 | 97 | 17 | 5 |
| 1250851 | 2806 | 63 | 15 | 3 |

Kidney and Liver Function

To evaluate the effect of Ionis oligonucleotides on hepatic and kidney function, blood samples were collected from all the study groups on day 87. The monkeys were fasted overnight prior to blood collection. Blood was collected in tubes without anticoagulant for serum separation. The tubes were kept at room temperature for a minimum of 90 minutes and then centrifuged at 3000 rpm for 10 minutes to obtain serum. Levels of various liver function markers were measured using a Toshiba 200FR NEO chemistry analyzer (Toshiba Co., Japan). Plasma levels of blood urea nitrogen (BUN), creatinine (CREA), total protein (TP), albumin (ALB), globulin (GLO), albumin/globulin (A/G) ratio calculated, alanine aminotransferase (ALT), aspartate aminotransferase (AST), total bilirubin (TBIL) were measured and the results are presented in the table below.

TABLE 25

Liver function markers in cynomolgus monkey plasma

| Compound No. | BUN (mg/dL) | CREA (mg/dL) | TP (g/dL) | ALB (g/dL) | GLO (g/dL) | A/G ratio | ALT (IU/L) | AST (IU/L) | TBIL (mg/dL) |
|---|---|---|---|---|---|---|---|---|---|
| saline | 28 | 0.8 | 6.9 | 4.1 | 2.8 | 1.5 | 50 | 57 | 0.25 |
| 1205407 | 23 | 0.8 | 6.9 | 4.0 | 2.9 | 1.4 | 67 | 55 | 0.20 |
| 1205408 | 26 | 0.8 | 6.7 | 4.0 | 2.7 | 1.5 | 53 | 50 | 0.27 |
| 1205410 | 21 | 0.9 | 6.9 | 3.9 | 3.0 | 1.3 | 145 | 72 | 0.26 |
| 1231463 | 22 | 0.8 | 7.3 | 4.0 | 3.4 | 1.2 | 112 | 75 | 0.26 |
| 1250835 | 19 | 0.9 | 7.4 | 3.8 | 3.6 | 1.1 | 129 | 82 | 0.25 |
| 1250836 | 23 | 1.1 | 7.7 | 3.9 | 3.8 | 1.1 | 150 | 95 | 0.34 |
| 1250837 | 21 | 0.8 | 6.9 | 4.2 | 2.7 | 1.6 | 91 | 68 | 0.28 |
| 1250850 | 21 | 0.8 | 7.4 | 4.0 | 3.4 | 1.2 | 85 | 86 | 0.25 |
| 1250851 | 20 | 0.8 | 6.8 | 4.1 | 2.7 | 1.6 | 63 | 64 | 0.27 |

Pro-Inflammatory Proteins Analysis

To evaluate any inflammatory effect of Ionis modified oligonucleotides in cynomolgus monkeys, blood samples were taken for analysis. The monkeys were fasted overnight prior to blood collection. On day 85 (pre-dose and 24 hours post-dose), approximately 0.8 mL of blood was collected from each animal and put into tubes without anticoagulant for serum separation. The tubes were kept at room temperature for a minimum of 90 min and then centrifuged at 3,000 rpm for 10 min at room temperature to obtain serum. Complement C3 were measured using a Toshiba 120 FR NEO chemistry analyzer (Toshiba Co., Japan). Another marker of inflammation, C-Reactive Protein (CRP) was tested together with the clinical chemistry parameters tested for liver function above.

TABLE 26

Pro-inflammatory protein analysis in cynomolgus monkeys

| Compound No. | Complement C3 (mg/dL) | | CRP (mg/L) Day 87 |
|---|---|---|---|
| | Day 85 (pre-dose) | Day 86 (24 hr post-dose) | |
| saline | 110 | 110 | 2 |
| 1205407 | 94 | 91 | 10 |
| 1205408 | 93 | 93 | 4 |
| 1205410 | 117 | 111 | 14 |
| 1231463 | 92 | 102 | 6 |
| 1250835 | 84 | 75 | 15 |
| 1250836 | 78 | 82 | 9 |
| 1250837 | 82 | 87 | 1 |
| 1250850 | 86 | 83 | 12 |
| 1250851 | 86 | 92 | 3 |

Hematology

To evaluate any effect of Ionis modified oligonucleotides in cynomolgus monkeys on hematologic parameters, blood samples of approximately 0.5 mL of blood was collected from each of the available study animals on day 87. The samples were collected in tubes containing $K_2$-EDTA. Samples were analyzed for red blood cell (RBC) count, Hemoglobin (HGB), Hematocrit (HCT), Mean corpuscular volume (MCV), mean corpuscular hemoglobin (MCH), mean corpuscular hemoglobin concentration (MCHC), platelet count (PLT), white blood cells (WBC) count, individual white blood cell counts, such as that of monocytes (MON), neutrophils (NEU), and lymphocytes (LYM) using an ADVIA2120i hematology analyzer (Siemens, USA).

TABLE 27

Blood cell counts in cynomolgus monkeys

| Compound No. | WBC (^3/μL) | RBC (^6/μL) | HGB (g/dL) | HCT (%) | MCV (fL) | MCH (pg) | MCHC (g/dL) | NEU (%) | LYM (%) | MON (%) | PLT (^3/μL) |
|---|---|---|---|---|---|---|---|---|---|---|---|
| saline | 13 | 6 | 14 | 45 | 78 | 24 | 30 | 39 | 55 | 4 | 403 |
| 1205407 | 11 | 6 | 13 | 43 | 77 | 23 | 30 | 40 | 56 | 3 | 377 |
| 1205408 | 12 | 6 | 13 | 44 | 78 | 23 | 30 | 43 | 51 | 3 | 375 |
| 1205410 | 8 | 6 | 13 | 45 | 81 | 24 | 30 | 32 | 63 | 2 | 312 |
| 1231463 | 10 | 6 | 13 | 45 | 78 | 24 | 30 | 28 | 66 | 3 | 338 |
| 1250835 | 10 | 6 | 14 | 47 | 79 | 24 | 30 | 28 | 65 | 4 | 370 |
| 1250836 | 12 | 6 | 14 | 45 | 75 | 23 | 31 | 29 | 66 | 3 | 354 |
| 1250837 | 7 | 6 | 13 | 43 | 77 | 24 | 31 | 37 | 59 | 3 | 288 |
| 1250850 | 8 | 5 | 13 | 42 | 78 | 23 | 30 | 29 | 66 | 3 | 376 |
| 1250851 | 9 | 6 | 14 | 45 | 77 | 24 | 31 | 45 | 51 | 2 | 356 |

Urine Analysis

Food was removed overnight the day before fresh urine collection, but water was supplied. Fresh urine samples for urinalysis and urine chemistry were collected from all animals using a clean cage pan on wet ice (first in the morning) on day 87. Urinalysis/Urine Chemistry parameters include creatinine (UCRE), protein/creatinine (P/C) ratio, microprotein (UTP) and urine microalbumin (UALB), which were measured using a Toshiba 120FR automated chemistry analyzer (Toshiba Co., Japan).

TABLE 28

Urinalysis and Urine Chemistry Markers in cynomolgus monkeys

| Compound No. | UTP (mg/dL) | UALB (mg/dL) | P/C ratio | UCRE (mg/dL) |
|---|---|---|---|---|
| saline | 7 | 0.57 | 0.15 | 55 |
| 1205407 | 7 | 0.29 | 0.19 | 37 |
| 1205408 | 7 | 0.47 | 0.14 | 52 |
| 1205410 | 7 | 0.34 | 0.19 | 52 |
| 1231463 | 7 | 0.37 | 0.13 | 63 |
| 1250835 | 12 | 0.58 | 0.14 | 95 |
| 1250836 | 10 | 0.54 | 0.11 | 114 |
| 1250837 | 7 | 0.41 | 0.16 | 49 |
| 1250850 | 7 | 0.55 | 0.08 | 105 |
| 1250851 | 9 | 0.74 | 0.07 | 140 |

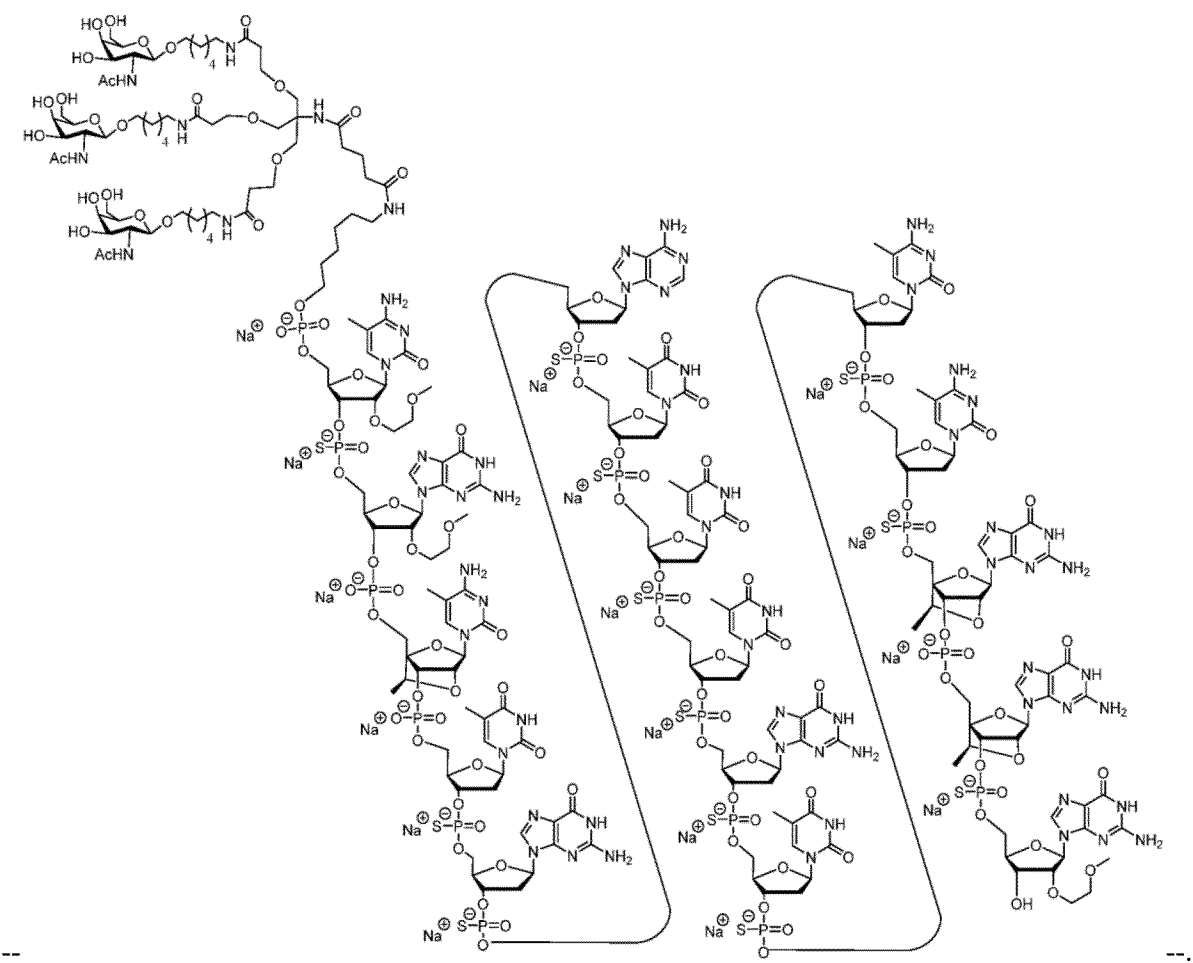

The invention claimed is:

1. An oligomeric compound according to the following chemical structure:

207
-continued
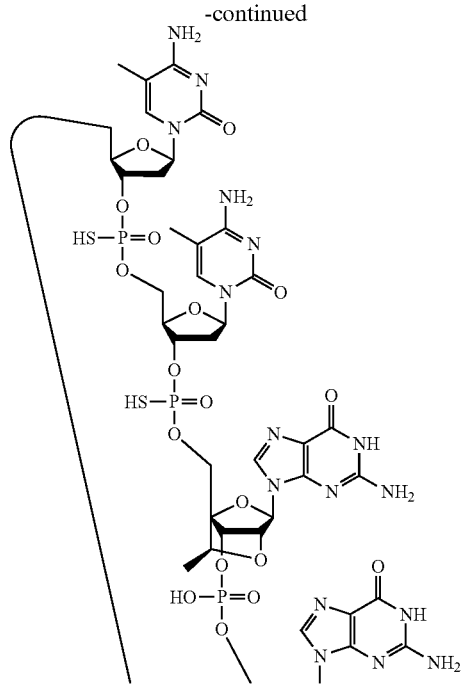
208
-continued
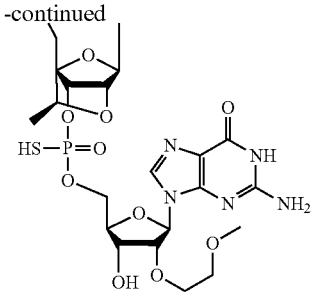
(SEQ ID NO: 12), or a salt thereof.
2. The oligomeric compound of claim 1, which is the sodium salt or potassium salt.
3. An oligomeric compound according to the following chemical structure:
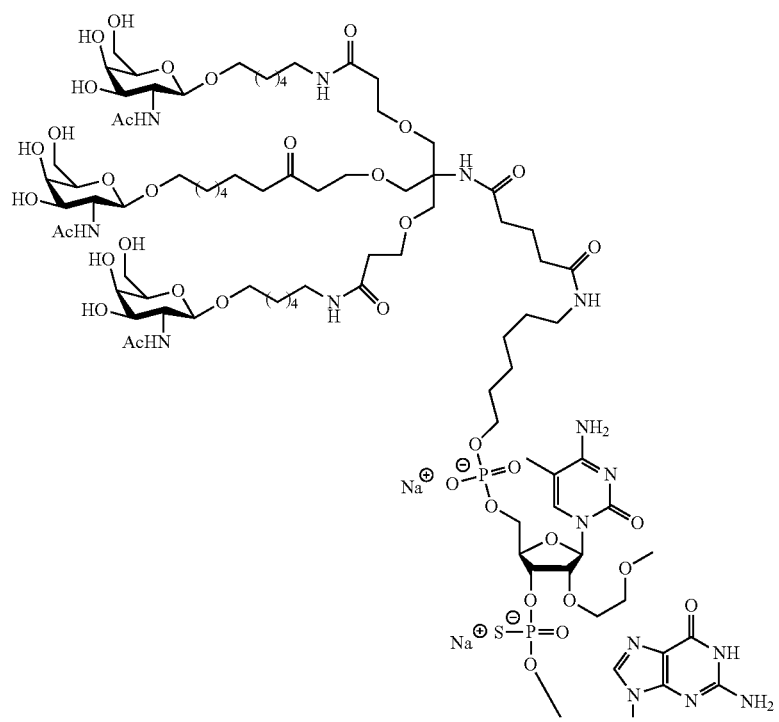

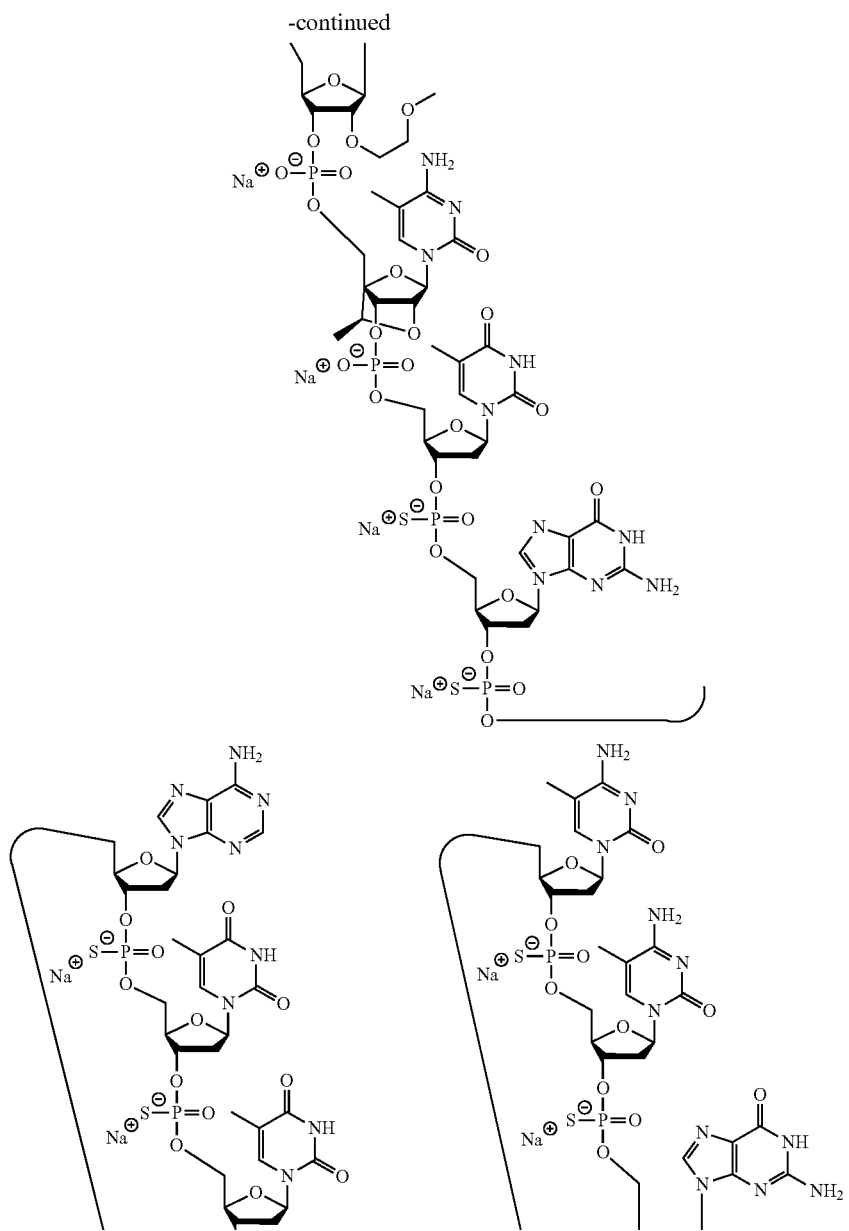

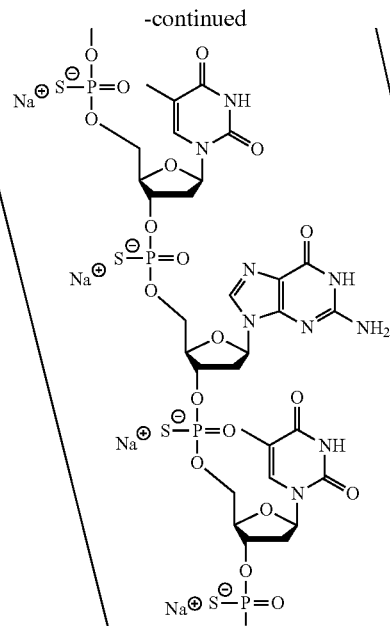
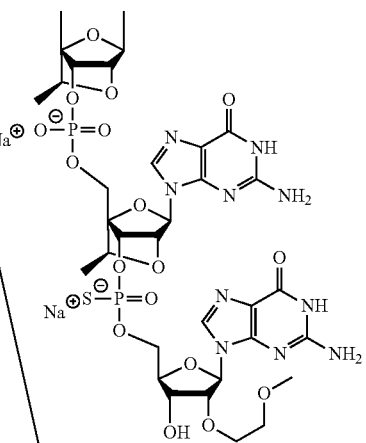

(SEQ ID NO: 12).

4. An oligomeric compound comprising a modified oligonucleotide according to the following chemical notation: $^mC_{es}G_{eo}{}^mC_{ko}T_{ds}G_{ds}A_{ds}T_{ds}T_{ds}T_{ds}G_{ds}T_{ds}{}^mC_{ds}{}^mC_{ds}G_{ko}G_{ks}G_e$ (SEQ ID NO: 12), wherein:

A=an adenine nucleobase,
$^mC$=a 5-methyl cytosine nucleobase,
G=a guanine nucleobase,
T=a thymine nucleobase,
e=a 2'-β-D-MOE sugar moiety,
k=a cEt sugar moiety,
d=a 2'-β-D-deoxyribosyl sugar moiety,
s=a phosphorothioate internucleoside linkage, and
o=a phosphodiester internucleoside linkage.

5. The oligomeric compound of claim 4, comprising the modified oligonucleotide covalently linked to a conjugate group.

6. A population of oligomeric compounds of claim 1, in which all phosphorothioate internucleoside linkages of the oligomeric compound are stereorandom.

7. A pharmaceutical composition comprising the oligomeric compound of claim 1 and a pharmaceutically acceptable carrier or diluent.

8. The pharmaceutical composition of claim 7, wherein the pharmaceutically acceptable diluent is water or PBS.

9. A pharmaceutical composition comprising the population of claim 6 and a pharmaceutically acceptable carrier or diluent.

10. A population of oligomeric compounds of claim 2, in which all phosphorothioate internucleoside linkages of the oligomeric compound are stereorandom.

11. A pharmaceutical composition comprising the oligomeric compound of claim 2 and a pharmaceutically acceptable carrier or diluent.

12. The pharmaceutical composition of claim 11, wherein the pharmaceutically acceptable diluent is water or PBS.

13. A pharmaceutical composition comprising the population of claim 10 and a pharmaceutically acceptable carrier or diluent.

14. A population of oligomeric compounds of claim 3, in which all phosphorothioate internucleoside linkages of the oligomeric compound are stereorandom.

15. A pharmaceutical composition comprising the oligomeric compound of claim 3 and a pharmaceutically acceptable carrier or diluent.

16. The pharmaceutical composition of claim 15, wherein the pharmaceutically acceptable diluent is water or PBS.

17. A pharmaceutical composition comprising the population of claim 14 and a pharmaceutically acceptable carrier or diluent.

18. A population of oligomeric compounds of claim 4 in which all phosphorothioate internucleoside linkages of the oligomeric compound are stereorandom.

19. A pharmaceutical composition comprising the oligomeric compound of claim 4 and a pharmaceutically acceptable carrier or diluent.

20. The pharmaceutical composition of claim 19, wherein the pharmaceutically acceptable diluent is water or PBS.

21. A pharmaceutical composition comprising the population of claim 18 and a pharmaceutically acceptable carrier or diluent.

22. A population of oligomeric compounds of claim 5, in which all phosphorothioate internucleoside linkages of the oligomeric compound are stereorandom.

23. A pharmaceutical composition comprising the oligomeric compound of claim 5 and a pharmaceutically acceptable carrier or diluent.

24. The pharmaceutical composition of claim 23, wherein the pharmaceutically acceptable diluent is water or PBS.

25. A pharmaceutical composition comprising the population of claim 22 and a pharmaceutically acceptable carrier or diluent.

* * * * *

UNITED STATES PATENT AND TRADEMARK OFFICE
CERTIFICATE OF CORRECTION

PATENT NO. : 11,447,521 B2
APPLICATION NO. : 17/529897
DATED : September 20, 2022
INVENTOR(S) : Adam Mullick and Susan M. Freier Page 1 of 46

It is certified that error appears in the above-identified patent and that said Letters Patent is hereby corrected as shown below:

In the Specification

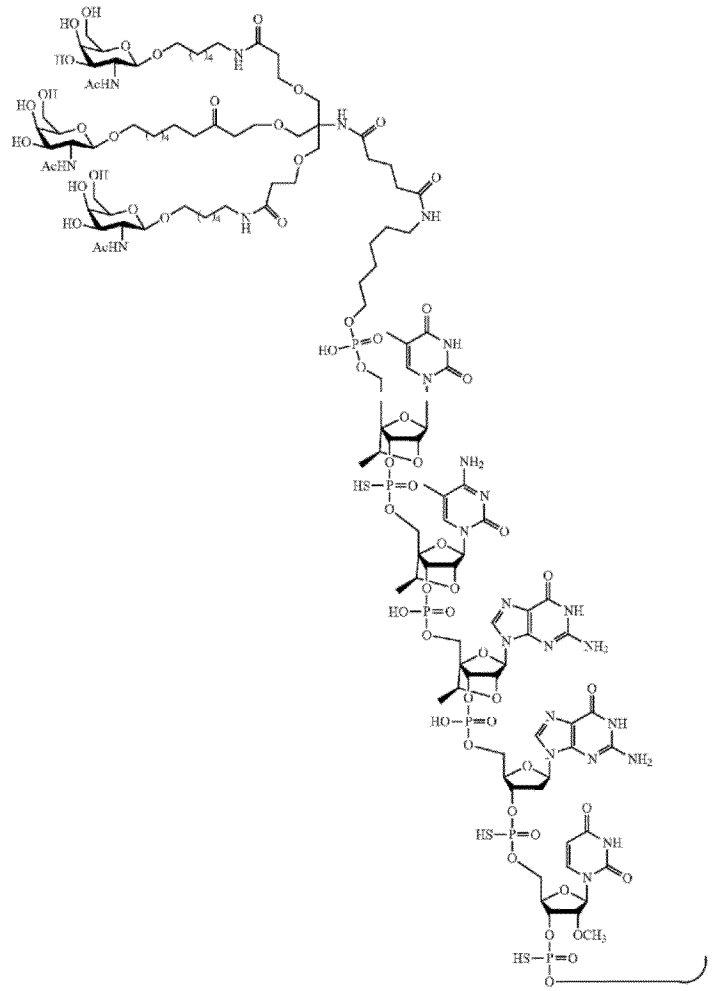

Columns 65-68, change "

Signed and Sealed this
Thirty-first Day of October, 2023

Katherine Kelly Vidal
*Director of the United States Patent and Trademark Office*

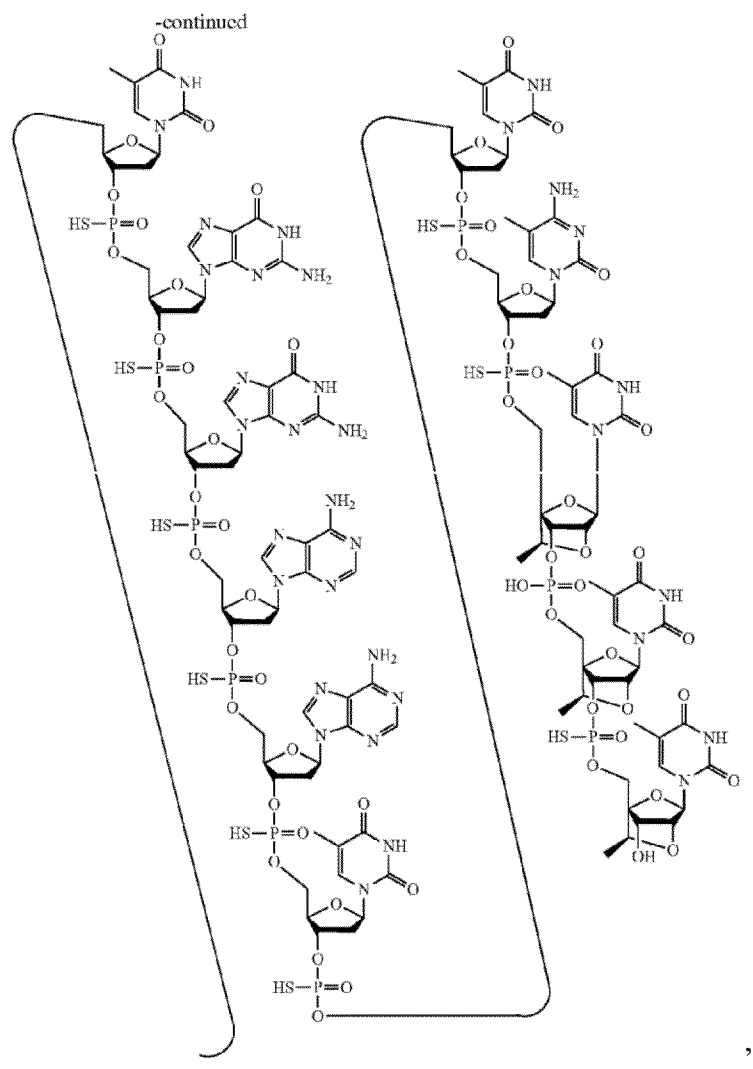
" to

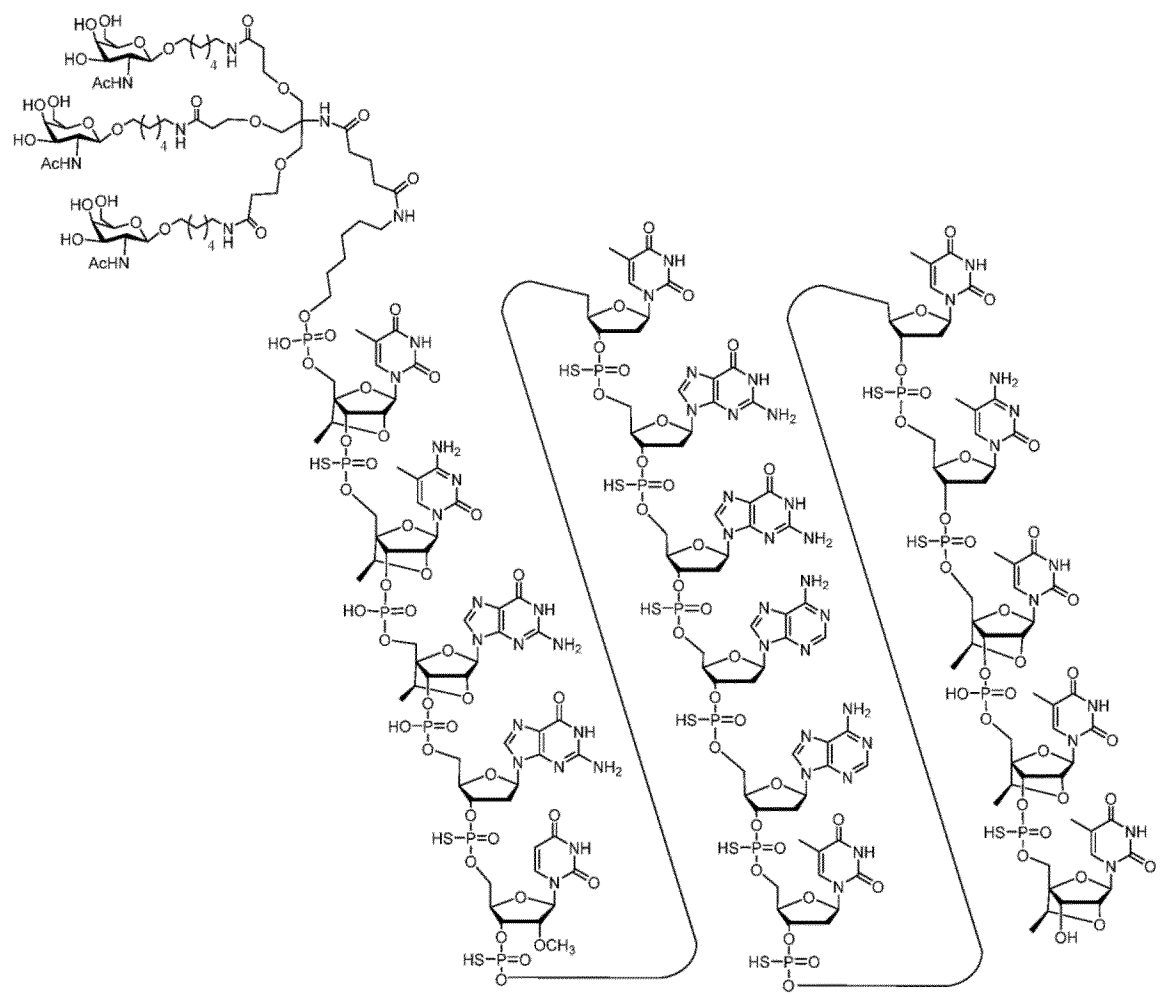
--  --.

CERTIFICATE OF CORRECTION (continued)
U.S. Pat. No. 11,447,521 B2

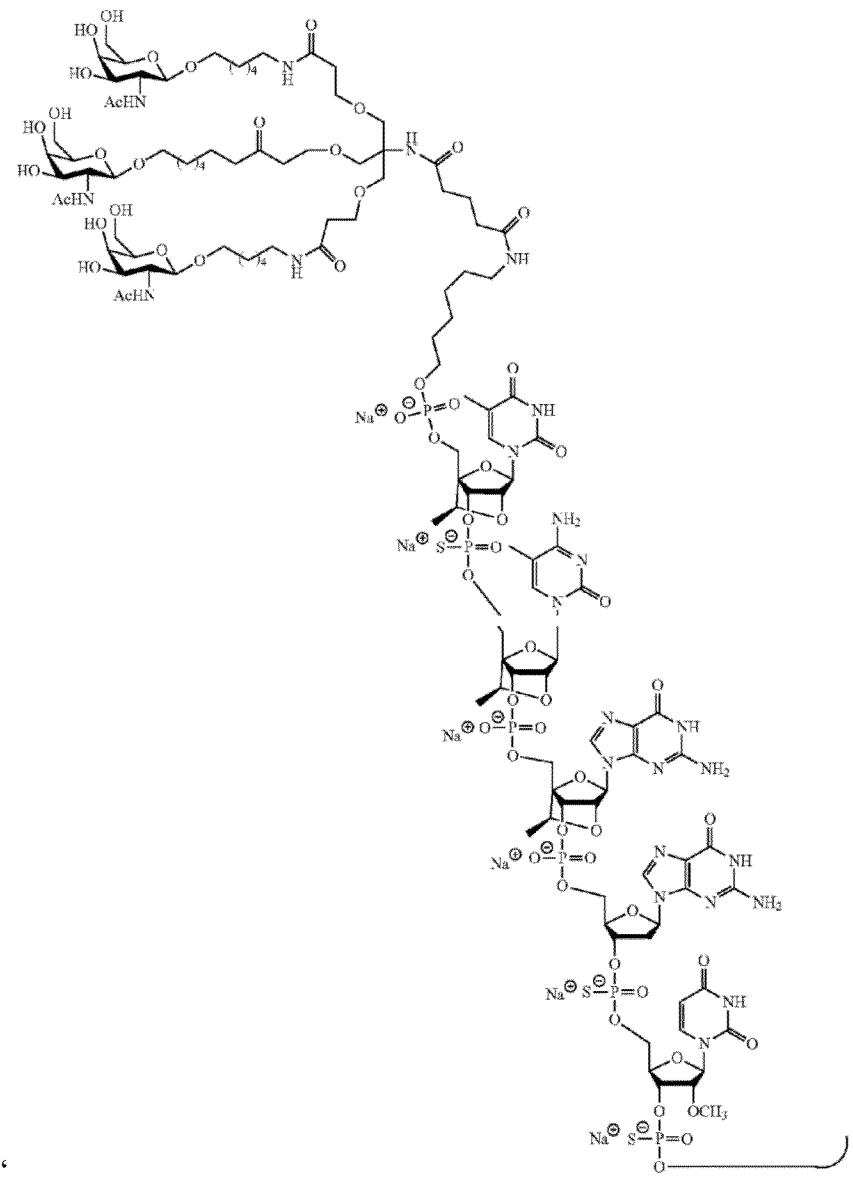

Columns 69-72, change "

-continued
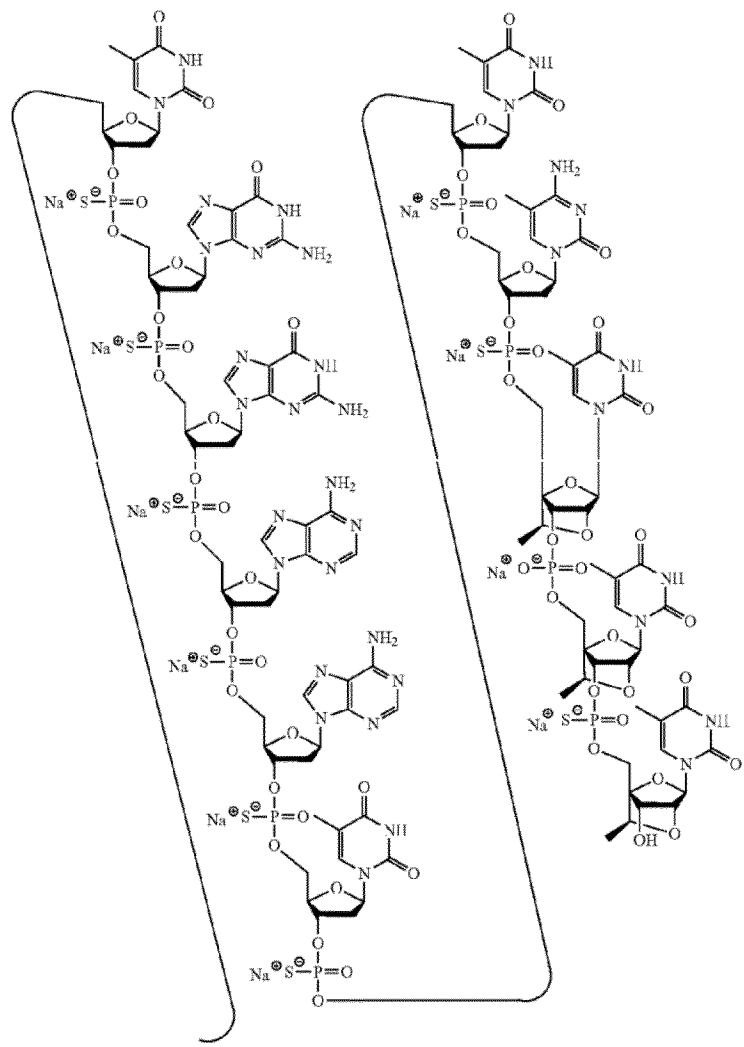
” to

CERTIFICATE OF CORRECTION (continued)
U.S. Pat. No. 11,447,521 B2

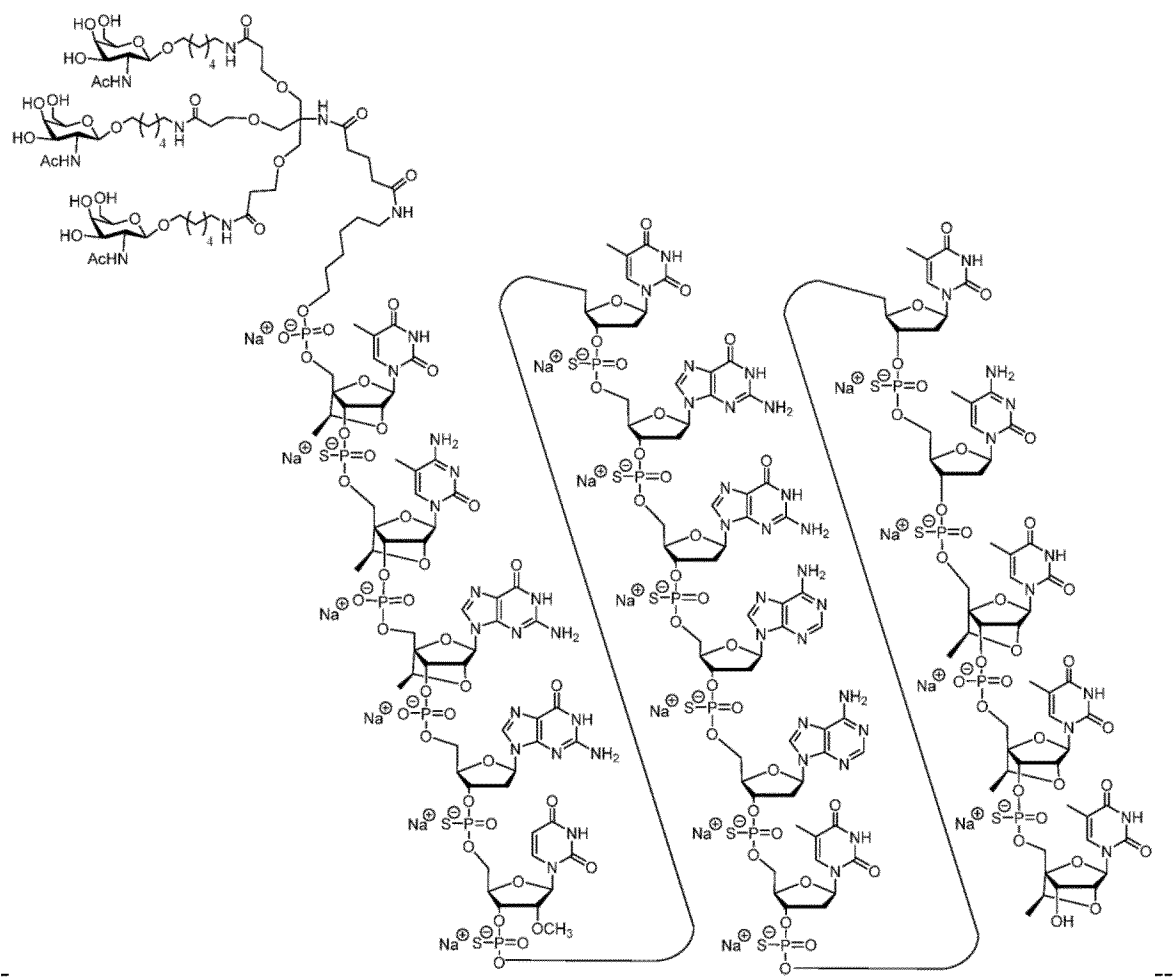

-- --.

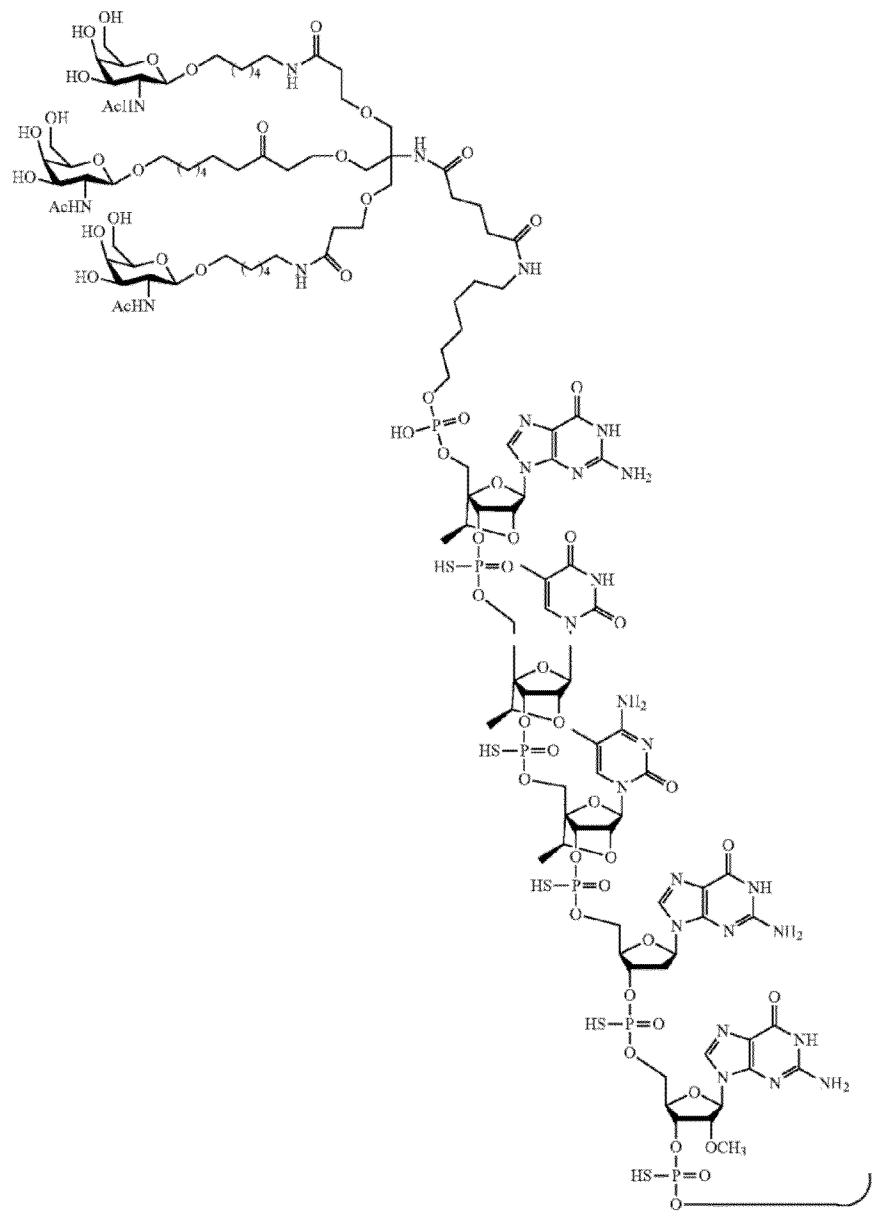
Columns 73-76, change "

-continued
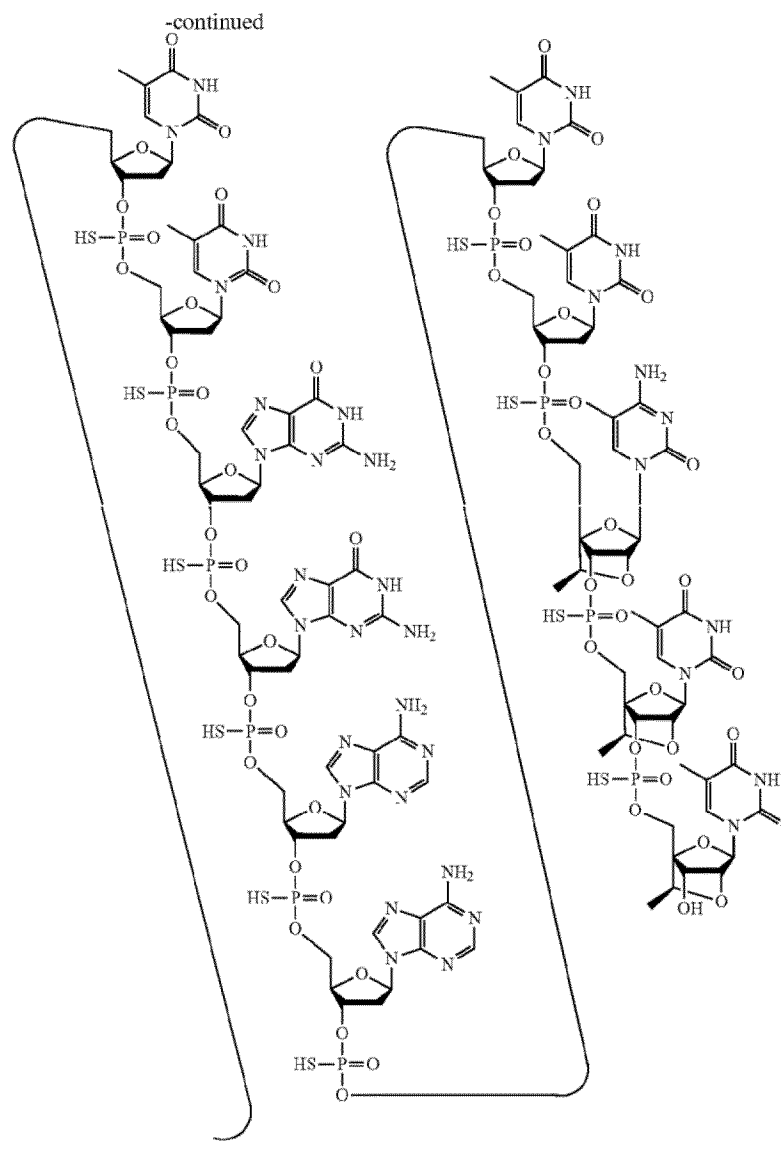
" to

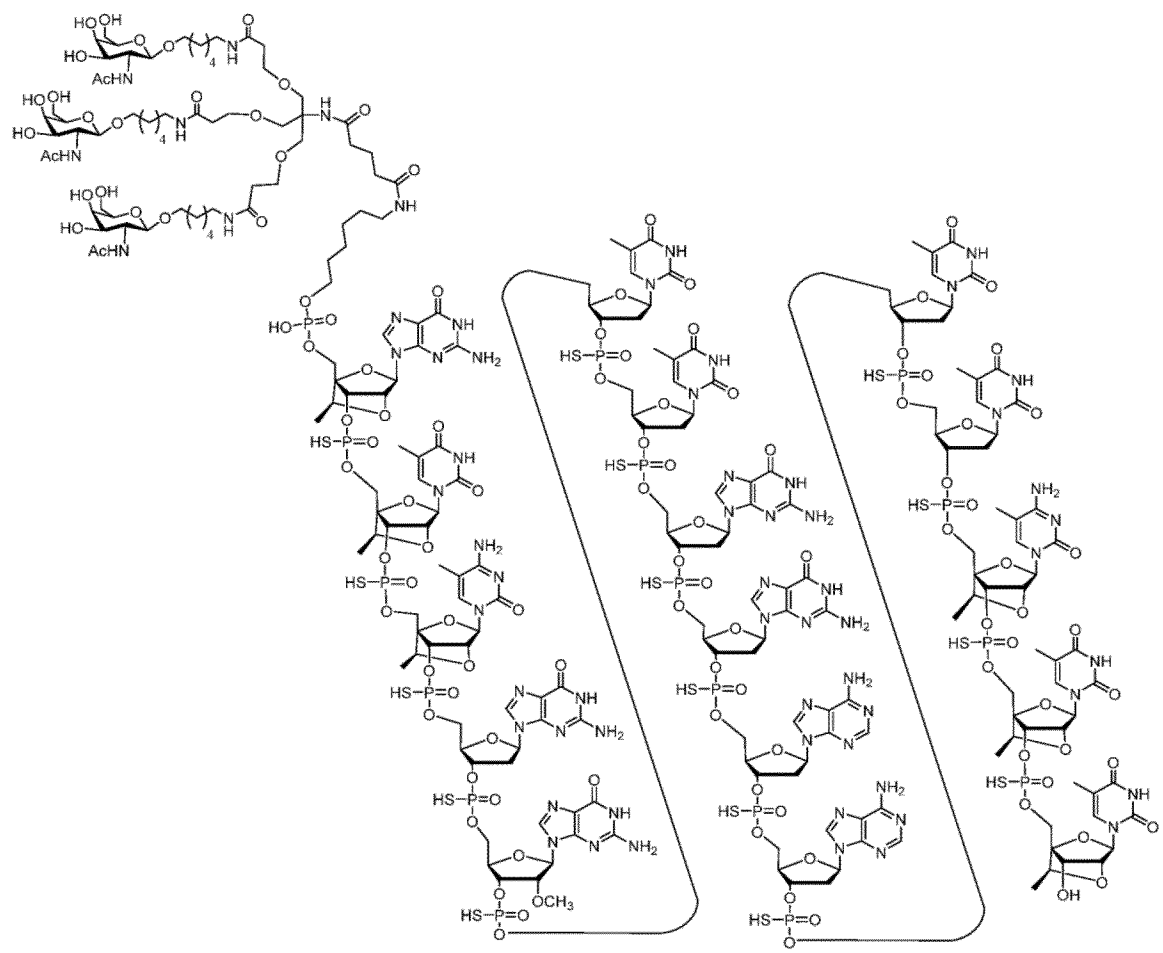

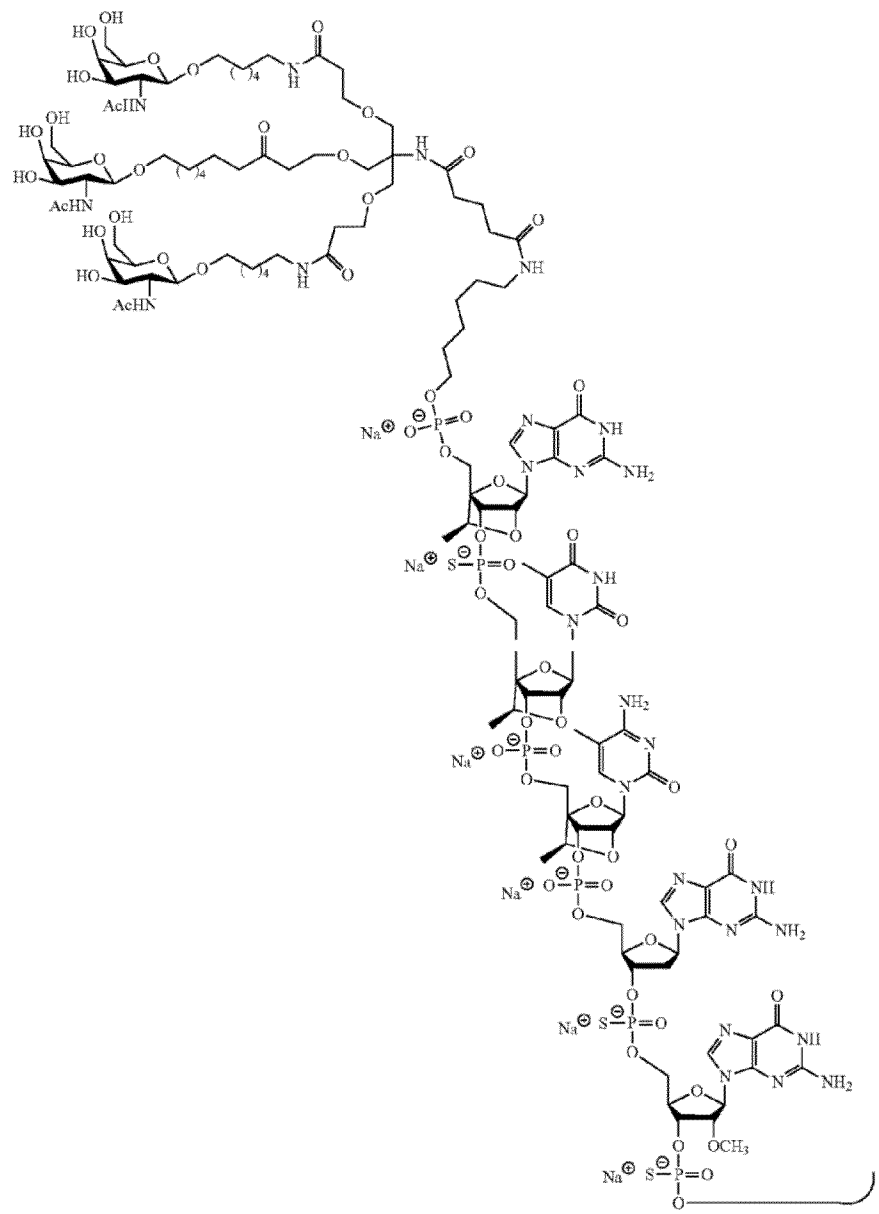
Columns 77-80, change "

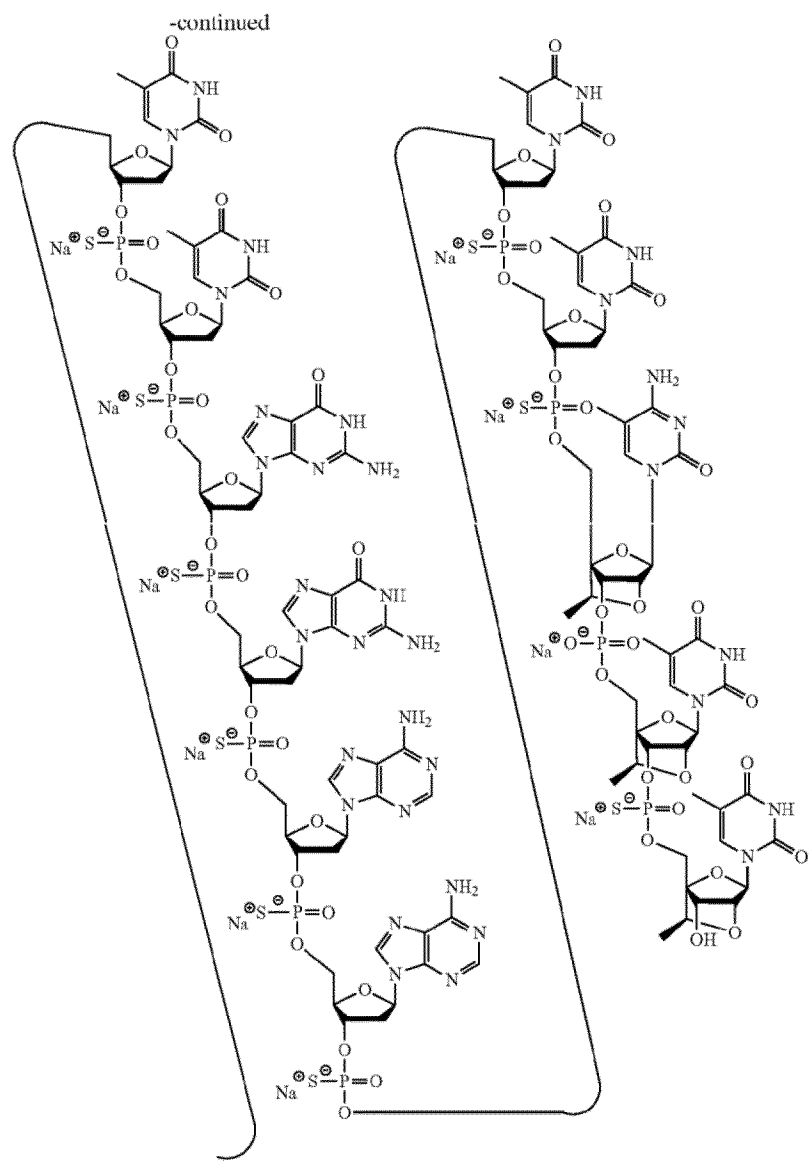
" to

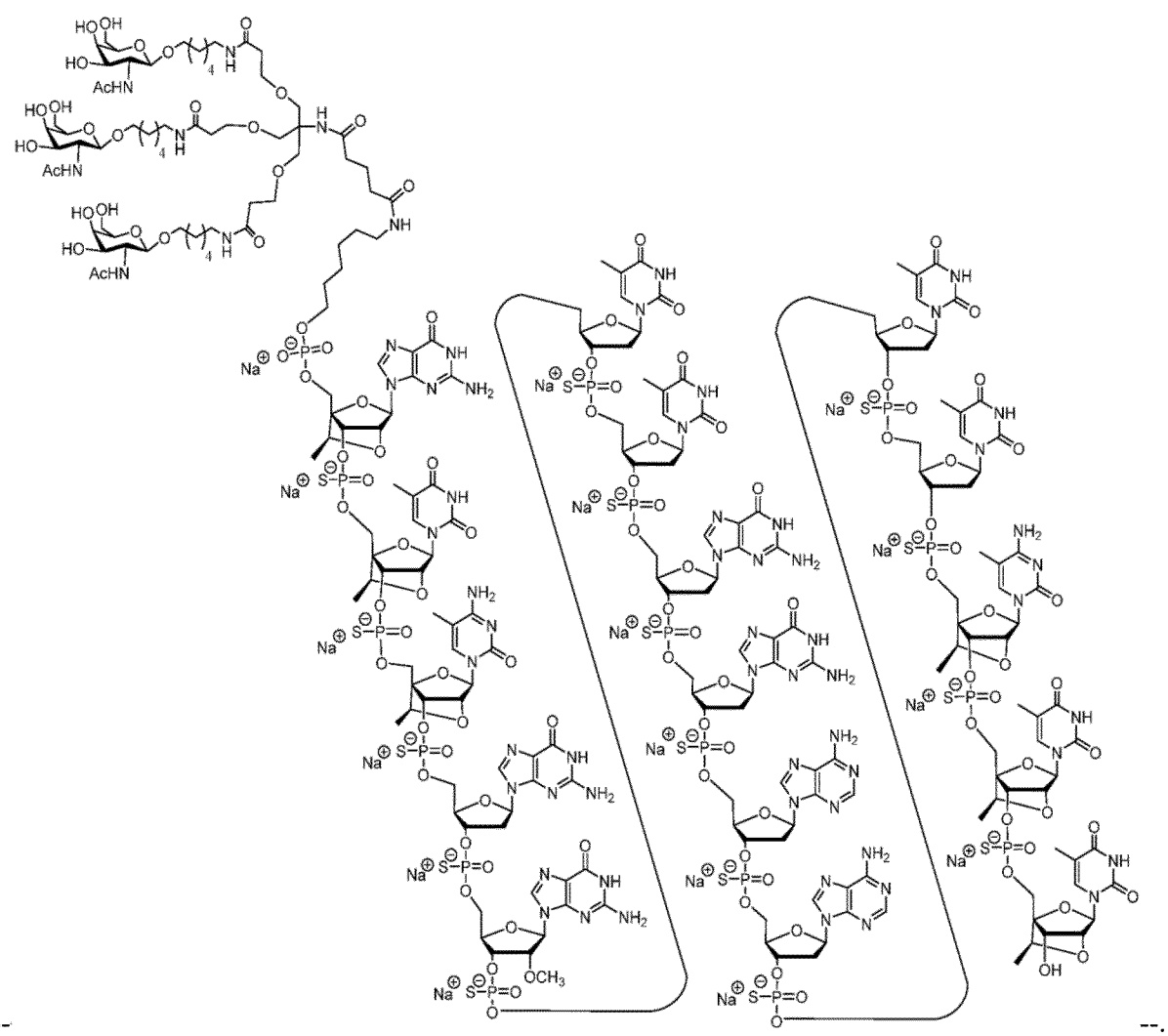
--    --.

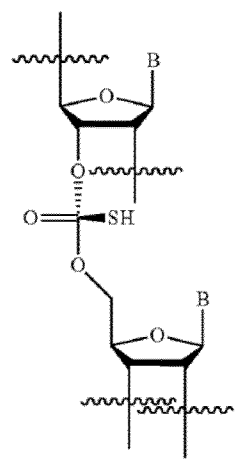
-continued
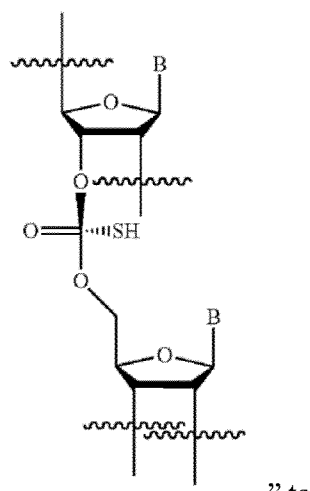
Columns 89-90, change " 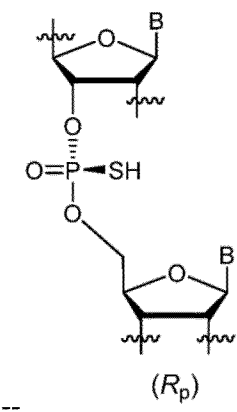 " to 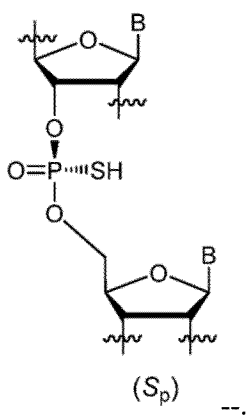 .

Columns 113-114, change
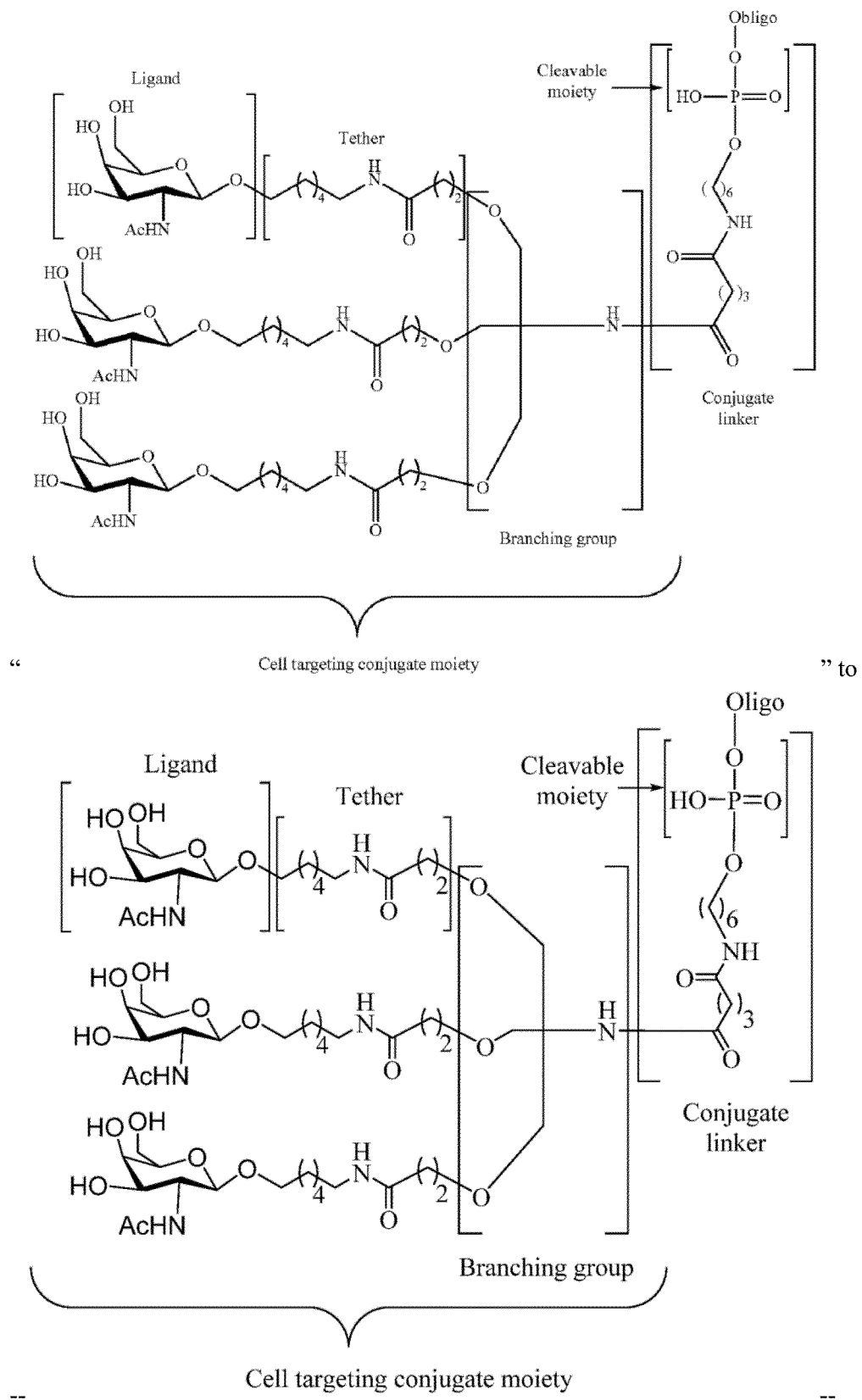

CERTIFICATE OF CORRECTION (continued)
U.S. Pat. No. 11,447,521 B2

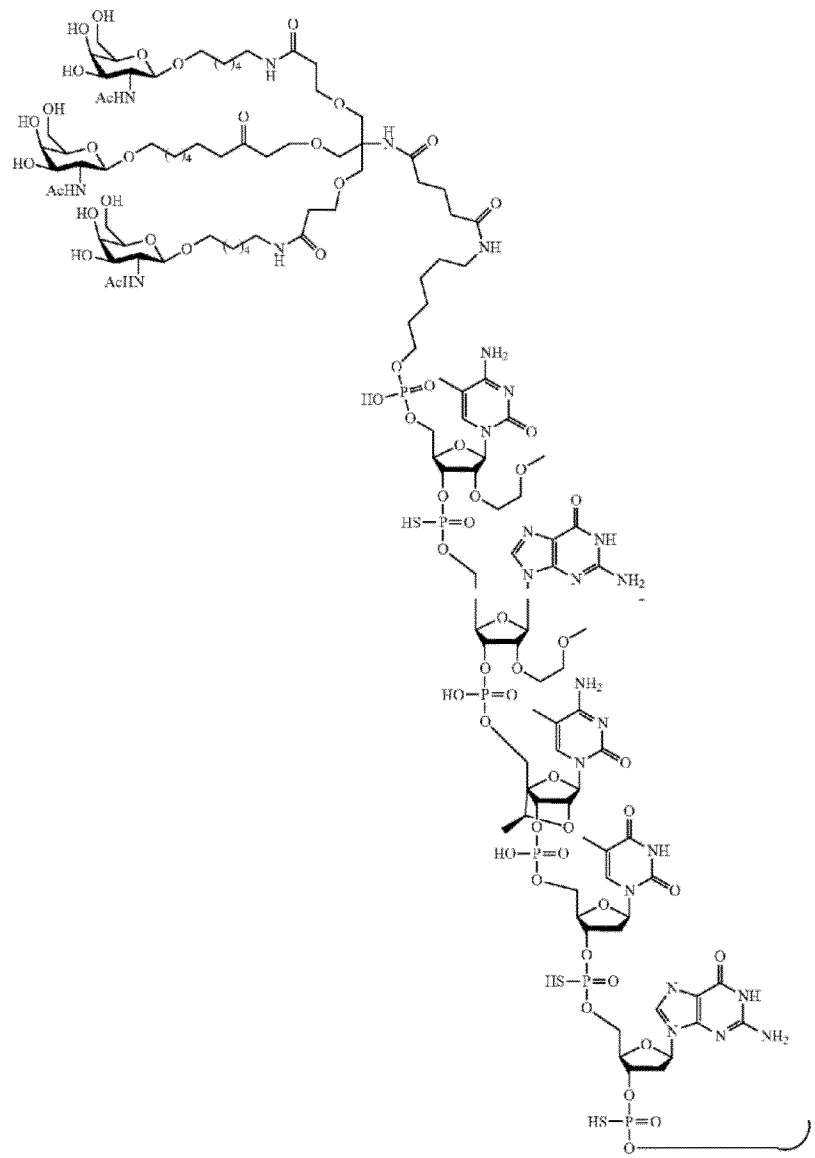

Columns 119-122, change "

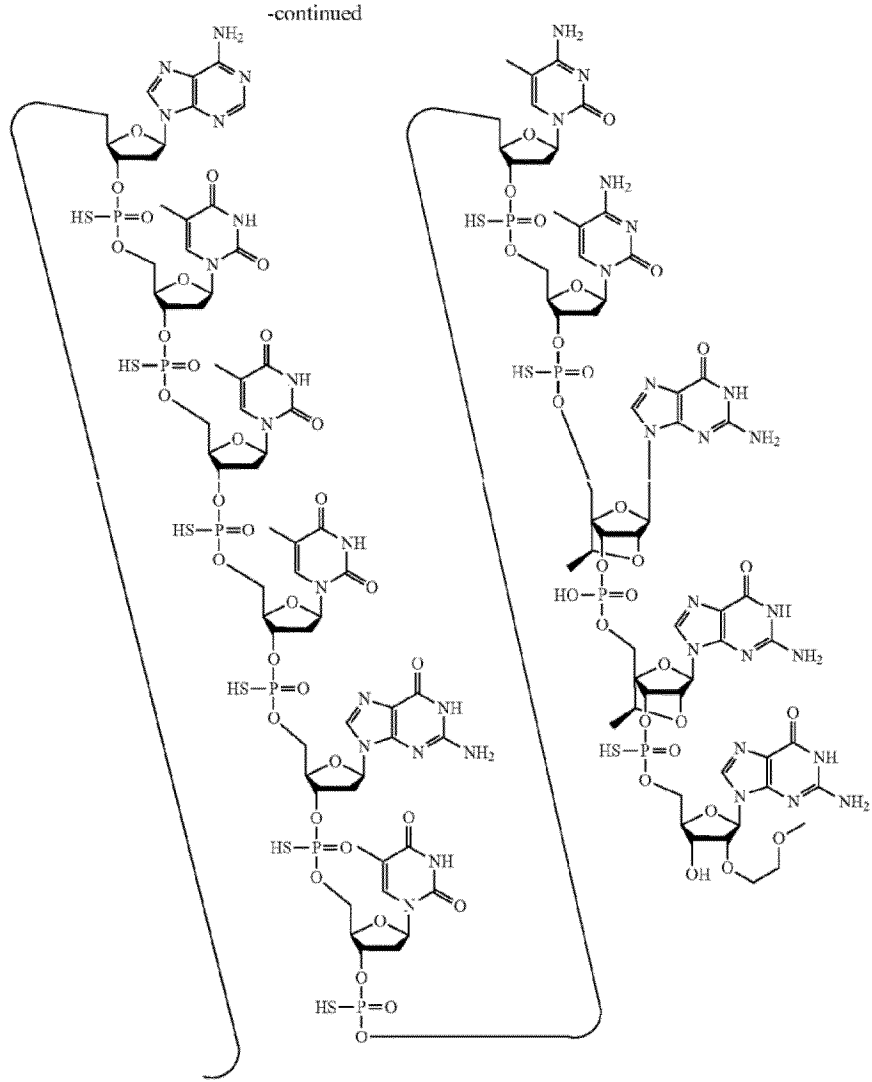
" to

CERTIFICATE OF CORRECTION (continued)
U.S. Pat. No. 11,447,521 B2

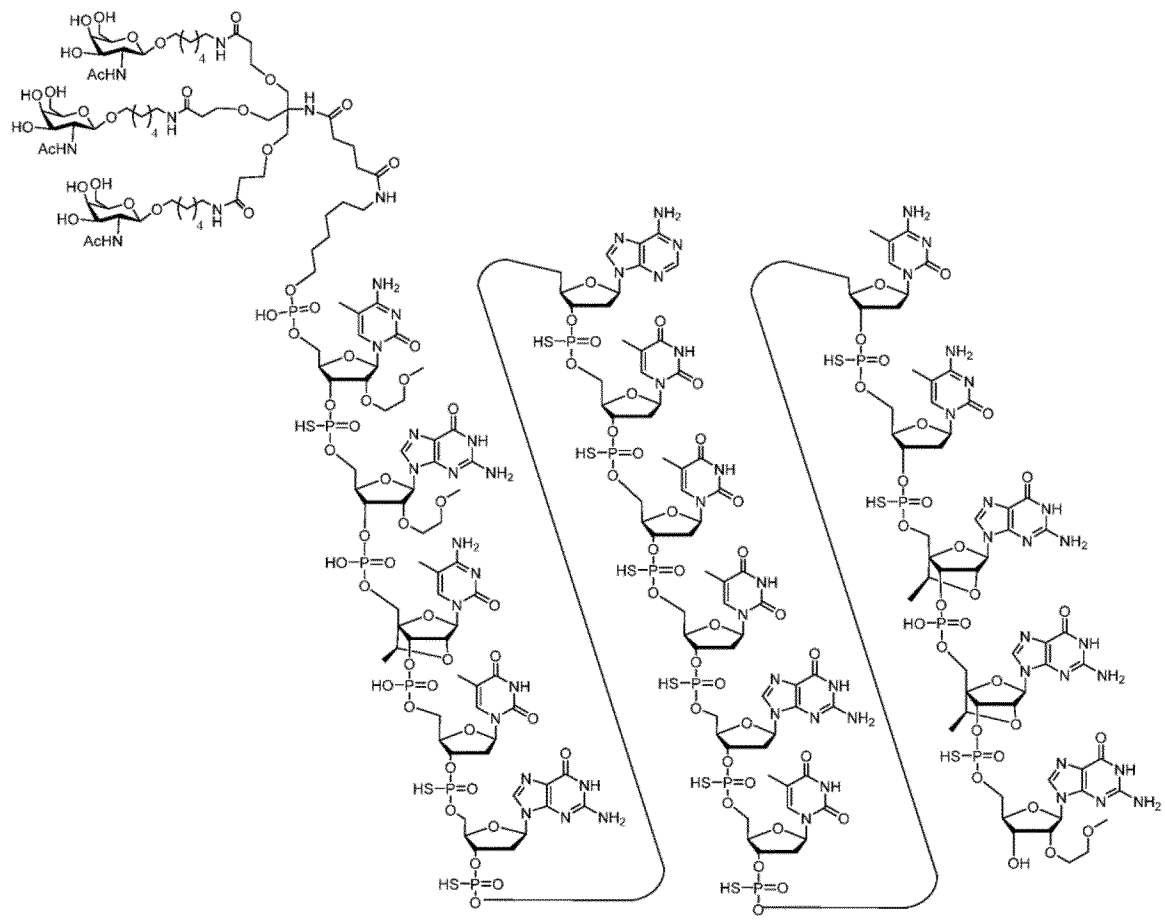

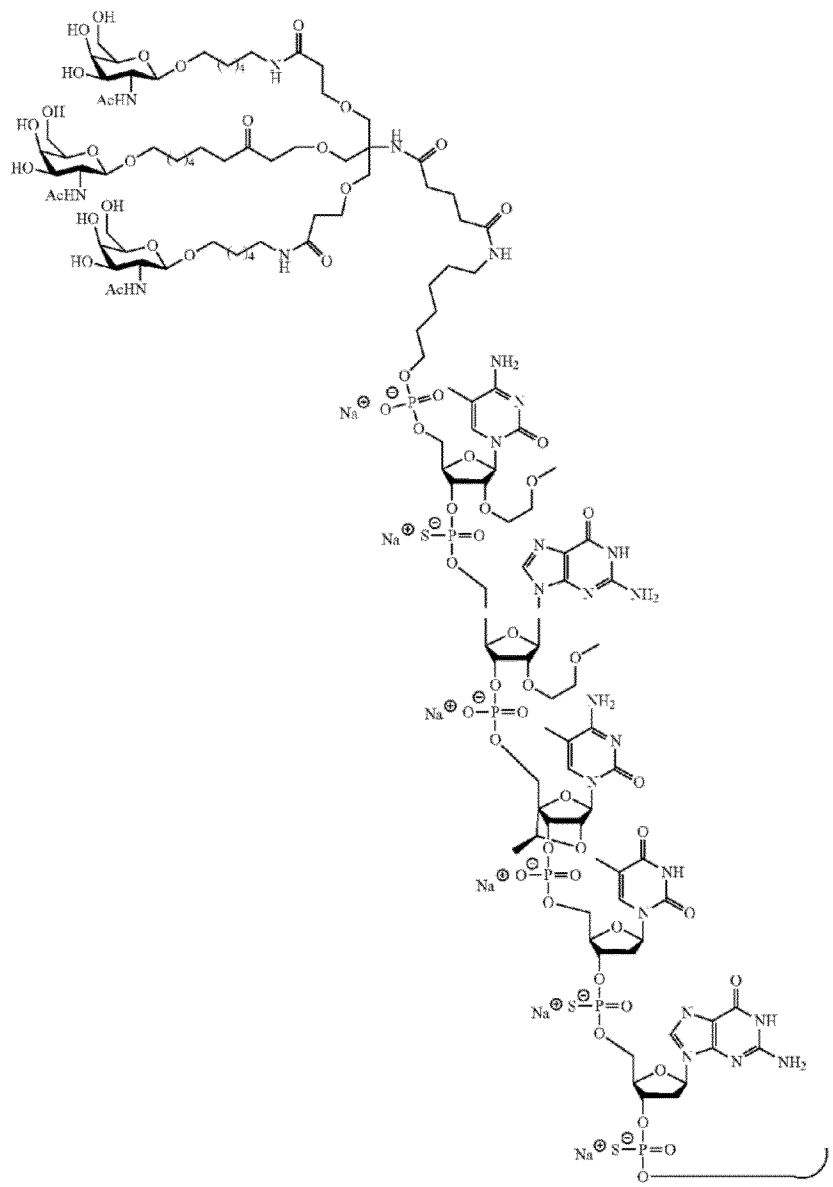
Columns 123-126, change "

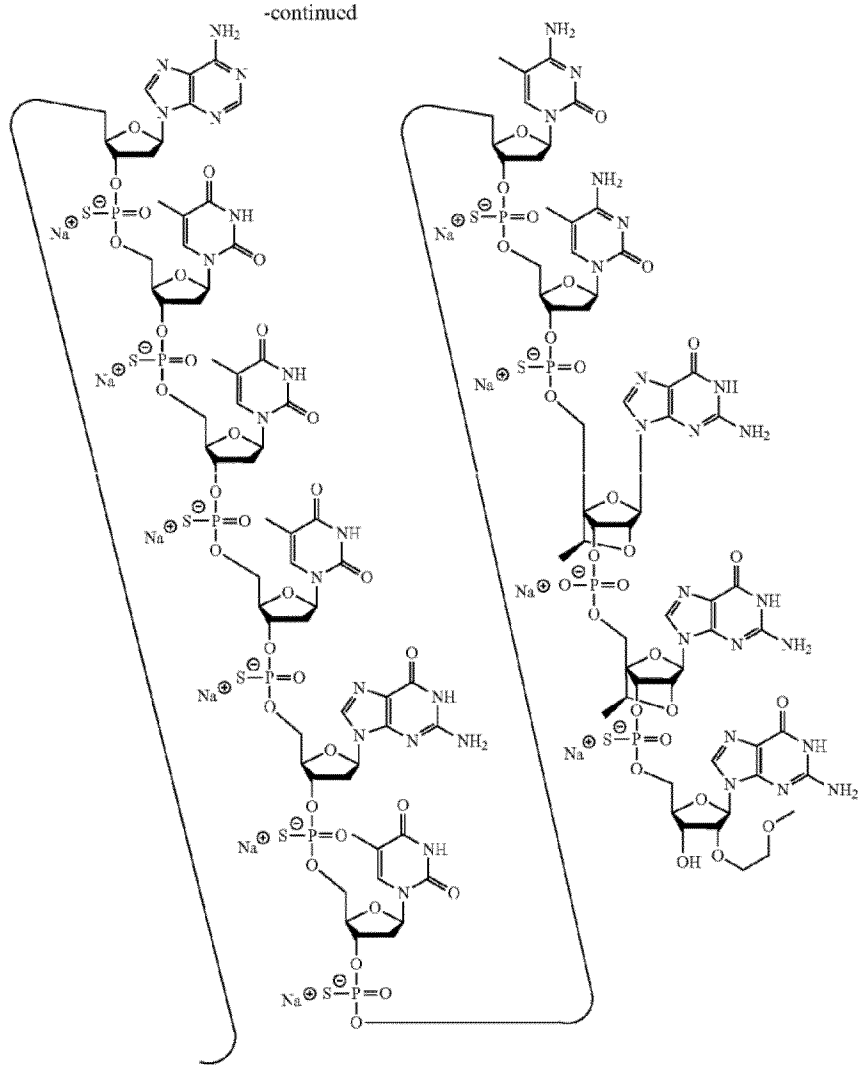
" to

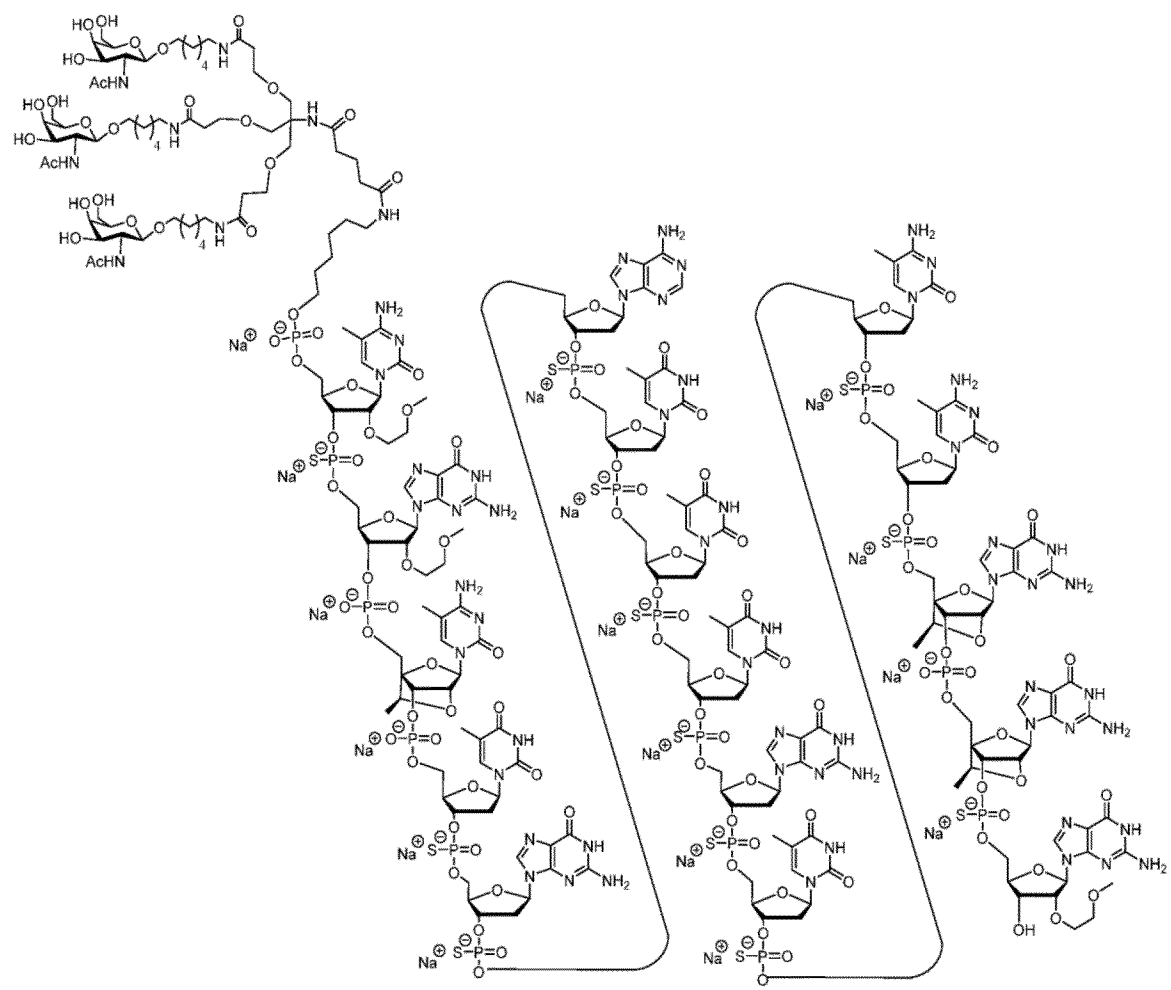

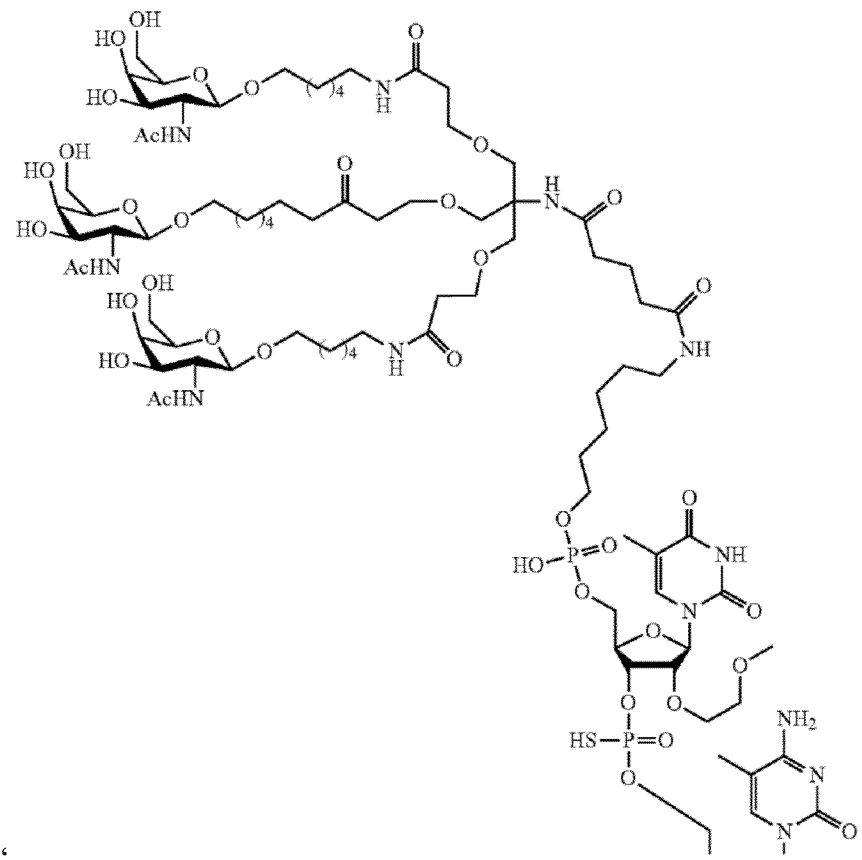
Columns 127-132, change "

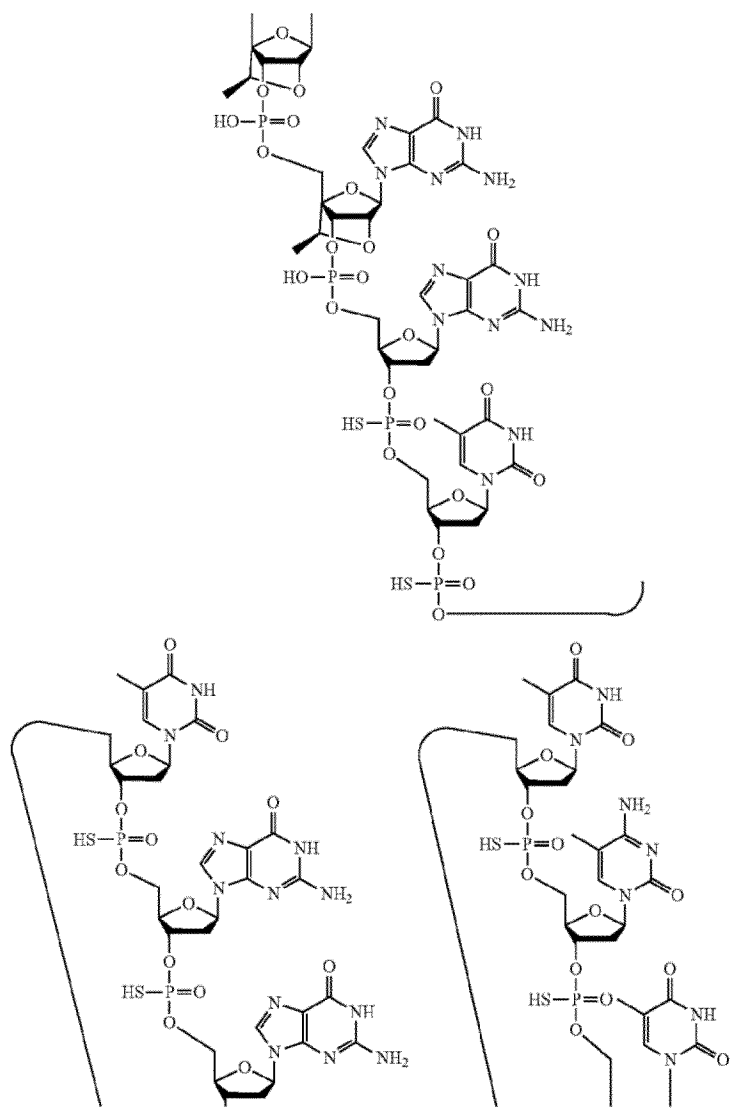

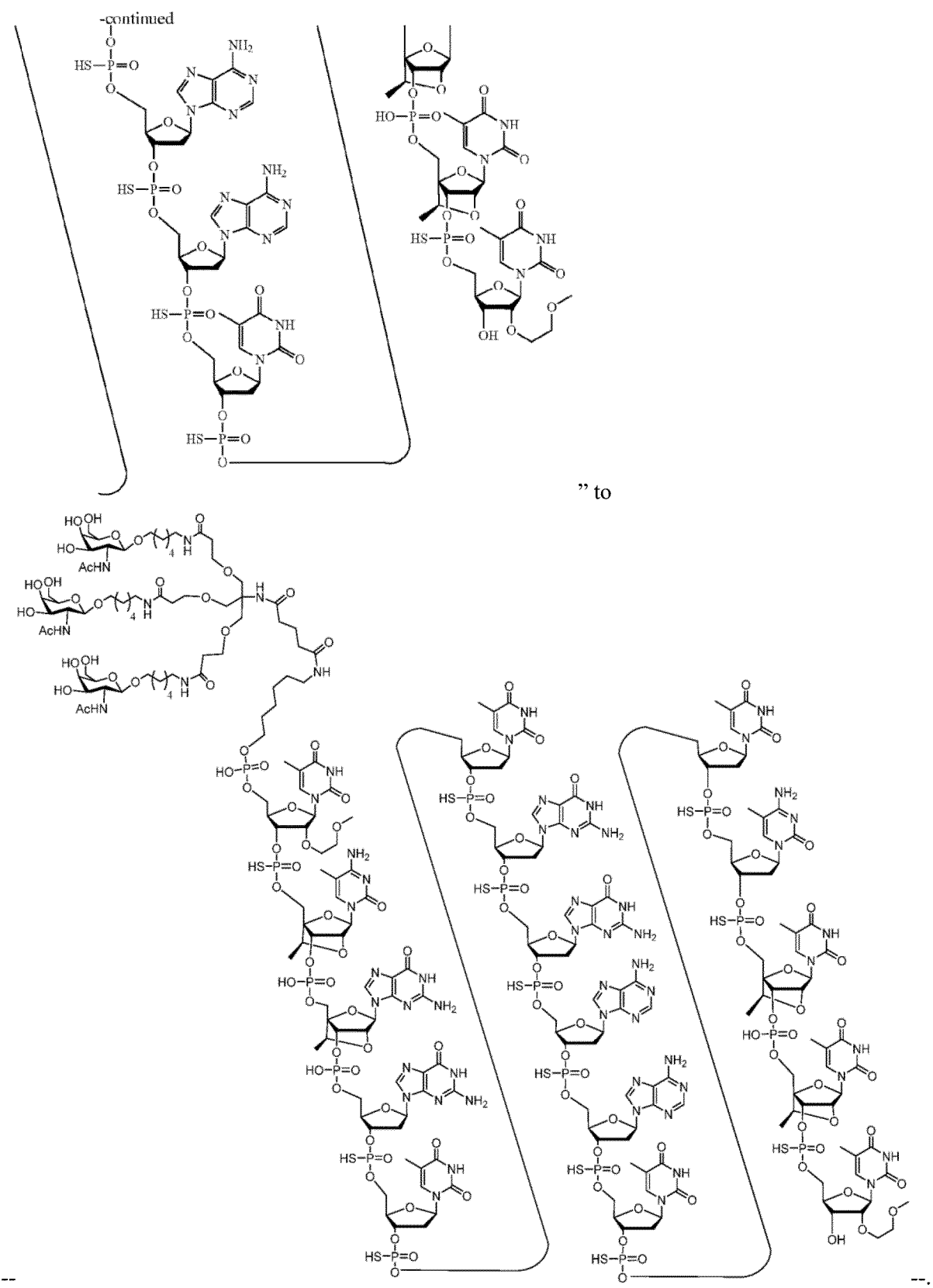

CERTIFICATE OF CORRECTION (continued)
U.S. Pat. No. 11,447,521 B2

Columns 131-136, change

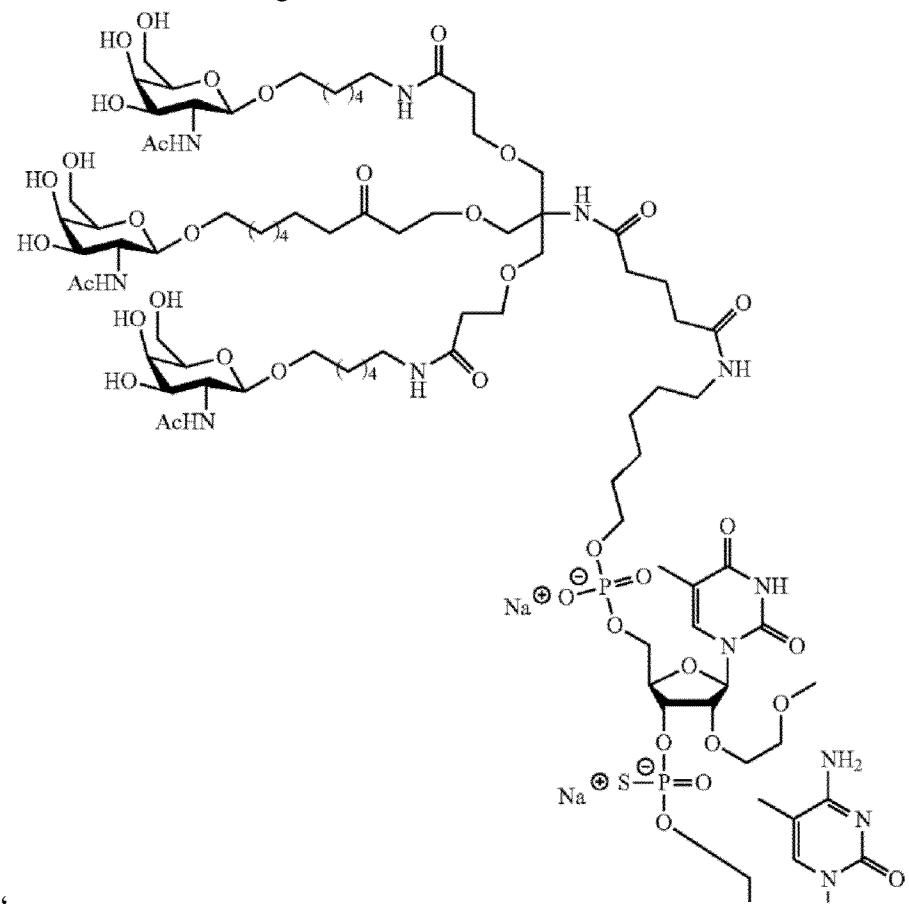

"

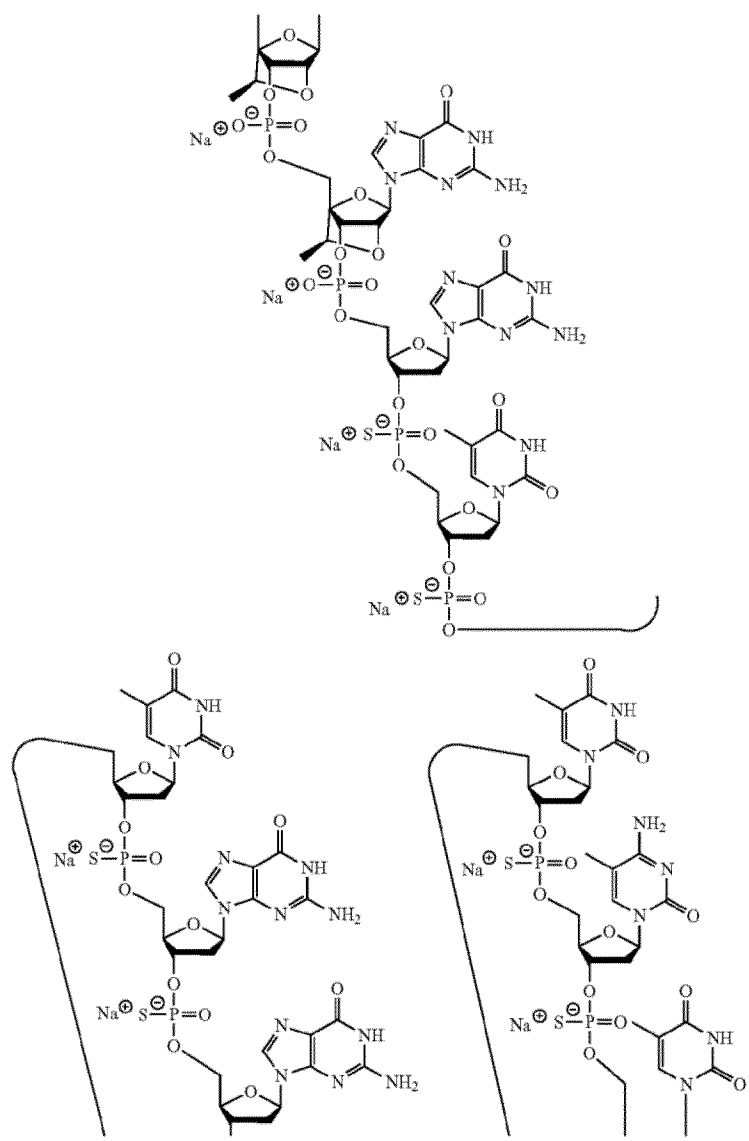

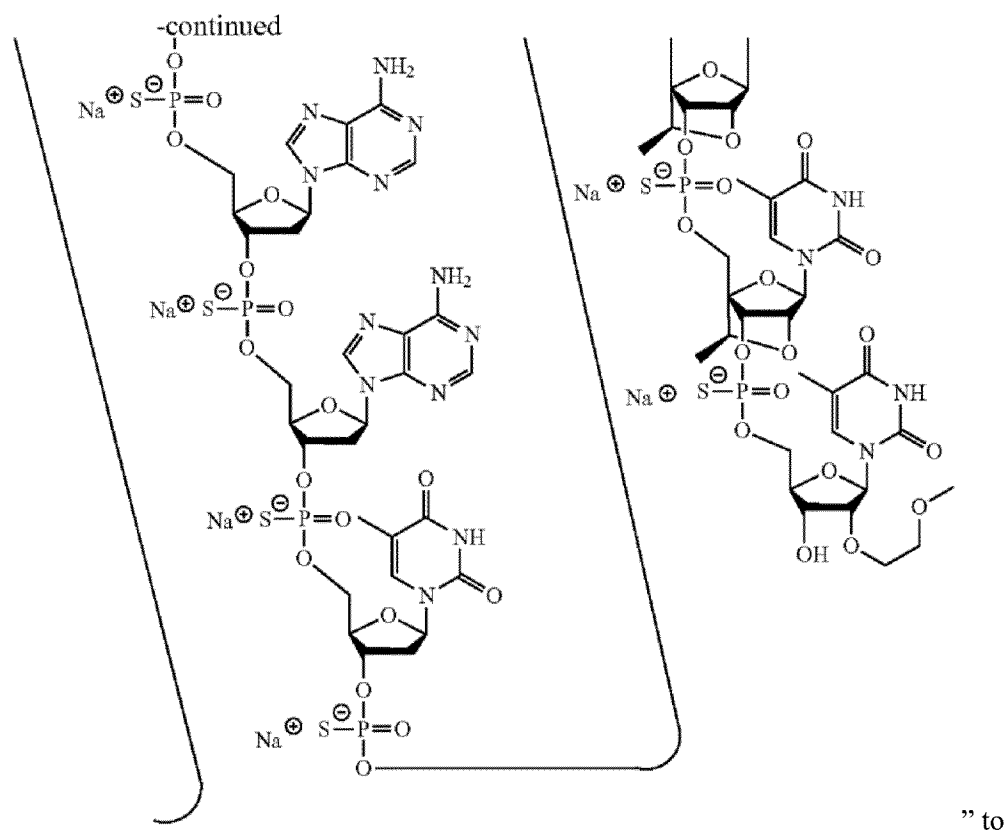
" to

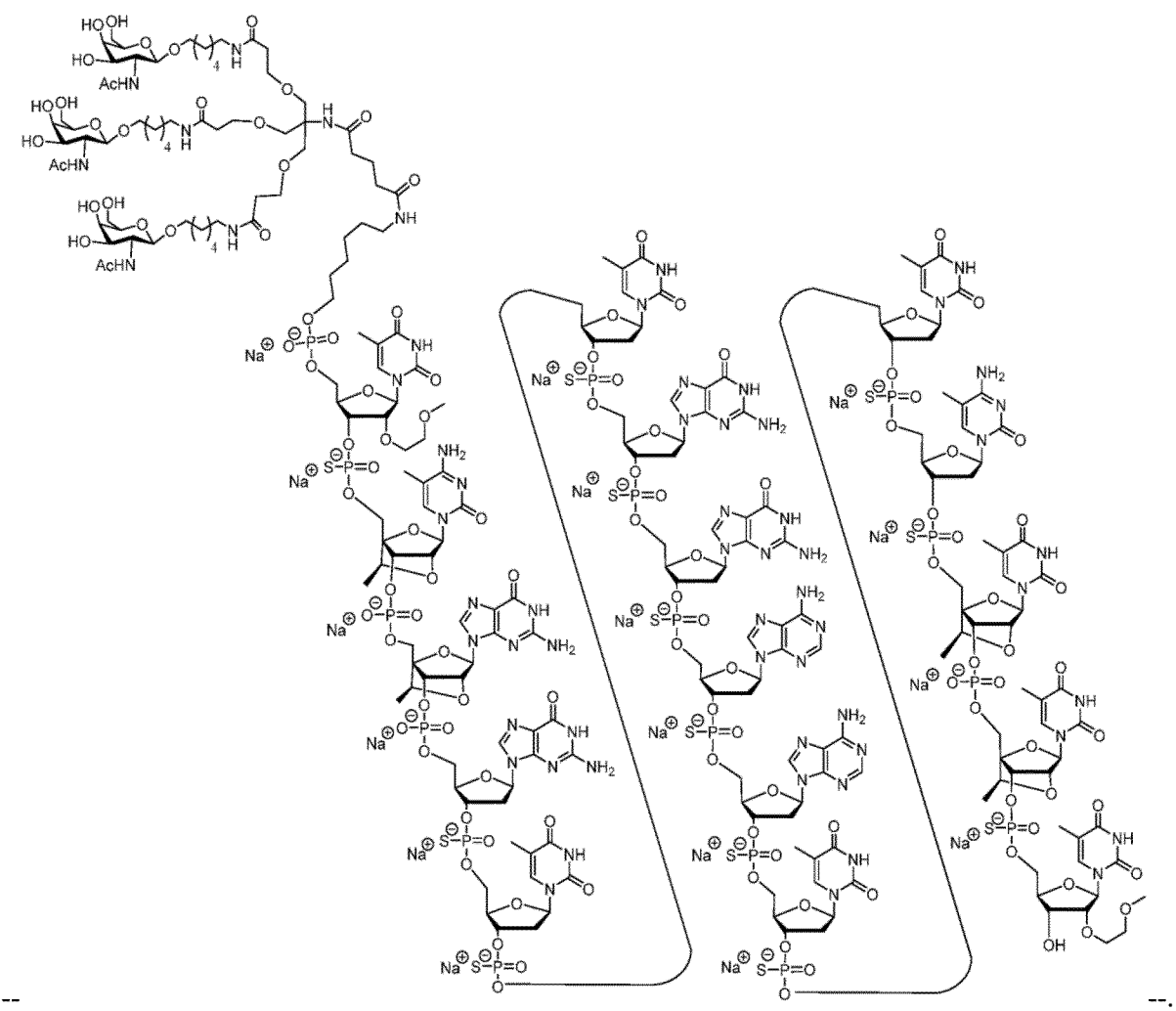

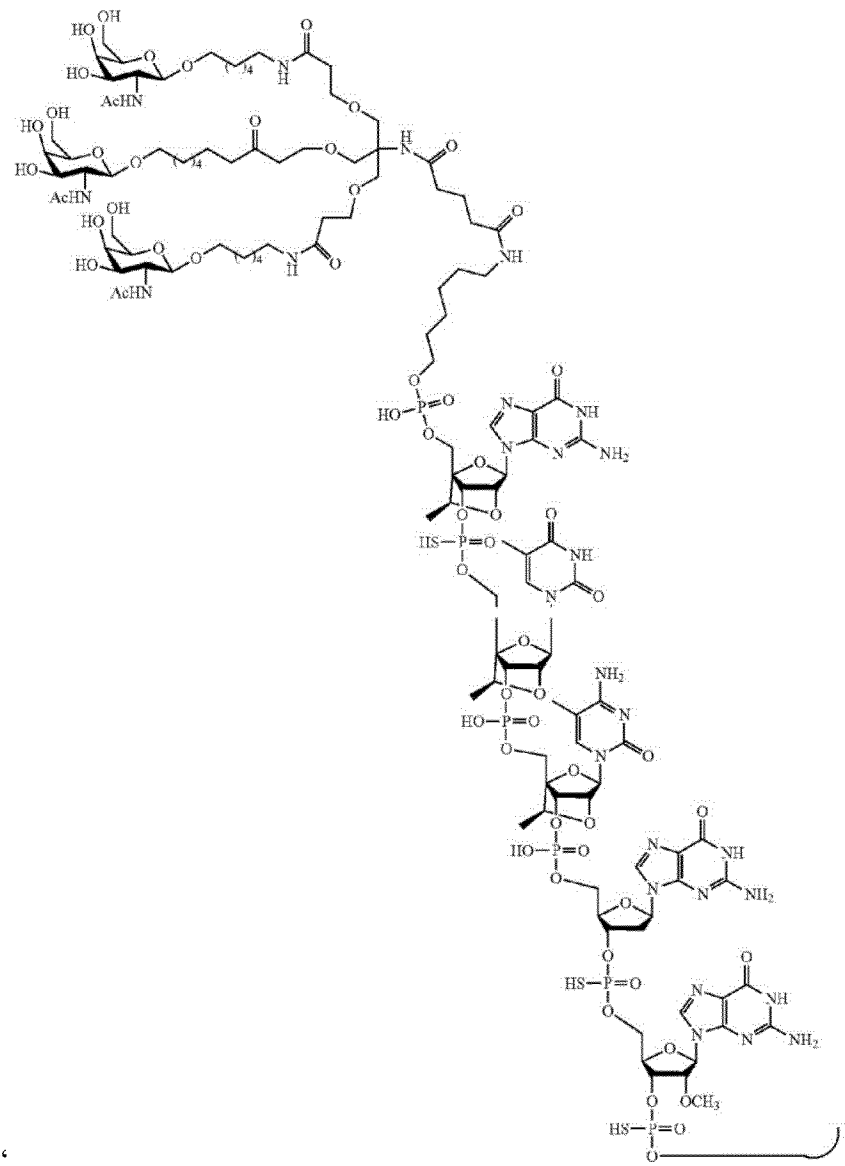
Columns 137-140, change "

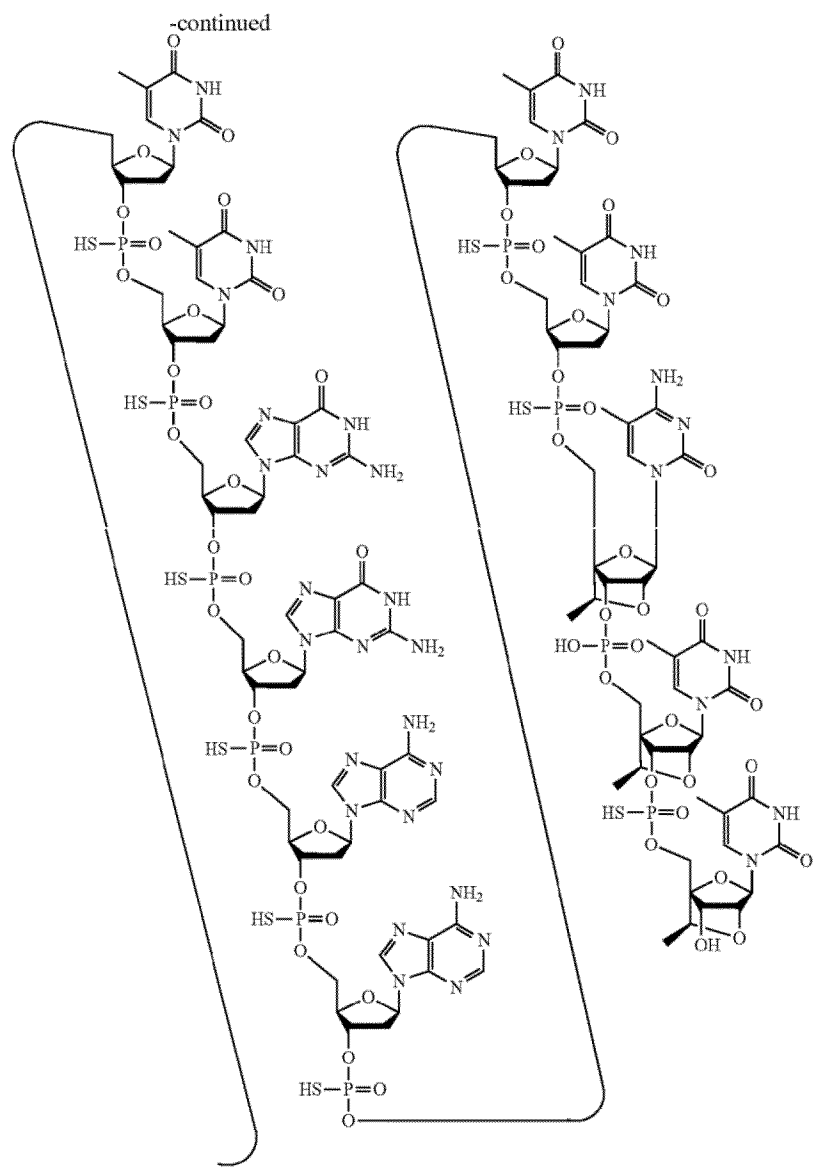
" to

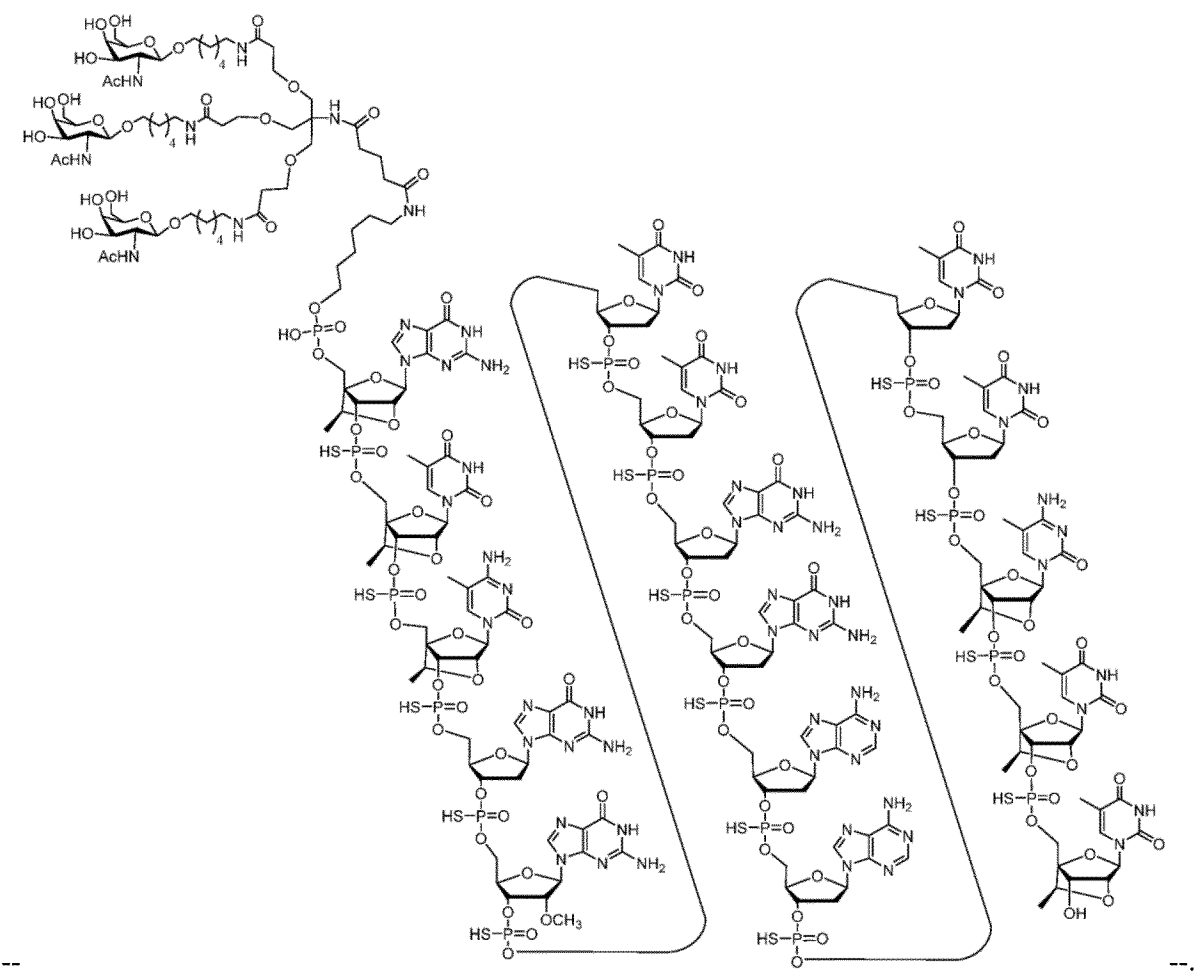

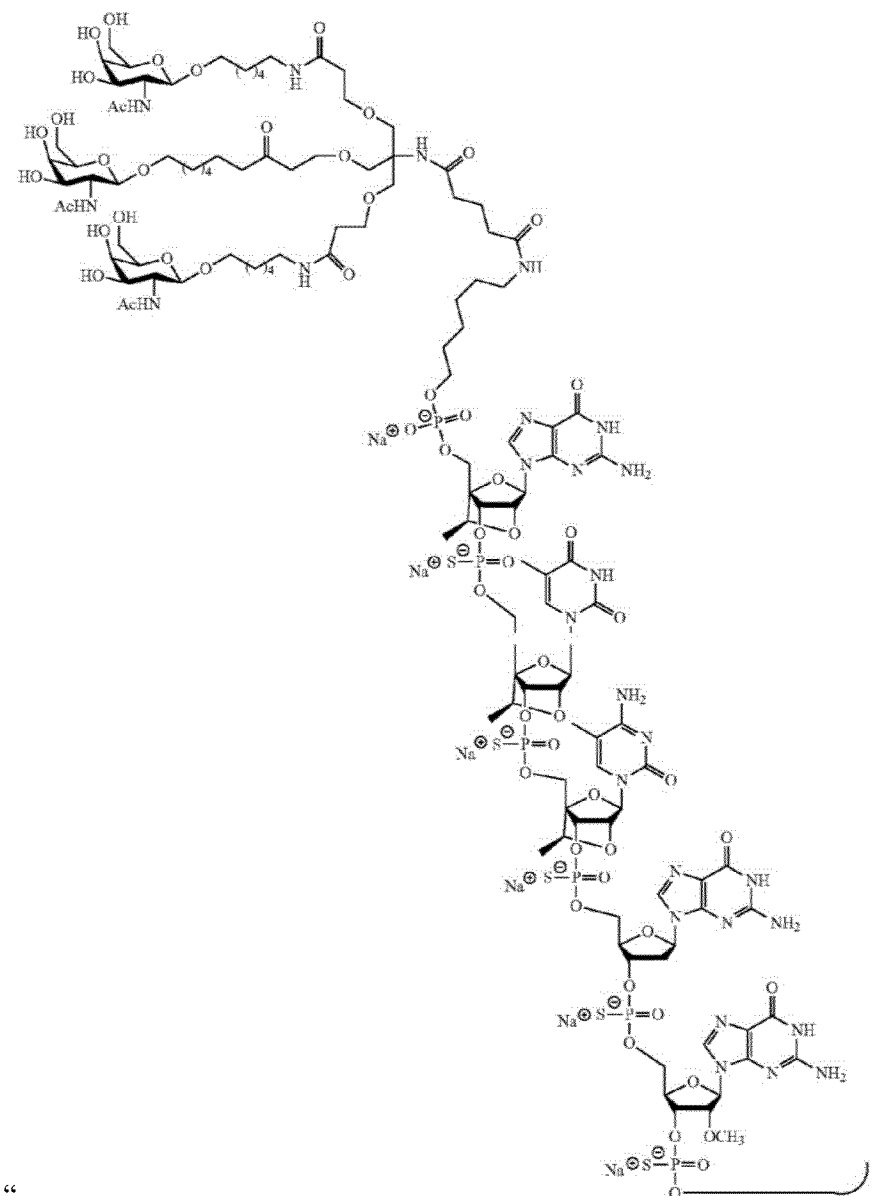
Columns 141-144, change "

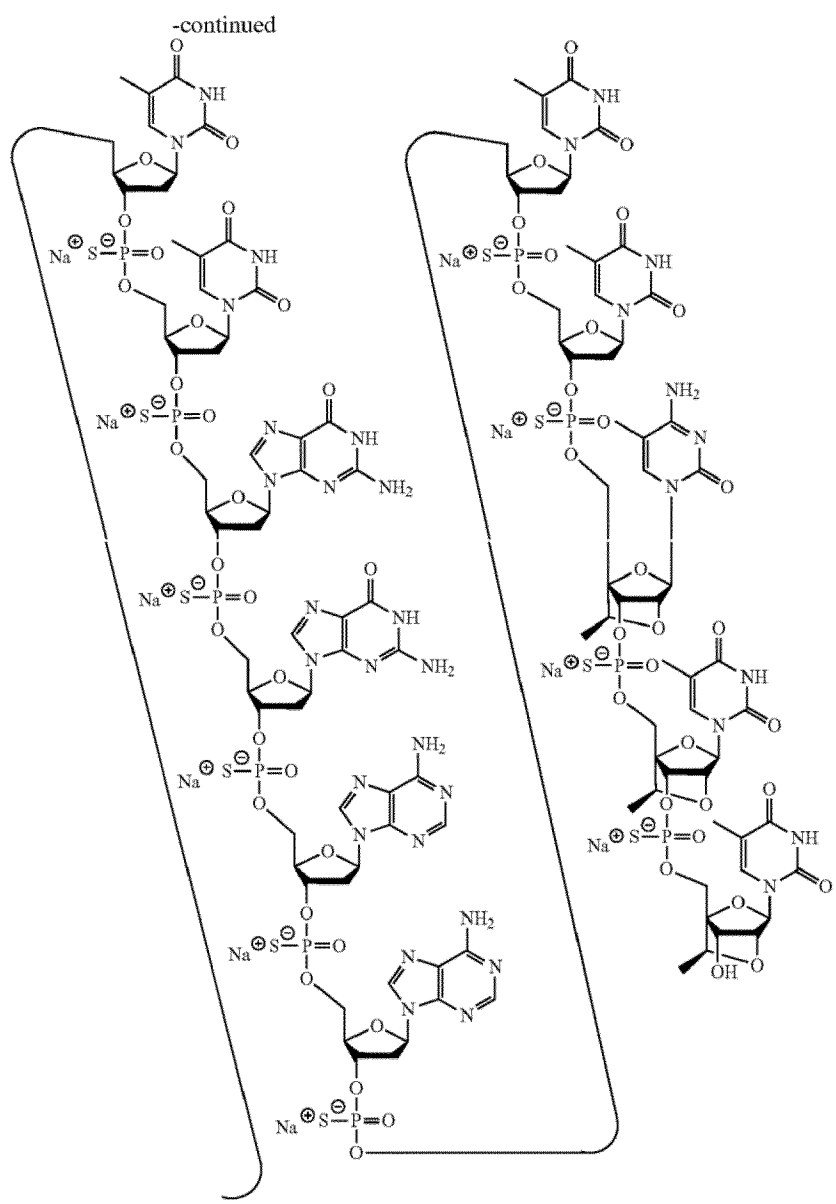
" to

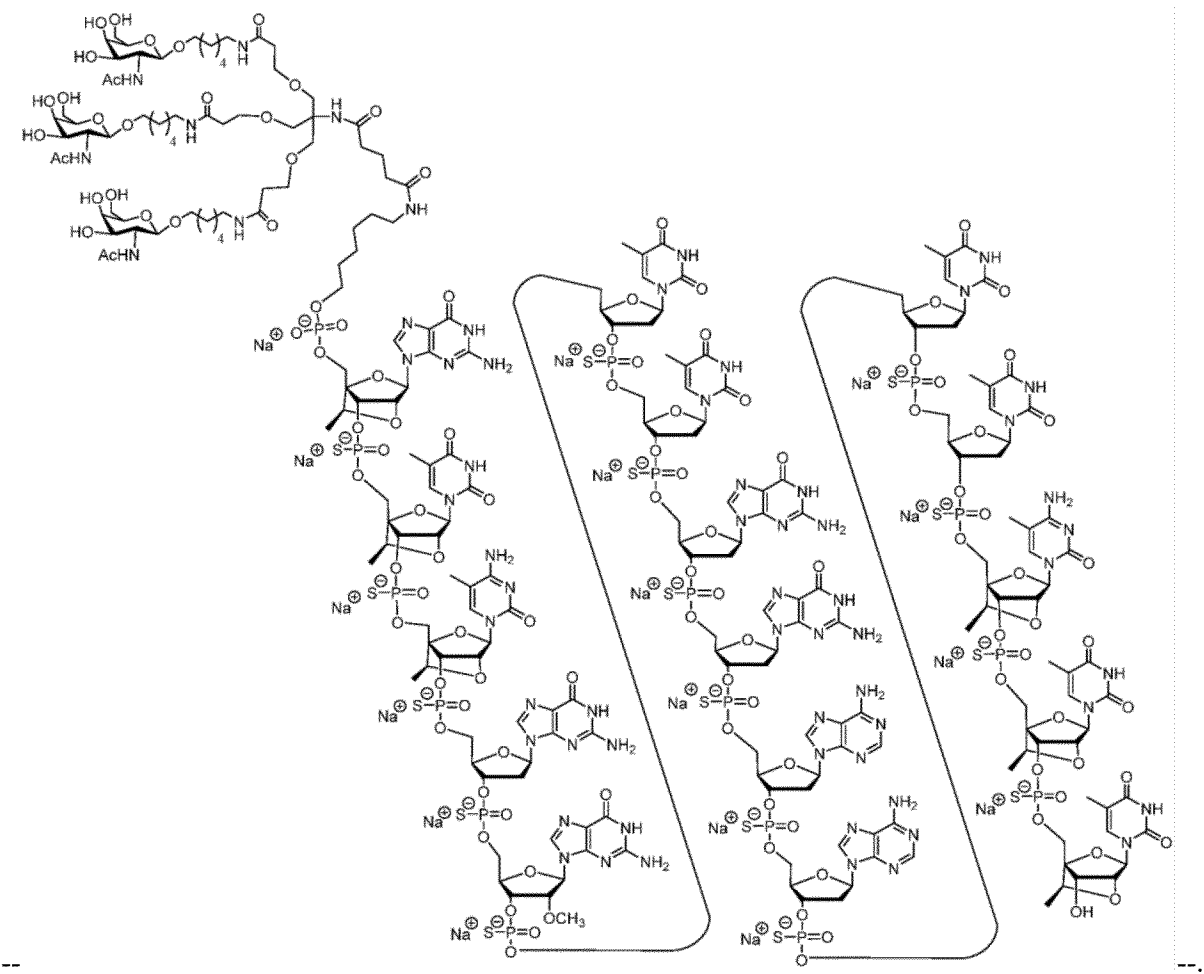
--                                                                                                                                          --.

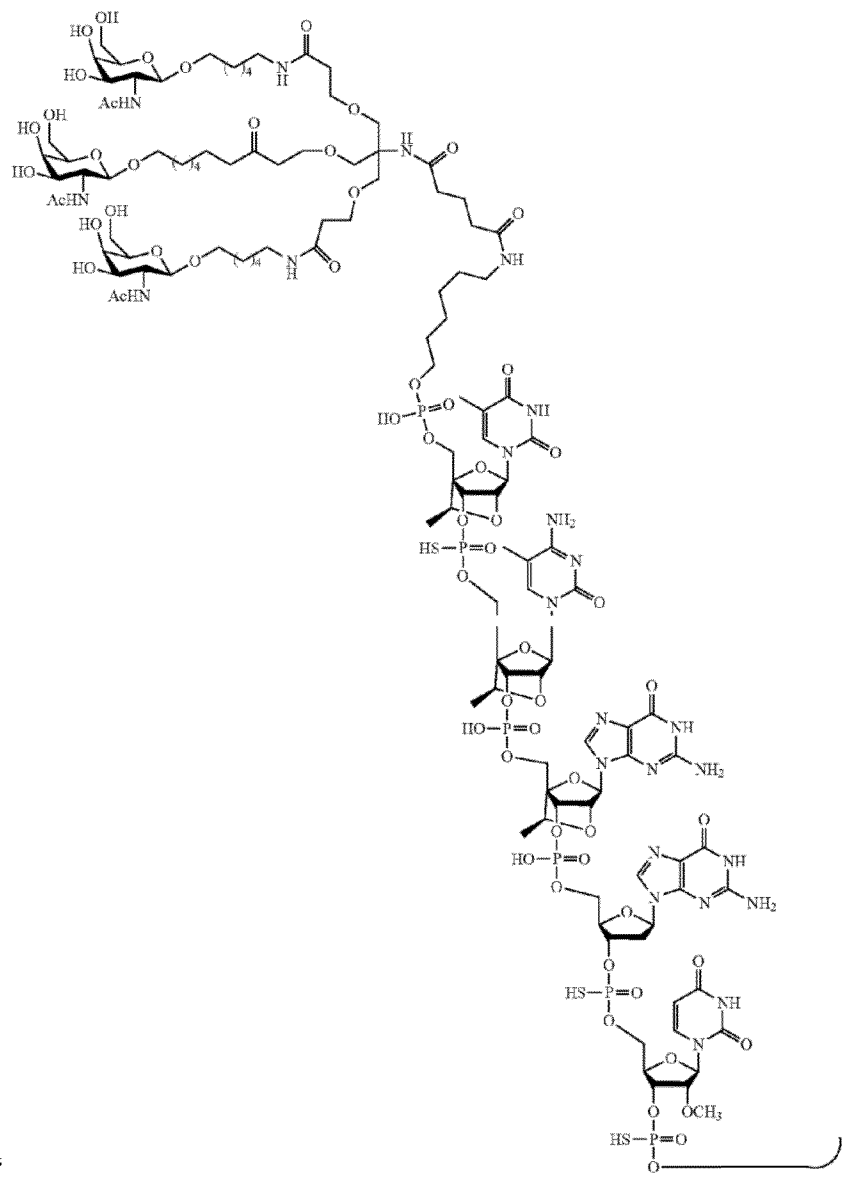
Columns 147-150, change "

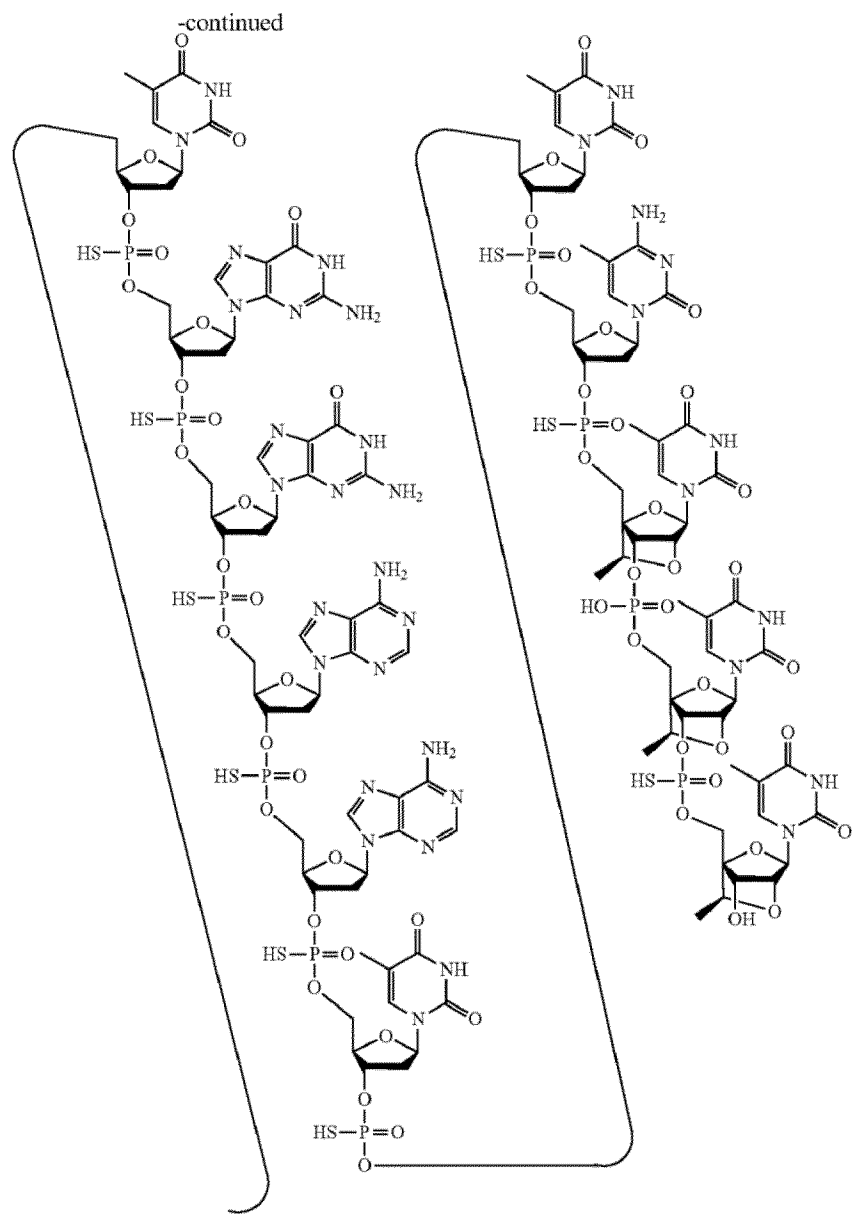
" to

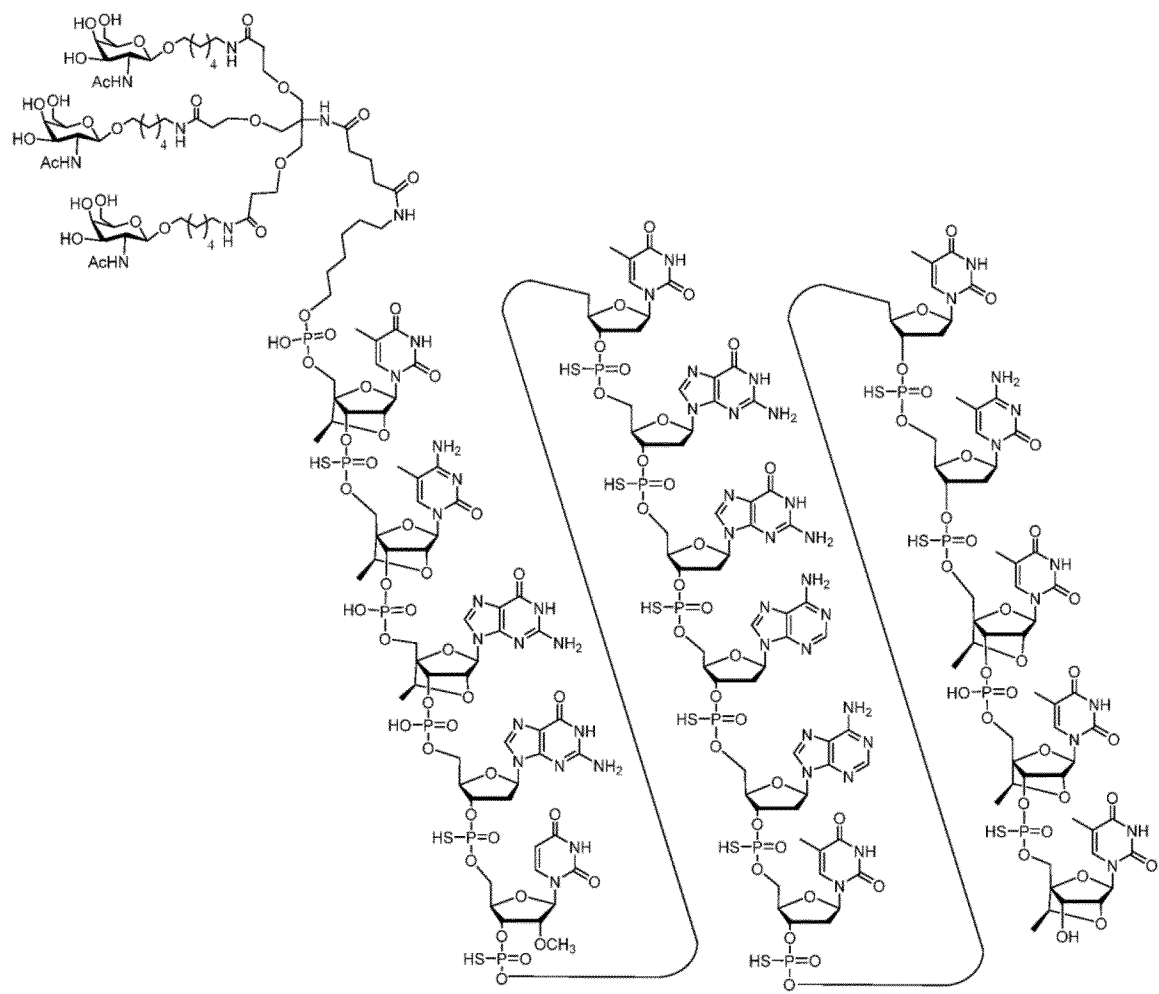
--                                                                                                                                  --.

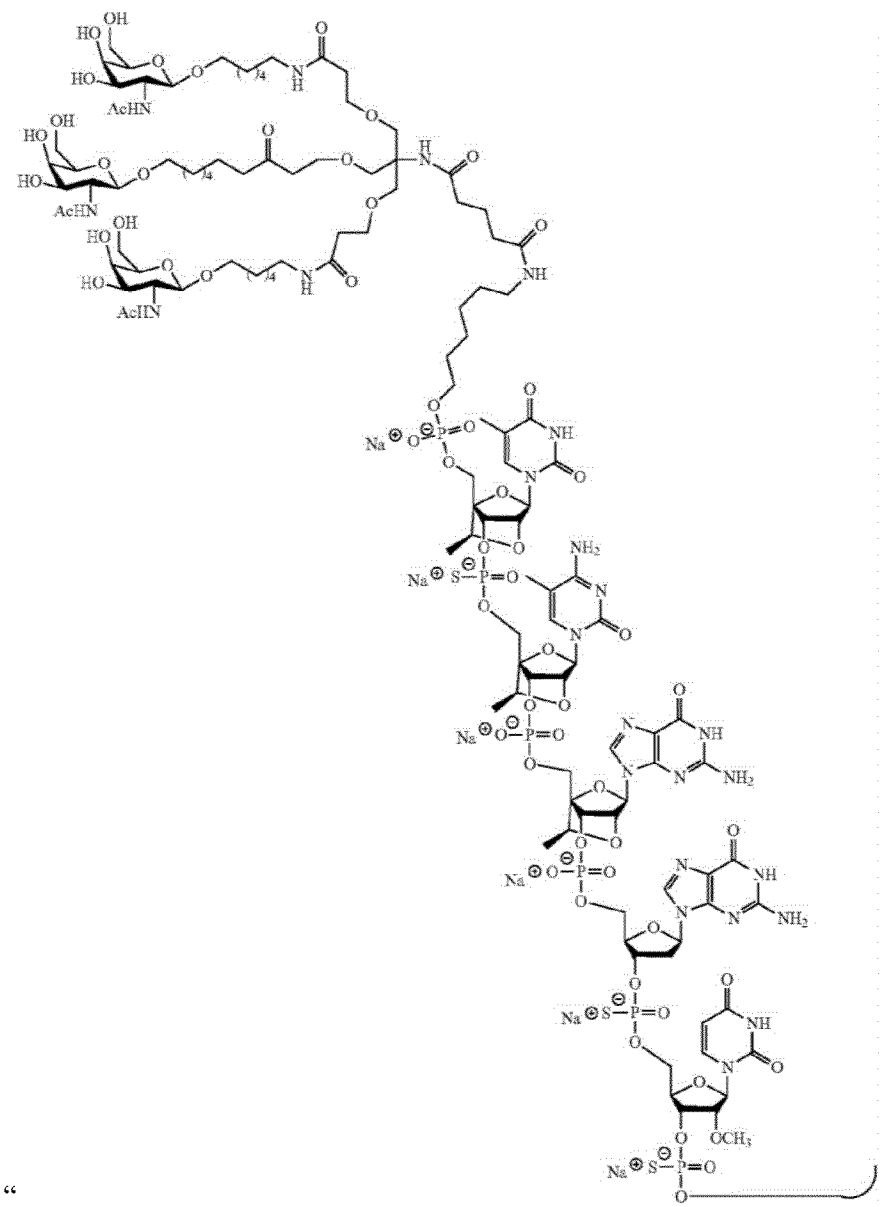
Columns 151-154, change "

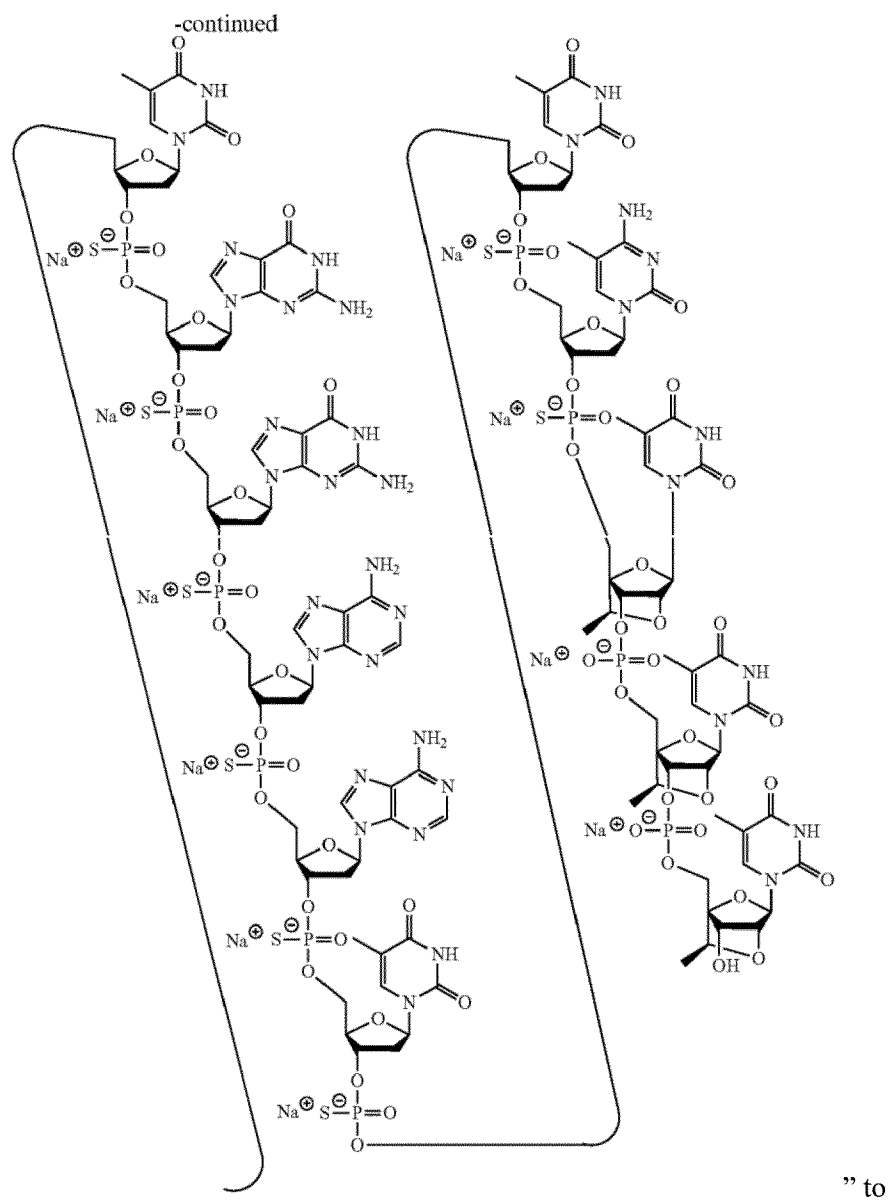
" to

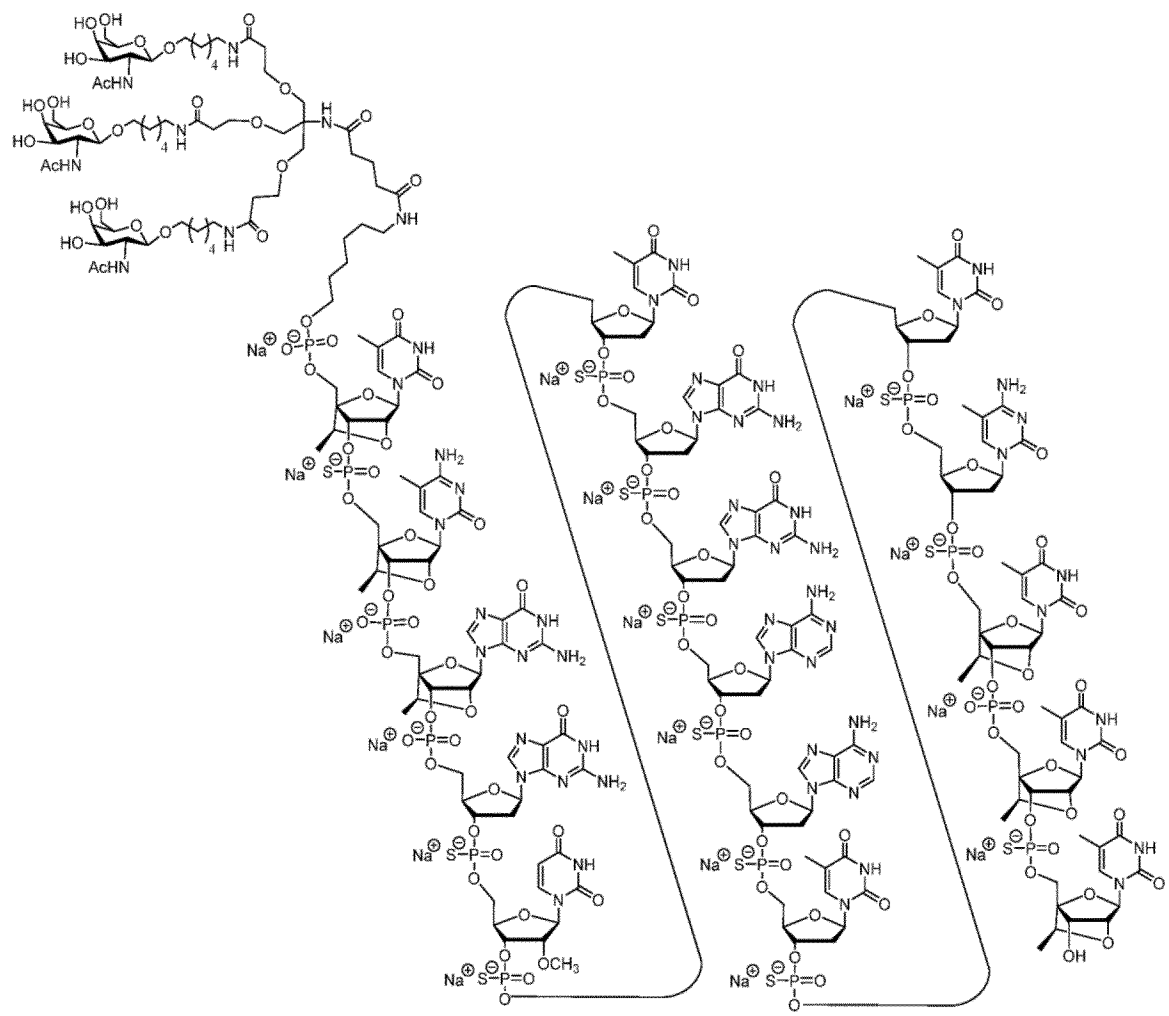
-- -- .

CERTIFICATE OF CORRECTION (continued)
U.S. Pat. No. 11,447,521 B2

In the Claims

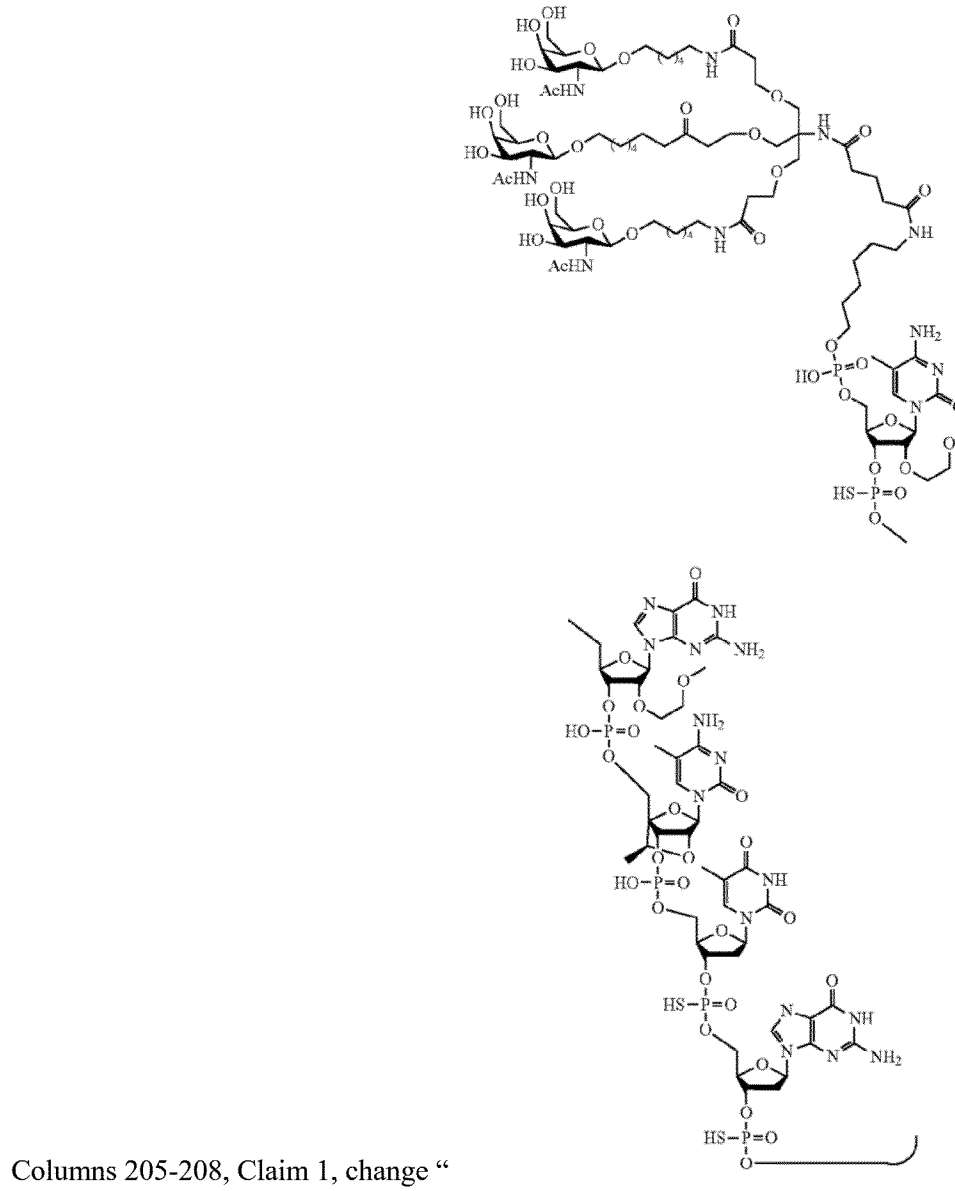

Columns 205-208, Claim 1, change "

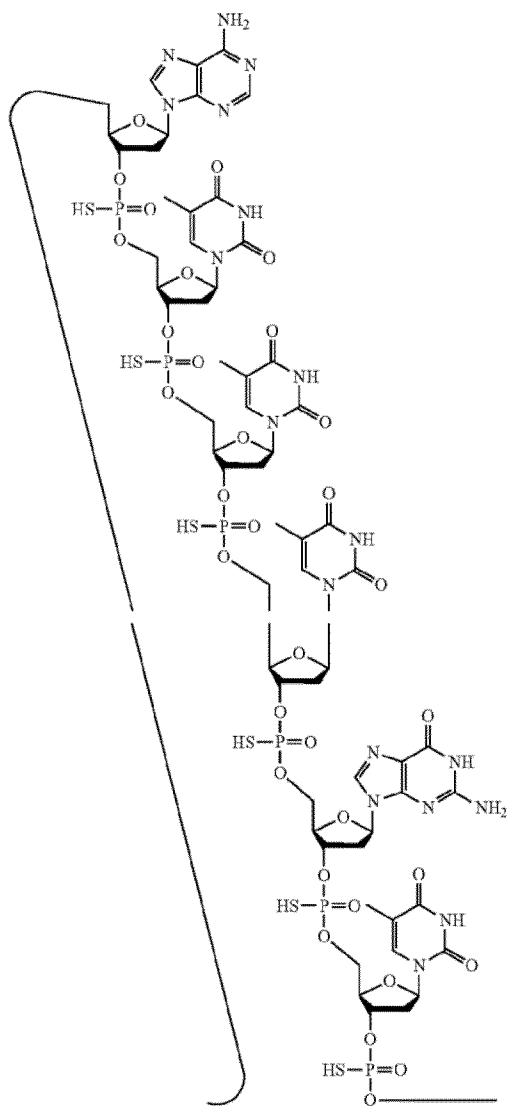

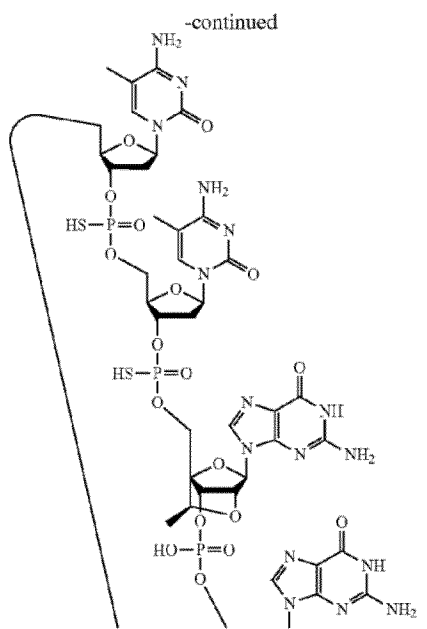
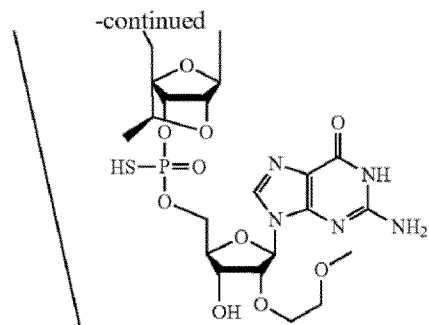
" to

CERTIFICATE OF CORRECTION (continued)
U.S. Pat. No. 11,447,521 B2

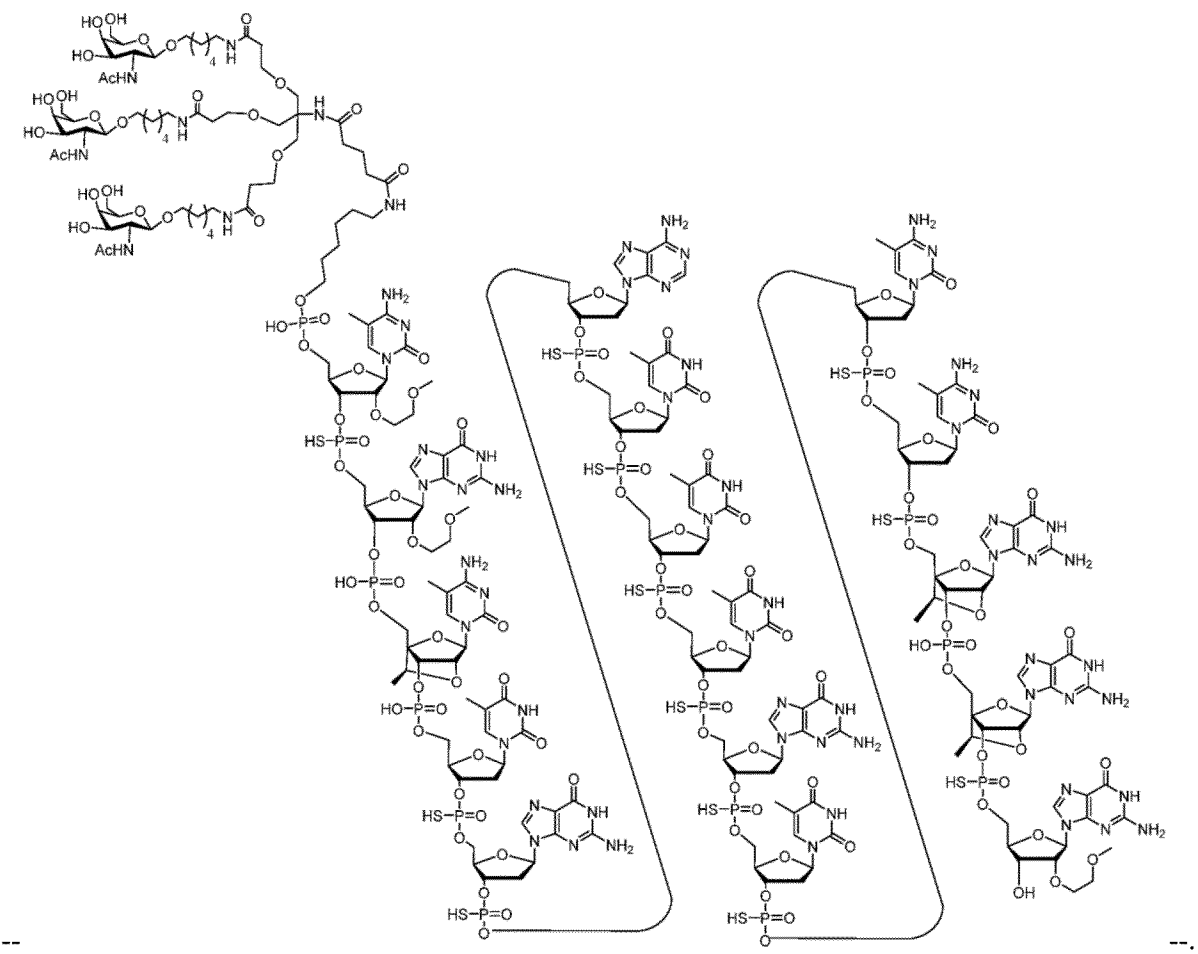

--

Columns 207-212, Claim 3, change

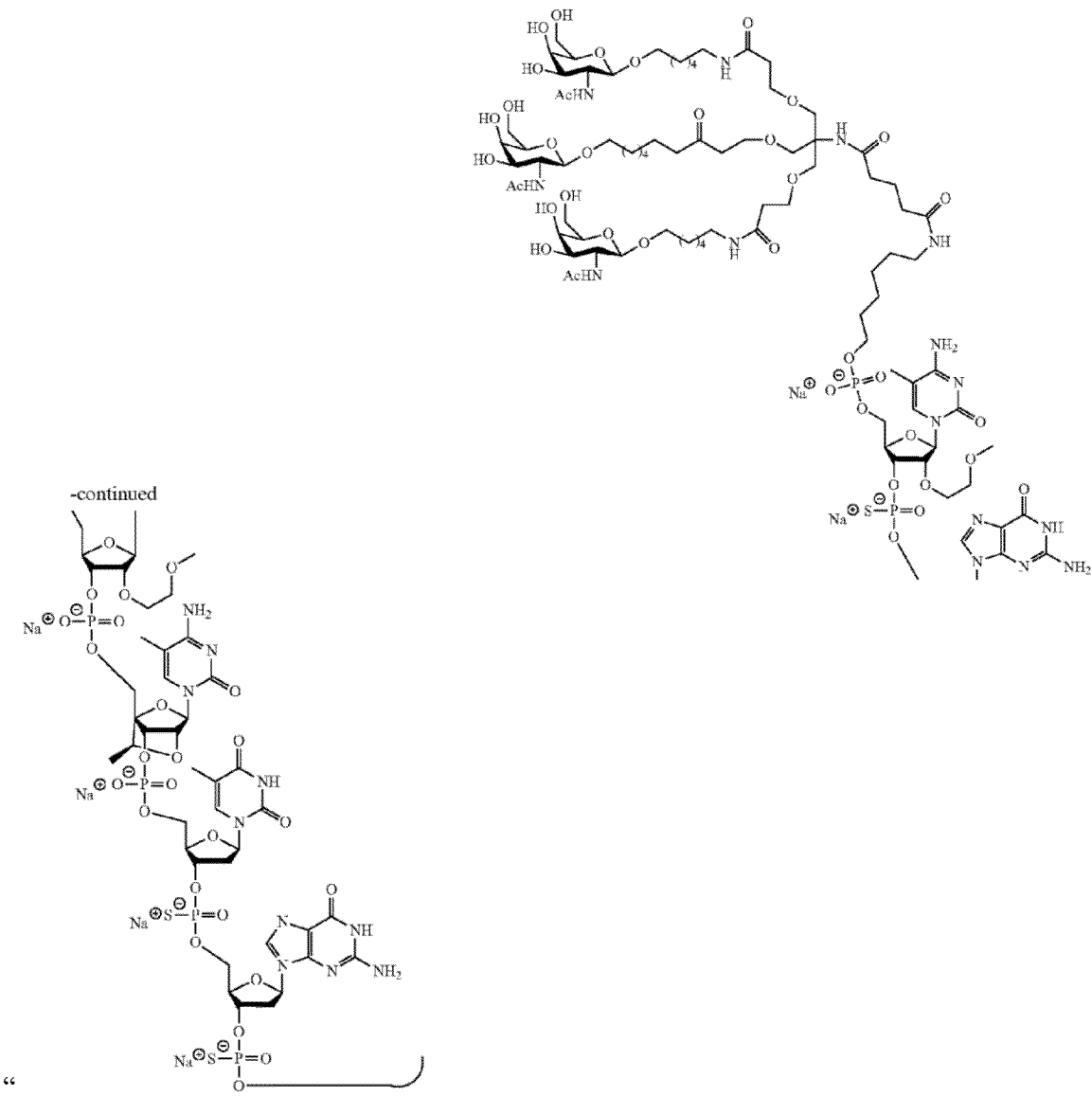

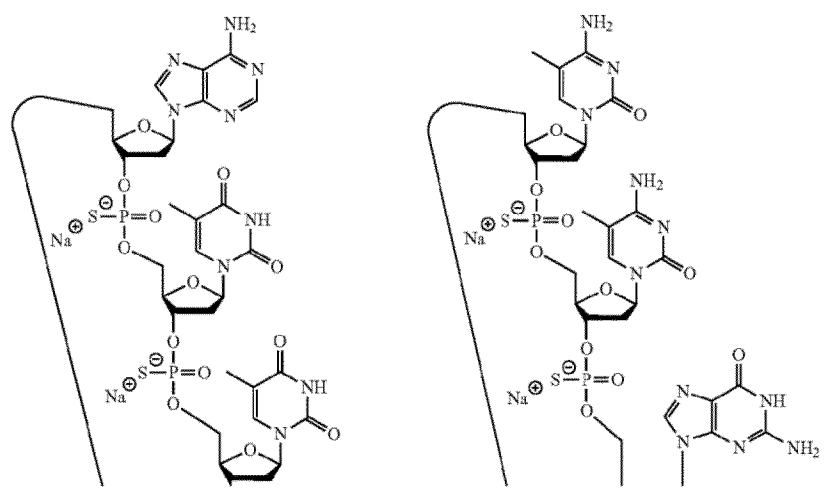
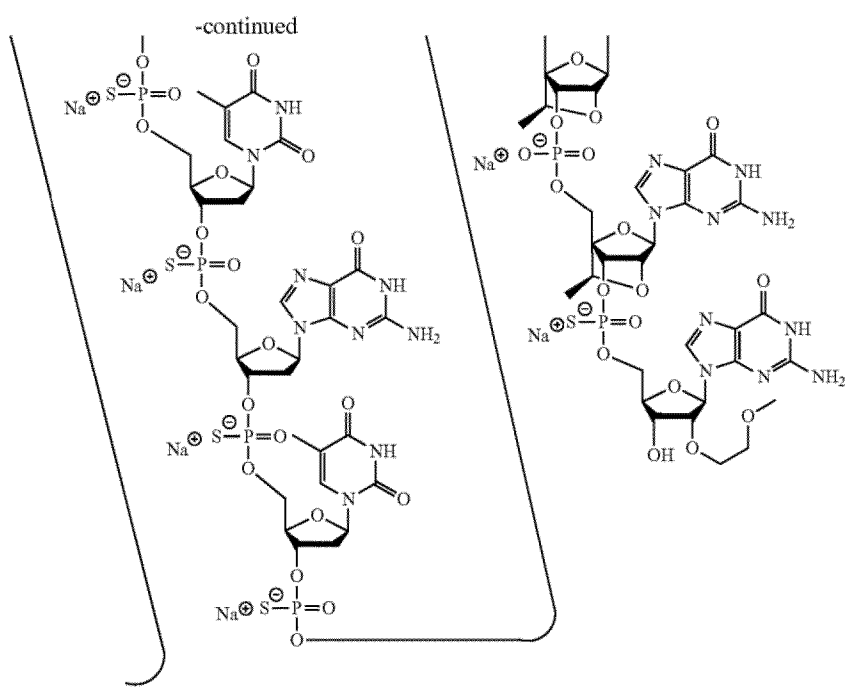
" to

SEQUENCE LISTING

```
<160> NUMBER OF SEQ ID NOS: 28

<210> SEQ ID NO 1
<211> LENGTH: 2587
<212> TYPE: DNA
<213> ORGANISM: Homo sapiens

<400> SEQUENCE: 1
atcccatgag cgggcagcag ggtcagaagt ggccccgtg ttgcctaagc aagactctcc      60
cctgccctct gccctctgca cctccggcct gcatgtccct gtggcctctt gggggtacat    120
ctcccggggc tgggtcagaa ggcctgggtg gttggcctca ggctgtcaca cacctaggga    180
gatgctcccg tttctgggaa ccttggcccc gactcctgca aacttcggta aatgtgtaac    240
tcgaccctgc accggctcac tctgttcagc agtgaaactc tgcatcgatc actaagactt    300
cctggaagag gtcccagcgt gagtgtcgct tctggcatct gtccttctgg ccagcctgtg    360
gtctggccaa gtgatgtaac cctcctctcc agcctgtgca caggcagcct gggaacagct    420
ccatccccac ccctcagcta taaatagggc atcgtgaccc ggccggggga agaagctgcc    480
gttgttctgg gtactacagc agaagggtat gcggaagcga gcacccagt ctgagatggc     540 tcctgccggt gtgagcctga gggccaccat cctctgcctc ctggcctggg ctggcctggc    600
tgcaggtgac cgggtgtaca tacacccctt ccacctcgtc atccacaatg agagtacctg    660
tgagcagctg gcaaaggcca atgccgggaa gcccaaagac cccaccttca tacctgctcc    720
```

```
aattcaggcc aagacatccc ctgtggatga aaaggccta caggaccagc tggtgctagt      780
cgctgcaaaa cttgacaccg aagacaagtt gagggccgca atggtcggga tgctggccaa     840
cttcttgggc ttccgtatat atggcatgca cagtgagcta tggggcgtgg tccatggggc     900
caccgtcctc tccccaacgg ctgtctttgg caccctggcc tctctctatc tgggagcctt     960
ggaccacaca gctgacaggc tacaggcaat cctgggtgtt ccttggaagg acaagaactg    1020
cacctcccgg ctgatgcgc acaaggtcct gtctgccctg caggctgtac agggcctgct    1080
agtggcccag ggcagggctg atagccaggc ccagctgctg ctgtccacgg tggtgggcgt    1140
gttcacagcc ccaggcctgc acctgaagca gccgtttgtg cagggcctgg ctctctatac    1200
ccctgtggtc ctcccacgct ctctggactt cacagaactg gatgttgctg ctgagaagat    1260
tgacaggttc atgcaggctg tgacaggatg gaagactggc tgctccctga tgggagccag    1320
tgtggacagc accctggctt tcaacaccta cgtccacttc aagggaaga tgaagggctt    1380
ctccctgctg gccgagcccc aggagttctg ggtggacaac agcacctcag tgtctgttcc    1440
catgctctct ggcatgggca ccttccagca ctggagtgac atccaggaca acttctcggt    1500
gactcaagtg cccttcactg agagcgcctg cctgctgctg atccagcctc actatgcctc    1560
tgacctggac aaggtggagg gtctcacttt ccagcaaaac tccctcaact ggatgaagaa    1620
actatctccc cggaccatcc acctgaccat gccccaactg gtgctgcaag gatcttatga    1680
cctgcaggac ctgctcgccc aggctgagct gcccgccatt ctgcacaccg agctgaacct    1740
gcaaaaattg agcaatgacc gcatcagggt gggggaggtg ctgaacagca ttttttttga    1800
gcttgaagcg gatgagagag agcccacaga gtctacccaa cagcttaaca gcctgaggt    1860
cttggaggtg accctgaacc gcccattcct gtttgctgtg tatgatcaaa gcgccactgc    1920
cctgcacttc ctgggccgcg tggccaaccc gctgagcaca gcatgaggcc agggccccag    1980
aacacagtgc ctggcaaggc ctctgcccct ggcctttgag gcaaaggcca gcagcagata    2040
acaaccccgg acaaatcagc gatgtgtcac ccccagtctc ccaccttttc ttctaatgag    2100
tcgactttga gctggaaagc agccgttct ccttggtcta agtgtgctgc atggagtgag    2160
cagtagaagc ctgcagcggc acaaatgcac ctcccagttt gctgggttta ttttagagaa    2220
tgggggtggg gaggcaagaa ccagtgtttta gcgcgggact actgttccaa aaagaattcc    2280
aaccgaccag cttgtttgtg aaacaaaaaa gtgttcccct ttcaagttga gaacaaaaat    2340
tgggttttaa aattaaagta tacattttttg cattgccttc ggtttgtatt tagtgtcttg    2400
aatgtaagaa catgacctcc gtgtagtgtc tgtaatacct tagttttttc cacagatgct    2460
tgtgattttt gaacaatacg tgaaagatgc aagcacctga atttctgttt gaatgcggaa    2520
ccatagctgg ttatttctcc cttgtgttag taataaacgt cttgccacaa taagcctcca    2580
aaaaaaa                                                              2587
```

<210> SEQ ID NO 2
<211> LENGTH: 18000
<212> TYPE: DNA
<213> ORGANISM: Homo sapiens

<400> SEQUENCE: 2

```
cagagcaaga ccccaactct aaaacaacac acaaaaatac agccatttct cctgggtgaa      60
atggggagc tcagactatt ttgttttatt tgtcaggagt ctaaagccca tgtgagccaa     120
cttaagaaaa ttctgtttgt atttgagtgt tctttattgg aaagaaatgg acttttccct    180
```

```
aatgagccca ttttacaaat cgagagctcc aaatgcccgg ttccagcccc catgatatag    240
atgggcagca atgaggacca gaaatgctgg gaagtgtcct tgtcatgcaa ggaaaacttg    300
gaacttcaag gatccatcat gggatgcagg acagtaggct ccaccccctct tcctgctttc    360 cagtaaatga tgttcagggc tcacatgcct cttccaaggc atgatgtggg gttgcagttc    420
tgatcccagc agagaacaag gctcctgtga acaattagt tttggctcag aggcaaaaaa    480
tggaaacccc attcctgtat ttacccttca ttctttcctt acctcataca gctggttcca    540
ggtttgattg catcatatac ataaataaat aatctgcttt cctggtttgg tttagttttg    600
ctggagagag gagtttatgt gttcatccca tgactagctg ggtggtcaag agattggaaa    660
gtaggagttc tagtttagac caagtctcat ctcagaaacc acagagtaga actgatccca    720
aacgtcatca tccctgtagg gaaaagaaag agagatcaga ctgttactgt gtctatatag    780
aaagggaaga cataagagac tccattttga aaaagagcta tactttaaac aattgctttg    840
ctgagatgtt gttaatttgt agctttgccc cagccacttt gacccaacct ggagctcaca    900
aaaacatgtg ttgtataaaa tcaaggttta agggatctag gctgtgtca aagtggctgg    960 ggcaaagcta caaattaaca acatctcagc aaagcaattg tttaaagtac agctcttttt   1020
caaaatggag tctcttatgt cttcccttc tatatagaca cagtaacagt ctgatctctc   1080
ttttttttcc ctacatatcc caatagcacc tgcctgacta atacatcatg ctctgctgac   1140
tccatatgtg gctggtttcc tggatccgat tctgactgat ggtatctgtt ctcacgctgc   1200
taataaagac ataccagaga ctgggtaatt tataaagaaa aagaggttta atggacttat   1260
gtgttccacg tggctgggga ggcctcacaa tcatggtgga aggtgaagga ggagcaaaag   1320
cacatcttac atggtggctg gcaaaagaga gaaagcatgt tcagggaac tccccttat   1380 aaaaccatca gatctcatga gacttatgca ctatcacaag aacagcatca gaaagatcca   1440
ccctcatgat tcaattacct cccactgggt ccctcccatg acacatggga attatgggag   1500
ctacaattgg agatttgggt ggggacacag ccaaaccata tcagatggct tatttggttt   1560
ctatgtagaa cctctgcttt tcattcaaca gtcttcattt agccacagat aagctctgtc   1620
cctaacttcc actgatggaa tgtacacata agaaacttcc actgatggaa tgaacacaga   1680
aggtgcctac tgggaagaaa actggcctga atctgagctg ggtcaaatgt ctgcagtcag   1740
tttgaatggc tgctccttat gggaataatt tacattctca ataaaattct ctagcaattt   1800
tctgattgat tttaatgagc tttaaagcct tacgtagaag atcccccagc tgatagtcag   1860
ccttgggcat ggattaaggg cttttaacca atccttgcaac aagtttaagc agatattctt   1920
tattgggtcc aatctaacca aaattatttt cttatgttct ccccagtaac gtgtcattat   1980
taagagaagt ttggcttgct tagaggccaa atttagaggg tcctgaaatt ttattttctt   2040
ttacaccact ttccagcatg ttacctgatc agttgtttat tatctttgct gttgaatgga   2100
gtgatcattc caagggcccg aggcaggagg cccaggcaca gtggaaactc tcccaaagac   2160
caggatcttt gttttgttcc ctgacatatg ctgagcacca ggaatagtga gtgaatgaaa   2220
caaattgtga ggctttaaag agccgaaata tttaaacact gggcacaagg ttgttgctta   2280
atcagtgcta gatccttacc tcccccttgt gtccaggtgg acttgttact gcagttaaac   2340
cacttgctga tcctcaaaca actagttagt ggcacagcca ggcctaggac cccagtctct   2400
actgttccaa ctaacccatt cgcaggcagg agcactttga atggtctctt attttaaaaa   2460
aattaaatta aaattgtcta tttatttaga gacagagtct tactctgtag cccaggctcg   2520
agtgcagtgg tgcaatcata gctcactgta acctccatct cctggcctca aaagtgtttt   2580
```

```
gaattacaga tgcgaggcac tgtacctggc ccgaatgttc tgttcagaca aagccacctc    2640
taagtcgctg tggggcccca gacaagtgat ttttgaggag tccctatcta taggaacaaa    2700
gtaattaaaa aaatgtattt cagaatttac aggcccatgt gagatatgat tttttttaaat   2760 gaagatttag agtaatgggt aaaaaagagg tatttgtgtg tttgttgatt gttcagtcag    2820
tgaatgtaca gcttctgcct catatccagg caccatctct tcctgctctt tgttgttaaa    2880
tgttccattc ctgggtaatt tcatgtctgc catcgtggat atgccgtggc tccttgaacc    2940
tgcttgtgtt gaagcaggat cttccttcct gtcccttcag tgccctaata ccatgtattt    3000
aaggctggac acatcaccac tcccaacctg cctcacccac tgcgtcactt gtgatcactg    3060
gcttctggcg actctcacca aggtctctgt catgccctgt tataatgact acaaaagcaa    3120
gtcttaccta taggaaaata agaattataa ccctttttact ggtcatgtga aacttaccat    3180
ttgcaatttg tacagcataa acacagaaca gcacatcttt caatgcctgc atcctgaagg    3240 catttttgttt tgtctttca atctggctgt gctattgttg gtgtttaaca gtctccccag   3300
ctacactgga aacttccaga aggcactttt cacttgcttg tgtgttttcc ccagtgtcta    3360
ttagaggcct ttgcacaggg taggctcttt ggagcagctg aaggtcacac atcccatgag    3420
cgggcagcag ggtcagaagt ggcccccgtg ttgcctaagc aagactctcc cctgccctct    3480
gccctctgca cctccggcct gcatgtccct gtggcctctt gggggtacat ctcccggggc    3540
tgggtcagaa ggcctgggtg gttggcctca ggctgtcaca cacctaggga gatgctcccg    3600
tttctgggaa ccttggcccc gactcctgca aacttcggta aatgtgtaac tcgaccctgc    3660
accggctcac tctgttcagc agtgaaactc tgcatcgatc actaagactt cctggaagag    3720
gtcccagcgt gagtgtcgct tctggcatct gtccttctgg ccagcctgtg gtctggccaa    3780
gtgatgtaac cctcctctcc agcctgtgca caggcagcct gggaacagct ccatcccac    3840 ccctcagcta taaataggc atcgtgaccc ggccggggga agaagctgcc gttgttctgg    3900
gtactacagc agaaggtaag ccggggggccc cctcagctcc ttctcggtct tgtctctctc    3960
agatgtaact gagctgtggg ctaggaggaa aaggccggga ggaggcacgg tgatgactga    4020
aaaacctctc ccctctcata agaccagtca tccggacgcg ggctttcccc cactcggtgc    4080
ccacctgggg tcttacagga ggagctgctc ctcctcagca ataggacaag atggtcaggt    4140
cttcctgctt ccgctgagaa aagttagggt cctcaggaac ggagcagact ggtacaggaa    4200
cagagtcatc atggccaaga gtccaccggg tcctcttgcc atcaggagga atagcagggc    4260
ttgtgcagga attggggctg gagggaaggg ccgggctcgg tcagtctcca gctgggatcc    4320
ccagagtggt caccctaccc ctccctcgag acagactgcc tgactgtgtg tcatcaggct    4380
ggtcaccatc tccctgaacc tcgatttgct cacctataaa atggaactaa taacgatgcc    4440
tgggctccct gtctcagggg ctctggtata gctgaagaga actaatataa catgaaagtg    4500
ctttctaagc tttgggataa gctaaaaggc agattccaat tttattcgag ggcagcgtag    4560
attggtgctt cagctcgtgg atgacagagt caggggggcct ggttctgagt cctagttctg    4620
tctcttccca gctgtgtgac gttgaacaag tcactggacc tctctgttcc tctgcaaaac    4680
agcatgaacc aattcattaa ctacttctcc aggatgcagt aggtcccagg gactatccta    4740
ggaatgtggg ctgtattagt aaacacaaca gcgggaaccc tgttccgggg ctcacattca    4800
catcagagca aacagacaaa gacgctggac agaataagtg cataactaca tggtacagag    4860
ggttataagg agggaaaagg ggagctggat gagagagttg agagtgcccg gtgtggtggg    4920
```

```
gaaagctgca gggtgaaata ctgcatcagg gaaacctcag ggaaggtgag gactatggtg    4980
aggtcagagg ggttgatatg agaacagtgc cctgcaaatg gcaggcacca caggagcatg    5040
agccgtcatc ttcacctta gcattcagcc cgggagaagt agggagacat agaaggggca    5100
ggtgctggcc aagaggcagg ggcaggagag gagaaggcgg aggggcactc agggcgaggg    5160
tgtcaggccc gccacccag agcaccatta ctcccaggac gcggctgcgt gcagacctgg    5220
aaccagccta gggagcagcc gcagatcaca actgagaaca aacgacagtc tctgcctcaa    5280
aaatggccca tggaattgcg tctctggaga cgctgcctga gcaggagcag cacagtgagc    5340
gggctgcatc gaccagcgcc atccaaaccc gaacagttg gcgcttgtca ggcaggactt    5400
cccagcagtc ggttcccaca ggtttcccct gttgacctga tttgatgtga ctgtctagat    5460
taggtgtgaa ctggtggctt aggcttctct gcacagaaag gcctgcaagc agcagagaga    5520
gttttctgtt ccattttcc atgtcatgtg gctcttcctg agaacagcgg atggagtcaa    5580
atgcatgggg agtggggtga gatggtagct gaggtcagaa tttggcattt gaatgactga    5640
agcagaacaa aacacaccag gtacttcagc agctgcaccg tgttgagggc aggtgctggt    5700
tacgggtctg ggtgagggaa gccagctgcc aatgtaagaa gaatgactgg gtatgcttag    5760
atgaagcaga aaaatctagg catcaaggtg gccttgagtc agtgatgaca cgctacagct    5820
ccaaggaagc ctggcctagc cctgggggga cagaaaaggc caagaagtga cgatattgca    5880
gtacaccccc ctccacaaga aatgagtgag atgtggtaca aaatgttaga attgaatgaa    5940
tcaatagaat aaacgttcat cccttcaatc aagaagagtc agatgaaatg aattagcagg    6000
gccagcccaa gaacctcttc tgggggtctc agggtagctt tcatttgtag cagctgaggc    6060
tgaagcccag ctgcaaggcc tttgagagaa cgtggtgctg gacccgtgtc tagggcaggg    6120
gttctaaacc ctgcttacat atcagagtca cctgagaatt ttctatttt tttttttttt    6180
ttttatacgt ggtcccagca cagactaagg aatccaacta tcattgggca agccatgcta    6240
ggtatgcatg cctttgggc tctgcagggg atagcgctat gcaggatgg ttgagagctg    6300
gttttggggt tgagacacgt gggaaatact tggactttgg gctgagcctg tggtgctcaa    6360
tcccggctgc atgttgggac cacagggaga tgacaaaacc atccccagcc ctcaccctag    6420
ggccctcgaa tgagcatctc aggggtctag gaggcctcca caaagaccta ctgattggca    6480
cacacttgtt tctctaggaa gagaacttac agctgcaggc aggagcatgt cttaatctgc    6540
ttgggctgcc ataagtacca cagactggga gggtttaaca acagaaatgt gttatctcac    6600
agttctggaa gctagaagcc tgggagccag ccatcagcag agttggtttc ctctgggtcc    6660
tctatccttg gcttgtagat ggccgtcttc tctctgtgtc cccacatggt cttccctctg    6720
tgtccccaca tggtcttccc tctgtgtgtg tccatgtcct catctcctct tctcataagg    6780
acacaggtca tattagatca gggctcaccc tcatggcctc attttaactt aatcatctct    6840
ttaaagatcc tgtctccaaa taatggtcac attctgaggt cctggggttg aggcttcaa    6900
cacgggcatt atggccgttg ggggaggtag gacataattc agctgatatt ggtgcatttt    6960
gcacttggat catgtagata ttttccatgg agctttgaat ccatttcttc ttttttttgt    7020
agacatgaat ggatttattc tgggctaaat ggtgacaggg aatattgaga caatgaaaga    7080
tctggttaga tggcacttaa aggtcagtta ataaccacct ttcaccctt gcaaaatgat    7140
atttcagggt atgcggaagc gagcacccca gtctgagatg gctcctgccg gtgtgagcct    7200
gagggccacc atcctctgcc tcctggcctg ggctggcctg gctgcaggtg accgggtgta    7260
catacacccc ttccacctcg tcatccacaa tgagagtacc tgtgagcagc tggcaaaggc    7320
```

-continued

```
caatgccggg aagcccaaag accccacctt catacctgct ccaattcagg ccaagacatc    7380
ccctgtggat gaaaaggccc tacaggacca gctggtgcta gtcgctgcaa aacttgacac    7440
cgaagacaag ttgagggccg caatggtcgg gatgctggcc aacttcttgg gcttccgtat    7500
atatggcatg cacagtgagc tatggggcgt ggtccatggg gccaccgtcc tctcccaac    7560
ggctgtcttt ggcaccctgg cctctctcta tctgggagcc ttggaccaca cagctgacag    7620
gctacaggca atcctgggtg ttccttggaa ggacaagaac tgcacctccc ggctggatgc    7680
gcacaaggtc ctgtctgccc tgcaggctgt acagggcctg ctagtggccc agggcagggc    7740
tgatagccag gccagctgc tgctgtccac ggtggtgggc gtgttcacag ccccaggcct    7800
gcacctgaag cagccgtttg tgcagggcct ggctctctat accctgtgg tcctcccacg    7860
ctctctggac ttcacagaac tggatgttgc tgctgagaag attgacaggt tcatgcaggc    7920
tgtgacagga tggaagactg gctgctccct gatgggagcc agtgtggaca gcaccctggc    7980
tttcaacacc tacgtccact tccaaggtaa ggcaaacctc tctgctggct ctggccctag    8040
gacttagtat ccaatgtgta gctgagatca gccagtcagg ccttggagat gggcaggggg    8100
cagccctgcg gacatacctg gtgaccaccc ttgagaagtg gggaagtggc tgctccgctg    8160
ggtccctgga tgggccgtcc acctcctgga cctgctgccc tactatgtgc acgactatac    8220
aacatccttt ttcttacatc atttaatccc cttatgatgt ggtgaagagg tatttgtgcc    8280
tttgtttacc agtgaagaaa tagagactcg gagaaacaaa gtgccttgct caagatggca    8340
cagccaccag tgggggtcct gggattgaaa cccacatctc ctggcccac agcccagttc    8400
tacactcaga agggtcaggt tcatatctct tgagaaggtc aggaactggg gtccctggcc    8460
catgcagaaa taagcaattg gcttgcttaa atccctttca tgttaggagg ggcattactg    8520
aaaaccctct actacaaaga ttgttgattt tttttttttt tttattgag acagggtctt    8580
gttctgtcac ccaggctgca gtgtagtggt gccatcattg ctcactgtag ccttgaactc    8640
ctggcctcaa gcgatcctcc cacctctgcc ttccaaagtg ttgggattaa aggtgtgagc    8700
cactgcaccc agccacagat tgcttaaagc attcatttaa caaatacttg ttgaggattt    8760
gctacttgta agactttaag cctggcatct cagaggaggc cagaggaggg ctgtataggc    8820
cctgcctcca ggcttttaaa ggtcaatggg caaatgccta ggatttggag ctgcagggaa    8880
acgtgctcca caaggtaact cagggaagcc tcggggctct cagaggacag aggtcactgg    8940
ggagcggaga gcaggccttg cctggcagtg agggcaacag ggctggtgaa gctaggagca    9000
agcatgatga gcccagcctg cagagtttgg ggcaaggaac gaggatgggg cggttggctt    9060
ggcatgagtg ttgaaccaga aaatgggcct ggggagggca gagctggaga cactttgaac    9120
gccatgcttg gtaggtgtgg gaatgggac gcgttctgtt cagaggtcat cccggaagcc    9180
tgccgtgtgc agactggagg cagggaggat tgtttgaagg ttacgcaaga gtccaggcac    9240
acagtcacgg gaacacgtgc tcaggagca gctcggcaaa tccatgggtg gggtggggct    9300
gaggggtgtg tctaagagac actgaggagg ctctgtcaag atgttaacct cgtgagggac    9360
agagagccag gcgggaggtg aaagacaaga ctgtggagaa agaggttcag tggcgcatag    9420
tgattttct taccacaaca acctccttga ggtctttccc ttcgggttca gggagaggtg    9480
atagatgggg ggattgctca gccctggcac tgactggtca caggggcaga ggccagcccg    9540
agggttgccc ggttgagggt ggcagcacac tgtgcagggc agagcaggga cacatggact    9600
tagcctgctg tccctaggag aagtgctggg aggagcgctc actgagaagg agggtcctgc    9660
```

| | |
|---|---|
| agaaggcaaa ggcaagaaag ccagtggcat ctgaaatggg tctcccttcg aaagagagca | 9720 |
| catccacctg acccagaccg cagagccagg ccaggaggaa gaggaggaag aataaaaaag | 9780 |
| ccaaccacat cgggactcaa aggaagccca ggatcctcgc cggcctccac cgcatgctgc | 9840 |
| cctgaccctg ccccacttcc taactttgct ggcctcagtt ccgtcaaag gaggcagcca | 9900 |
| cttcctgccc acatggtctg tccagtgagg agatcggggg ctgtctcggg acctctaggt | 9960 |
| ttcccttag caatgatgtt ctatttacat gacctcagca ggcagctaga tgtgtcccac | 10020 |
| tagagaggac ctgaggatct ggggcctgat gggctccagg gtaccgtctg cccagtgctt | 10080 |
| gctgtgctcc tgagcatggg gcgctggccc tggtggtttc catgacacca ggtcctgact | 10140 |
| tgacctcgac agatttacct agcctccgga tgagaatggt gagctgtgca tgtcagacga | 10200 |
| gcagagggaa gacggcagcc actctcatgt caaatcccag cgtctttgg gaggcagctt | 10260 |
| cccttttta gtttagtttg ttggaagaaa agaattgtcc ctttcccccc tctaaactaa | 10320 |
| aagccttgcc agcccaggtg ggcagcaccg aggtccctgc agggaacgtg caaggggaac | 10380 |
| cctgcagttt cccgctcaca tgcccttccg agactgagtg ctccgaggac tgaggacgag | 10440 |
| aaatatgcca ggtctgccac tgccttctta cgagacccgg acccagggga ggcacagcca | 10500 |
| tgcccagctc ctgcctgcca gttctgtcct cccagctgcc ctactttcat gctgggacct | 10560 |
| ccaattcagt acaaagggag acctcactgt ttctgaacca tctctactca gactcccaag | 10620 |
| tgccacgtgc ccaggggact gttctgtgac aaacttatac acaacttcac cctattctcc | 10680 |
| taagaacaac cgcagaatag gcctttcagg atgagtggga ggacagccga gggcagggat | 10740 |
| gtgctagtgt aaggtcgagg cagagggtgg gctgctgtca tggaaagacc ccaggtaact | 10800 |
| gcgtcacaca caaatttgtg tccttctccc acaacgggct ctcccgagtt ctctgtcatc | 10860 |
| tgcacggccc tgtgagcagg aggggaaaca gagggctcac ccctgccccc aaggcccagt | 10920 |
| gtgcaaatcc attcatcaca acgaggttgt gtgagtctcc ccagtagcaa gggctgctga | 10980 |
| ggaatggagc cctcgtttcc ggggcctgcg tggcccactc tgtattctat gactgtgatg | 11040 |
| ggggagggtg ggggccacag gacagctggt gggctctgcc atggctgggg ctagacatgg | 11100 |
| attaaaaagt gagtatgagc aggggcctct aggagtggtg ggatagtgcg gtggtggcca | 11160 |
| catgtcattc tacgtgcgtc caaacctaca gaatgtaaaa caccaggagg gagactcaaa | 11220 |
| gaaaactatc aactttgagt gctgaggacg tgtcagtgta ggttcgtcag ttgcaacaaa | 11280 |
| tgggccacgc tggtgtgaga tgttgatcac gggggaggct gtgtagtggg ggacaagagt | 11340 |
| tatatgggaa ctttctgtac tttctgctcg attttgctgt gaacctaaag tcactctaaa | 11400 |
| aaataacatc tcttaaattt tttaaaaagt gagtgtgtca aaccacagcc tttgggtcag | 11460 |
| gacagttcta ggtttgagtt gacctggcag gtaccagtgg cttatgtccc ttaaggtgac | 11520 |
| agatgcaaaa ccccggttt ggtgcctggc atgttgtgtg tcttgcaggt ggcggttagg | 11580 |
| gctgcctcag tgaactcaaa tggctgcatt ttacaggaga aatatttgag ccacacttgc | 11640 |
| ggtcctgtgg ccaggagaat gcagagtggc ctgggggggg ccaaggaagg aggctgaggc | 11700 |
| agggcgaggg gcaggatctg ggcctttggt gtctgccagc cctcattcct gcccctgtct | 11760 |
| tgggtgactc ttccctccct gtctcctgtc tggatttcag ggaagatgaa gggcttctcc | 11820 |
| ctgctggccg agcccagga gttctgggtg acaacagca cctcagtgtc tgttcccatg | 11880 |
| ctctctggca tgggcacctt ccagcactgg agtgacatcc aggacaactt ctcggtgact | 11940 |
| caagtgccct tcactgagag cgcctgcctg ctgctgatcc agcctcacta tgcctctgac | 12000 |
| ctggacaagg tggagggtct cactttccag caaaactccc tcaactggat gaagaaacta | 12060 |

```
tctccccggt aggagcctcc cggtctcccc tggaatgtgg gagccacact gtcctgccca   12120
ggctgggggc ggggtgggga gtagacacac ctgagctgag ccttgggtgc agagcagggc   12180
agggccgcgg tggcacgggg ctgggcaggc ggcctgtgtg tctgtctacc agtcctctat   12240
ccagccagca cccagctctc cagttagtgt ctgtctttca agtgcaggca aggtaaagga   12300
ggagaggaag aatgcttttt ctacacttac acttgcctgg tagttttgga gggggagaaa   12360
acattgcaat ccgccctctg agagaggacc attttggtcc cacacctgac acacagcaca   12420
cctgtgacat ccaagagctt cttggaactg acttgccagg agggttcgga cttcgcgtga   12480 gcggggtgg ggccttctca gggagcgtcc cttgactcca gaacgccctt gctggcggct   12540
ggcggctggg tggggatagg tgttgttagc tcctctttcc tgctgcaatt cctttccaca   12600
gagccctgga ctcaaactac acatcacccc agatcatcga ggcctggaaa tctgctccca   12660
gaggcaggca ttgagtgaca cgatggcttg acatcaactc tgggtgtttt ttatgtttta   12720
aaaattgtga tggtaaaata tacgtaacaa aatttgccat cgtaaccatt ttcgagtgca   12780
cagttcagtg gtactaggcc cattcacact gttgtgcagc catcaccccc gtccatctcc   12840
atttatcttc tcaacttccc aaactgaagc tctgtcctgc tgaaacacta actctccatt   12900
tccccttccc cttggccccg gcaaccacca cgatgtcctc gaggttcacc catgttgtag   12960
cacatgtcag aatgtccttc cttttgaagg ctgaataata ttccattgca tgtggttacc   13020
accttttgtg tatccactca tccatcgatg gacacgtggg ttgcttccac ctttgagctg   13080
ctgtgaatag tgcagtgtac cctgtaaaca tgggtgtact gtcagctctt ataagtgctt   13140
gatacatcac tggaaatgtc catgggctct gaaggatgcc aaaagatgga agaggctcta   13200
tacgaagatc aatcgagttg acatagcaac gtgtccagca cgaggttgac actgtaccct   13260
cctgcctctc tccttttcat gggtgtcatg tcatcaagaa cactgctgtg gcagtagtaa   13320
gacacagtgc attatttcag agaatagcat ttaaaaatta cccaagtaac acaccttcaa   13380
tgcagccaac ctaaaaacag aatgcaccaa aggacaacca ttcctaggtc ctcatcggta   13440
aatcttctat gtccctcaca tagtattgca aatgacatga aggatttta ttgtaggttt   13500 tgctgaaatt ttccccaagg gggaggatga cttagttggg tgatgggggg agcaaacatc   13560
cctgtcgtca gggttgggtg caaggagcat aagcctgcct ggcctctggg agagccctca   13620
ctgtgtggcc tggagccttc ctaactgtgc atcatctccc caggaccatc cacctgacca   13680
tgccccaact ggtgctgcaa ggatcttatg acctgcagga cctgctcgcc caggctgagc   13740
tgcccgccat tctgcacacc gagctgaacc tgcaaaaatt gagcaatgac cgcatcaggg   13800 tggggaggt atgtgtgagc ctgtgtctgt gcctgacctg ggttccaagt gtgcacaggg   13860
tgggaggcat ggatgtaagg gacacagagg aggctatggg tggggccagc agggcaagag   13920
ggagcggaga gtagggccaa aggtgggaga gaagtagcca gagcattctg gggccttcca   13980
ggtgcagagc agcaaatccc tccccatccc tgctgtgcct cctcctgcta ggtgtgtgtt   14040
ccatggtcct gcttggcctt gccttgcctc agggtcctcc agggttccta tagtggagtt   14100
gaaaccggga tgaagacagc aagcacccct ggacctggtg ccctgggccc agccccttct   14160
tcagggaaat gctgagcagc agacagaatg tcccctgcc atgtggcacc atgcacatct   14220
gcagctacca aggatgtgcc ttgatgttct gggccctgtg ctcagtgctg gggagaaagt   14280
gggagttctt acggggccca gcgggaagag ccctctgtgc taagttagct aagccctggc   14340
actggtgggc catggccaag ggagccagga attctgcctg gacatcagg gcagaatgtg   14400
```

```
aagatgggag gatgtaaggg gtgtgttagg gaggagccgg catgtgagtt tggccattgt   14460
ggccaattaa cggtcatcta cacacagaca caccccttgcc tacactgagg ggcaggcata   14520
cactgtgcat cctcctggca ggctggaaaa tgtcccccctc caggacagtg cacagcacag   14580
aggtcctgag cccaccccgg ccctctagcc ctcagcaccc tgggtcaccc agtgcgccct   14640
cagaatgatc ctgatgtctg ctgctttgca ggtgctgaac agcatttttt ttgagcttga   14700
agcggatgag agagagccca cagagtctac ccaacagctt aacaagcctg aggtcttgga   14760
ggtgaccctg aaccgcccat cctgtttgc tgtgtatgat caaagcgcca ctgccctgca   14820
cttcctgggc cgcgtggcca acccgctgag cacagcatga ggccagggcc ccagaacaca   14880
gtgcctggca aggcctctgc ccctggcctt tgaggcaaag gccagcagca gataacaacc   14940
ccggacaaat cagcgatgtg tcaccccag tctcccacct tttcttctaa tgagtcgact   15000
ttgagctgga aagcagccgt ttctccttgg tctaagtgtg ctgcatggag tgagcagtag   15060
aagcctgcag cggcacaaat gcacctccca gtttgctggg tttatttag agaatgggg   15120 tggggaggca agaaccagtg tttagcgcgg gactactgtt ccaaaaagaa ttccaaccga   15180
ccagcttgtt tgtgaaacaa aaaagtgttc ccttttcaag ttgagaacaa aaattgggtt   15240
ttaaaattaa agtatacatt tttgcattgc cttcggtttg tatttagtgt cttgaatgta   15300
agaacatgac ctccgtgtag tgtctgtaat accttagttt tttccacaga tgcttgtgat   15360
ttttgaacaa tacgtgaaag atgcaagcac ctgaatttct gtttgaatgc ggaaccatag   15420
ctggttattt ctcccttgtg ttagtaataa acgtcttgcc acaataagcc tccaaaaatt   15480
ttatctttca tttagcagcc aaacagatgt atacaattca gcagatagac tgtgcaaacg   15540
aaagtgcttt cctggacttt ggatggaatt ccatgggag gtctgagcca gtacttagca   15600 gtccttgaa gttttaggtg atgcttttct ctggacactt ccattggtaa gcagtggtgg   15660
ccatctgtgt gatggacagg gggcgggaag agggtgacag ggaaggcccc atacccatg   15720 tggcacctgg gaaaggaacc aggcagatgg gacttcttcc gtcctggtga cacagggcca   15780
gactgctgct ggtattgtgc cccgggagtg gaaggtagag aaataaatct tcacaaataa   15840
atatttgcaa ttttccccca tctgttgagt gcctctgcct gctcctcctc gatgggatta   15900
ggcccacagt tcggaatctt ggggagagcc aaggaagcgg taggcaccca gtaggcccac   15960
ggccgtcggc tgatagcaat ggtgatgctg tcctacctac ttgtgtaagg cattcgatct   16020
tcctcccttc catacatatt gaaataaata agccgcgcaa tgtgttagct attgatcaga   16080
actaaagtga agtcagccac ggggattaca aatctcggct tctcccctca tgttcctgag   16140
agtcttcccc tggttttgaa cacatctccc tagctcgatg tcaaggtgag ggattctgtc   16200
ggcaacagca gtgcccttag ttgcttcgtc gtaactcccc gtcaccggtt ttattcagtt   16260
accttccagt cccactctca gagcttcctg gcttgttctg ctctcaaagc gggtagagct   16320
ggcacacatg gactctccga aacggctgca agatgccaag tttctcggaa gaactggaag   16380
cacagagacc agaagtgcct taaggtctcg ctattcagtg tggcgcttag accggcagtg   16440
gcggcagctg ccctgggagc ttgttagaat gtggcttctc acgcccctcc tggacctaca   16500
gagtcagaat ctgcagtttt acaggaggtc caggcttgga agttgctcgt agagacctga   16560
gacagcgcag ccacgtgctg gaaacaaagc atttaagttt gtgactttat tttaaaaggc   16620
agcaggcagt cgacaaacca atttcttcta cttagaggcg gcttcggctt ctggaagtcg   16680
ctaggagtat aaagttgcca accagcgctg ttctcccgct gttttctgtg cacttataaa   16740
tgggaagtta ggtcaggata gatctctcag ctattacaag gatacaaaat acgaacattc   16800
```

-continued

```
tacaagttac ttaacacaca cacacacaca cacacacaca caaaattaat      16860
tccacaggtc agtttctctg aaacattttt tcactaaatt ctaagtcttc ctggagttgc 16920
aagtgcctat ctcctagaca aggcaattac tcaccaacta aaatcactgt caatctgaga 16980
tttcggctgg gcatgagacc atggtcaggg gatgctttga acagcctctg aggaaattag 17040
tgagtttgaa aaatggaaag attttatta ctcacttggc agtaaaacct gatggggaca  17100
gacgtcaggc tgtttaagat cctcagaaga aaaagttgat agtgtgaata ttcctaaatt 17160
tgccacacga agatgtacat gtgattataa ggtgctgttg cagaagcccc tgggggtgtt 17220
atgggatata cactatatgg gccactttac cttcctaaaa tctgaaaaac ttcaactact 17280
gaaacatgga ctgaaggttt tgaatagtgg atggtgaatt tgaataccat cccgtgtgat 17340
ttttttttct agcagacttt agttttttag agcagtttta agcccacacc aaaactgaga 17400
ggaagataca gcaatttctc atataccccc tactaccttc cagtctcccc cattattgac 17460
atcccccacc cagagtggtc catttcttac aacccacgaa cctacattga cacatcatta 17520
ttactcaacg tccatagttt acattagggt tggctcttgg tgttgtacat tctatgggtt 17580
tagacaattt tcaggagttt cactgacctg aaaatcctct gtgtccctcc tattcacccc 17640
tccttccctc ctaaccactg gtaaccaccg atcctattcc catcttctcc atagttttgc 17700
ctttcccacc caggatgtca tatagtggaa tcattcagta tgtggccttt ccagattagc 17760
ctctttcact tagtaatgtg catttaagtt tcctccatgt cttttcatga tcgctcattt 17820
cttttttatt gctaaatact atgccactgt ctggatgtgt cacagtttat ttattcacct 17880
actgaaggac atcttgcttg tttccaagtt gtggcaattg cgaattaagc tgctacagac 17940
acccatgtgt gggttttgt gtggacatgt ttaccccaca caatttttaa agttgctcaa 18000
```

<210> SEQ ID NO 3
<211> LENGTH: 19
<212> TYPE: DNA
<213> ORGANISM: Artificial sequence
<220> FEATURE:
<223> OTHER INFORMATION: Primer

<400> SEQUENCE: 3
ccctgatggg agccagtgt                                           19

<210> SEQ ID NO 4
<211> LENGTH: 19
<212> TYPE: DNA
<213> ORGANISM: Artificial sequence
<220> FEATURE:
<223> OTHER INFORMATION: Primer

<400> SEQUENCE: 4
agcagggaga agcccttca                                           19

<210> SEQ ID NO 5
<211> LENGTH: 27
<212> TYPE: DNA
<213> ORGANISM: Artificial sequence
<220> FEATURE:
<223> OTHER INFORMATION: Probe

<400> SEQUENCE: 5
ccctggcttt caacacctac gtccact                                  27

<210> SEQ ID NO 6

```
<211> LENGTH: 20
<212> TYPE: DNA
<213> ORGANISM: Artificial sequence
<220> FEATURE:
<223> OTHER INFORMATION: Primer

<400> SEQUENCE: 6
ggacaaggtg gagggtctca                                                      20

<210> SEQ ID NO 7
<211> LENGTH: 21
<212> TYPE: DNA
<213> ORGANISM: Artificial sequence
<220> FEATURE:
<223> OTHER INFORMATION: Primer

<400> SEQUENCE: 7
agatccttgc agcaccagtt g                                                    21

<210> SEQ ID NO 8
<211> LENGTH: 29
<212> TYPE: DNA
<213> ORGANISM: Artificial sequence
<220> FEATURE:
<223> OTHER INFORMATION: Probe

<400> SEQUENCE: 8
atgaagaaac tatctccccg gaccatcca                                            29

<210> SEQ ID NO 9
<211> LENGTH: 19
<212> TYPE: DNA
<213> ORGANISM: Artificial sequence
<220> FEATURE:
<223> OTHER INFORMATION: Primer

<400> SEQUENCE: 9
gaaggtgaag gtcggagtc                                                       19

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
gaagatggtg atgggatttc                                                      20

<210> SEQ ID NO 11
<211> LENGTH: 20
<212> TYPE: DNA
<213> ORGANISM: Artificial sequence
<220> FEATURE:
<223> OTHER INFORMATION: Probe

<400> SEQUENCE: 11
caagcttccc gttctcagcc                                                      20

<210> SEQ ID NO 12
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 12
```
cgctgatttg tccggg                                                    16

<210> SEQ ID NO 13
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 13
tcggttggaa ttcttt                                                    16

<210> SEQ ID NO 14
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: bases at these positions are RNA

<400> SEQUENCE: 14
tcggutggaa ttcttt                                                    16

<210> SEQ ID NO 15
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 15
gtcggttgga attctt                                                    16

<210> SEQ ID NO 16
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (6)..(6)
<223> OTHER INFORMATION: bases at these positions are RNA

<400> SEQUENCE: 16
ctcatugtgg atgacg                                                    16

<210> SEQ ID NO 17
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 17
ctcattgtgg atgacg                                                    16

<210> SEQ ID NO 18
<211> LENGTH: 16
<212> TYPE: DNA
<213> ORGANISM: Artificial sequence
<220> FEATURE:
<223> OTHER INFORMATION: Synthetic oligonucleotide
<220> FEATURE:

<221> NAME/KEY: misc_feature
<222> LOCATION: (6)..(6)
<223> OTHER INFORMATION: bases at these positions are RNA

<400> SEQUENCE: 18
tgaatuggag caggta                                                    16

<210> SEQ ID NO 19
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 19
tgaattggag caggta                                                    16

<210> SEQ ID NO 20
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 20
cggtgtcaag ttttgc                                                    16

<210> SEQ ID NO 21
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 21
gttgggtaga ctctgt                                                    16

<210> SEQ ID NO 22
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 22
gttggaattc tttttg                                                    16

<210> SEQ ID NO 23
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 23

```
gttaagctgt tgggta                                               16

<210> SEQ ID NO 24
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (5)..(5)
<223> OTHER INFORMATION: bases at these positions are RNA

<400> SEQUENCE: 24
tgaautggag caggta                                               16

<210> SEQ ID NO 25
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 25
ttgcaggttc agctcg                                               16

<210> SEQ ID NO 26
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 26
ggtagactct gtgggc                                               16

<210> SEQ ID NO 27
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 27
gttggaattc tttttg                                               16

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
cacaaacaag ctggtcggtt                                           20
```